(12) United States Patent
Dai et al.

(10) Patent No.: US 10,047,098 B2
(45) Date of Patent: Aug. 14, 2018

(54) C5-C6-OXACYCLIC FUSED IMINOPYRIMIDINONE COMPOUNDS AS BACE INHIBITORS, COMPOSITIONS, AND THEIR USE

(71) Applicant: Merck Sharp & Dohme Corp., Rahway, NJ (US)

(72) Inventors: Xing Dai, Cranford, NJ (US); Jared N. Cumming, Winchester, MA (US); Hong Liu, Hillsborough, NJ (US); Jack D. Scott, Scotch Plains, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

(21) Appl. No.: 15/527,975

(22) PCT Filed: Nov. 20, 2015

(86) PCT No.: PCT/US2015/061727
§ 371 (c)(1),
(2) Date: May 18, 2017

(87) PCT Pub. No.: WO2016/085780
PCT Pub. Date: Jun. 2, 2016

(65) Prior Publication Data
US 2017/0362248 A1 Dec. 21, 2017

Related U.S. Application Data

(60) Provisional application No. 62/084,234, filed on Nov. 25, 2014.

(51) Int. Cl.
*A61K 31/519* (2006.01)
*C07D 491/048* (2006.01)
*C07D 491/052* (2006.01)

(52) U.S. Cl.
CPC ............................... *C07D 491/052* (2013.01)

(58) Field of Classification Search
CPC .............. A61K 31/519; C07D 491/048; C07D 491/052
USPC ........................................ 514/260.1; 544/278
See application file for complete search history.

(56) References Cited

U.S. PATENT DOCUMENTS

| | | | |
|---|---|---|---|
| 6,930,112 B2 | 8/2005 | Weaver et al. | |
| 7,763,609 B2 | 7/2010 | Zhu et al. | |
| 8,183,252 B2 | 5/2012 | Zhu et al. | |
| 8,691,831 B2 | 4/2014 | Zhu et al. | |
| 8,691,833 B2 | 4/2014 | Zhu et al. | |
| 8,729,071 B2 | 5/2014 | Scott et al. | |
| 8,829,036 B2 | 9/2014 | Zhu et al. | |
| 8,940,748 B2 | 1/2015 | Scott et al. | |
| 9,029,362 B2 | 5/2015 | Scott et al. | |
| 9,221,839 B2 | 12/2015 | Cumming et al. | |
| 9,365,589 B2 | 6/2016 | Cumming et al. | |
| 9,428,475 B2 | 8/2016 | Scott et al. | |
| 9,475,785 B2 | 10/2016 | Scott | |
| 9,489,013 B2 | 11/2016 | Cumming et al. | |
| 9,580,396 B2 | 2/2017 | Cumming et al. | |
| 2011/0237576 A1 | 9/2011 | Yonezawa et al. | |
| 2012/0202828 A1 | 8/2012 | Castro Pineiro et al. | |
| 2014/0200213 A1 | 7/2014 | Wu et al. | |
| 2016/0367563 A1 | 12/2016 | Scott et al. | |

FOREIGN PATENT DOCUMENTS

| WO | 2016044120 A1 | 3/2016 |
|---|---|---|
| WO | 2016085780 A1 | 6/2016 |

OTHER PUBLICATIONS

International Search Report for PCT/US2015/061727 dated Mar. 16, 2016, 11 pages.

*Primary Examiner* — Brenda L Coleman
(74) *Attorney, Agent, or Firm* — Keith D. MacMillan; Catherine D. Fitch

(57) ABSTRACT

In its many embodiments, the present invention provides certain C5-C6-oxacyclic fused iminopyrimidinone compounds, including compounds Formula (I): or a tautomer thereof, and pharmaceutically acceptable salts of said compounds and said tautomers, wherein $R^N$, $R^1$, $R^A$, ring A, m, n, $-L_1-$, ring B, $R^B$, and p are as defined herein. The novel compounds of the invention are useful as BACE inhibitors and/or for the treatment and prevention of various pathologies related thereto. Pharmaceutical compositions comprising one or more such compounds (alone and in combination with one or more other active agents), and methods for their preparation and use, including for the possible treatment of Alzheimer's disease, are also disclosed.

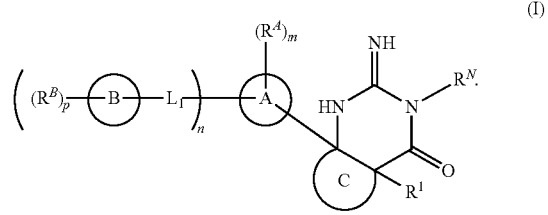

(I)

12 Claims, No Drawings

C5-C6-OXACYCLIC FUSED IMINOPYRIMIDINONE COMPOUNDS AS BACE INHIBITORS, COMPOSITIONS, AND THEIR USE

FIELD OF THE INVENTION

This invention provides certain C5-C6-oxacyclic fused iminopyrimidinone compounds, and compositions comprising these compounds, as inhibitors of BACE, which may be useful for treating or preventing pathologies related thereto, including, but not limited to, Alzheimer's disease.

BACKGROUND

Amyloid beta peptide ("Aβ") is a primary component of β amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease ("AD"), Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis β2 microglobulins and complications arising therefrom), neurodegenerative diseases such as scrapie, bovine spongiform encephalitis, Creutzfeld-Jakob disease, traumatic brain injury and the like.

Aβ peptides are short peptides which are made from the proteolytic break-down of the transmembrane protein called amyloid precursor protein ("APP"). Aβ peptides are made from the cleavage of APP by β-secretase activity at a position near the N-terminus of Aβ, and by gamma-secretase activity at a position near the C-terminus of Aβ. (APP is also cleaved by α-secretase activity, resulting in the secreted, non-amyloidogenic fragment known as soluble APPα.) Beta site APP Cleaving Enzyme ("BACE-1") is regarded as the primary aspartyl protease responsible for the production of Aβ by β-secretase activity. The inhibition of BACE-1 has been shown to inhibit the production of Aβ.

AD is estimated to afflict more than 20 million people worldwide and is believed to be the most common cause of dementia. AD is a disease characterized by degeneration and loss of neurons and also by the formation of senile plaques and neurofibrillary tangles. Presently, treatment of Alzheimer's disease is limited to the treatment of its symptoms rather than the underlying causes. Symptom-improving agents approved for this purpose include, for example, N-methyl-D-aspartate receptor antagonists such as memantine (Namenda®, Forest Pharmaceuticals, Inc.), cholinesterase inhibitors such as donepezil (Aricept®, Pfizer), rivastigmine (Exelon®, Novartis), galantamine (Razadyne Reminyl®), and tacrine (Cognex®).

In AD, Aβ peptides, formed through β-secretase and gamma-secretase activity, can form tertiary structures that aggregate to form amyloid fibrils. Aβ peptides have also been shown to form Aβ oligomers (sometimes referred to as "Aβ aggregates" or "Abeta oligomers"). Aβ oligomers are small multimeric structures composed of 2 to 12 Aβ peptides that are structurally distinct from Aβ fibrils. Amyloid fibrils can deposit outside neurons in dense formations known as senile plaques, neuritic plaques, or diffuse plaques in regions of the brain important to memory and cognition. Aβ oligomers are cytotoxic when injected in the brains of rats or in cell culture. This Aβ plaque formation and deposition and/or Aβ oligomer formation, and the resultant neuronal death and cognitive impairment, are among the hallmarks of AD pathophysiology. Other hallmarks of AD pathophysiology include intracellular neurofibrillary tangles comprised of abnormally phosphorylated tau protein, and neuroinflammation.

Evidence suggests that Aβ, Aβ fibrils, aggregates, oligomers, and/or plaque play a causal role in AD pathophysiology. (Ohno et al., Neurobiology of Disease, No. 26 (2007), 134-145). Mutations in the genes for APP and presenilins 1/2 (PS1/2) are known to cause familial AD and an increase in the production of the 42-amino acid form of Aβ is regarded as causative. Aβ has been shown to be neurotoxic in culture and in vivo. For example, when injected into the brains of aged primates, fibrillar Aβ causes neuronal cell death around the injection site. Other direct and circumstantial evidence of the role of Aβ in Alzheimer etiology has also been published.

BACE-1 has become an accepted therapeutic target for the treatment of Alzheimer's disease. For example, McConlogue et al., J. Bio. Chem., Vol. 282, No. 36 (September 2007), have shown that partial reductions of BACE-1 enzyme activity and concomitant reductions of Aβ levels lead to a dramatic inhibition of Aβ-driven AD-like pathology, making β-secretase a target for therapeutic intervention in AD. Ohno et al. Neurobiology of Disease, No. 26 (2007), 134-145, report that genetic deletion of BACE-1 in 5XFAD mice abrogates Aβ generation, blocks amyloid deposition, prevents neuron loss found in the cerebral cortex and subiculum (brain regions manifesting the most severe amyloidosis in 5XFAD mice), and rescues memory deficits in 5XFAD mice. The group also reports that Aβ is ultimately responsible for neuron death in AD and concludes that BACE-1 inhibition has been validated as an approach for the treatment of AD. Roberds et al., Human Mol. Genetics, 2001, Vol. 10, No. 12, 1317-1324, established that inhibition or loss of β-secretase activity produces no profound phenotypic defects while inducing a concomitant reduction in Aβ. Luo et al., Nature Neuroscience, Vol. 4, No. 3, March 2001, report that mice deficient in BACE-1 have normal phenotype and abolished β-amyloid generation.

More recently, Jonsson, et al. have reported in Nature, Vol. 488, pp. 96-99 (August 2012), that a coding mutation (A673T) in the APP gene protects against Alzheimer's disease and cognitive decline in the elderly without Alzheimer's disease. More specifically, the A allele of rs63750847, a single nucleotide polymorphism (SNP), results in an alanine to threonine substitution at position 673 in APP (A673T). This SNP was found to be significantly more common in a healthy elderly control group than in an Alzheimer's disease group. The A673T substitution is adjacent to the aspartyl protease beta-site in APP, and results in an approximately 40% reduction in the formation of amyloidogenic peptides in a heterologous cell expression system in vitro. Jonsson, et al. report that an APP-derived peptide substrate containing the A673T mutation is processed 50% less efficiently by purified human BACE1 enzyme when compared to a wild-type peptide. Jonsson et al. indicate that the strong protective effect of the APP-A673T substitution against Alzheimer's disease provides proof of principle for the hypothesis that reducing the beta-cleavage of APP may protect against the disease.

BACE-1 has also been identified or implicated as a therapeutic target for a number of other diverse pathologies in which Aβ or Aβ fragments have been identified to play a causative role. One such example is in the treatment of AD-type symptoms of patients with Down's syndrome. The gene encoding APP is found on chromosome 21, which is also the chromosome found as an extra copy in Down's syndrome. Down's syndrome patients tend to acquire AD at an early age, with almost all those over 40 years of age showing Alzheimer's-type pathology. This is thought to be due to the extra copy of the APP gene found in these patients, which leads to overexpression of APP and therefore to increased levels of Aβ causing the prevalence of AD seen in this population. Furthermore, Down's patients who have a duplication of a small region of chromosome 21 that does not include the APP gene do not develop AD pathology. Thus, it is thought that inhibitors of BACE-1 could be useful in reducing Alzheimer's type pathology in Down's syndrome patients.

Another example is in the treatment of glaucoma (Guo et al., PNAS, Vol. 104, No. 33, Aug. 14, 2007). Glaucoma is a retinal disease of the eye and a major cause of irreversible blindness worldwide. Guo et al. report that Aβ colocalizes with apoptotic retinal ganglion cells (RGCs) in experimental glaucoma and induces significant RGC cell loss in vivo in a dose- and time-dependent manner. The group report having demonstrated that targeting different components of the Aβ formation and aggregation pathway, including inhibition of β-secretase alone and together with other approaches, can effectively reduce glaucomatous RGC apoptosis in vivo. Thus, the reduction of Aβ production by the inhibition of BACE-1 could be useful, alone or in combination with other approaches, for the treatment of glaucoma.

Another example is in the treatment of olfactory impairment. Getchell et al., Neurobiology of Aging, 24 (2003), 663-673, have observed that the olfactory epithelium, a neuroepithelium that lines the posterior-dorsal region of the nasal cavity, exhibits many of the same pathological changes found in the brains of AD patients, including deposits of Aβ, the presence of hyperphosphorylated tau protein, and dystrophic neurites among others. Other evidence in this connection has been reported by Bacon A W, et al., Ann NY Acad Sci 2002; 855:723-31; Crino P B, Martin J A, Hill W D, et al., Ann Otol Rhinol Laryngol, 1995; 104:655-61; Davies D C, et al., Neurobiol Aging, 1993; 14:353-7; Devanand D P, et al., Am J Psychiatr, 2000; 157:1399-405; and Doty R L, et al., Brain Res Bull, 1987; 18:597-600. It is reasonable to suggest that addressing such changes by reduction of Aβ by inhibition of BACE-1 could help to restore olfactory sensitivity in patients with AD.

For compounds which are inhibitors of BACE-2, another example is in the treatment of type-II diabetes, including diabetes associated with amyloidogenesis. BACE-2 is expressed in the pancreas. BACE-2 immunoreactivity has been reported in secretory granules of beta cells, co-stored with insulin and IAPP, but lacking in the other endocrine and exocrine cell types.

Stoffel et al., WO2010/063718, disclose the use of BACE-2 inhibitors in the treatment of metabolic diseases such as Type-II diabetes. The presence of BACE-2 in secretory granules of beta cells suggests that it may play a role in diabetes-associated amyloidogenesis. (Finzi, G. Franzi, et al., Ultrastruct Pathol. 2008 November-December; 32(6):246-51.)

Other diverse pathologies characterized by the formation and deposition of Aβ or fragments thereof, and/or by the presence of amyloid fibrils, oligomers, and/or plaques, include neurodegenerative diseases such as scrapie, bovine spongiform encephalitis, traumatic brain injury ("TBI"), Creutzfeld-Jakob disease and the like, type II diabetes (which is characterized by the localized accumulation of cytotoxic amyloid fibrils in the insulin producing cells of the pancreas), and amyloid angiopathy. In this regard reference can be made to the patent literature. For example, Kong et al., US2008/0015180, disclose methods and compositions for treating amyloidosis with agents that inhibit Aβ peptide formation. As another example, certain groups have suggested the potential of BACE inhibition may be useful for traumatic brain injury. (Loane et al., "Amyloid precursor protein secretases as therapeutic targets for traumatic brain injury", Nature Medicine, 15, 377-379 (2009); Yu, et al., "Lithium reduces BACE1 overexpression, β amyloid accumulation, and spatial learning deficits in mice with traumatic brain injury", J Neurotrauma, 2012 September; 29(13): 2342-51; Tran, et al., "Controlled cortical impact traumatic brain injury in 3×Tg-AD mice causes acute intra-axonal amyloid-β accumulation and independently accelerates the development of tau abnormalities", J Neurosci. 2011 Jun. 29; 31(26):9513-25). Still other diverse pathologies characterized by the inappropriate formation and deposition of Aβ or fragments thereof, and/or by the presence of amyloid fibrils, and/or for which inhibitor(s) of BACE are expected to be of therapeutic value are discussed further hereinbelow.

SUMMARY OF THE INVENTION

The present invention provides certain C5-C6-oxacyclic fused iminopyrimidinone compounds, which are collectively or individually referred to herein as "compound(s) of the invention", as described herein. The compounds of the invention are inhibitors of BACE-1 and/or BACE-2, and may be useful for treating or preventing diseases or pathologies related thereto.

In one embodiment, the compounds of the invention have the structural Formula (I):

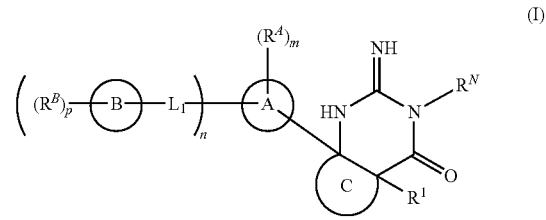

or a tautomer thereof having the structural Formula (I'):

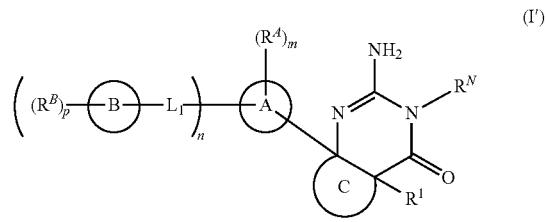

or pharmaceutically acceptable salt thereof, wherein:

ring C is selected from the group consisting of tetrahydrofuranyl and tetrahydropyranyl, wherein 1 or 2 of the ring carbon atoms having two available substitutable hydrogen atoms of said tetrahydrofuranyl and tetrahydropyranyl rings are optionally independently replaced with a —C($R^{C1}R^{C2}$)— group, wherein $R^{C1}$ and $R^{C2}$ are each independently selected from the group consisting of H, halogen, —$CO_2$-(lower alkyl), alkyl, cycloalkyl, -alkyl-cycloalkyl, -heterocycloalkyl, -alkyl-heterocycloalkyl, aryl, -alkyl-aryl, heteroaryl, and -alkyl-heteroaryl, wherein said alkyl, cycloalkyl, -alkyl-cycloalkyl, -heterocycloalkyl, -alkyl-heterocycloalkyl, aryl, -alkyl-aryl, heteroaryl, and -alkyl-heteroaryl of $R^{C1}$ and $R^{C2}$ are optionally substituted with one or more $R^3$, and wherein 1 to 2 non-adjacent, non-terminal carbon atoms in each said alkyl of $R^{C1}$ and $R^{C2}$ are optionally independently replaced with —O—, —NH—, —N(alkyl)-, —S—, —S(O)—, or —S(O)$_2$—, or, alternatively, wherein said $R^{C1}$ and $R^{C2}$ of one said —C($R^{C1}R^{C2}$)— group are taken together with the carbon to which they are attached form a spirocyclic ring consisting of from 3 to 6 carbon atoms, wherein 1 of said carbon atoms may be replaced with —O—, —NH—, —N(lower alkyl)-, —N(lower haloalkyl)-, —S—, —S(O)—, or —S(O)$_2$—, and wherein each of the carbon atoms of said spirocyclic ring may be optionally independently substituted with 1 to 4 fluorine, lower alkyl, lower haloalkyl, or —$CH_2$O-(lower alkyl).

$R^N$ is selected from the group consisting of H, alkyl, cycloalkyl, and -alkyl-cycloalkyl, wherein said alkyl, cycloalkyl, and -alkyl-cycloalkyl are optionally substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—;

$R^1$ is selected from the group consisting of H, halogen, and alkyl, wherein said alkyl is optionally substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—;

ring A is selected from the group consisting of aryl and heteroaryl;

m is 0 or more, with the proviso that the value of m does not exceed the number of available substitutable hydrogen atoms on ring A;

each $R^A$ (when present) is independently selected from the group consisting of halogen, oxo, —OH, —CN, lower alkyl, —O-(lower alkyl), lower alkenyl, —O-(lower alkenyl), and -(lower alkyl)-(lower cycloalkyl).

wherein said lower alkyl, —O-(lower alkyl), lower alkenyl, —O-(lower alkenyl), and -(lower alkyl)-(lower cycloalkyl) of $R^A$ are each optionally independently unsubstituted or substituted with one or more fluorine, and wherein 1 to 2 non-adjacent, non-terminal carbon atoms in said lower alkyl and are optionally independently replaced with —O—, —NH—, —N(alkyl)-, —S—, —S(O)—, or —S(O)$_2$—;

n is 0 or 1;

-$L_1$- (when present) independently represents a bond or a divalent moiety selected from the group consisting of —O—, —$CH_2$—O—, —CH($CH_3$)—O—, —CH($CF_3$)—O—, and —CH($CHF_2$)—O—;

ring B is selected from the group consisting of aryl, heteroaryl, cycloalkyl, and heterocycloalkyl;

p is 0 or more, with the proviso that the value of p does not exceed the number of available substitutable hydrogen atoms on ring B; and each $R^B$ (when present) is independently selected from the group consisting of halogen, oxo, —OH, —CN, —$SF_5$, —$OSF_5$, —$OR^{2B}$, —$SR^{2B}$, alkyl, alkenyl, alkynyl, cycloalkyl, -alkyl-cycloalkyl, heterocycloalkyl, -alkyl-heterocycloalkyl, aryl, and heteroaryl, wherein said alkyl, alkenyl, alkynyl, cycloalkyl, -alkyl-cycloalkyl, heterocycloalkyl, -alkyl-heterocycloalkyl, aryl, and heteroaryl of $R^B$ are each optionally independently unsubstituted or substituted with one or more groups independently selected from $R^3$, and wherein 1 to 2 non-adjacent, non-terminal carbon atoms in said alkyl are optionally independently replaced with —O—, —NH—, —N(alkyl)-, —S—, —S(O)—, or —S(O)$_2$—;

each $R^{2B}$ is independently selected from the group consisting of H, alkyl, alkenyl, alkynyl, cycloalkyl, -alkyl-cycloalkyl, heterocycloalkyl, and -alkyl-heterocycloalkyl, wherein each said alkyl, alkenyl, alkynyl, cycloalkyl, -alkyl-cycloalkyl, heterocycloalkyl, and -alkyl-heterocycloalkyl of $R^{2B}$ is unsubstituted or optionally substituted with one or more fluorine, and wherein 1 to 2 non-adjacent, non-terminal carbon atoms in said alkyl are optionally independently replaced with —O—, —NH—, —N(alkyl)-, —S—, —S(O)—, or —S(O)$_2$—;

each $R^3$ (when present) is independently selected from the group consisting of halogen, —OH, —CN, alkyl, -alkyl-OH, —O-alkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl, wherein each said alkyl, -alkyl-OH, —O-alkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl, are optionally substituted with one or more halogen, and wherein 1 to 2 non-adjacent, non-terminal carbon atoms in said alkyl and —O-alkyl, are optionally independently replaced with —O—, —NH—, —N(alkyl)-, —S—, —S(O)—, or —S(O)$_2$—.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

DETAILED DESCRIPTION

For each of the following embodiments, any variable not explicitly defined in the embodiment is as defined in Formula (I), (I'), (IA), or (IA'). In each of the embodiments described herein, each variable is selected independently of the other unless otherwise noted.

In one embodiment, the compounds of the invention have the structural Formula (IA):

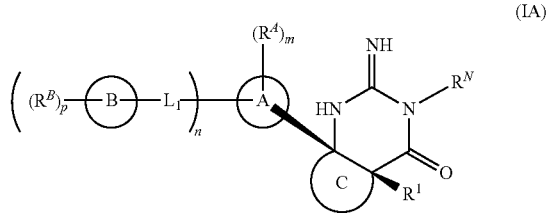
(IA)

or a tautomer thereof having the structural Formula (IA'):

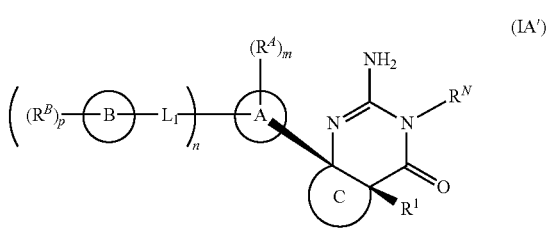
(IA')

or pharmaceutically acceptable salt thereof, wherein each variable is as described in Formula (I).

In one embodiment, in each of Formulas (I), (I'), (IA), and (IA'):

ring C is selected from the group consisting of

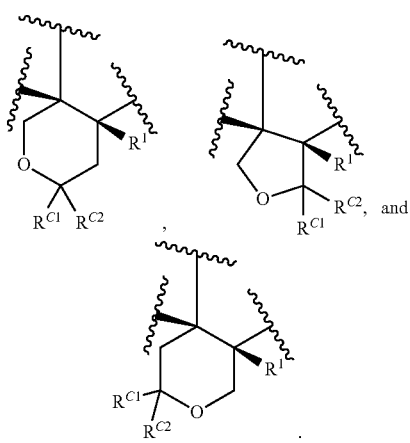

In one embodiment, in each of Formulas (I), (I'), (IA), and (IA'):

ring C is

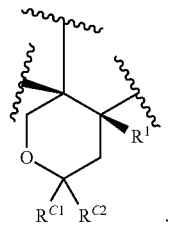

The following alternative embodiments of $R^{C1}$ and $R^{C2}$ are contemplated in combination with any of the embodiments described above.

In one embodiment, in each of Formulas (I), (I'), (IA), and (IA'):

$R^{C1}$ and $R^{C2}$ are each independently selected from the group consisting of H, —$CO_2CH_3$, —$CO_2CH_2CH_3$, —$CO_2CH(CH_3)_3$, methyl, ethyl, propyl, butyl, cyclopropyl, —$CH_2$-cyclopropyl, cyclobutyl, —$CH_2$-cyclobutyl, —$CH_2OH$, —$CH_2OCH_3$, —$CH_2OCH_2CH_3$, phenyl, pyridyl, pyrimidinyl, pyrazinyl, oxazoyl, isooxazoyl, thiazoyl, isothiazolyl, pyrazolyl, benzodioxolyl, benzofuranyl, dihydrobenzofuranyl, benzyl, —$CH_2$-pyridyl, —$CH_2$-pyrimidinyl, and —$CH_2$-pyrazinyl, wherein each said methyl, ethyl, propyl, butyl, cyclopropyl, —$CH_2$-cyclopropyl, cyclobutyl, —$CH_2$-cyclobutyl, —$CH_2OCH_3$, and —$CH_2OCH_2CH_3$ of $R^{C1}$ and $R^{C2}$ is optionally substituted with one or more fluorine, and wherein each said phenyl, pyridyl, pyrimidinyl, pyrazinyl, oxazoyl, isoxazoyl, thiazoyl, isothiazolyl, pyrazolyl, benzodioxolyl, benzofuranyl, dihydrobenzofuranyl, benzyl, —$CH_2$-pyridyl, —$CH_2$-pyrimidinyl, and —$CH_2$-pyrazinyl of $R^{C1}$ and $R^{C2}$ is unsubstituted or substituted with one or more groups independently selected from the group consisting of fluorine, chlorine, bromine, methyl, ethyl, propyl, cyclopropyl, —$OCH_3$, —$OCH_2CH_3$, and —O-cyclopropyl, wherein each said methyl, ethyl, propyl, cyclopropyl, —$OCH_3$, —$OCH_2CH_3$, and —O-cyclopropyl is each optionally substituted with from 1 to 3 fluorine.

In one embodiment, in each of Formulas (I), (I'), (IA), and (IA'):

$R^{C1}$ and $R^{C2}$ are each independently selected from the group consisting of H, —$CO_2CH_3$, methyl, ethyl, cyclopropyl, —$CH_2OH$, —$CH_2OCH_3$, phenyl, pyridyl, pyrimidinyl, oxazoyl, isoxazoyl, and pyrazolyl, wherein each said methyl, ethyl, cyclopropyl, and —$CH_2OCH_3$, of $R^{C1}$ and $R^{C2}$ is optionally substituted with one or more fluorine, and wherein each said phenyl, pyridyl, pyrimidinyl, oxazoyl, isoxazoyl, and pyrazolyl of $R^{C1}$ and $R^{C2}$ is unsubstituted or substituted with one or more groups independently selected from the group consisting of fluorine, methyl, ethyl, cyclopropyl, and —$OCH_3$, wherein each said methyl, ethyl, cyclopropyl, and —$OCH_3$ is each optionally substituted with from 1 to 3 fluorine.

In one embodiment, in each of Formulas (I), (I'), (IA), and (IA'):

$R^{C1}$ and $R^{C2}$ are each independently selected from the group consisting of H, —$CO_2CH_3$, methyl, —$CHF_2$, cyclopropyl, —$CH_2OCH_3$, phenyl, and isoxazoyl, wherein each said phenyl and isoxazoyl of $R^{C1}$ and $R^{C2}$ is unsubstituted or substituted with one or more groups independently selected from the group consisting of fluorine and methyl.

In one embodiment, in each of Formulas (I), (I'), (IA), and (IA'):

$R^{C2}$ is selected from the group consisting of H and methyl.

In one embodiment, in each of Formulas (I), (I'), (IA), and (IA'):

$R^{C2}$ is H.

In one embodiment, in each of Formulas (I), (I'), (IA), and (IA'):

$R^{C1}$ is selected from the group consisting of H, —$CO_2CH_3$, methyl, ethyl, cyclopropyl, —$CH_2OH$, —$CH_2OCH_3$, phenyl, pyridyl, pyrimidinyl, oxazoyl, isoxazoyl, and pyrazolyl, wherein each said methyl, ethyl, cyclopropyl, and —$CH_2OCH_3$, of $R^{C1}$ is optionally substituted with one or more fluorine, and wherein each said phenyl, pyridyl, pyrimidinyl, oxazoyl, isoxazoyl, and pyrazolyl of $R^{C1}$ is unsubstituted or substituted with one or more groups independently selected from the group consisting of fluorine, methyl, ethyl, cyclopropyl, and —$OCH_3$, wherein each said methyl, ethyl, cyclopropyl, and —$OCH_3$ is each optionally substituted with from 1 to 3 fluorine; and $R^{C2}$ is selected from the group consisting of H and methyl.

In one embodiment, in each of Formulas (I), (I'), (IA), and (IA'):

$R^{C1}$ is selected from the group consisting of H, —$CO_2CH_3$, methyl, —$CHF_2$, cyclopropyl, —$CH_2OCH_3$, phenyl, and isoxazoyl, wherein each said phenyl and isoxazoyl of $R^{C1}$ is unsubstituted or substituted with one or more groups independently selected from the group consisting of fluorine and methyl; and $R^{C2}$ is selected from the group consisting of H and methyl.

In one embodiment, in each of Formulas (I), (I'), (IA), and (IA'):

$R^{C1}$ is selected from the group consisting of H, —$CO_2CH_3$, methyl, —$CHF_2$, cyclopropyl, —$CH_2OCH_3$, phenyl, and isoxazoyl, wherein each said phenyl and isoxazoyl of $R^{C1}$ is unsubstituted or substituted with one or more groups independently selected from the group consisting of fluorine and methyl; and $R^{C2}$ is H.

In one embodiment, in each of Formulas (I), (I'), (IA), and (IA'):

ring C is and $R^{C1}$ and $R^{C2}$ are each independently selected from the group consisting of H, —$CO_2CH_3$, methyl, —$CHF_2$, cyclopropyl, —$CH_2OCH_3$, phenyl, and isoxazoyl, wherein each said phenyl and isoxazoyl of $R^{C1}$ and $R^{C2}$ is unsubstituted or substituted with one or more groups independently selected from the group consisting of fluorine and methyl.

In one embodiment, in each of Formulas (I), (I'), (IA), and (IA'):

ring C is $R^{C1}$ is selected from the group consisting of H, —$CO_2CH_3$, methyl, —$CHF_2$, cyclopropyl, —$CH_2OCH_3$, phenyl, and isoxazoyl, wherein each said phenyl and isoxazoyl of $R^{C1}$ is unsubstituted or substituted with one or more groups independently selected from the group consisting of fluorine and methyl; and $R^{C2}$ is H.

In one embodiment, in each of Formulas (I), (I'), (IA), and (IA'):

ring C is and $R^{C1}$ and $R^{C2}$ taken together with the carbon to which they are attached form a spirocyclic ring selected from the group consisting of spirocyclopropyl, spirocyclobutyl, spirocyclopentyl, spirocyclohexyl, spiroazetidinyl, spiropyrrolidinyl, spiropiperidinyl, spiroxetanyl, spirotetrahydrofuranyl, spirotetrahydropyranyl, wherein each of the carbon atoms of said spirocyclopropyl, spirocyclobutyl, spirocyclopentyl, spirocyclohexyl, spiroazetidinyl, spiropyrrolidinyl, spiropiperidinyl, spiroxetanyl, spirotetrahydrofuranyl, spirotetrahydropyranyl is unsubstituted or substituted with 1 to 4 groups independently selected from the group consisting of fluorine, methyl, cyclopropyl, and —$OCH_3$, wherein each said methyl, cyclopropyl, and —$OCH_3$ is each optionally substituted with from 1 to 3 fluorine, and wherein each of the nitrogen atoms of said spiroazetidinyl, spiropyrrolidinyl, and spiropiperidinyl is unsubstituted or substituted with methyl, ethyl, propyl, and —$CH_2CF_3$.

The following alternative embodiments of $R^N$ are contemplated in combination with any of the embodiments described above.

In one embodiment, in each of Formulas (I), (I'), (IA), and (IA'):

$R^N$ is selected from the group consisting of H, methyl, ethyl, cyclopropyl, —$CH_2$-cyclopropyl, and —$CH_2CH_2OCH_3$, wherein each said methyl, ethyl, cyclopropyl, —CH$_2$-cyclopropyl, and —CH$_2$CH$_2$OCH$_3$ is each optionally substituted with from 1 to 3 fluorine.

In one embodiment, in each of Formulas (I), (I'), (IA), and (IA'):
R$^N$ is selected from the group consisting of H and methyl.

In one embodiment, in each of Formulas (I), (I'), (IA), and (IA'):
R$^N$ is methyl.

The following alternative embodiments of R$^1$ are contemplated in combination with any of the embodiments described above.

In one embodiment, in each of Formulas (I), (I'), (IA), and (IA'):
R$^1$ is selected from the group consisting of H, fluoro, methyl, and —CH$_2$OCH$_3$.

In one embodiment, in each of Formulas (I), (I'), (IA), and (IA'):
R$^1$ is H.

In one embodiment, in each of Formulas (I), (I'), (IA), and (IA'):
R$^N$ is selected from the group consisting of H, methyl, ethyl, cyclopropyl, —CH$_2$-cyclopropyl, and —CH$_2$CH$_2$OCH$_3$,
wherein each said methyl, ethyl, cyclopropyl, —CH$_2$-cyclopropyl, and —CH$_2$CH$_2$OCH$_3$ is each optionally substituted with from 1 to 3 fluorine; and
R$^1$ is selected from the group consisting of H, fluoro, methyl, and —CH$_2$OCH$_3$.

In one embodiment, in each of Formulas (I), (I'), (IA), and (IA'):
R$^N$ is selected from the group consisting of H and methyl; and
R$^1$ is H.

In one embodiment, in each of Formulas (I), (I'), (IA), and (IA'):
R$^N$ is methyl; and
R$^1$ is H.

In some embodiments, in each of Formulas (I), (I'), (IA), and (IA'):
n is 1. In these embodiments, the moiety:

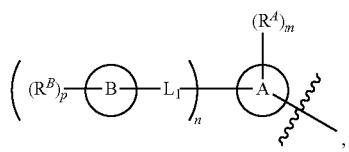

has the form:

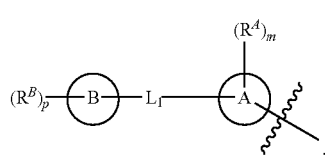

The following alternative embodiments of ring A, R$^A$, m, n, -L$_1$-, ring B, p, and R$^B$ are contemplated in combination with any of the embodiments described above.

In one embodiment, in each of Formulas (I), (I'), (IA), and (IA'):
n is 1;
-L$_1$- independently represents a bond or a divalent moiety selected from the group consisting of —O— and —CH$_2$—O—.

In one embodiment, in each of Formulas (I), (I'), (IA), and (IA'):
n is 1;
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, or 3; with the proviso that the value of m does not exceed the number of available substitutable hydrogen atoms on ring A; and
each R$^A$ (when present) is independently selected from the group consisting of fluoro, chloro, bromo, —CN, methyl, ethyl, cyclopropyl, —CH$_2$OCH$_3$, —CF$_3$, —CHF$_2$, —CH$_2$F, —OCH$_3$, —OCF$_3$, and —OCHF$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
n is 1;
ring A is selected from the group consisting of phenyl, pyridinyl, and thienyl;
m is 0, 1, 2, or 3; and
each R$^A$ (when present) is independently selected from the group consisting of fluoro, chloro, methyl, and —CHF$_2$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
n is 1;
ring A is selected from the group consisting of phenyl and pyridinyl;
m is 0, 1, 2, or 3; and
each R$^A$ (when present) is independently selected from the group consisting of fluoro, chloro, methyl, and —CHF$_2$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
n is 1;
ring A is selected from the group consisting of phenyl and pyridinyl;
m is 0, 1, 2, or 3; and
each R$^A$ (when present) is fluoro.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In one embodiment, in each of Formulas (I), (I'), (IA), and (IA'):
n=1;
-L$_1$- is —O—;
ring B is selected from the group consisting of azetidinyl, benzimidazolyl, benzoisothiazolyl, benzoisoxazolyl, benzothiazolyl, benzoxazolyl, cyclobutyl, cyclohexyl, cyclopentyl, cyclopropyl, dihydroindenyl, furanyl, imidazolyl, imidazopyridinyl, imidazopyrimidinyl, imidazothiazolyl, indenyl, indolyl, isoquinolinyl, isothiazolyl, isoxazolyl, morpholinyl, oxadiazolyl, oxazolyl, oxetanyl, phenyl, piperazinyl, piperidinyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, quinolinyl, tetrahydrofuranyl, tetrahydropyranyl, tetrazolyl, thiadiazolyl, thiazolyl, thienyl, thienylpyridine, thiomorpholinyl, thiomorpholinyl dioxide, and triazolyl;

p is 0, 1, 2, or 3, with the proviso that the value of p does not exceed the number of available substitutable hydrogen atoms on ring B; and each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, —OCH$_2$CH$_2$F, phenyl, pyridinyl, oxadiazolyl, isoxazolyl, oxazolyl, pyrazolyl, pyrrolyl, and triazolyl, wherein each said phenyl, pyridinyl, oxadiazolyl, isoxazolyl, oxazolyl, pyrazolyl, pyrrolyl, and triazolyl is optionally substituted with from 1 to 3 substituents independently selected from the group consisting of fluoro, chloro, —CN, methyl, —OCH$_3$, and —CF$_3$;

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-L$_1$- is —O—;
ring B is selected from the group consisting of cyclobutyl, cyclopentyl, cyclopropyl, isoquinolinyl, phenyl, piperidinyl, pyrazinyl, pyrazolyl, pyridazinyl, pyridinyl, pyrimidinyl, pyrrolidinyl, quinolinyl, tetrahydrofuranyl, and tetrahydropyranyl;
p is 0, 1, 2, or 3, with the proviso that the value of p does not exceed the number of available substitutable hydrogen atoms on ring B; and
each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, oxazolyl, pyrazolyl, pyrrolyl, and triazolyl,
wherein each said oxadiazolyl, isoxazolyl, oxazolyl, pyrazolyl, pyrrolyl, and triazolyl, is optionally substituted with one substituent from the group consisting of fluoro and methyl.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-L$_1$- is —O—;
ring B is selected from the group consisting of cyclobutyl, isoquinolinyl, phenyl, pyrazinyl, pyridazinyl, pyridinyl, and pyrimidinyl;
p is 0, 1, or 2; and
each $R^B$ group (when present) is independently selected from the group consisting of fluoro, chloro, methyl, —CN, —OMe, —CHF$_2$, oxazolyl, pyrazolyl, and triazolyl.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):
n=1;
-L$_1$- is —O—;
ring A is selected from the group consisting of phenyl and pyridinyl;
m is 0, 1, 2, or 3;
each $R^A$ (when present) is fluoro;
ring B is selected from the group consisting of cyclobutyl, cyclopentyl, cyclopropyl, isoquinolinyl, phenyl, piperidinyl, pyrazinyl, pyrazolyl, pyridazinyl, pyridinyl, pyrimidinyl, pyrrolidinyl, quinolinyl, tetrahydrofuranyl, and tetrahydropyranyl;
p is 0, 1, 2, or 3, with the proviso that the value of p does not exceed the number of available substitutable hydrogen atoms on ring B; and
each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, oxazolyl, pyrazolyl, pyrrolyl, and triazolyl,
wherein each said oxadiazolyl, isoxazolyl, oxazolyl, pyrazolyl, pyrrolyl, and triazolyl, is optionally substituted with one substituent from the group consisting of fluoro and methyl.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):
n=1;
-L$_1$- is —O—;
ring A is selected from the group consisting of phenyl and pyridinyl;
m is 0, 1, or 2;
each $R^A$ (when present) is fluoro;
ring B is selected from the group consisting of cyclobutyl, isoquinolinyl, phenyl, pyrazinyl, pyridazinyl, pyridinyl, and pyrimidinyl;
p is 0, 1, or 2; and each $R^B$ group (when present) is independently selected from the group consisting of fluoro, chloro, methyl, —CN, —OMe, —CHF$_2$, oxazolyl, pyrazolyl, and triazolyl.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n=1;
-L$_1$- is —CH$_2$O—;
ring B is selected from the group consisting of azetidinyl, bicyclo[2.1.1]hexane, bicyclo[3.1.1]heptane, bicyclo[2.2.1]heptane, bicyclo[2.2.2]octane, [1.1.1]-bicyclopentane, cyclobutyl, cyclohexyl, cyclopentyl, cyclopropyl, furanyl, isothiazolyl, isoxazolyl, morpholinyl, oxadiazolyl, oxazolyl, oxetanyl, phenyl, piperazinyl, piperidinyl, pyrazinyl, pyrazolyl, pyridazinyl, pyridinyl, pyrimidinyl, pyrrolidinyl, pyrrolyl, tetrahydrofuranyl, tetrahydropyranyl, tetrazolyl, thiadiazolyl, thiazolyl, thienyl, thiomorpholinyl, thiomorpholinyl dioxide, and triazolyl;
p is 0, 1, 2, or 3, with the proviso that the value of p does not exceed the number of available substitutable hydrogen atoms on ring B; and
each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, and —OCH$_2$CH$_2$F.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;
-L$_1$- is —CH$_2$O—;
ring B is selected from the group consisting of [1.1.1]-bicyclopentane, cyclobutyl, cyclopropyl, oxazolyl, phenyl, pyrazinyl, pyridinyl, pyrimidinyl, tetrahydropyranyl, and thiazolyl;
p is 0, 1, 2, or 3, with the proviso that the value of p does not exceed the number of available substitutable hydrogen atoms on ring B; and
each $R^B$ group (when present) is independently selected from the group consisting of fluoro, chloro, —CN, —OCH$_3$, —OCH$_2$—C≡C—H, —OCH$_2$—C≡C—CH$_3$, methyl, cyclopropyl, —CH$_2$OCH$_3$, —C≡CH, —C≡C—CH$_3$, —CF$_3$, —CHF$_2$, —OCF$_3$, and —OCHF$_2$.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;
-L$_1$- is —CH$_2$O—;
ring B is selected from the group consisting of [1.1.1]-bicyclopentane, cyclobutyl, and cyclopropyl;
p is 0, 1, or 2; and
each $R^B$ group (when present) is independently selected from the group consisting of fluoro, —CN, and —OMe.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n is 1;
-L$_1$- is —CH$_2$O—;
ring A is selected from the group consisting of phenyl and pyridinyl;
m is 0, 1, 2, or 3;
each $R^A$ (when present) is fluoro;
ring B is selected from the group consisting of [1.1.1]-bicyclopentane, cyclobutyl, cyclopropyl, oxazolyl, phenyl, pyrazinyl, pyridinyl, pyrimidinyl, tetrahydropyranyl, and thiazolyl;
p is 0, 1, 2, or 3, with the proviso that the value of p does not exceed the number of available substitutable hydrogen atoms on ring B; and
each $R^B$ group (when present) is independently selected from the group consisting of fluoro, chloro, —CN, —OCH$_3$, —OCH$_2$—C≡C—H, —OCH$_2$—C≡C—CH$_3$, methyl, cyclopropyl, —CH$_2$OCH$_3$, —C≡CH, —C≡C—CH$_3$, —CF$_3$, —CHF$_2$, —OCF$_3$, and —OCHF$_2$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;
-L$_1$- is —CH$_2$O—;
ring A is selected from the group consisting of phenyl and pyridyl;
m is 0, 1, or 2;
each $R^A$ (when present) is fluoro;
ring B is selected from the group consisting of [1.1.1]-bicyclopentane, cyclobutyl, and cyclopropyl;
p is 0, 1, or 2; and
each $R^B$ group (when present) is independently selected from the group consisting of fluoro, —CN, and —OMe.

In an alternative of the immediately preceding embodiment, m is 0. In another alternative of the immediately preceding embodiment, m is 1. In another alternative of the immediately preceding embodiment, m is 2.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n=1;

-$L_1$- is a bond;

ring B is selected from the group consisting of benzimidazolyl, benzoisothiazolyl, benzoisoxazolyl, benzothiazolyl, benzoxazolyl, cyclopropyl, dihydroindenyl, dihydrooxazolyl, furanyl, imidazolyl, imidazopyridinyl, imidazopyrimidinyl, imidazothiazolyl, indenyl, indolyl, isothiazolyl, isoxazolyl, oxadiazolyl, oxazolyl, phenyl, pyrazinyl, pyrazolyl, pyrazolopyridinyl, pyrazolopyrimidinyl, pyridazinyl, pyridinyl, pyrimidinyl, pyrazolopyridinyl, pyrrolidinyl, pyrrolyl, pyrrolopyridinyl, pyrrolopyrimidinyl, tetrazolyl, thiadiazolyl, thiazolyl, thienyl, thienylpyridine, and triazolyl;

p is 0, 1, 2, or 3, with the proviso that the value of p does not exceed the number of available substitutable hydrogen atoms on ring B; and each $R^B$ group (when present) is independently selected from the group consisting of halogen, oxo, —OH, —CN, —OCH$_3$, —OCH$_2$CH$_3$, —O-cyclopropyl, —O—CH$_2$-cyclopropyl, —OCH$_2$—C≡C—H, —OCH$_2$—C≡C—CH$_3$, methyl, ethyl, propyl, cyclopropyl, —CH$_2$-cyclopropyl, —CH$_2$OCH$_3$, —CH$_2$OCH$_2$CH$_3$, —C≡CH, —C≡C—CH$_3$, —CF$_3$, —CHF$_2$, —CH$_2$F, —OCF$_3$, —OCH$_2$CF$_3$, —OCHF$_2$, —OCH$_2$F, and —OCH$_2$CH$_2$F.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;

-$L_1$- is a bond;

ring B is selected from the group consisting of imidazopyridinyl, imidazopyrimidinyl, indolyl, isothiazolyl, isoxazolyl, oxadiazolyl, oxazolyl, phenyl, pyrazinyl, pyrazolyl, pyrazolopyridinyl, pyrazolopyrimidinyl, pyridinyl, pyrimidinyl, pyrazolopyridinyl, pyrrolyl, pyrrolopyridinyl, pyrrolopyrimidinyl, thiadiazolyl, thiazolyl, thienyl, and triazolyl;

p is 0, 1, 2, or 3, with the proviso that the value of p does not exceed the number of available substitutable hydrogen atoms on ring B; and each $R^B$ group (when present) is independently selected from the group consisting of fluoro, chloro, —CN, —OCH$_3$, —O—CH$_2$-cyclopropyl, —OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$.

In an alternative of the immediately preceding embodiment, p is 0. In another alternative of the immediately preceding embodiment, p is 1. In another alternative of the immediately preceding embodiment, p is 2. In another alternative of the immediately preceding embodiment, p is 3, with the proviso that the value of p does not exceed the number of available substitutable hydrogen atoms on ring B.

In one embodiment, in each of Formulas (I), (I'), (IA), and (IA'):

n=1;

-$L_1$- is a bond;

ring B is selected from the group consisting of phenyl, pyridinyl, and pyrimidinyl;

p is 0, 1, or 2; and each $R^B$ group (when present) is independently selected from the group consisting of fluoro, chloro, methyl, —CN, —OMe, —C≡CH, —C≡C—CH$_3$, —CHF$_2$.

In an alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n=1;

-$L_1$- is a bond; and ring B is pyrimidinyl.

In one embodiment, in each of Formulas (I), (I'), (IA), and (IA'):

n=1;

-$L_1$- is a bond;

ring A is selected from the group consisting of phenyl, pyridinyl, and thienyl;

m is 0, 1, 2, or 3;

each $R^A$ (when present) is independently selected from the group consisting of fluoro, chloro, methyl, and —CHF$_2$;

ring B is selected from the group consisting of phenyl, pyridinyl, and pyrimidinyl;

p is 0, 1, or 2; and each $R^B$ group (when present) is independently selected from the group consisting of fluoro, chloro, methyl, —CN, —OMe, —C≡CH, —C≡C—CH$_3$, —CHF$_2$.

In an alternative of the immediately embodiment, m is 0. In another alternative of the immediately preceding embodiment, m is 1. In another alternative of the immediately preceding embodiment, m is 2. In another alternative of the immediately preceding embodiment, m is 3.

In another alternative of the immediately preceding embodiment, p is 0. In another alternative of the immediately preceding embodiment, p is 1. In another alternative of the immediately preceding embodiment, p is 2.

In one embodiment, in each of Formulas (I), (I'), (IA), and (IA'):

n is 1;

-$L_1$- is a bond;

ring A is selected from the group consisting of phenyl and pyridinyl;

m is 0, 1, or 2;

each $R^A$ (when present) is fluoro; and ring B is pyrimidinyl.

In an alternative of the immediately preceding embodiment, m is 0. In another alternative of the immediately preceding embodiment, m is 1. In another alternative of the immediately preceding embodiment, m is 2.

In some embodiments, in each of Formulas (I), (I'), (IA), and (IA'):

n is 0. In these embodiments, the moiety:

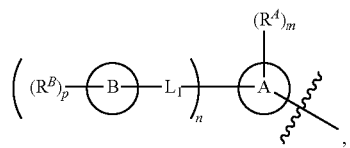

has the form:

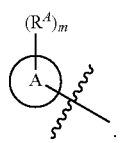

In one embodiment, in each of Formulas (I), (I'), (IA), and (IA'):

n=0;

ring A is selected from the group consisting of phenyl, pyridazinyl, pyridinyl, pyrimidinyl, pyrazinyl, pyrazolyl, triazinyl, thiazolyl, and thienyl;

m is 0, 1, 2, 3, or 4, with the proviso that the value of m does not exceed the number of available substitutable hydrogen atoms on ring A; and each $R^A$ (when present) is independently selected from the group consisting of fluoro, chloro, bromo, oxo, —OH, —CN, methyl, ethyl, propyl, butyl, cyclopropyl, —CH$_2$-cyclopropyl, —CH$_2$CH$_2$CH=CH$_2$, —CH$_2$OCH$_3$, —CH$_2$OCF$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$NHCH$_2$CF$_3$, —CF$_3$, —CHF$_2$, —CH$_2$F, —OCH$_3$, —OCH$_2$CH$_3$, —OCH$_2$CH$_2$CH$_3$, —OCH$_2$CH(CH$_3$)$_2$, —OCH$_2$CH$_2$OCH$_3$, —OCF$_3$, —OCHF$_2$, —OCH$_2$F, —OCH$_2$CF$_3$, —OCH$_2$CHF$_2$, —OCH$_2$CH$_2$F, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3, with the proviso that the value of m does not exceed the number of available substitutable hydrogen atoms on ring A. In another alternative of the immediately preceding embodiment, m is 4, with the proviso that the value of m does not exceed the number of available substitutable hydrogen atoms on ring A.

In one embodiment, in each of Formulas (I), (I'), (IA), and (IA'):

n=0;

ring A is selected from the group consisting of phenyl and pyridinyl;

m is 0, 1, 2, 3, or 4, with the proviso that the value of m does not exceed the number of available substitutable hydrogen atoms on ring A; and each $R^A$ (when present) is independently selected from the group consisting of fluoro, bromo, oxo, —OH, —CN, methyl, ethyl, cyclopropyl, —CH$_2$-cyclopropyl, —CH$_2$CH$_2$CH=CH$_2$, —CH$_2$OCH$_3$, —CH$_2$OCF$_3$, —CH$_2$NHCH$_2$CH$_3$, —CH$_2$NHCH$_2$CF$_3$, —CF$_3$, —CHF$_2$, —CH$_2$F, —OCH$_3$, —OCH$_2$CH$_2$CH$_3$, —OCH$_2$CH(CH$_3$)$_2$, —OCH$_2$CH$_2$OCH$_3$, —OCF$_3$, —OCHF$_2$, —OCH$_2$CF$_3$, —OCH$_2$CHF$_2$, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3. In another alternative of the immediately preceding embodiment, m is 4.

In one embodiment, in each of Formulas (I), (I'), (IA), and (IA'):

n=0;

ring A is selected from the group consisting of phenyl and pyridinyl;

m is 0, 1, 2, or 3; and each $R^A$ (when present) is independently selected from the group consisting of fluoro, bromo, —CN, —CH$_2$NHCH$_2$CF$_3$, —OCH$_2$CH$_2$OCH$_3$, —OCH$_2$CF$_3$, and —OCH$_2$CH$_2$CF$_3$.

each $R^A$ (when present) is independently selected from the group consisting of fluoro, bromo, oxo, —OH, —CN, —CH$_2$-cyclopropyl, —CH$_2$CH$_2$CH=CH$_2$, —CH$_2$NHCH$_2$CF$_3$, —OCH$_3$, —OCH$_2$CH$_2$CH$_3$, —OCH$_2$CH(CH$_3$)$_2$, —OCH$_2$CH$_2$OCH$_3$, —OCH$_2$CF$_3$, —OCH$_2$CHF$_2$, and —OCH$_2$CH$_2$CF$_3$.

In an alternative of the immediately preceding embodiment, m is 0. In another alternative of the immediately preceding embodiment, m is 1. In another alternative of the immediately preceding embodiment, m is 2. In another alternative of the immediately preceding embodiment, m is 3.

Specific non-limiting examples of compounds of the invention are shown in the table of examples below. While only one tautomeric form of each compound is shown in the tables, it shall be understood that all tautomeric forms of the compounds are contemplated as being within the scope of the non-limiting examples.

In other embodiments, the invention provides compositions, including pharmaceutical compositions, comprising one or more compounds of the invention (e.g., one compound of the invention), or a tautomer thereof, or a pharmaceutically acceptable salt or solvate of said compound(s) and/or said tautomer(s), optionally together with one or more additional therapeutic agents, optionally in an acceptable (e.g., pharmaceutically acceptable) carrier or diluent.

In other embodiments, the invention provides various methods of treating, preventing, ameliorating, and/or delaying the onset of an Aβ pathology and/or a symptom or symptoms thereof, comprising administering a composition comprising an effective amount of one or more compounds of the invention, or a tautomer thereof, or pharmaceutically acceptable salt or solvate of said compound(s) and/or said tautomer(s), to a patient in need thereof. Such methods optionally additionally comprise administering an effective amount of one or more additional therapeutic agents, simultaneously or sequentially, suitable for treating the patient being treated.

These and other embodiments of the invention, which are described in detail below or will become readily apparent to those of ordinary skill in the art, are included within the scope of the invention.

Specific non-limiting examples of compounds of the invention are shown in the table of examples below. While only one tautomeric form of each compound is shown in the tables, it shall be understood that both tautomeric forms of the compounds are contemplated as being within the scope of the non-limiting examples.

In another embodiment, in each of Formulas (I), (I'), (IA), and (IA'), 1 to 3 carbon atoms of the compounds of the invention may be replaced with 1 to 3 silicon atoms so long as all valency requirements are satisfied.

Another embodiment provides a composition comprising a compound of the invention and a pharmaceutically acceptable carrier or diluent.

Another embodiment provides a composition comprising a compound of the invention, either as the sole active agent, or optionally in combination with one or more additional therapeutic agents, and a pharmaceutically acceptable carrier or diluent. Non-limiting examples of additional therapeutic agents which may be useful in combination with the compounds of the invention include those selected from the group consisting of: (a) drugs that may be useful for the treatment of Alzheimer's disease and/or drugs that may be useful for treating one or more symptoms of Alzheimer's disease, (b) drugs that may be useful for inhibiting the synthesis Aβ, (c) drugs that may be useful for treating neurodegenerative diseases, and (d) drugs that may be useful for the treatment of type II diabetes and/or one or more symptoms or associated pathologies thereof.

Non-limiting examples of additional therapeutic agents which may be useful in combination with the compounds of the invention include drugs that may be useful for the treatment, prevention, delay of onset, amelioration of any pathology associated with Aβ and/or a symptom thereof. Non-limiting examples of pathologies associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $β_2$ microglobulins and complications arising therefrom in hemodialysis patients), scrapie, bovine spongiform encephalitis, and Creutzfeld-Jakob disease, comprising administering to said patient at least one compound of the invention, or a tautomer or isomer thereof, or pharmaceutically acceptable salt or solvate of said compound or said tautomer, in an amount effective to inhibit or treat said pathology or pathologies.

Non-limiting examples of additional therapeutic agents for that may be useful in combination with compounds of the invention include: muscarinic antagonists (e.g., $m_1$ agonists (such as acetylcholine, oxotremorine, carbachol, or McNa343), or $m_2$ antagonists (such as atropine, dicycloverine, tolterodine, oxybutynin, ipratropium, methoctramine, tripitamine, or gallamine)); cholinesterase inhibitors (e.g., acetyl- and/or butyrylchlolinesterase inhibitors such as donepezil (Aricept®, (±)-2,3-dihydro-5,6-dimethoxy-2-[[1-(phenylmethyl)-4-piperidinyl]methyl]-1H-inden-1-one hydrochloride), galantamine (Razadyne®), and rivastigimine (Exelon®); N-methyl-D-aspartate receptor antagonists (e.g., Namenda® (memantine HCl, available from Forrest Pharmaceuticals, Inc.); combinations of cholinesterase inhibitors and N-methyl-D-aspartate receptor antagonists; gamma secretase modulators; gamma secretase inhibitors; non-steroidal anti-inflammatory agents; anti-inflammatory agents that can reduce neuroinflammation; anti-amyloid antibodies (such as bapineuzemab, Wyeth/Elan); vitamin E; nicotinic acetylcholine receptor agonists; CB1 receptor inverse agonists or CB1 receptor antagonists; antibiotics; growth hormone secretagogues; histamine H3 antagonists; AMPA agonists; PDE4 inhibitors; $GABA_A$ inverse agonists; inhibitors of amyloid aggregation; glycogen synthase kinase beta inhibitors; promoters of alpha secretase activity; PDE-10 inhibitors; Tau kinase inhibitors (e.g., GSK3beta inhibitors, cdk5 inhibitors, or ERK inhibitors); Tau aggregation inhibitors (e.g., Rember®); RAGE inhibitors (e.g., TTP 488 (PF-4494700)); anti-Abeta vaccine; APP ligands; agents that upregulate insulin, cholesterol lowering agents such as HMG-CoA reductase inhibitors (for example, statins such as Atorvastatin, Fluvastatin, Lovastatin, Mevastatin, Pitavastatin, Pravastatin, Rosuvastatin, Simvastatin) and/or cholesterol absorption inhibitors (such as Ezetimibe), or combinations of HMG-CoA reductase inhibitors and cholesterol absorption inhibitors (such as, for example, Vytorin®); fibrates (such as, for example, clofibrate, Clofibride, Etofibrate, and Aluminium Clofibrate); combinations of fibrates and cholesterol lowering agents and/or cholesterol absorption inhibitors; nicotinic receptor agonists; niacin; combinations of niacin and cholesterol absorption inhibitors and/or cholesterol lowering agents (e.g., Simcor® (niacin/simvastatin, available from Abbott Laboratories, Inc.); LXR agonists; LRP mimics; H3 receptor antagonists; histone deacetylase inhibitors; hsp90 inhibitors; 5-HT4 agonists (e.g., PRX-03140 (Epix Pharmaceuticals)); 5-HT6 receptor antagonists; mGluR1 receptor modulators or antagonists; mGluR5 receptor modulators or antagonists; mGluR2/3 antagonists; Prostaglandin EP2 receptor antagonists; PAI-1 inhibitors; agents that can induce Abeta efflux such as gelsolin; Metal-protein attenuating compound (e.g, PBT2); and GPR3 modulators; and antihistamines such as Dimebolin (e.g., Dimebon®, Pfizer).

Another embodiment provides a method of preparing a pharmaceutical composition comprising the step of admixing at least one compound of the invention or pharmaceutically acceptable salt thereof, and a pharmaceutically acceptable carrier or diluent.

Another embodiment provides a method of inhibiting β-secretase comprising exposing a population of cells expressing β-secretase to at least one compound of the invention, or a tautomer thereof, in an amount effective to inhibit β-secretase. In one such embodiment, said population of cells is in vivo. In another such embodiment, said population of cells is ex vivo. In another such embodiment, said population of cells is in vitro.

Additional embodiments in which the compounds of the invention may be useful include: a method of inhibiting β-secretase in a patient in need thereof. A method of inhibiting the formation of Aβ from APP in a patient in need thereof. A method of inhibiting the formation of Aβ plaque and/or Aβ fibrils and/or Aβ oligomers and/or senile plaques and/or neurofibrillary tangles and/or inhibiting the deposition of amyloid protein (e.g., amyloid beta protein) in, on or around neurological tissue (e.g., the brain), in a patient in need thereof. Each such embodiment comprises administering at least one compound of the invention, or a tautomer thereof, or pharmaceutically acceptable salt of said compound or said tautomer, in a therapeutically effective amount to inhibit said pathology or condition in said patient.

Additional embodiments in which the compounds of the invention may be useful include: a method of treating, preventing, and/or delaying the onset of one or more pathologies associated with Aβ and/or one or more symptoms of one or more pathologies associated with Aβ. Non-limiting examples of pathologies which may be associated with Aβ include: Alzheimer's Disease, Down's syndrome, Parkinson's disease, memory loss, memory loss associated with Alzheimer's disease, memory loss associated with Parkinson's disease, attention deficit symptoms, attention deficit symptoms associated with Alzheimer's disease ("AD"), Parkinson's disease, and/or Down's syndrome, dementia, stroke, microgliosis and brain inflammation, pre-senile dementia, senile dementia, dementia associated with Alzheimer's disease, Parkinson's disease, and/or Down's syndrome, progressive supranuclear palsy, cortical basal degeneration, neurodegeneration, olfactory impairment, olfactory impairment associated with Alzheimer's disease, Parkinson's disease, and/or Down's syndrome, β-amyloid angiopathy, cerebral amyloid angiopathy, hereditary cerebral hemorrhage, mild cognitive impairment ("MCI"), glaucoma, amyloidosis, type II diabetes, hemodialysis complications (from $\beta_2$ microglobulins and complications arising therefrom in hemodialysis patients), scrapie, bovine spongiform encephalitis, and Creutzfeld-Jakob disease, said method(s) comprising administering to said patient in need thereof at least one compound of the invention, or a tautomer thereof, or pharmaceutically acceptable salt of said compound or said tautomer, in an amount effective to inhibit said pathology or pathologies.

Another embodiment in which the compounds of the invention may be useful includes a method of treating Alzheimer's disease, wherein said method comprises administering an effective (i.e., therapeutically effective) amount of one or more compounds of the invention (or a tautomer thereof, or pharmaceutically acceptable salt of said compound or said tautomer), optionally in further combination with one or more additional therapeutic agents which may be effective to treat Alzheimer's disease or a disease or condition associated therewith, to a patient in need of treatment. In embodiments wherein one or more additional therapeutic agents are administered, such agents may be administered sequentially or together. Non-limiting examples of associated diseases or conditions, and non-limiting examples of suitable additional therapeutically active agents, are as described above.

Another embodiment in which the compounds of the invention may be useful includes a method of treating mild cognitive impairment ("MCI"), wherein said method comprises administering an effective (i.e., therapeutically effective) amount of one or more compounds of the invention (or a tautomer thereof, or pharmaceutically acceptable salt of said compound or said tautomer) to a patient in need of treatment. In one such embodiment, treatment is commenced prior to the onset of symptoms.

Another embodiment in which the compounds of the invention may be useful includes a method of preventing, or alternatively of delaying the onset, of mild cognitive impairment or, in a related embodiment, of preventing or alternatively of delaying the onset of Alzheimer's disease. In such embodiments, treatment can be initiated prior to the onset of symptoms, in some embodiments significantly before (e.g., from several months to several years before) the onset of symptoms to a patient at risk for developing MCI or Alzheimer's disease. Thus, such methods comprise administering, prior to the onset of symptoms or clinical or biological evidence of MCI or Alzheimer's disease (e.g., from several months to several years before, an effective (i.e., therapeutically effective), and over a period of time and at a frequency of dose sufficient for the therapeutically effective degree of inhibition of the BACE enzyme over the period of treatment, an amount of one or more compounds of the invention (or a tautomer thereof, or pharmaceutically acceptable salt of said compound or said tautomer) to a patient in need of treatment.

Another embodiment in which the compounds of the invention may be useful includes a method of treating Down's syndrome, comprising administering an effective (i.e., therapeutically effective) amount of one or more compounds of the invention (or a tautomer thereof, or pharmaceutically acceptable salt or solvate of said compound or said tautomer) to a patient in need of treatment.

Another embodiment in which the compounds of the invention may be useful includes a kit comprising, in separate containers, in a single package, pharmaceutical compositions for use in combination, wherein one container comprises an effective amount of a compound of the invention (or a tautomer thereof, or pharmaceutically acceptable salt of said compound or said tautomer) in a pharmaceutically acceptable carrier, and another container (i.e., a second container) comprises an effective amount of another pharmaceutically active ingredient, the combined quantities of the compound of the invention and the other pharmaceutically active ingredient being effective to: (a) treat Alzheimer's disease, or (b) inhibit the deposition of amyloid protein in, on or around neurological tissue (e.g., the brain), or (c) treat neurodegenerative diseases, or (d) inhibit the activity of BACE-1 and/or BACE-2.

In various embodiments, the compositions and methods disclosed above and below wherein the compound(s) of the invention is a compound or compounds selected from the group consisting of the exemplary compounds of the invention described herein.

In another embodiment, the invention provides methods of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease. Such methods comprise administering a compound of the invention, or a pharmaceutically acceptable salt thereof, to a patient in need thereof in an amount effective to treat said disease or pathology.

In another embodiment, the invention provides for the use of any of the compounds of the invention for use as a medicament, or in medicine, or in therapy.

In another embodiment, the invention provides for use of a compound of the invention for the manufacture of a medicament for the treatment of a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease.

Definitions

The terms used herein have their ordinary meaning and the meaning of such terms is independent at each occurrence thereof. That notwithstanding and except where stated otherwise, the following definitions apply throughout the specification and claims. Chemical names, common names and chemical structures may be used interchangeably to describe that same structure. These definitions apply regardless of whether a term is used by itself or in combination with other terms, unless otherwise indicated. Hence the definition of "alkyl" applies to "alkyl" as well as the "alkyl" portion of "hydroxyalkyl", "haloalkyl", arylalkyl-, alkylaryl-, "alkoxy" etc.

It shall be understood that, in the various embodiments of the invention described herein, any variable not explicitly defined in the context of the embodiment is as defined in Formula (I). All valences not explicitly filled are assumed to be filled by hydrogen.

"Patient" includes both human and non-human animals. Non-human animals include those research animals and companion animals such as mice, primates, monkeys, great apes, canine (e.g., dogs), and feline (e.g., house cats).

"Pharmaceutical composition" (or "pharmaceutically acceptable composition") means a composition suitable for administration to a patient. Such compositions may contain the neat compound (or compounds) of the invention or mixtures thereof, or salts, solvates, prodrugs, isomers, or tautomers thereof, or they may contain one or more pharmaceutically acceptable carriers or diluents. The term "pharmaceutical composition" is also intended to encompass both the bulk composition and individual dosage units comprised of more than one (e.g., two) pharmaceutically active agents such as, for example, a compound of the present invention and an additional agent selected from the lists of the additional agents described herein, along with any pharmaceutically inactive excipients. The bulk composition and each individual dosage unit can contain fixed amounts of the afore-said "more than one pharmaceutically active agents". The bulk composition is material that has not yet been formed into individual dosage units. An illustrative dosage unit is an oral dosage unit such as tablets, pills and the like. Similarly, the herein-described method of treating a patient by administering a pharmaceutical composition of the present invention is also intended to encompass the administration of the afore-said bulk composition and individual dosage units.

"Halogen" (or "halo") means fluorine (F), chlorine (Cl), bromine (Br), or iodine (I). Preferred are fluorine, chlorine and bromine.

"Alkyl" means an aliphatic hydrocarbon group, which may be straight or branched, comprising 1 to 10 carbon atoms. "Lower alkyl" means a straight or branched alkyl group comprising 1 to 4 carbon atoms. Branched means that one or more lower alkyl groups such as methyl, ethyl or propyl, are attached to a linear alkyl chain. Non-limiting examples of suitable alkyl groups include methyl (Me), ethyl (Et), n-propyl, isopropyl, n-butyl, i-butyl, and t-butyl.

"Alkenyl" means an aliphatic hydrocarbon group containing at least one carbon-carbon double bond and which may be straight or branched and comprising 2 to 10 carbon atoms in the straight or branched chain. Branched means that one or more lower alkyl groups such as methyl, ethyl propyl, ethenyl or propenyl are attached to a linear or branched alkenyl chain. "Lower alkenyl" means 2 to 4 carbon atoms in the chain which may be straight or branched. Non-limiting examples of suitable alkenyl groups include ethenyl, propenyl, n-butenyl, 3-methylbut-2-enyl, n-pentenyl, octenyl and decenyl.

"Alkynyl" means an aliphatic hydrocarbon group containing at least one carbon-carbon triple bond and which may be straight or branched and comprising 2 to 10 carbon atoms in the chain. Branched means that one or more lower alkyl groups such as methyl, ethyl or propyl, or lower alkenyl or lower alkynyl groups, are attached to a linear alkynyl chain. "Lower alkynyl" means 2 to 4 carbon atoms in the chain which may be straight or branched. Non-limiting examples of suitable alkynyl groups include ethynyl, propynyl, 2-butynyl and 3-methylbutynyl.

"Aryl" means an aromatic monocyclic or multicyclic ring system comprising 6 to 14 carbon atoms, preferably 6 to 10 carbon atoms. The aryl group can be optionally substituted with one or more "ring system substituents" which may be the same or different, and are as defined herein. Non-limiting examples of suitable aryl groups include phenyl and naphthyl. "Monocyclic aryl" means phenyl.

"Heteroaryl" means an aromatic monocyclic or multicyclic ring system comprising 5 to 14 ring atoms, preferably 5 to 10 ring atoms, in which one or more of the ring atoms is an element other than carbon, for example nitrogen, oxygen or sulfur, alone or in combination. Preferred heteroaryls contain 5 to 6 ring atoms. The "heteroaryl" can be optionally substituted by one or more substituents, which may be the same or different, as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. "Heteroaryl" may also include a heteroaryl as defined above fused to an aryl as defined above. Non-limiting examples of suitable heteroaryls include pyridyl, pyrazinyl, furanyl, thienyl (which alternatively may be referred to as thiophenyl), pyrimidinyl, pyridone (including N-substituted pyridones), isoxazolyl, isothiazolyl, oxazolyl, oxadiazolyl, thiazolyl, thiadiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like. The term "monocyclic heteroaryl" refers to monocyclic versions of heteroaryl as described above and includes 4- to 7-membered monocyclic heteroaryl groups comprising from 1 to 4 ring heteroatoms, said ring heteroatoms being independently selected from the group consisting of N, O, and S, and oxides thereof. The point of attachment to the parent moiety is to any available ring carbon or ring heteroatom. Non-limiting examples of monocyclic heteroaryl moities include pyridyl, pyrazinyl, furanyl, thienyl, pyrimidinyl, pyridazinyl, pyridoneyl, thiazolyl, isothiazolyl, oxazolyl, oxadiazolyl, isoxazolyl, pyrazolyl, furazanyl, pyrrolyl, pyrazolyl, triazolyl, thiadiazolyl (e.g., 1,2,4-thiadiazolyl), imidazolyl, and triazinyl (e.g., 1,2,4-triazinyl), and oxides thereof.

"Cycloalkyl" means a non-aromatic monocyclic or multicyclic ring system comprising 3 to 10 carbon atoms, preferably 3 to 6 carbon atoms. The cycloalkyl can be optionally substituted with one or more substituents, which may be the same or different, as described herein. Monocyclic cycloalkyl refers to monocyclic versions of the cycloalkyl moieties described herein. Non-limiting examples of suitable monocyclic cycloalkyls include cyclopropyl, cyclopentyl, cyclohexyl, cycloheptyl and the like. Non-limiting examples of multicyclic cycloalkyls include [1.1.1]-bicyclopentane, 1-decalinyl, norbornyl, adamantyl and the like.

"Heterocycloalkyl" (or "heterocyclyl") means a non-aromatic saturated monocyclic or multicyclic ring system comprising 3 to 10 ring atoms, preferably 5 to 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain 5 to 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more substituents, which may be the same or different, as described herein. The nitrogen or sulfur atom of the heterocyclyl can be optionally oxidized to the corresponding N-oxide, S-oxide or S,S-dioxide. Thus, the term "oxide," when it appears in a definition of a variable in a general structure described herein, refers to the corresponding N-oxide, S-oxide, or S,S-dioxide. "Heterocyclyl" also includes rings wherein =O replaces two available hydrogens on the same carbon atom (i.e., heterocyclyl includes rings having a carbonyl group in the ring). Such =O groups may be referred to herein as "oxo." An example of such a moiety is pyrrolidinone (or pyrrolidone):

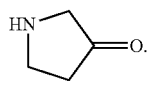

As used herein, the term "monocyclic heterocycloalkyl" refers monocyclic versions of the heterocycloalkyl moities described herein and include a 4- to 7-membered monocyclic heterocycloalkyl groups comprising from 1 to 4 ring heteroatoms, said ring heteroatoms being independently selected from the group consisting of N, N-oxide, O, S, S-oxide, S(O), and S(O)$_2$. The point of attachment to the parent moiety is to any available ring carbon or ring heteroatom. Non-limiting examples of monocyclic heterocycloalkyl groups include piperidyl, oxetanyl, pyrrolyl, piperazinyl, morpholinyl, thiomorpholinyl, thiazolidinyl, 1,4-dioxanyl, tetrahydrofuranyl, tetrahydrothiophenyl, beta lactam, gamma lactam, delta lactam, beta lactone, gamma lactone, delta lactone, and pyrrolidinone, and oxides thereof. Non-limiting examples of lower alkyl-substituted oxetanyl include the moiety:

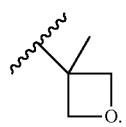

It should be noted that in hetero-atom containing ring systems of this invention, there are no hydroxyl groups on carbon atoms adjacent to a N, O or S, as well as there are no N or S groups on carbon adjacent to another heteroatom.

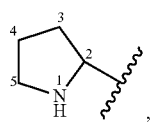

there is no —OH attached directly to carbons marked 2 and 5.

"Alkoxy" means an —O-alkyl group in which the alkyl group is as previously described. Non-limiting examples of alkoxy groups include methoxy, ethoxy, n-propoxy, isopropoxy and n-butoxy. The bond to the parent moiety is through the oxygen.

Any of the foregoing functional groups may be unsubstituted or substituted as described herein. The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

Substitution on a cycloalkylalkyl, heterocycloalkylalkyl, arylalkyl, heteroarylalkyl, arylfused cycloalkylalkyl-moiety or the like includes substitution on any ring portion and/or on the alkyl portion of the group.

When a variable appears more than once in a group, e.g., $R^6$ in —N($R^6$)$_2$, or a variable appears more than once in a structure presented herein, the variables can be the same or different.

The line -, as a bond generally indicates a mixture of, or either of, the possible isomers, e.g., containing (R)- and (S)-stereochemistry. For example:

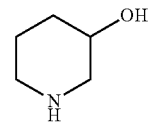

means containing both

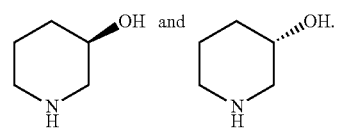

The wavy line ~~, as used herein, indicates a point of attachment to the rest of the compound. Lines drawn into the ring systems, such as, for example:

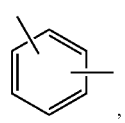

indicate that the indicated line (bond) may be attached to any of the substitutable ring carbon atoms.

"Oxo" is defined as a oxygen atom that is double bonded to a ring carbon in a cycloalkyl, cycloalkenyl, heterocyclyl, heterocyclenyl, or other ring described herein, e.g.,

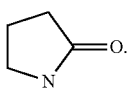

In this specification, where there are multiple oxygen and/or sulfur atoms in a ring system, there cannot be any adjacent oxygen and/or sulfur present in said ring system.

As well known in the art, a bond drawn from a particular atom wherein no moiety is depicted at the terminal end of the bond indicates a methyl group bound through that bond to the atom, unless stated otherwise. For example:

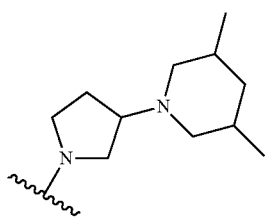 [SMILES: *N1CCC(N2CC(C)CC(C)C2)C1]

represents

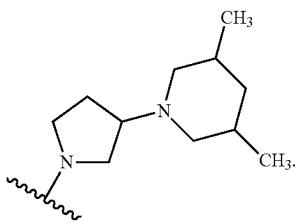 [SMILES: *N1CCC(N2CC(C)CC(C)C2)C1]

In another embodiment, the compounds of the invention, and/or compositions comprising them, are present in isolated and/or purified form. The term "purified", "in purified form" or "in isolated and purified form" for a compound refers to the physical state of said compound after being isolated from a synthetic process (e.g. from a reaction mixture), or natural source or combination thereof. Thus, the term "purified", "in purified form" or "in isolated and purified form" for a compound refers to the physical state of said compound (or a tautomer thereof, or pharmaceutically acceptable salt of said compound or said tautomer) after being obtained from a purification process or processes described herein or well known to the skilled artisan (e.g., chromatography, recrystallization and the like), in sufficient purity to be suitable for in vivo or medicinal use and/or characterizable by standard analytical techniques described herein or well known to the skilled artisan.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

Those skilled in the art will recognize those instances in which the compounds of the invention may be converted to prodrugs and/or solvates, another embodiment of the present invention. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of the invention or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

One or more compounds of the invention may exist in unsolvated as well as solvated forms with pharmaceutically acceptable solvents such as water, ethanol, and the like, and it is intended that the invention embrace both solvated and unsolvated forms where they exist. "Solvate" means a physical association of a compound of the invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

Those skilled in the art will recognize those instances in which the compounds of the invention may form salts. In such instances, another embodiment provides pharmaceutically acceptable salts of the compounds of the invention. The term "salt(s)", as employed herein, denotes any of the following: acidic salts formed with inorganic and/or organic acids, as well as basic salts formed with inorganic and/or organic bases. In addition, when a compound of the invention contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also potentially useful. Salts of the compounds of the invention may be formed by methods known to those of ordinary skill in the art, for example, by reacting a compound of the invention with an amount of acid or base, such as an equivalent amount, in a medium such as one in which the salt precipitates or in an aqueous medium followed by lyophilization.

Exemplary acid addition salts which may be useful include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use*. (2002) Zurich: Wiley-VCH; S. Berge et al, *Journal of Pharmaceutical Sciences* (1977) 66(1) 1-19; P. Gould, *International J. of Pharmaceutics* (1986) 33 201-217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered as potentially useful alternatives to the free forms of the corresponding compounds for purposes of the invention.

Another embodiment which may be useful includes pharmaceutically acceptable esters of the compounds of the invention. Such esters may include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di ($C_{6-24}$)acyl glycerol.

As mentioned herein, under certain conditions the compounds of the invention may form tautomers. Such tautomers, when present, comprise another embodiment of the invention. It shall be understood that all tautomeric forms of such compounds are within the scope of the compounds of the invention. For example, all keto-enol and imine-enamine forms of the compounds, when present, are included in the invention. Thus, compounds of the invention conforming to the formula:

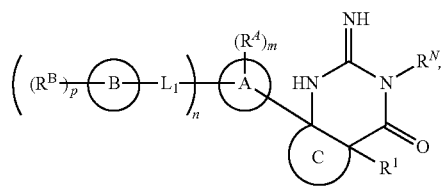

and its tautomer, which can be depicted as:

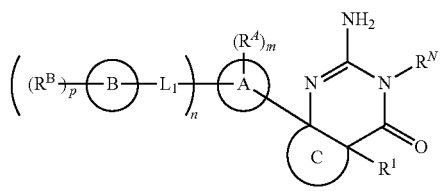

are both contemplated as being within the scope of the compounds of the invention. As noted above, while only one said tautomeric form of each example compound of the invention may be shown in the tables and appended claims, it shall be understood that both of these tautomeric forms of the compounds are contemplated as being within the scope of the non-limiting example compounds of the invention.

The compounds of the invention may contain asymmetric or chiral centers, and, therefore, exist in different stereoisomeric forms. It is intended that all stereoisomeric forms of the compounds of the invention as well as mixtures thereof, including racemic mixtures, form part of the present invention. In addition, the present invention embraces all geometric and positional isomers. For example, if a compound of the invention incorporates a double bond or a fused ring, both the cis- and trans-forms, as well as mixtures, are embraced within the scope of the invention.

Where various stereoisomers of the compounds of the invention are possible, another embodiment provides for diastereomeric mixtures and individual enantiomers of the compounds of the invention. Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of the invention may be atropisomers (e.g., substituted biaryls) and are considered as part of this invention. Enantiomers can also be separated by use of chiral HPLC column.

All stereoisomers (for example, geometric isomers, optical isomers and the like) of the compounds of the invention (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated as embodiments within the scope of this invention, as are positional isomers (such as, for example, 4-pyridyl and 3-pyridyl). (For example, if a compound of the invention incorporates a double bond or a fused ring, both the cis- and trans-forms, as well as mixtures, are embraced within the scope of the invention. Also, for example, all keto-enol and imine-enamine forms of the compounds are included in the invention.).

Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the *IUPAC* 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

Another embodiment which may be useful include isotopically-labelled compounds of the invention. Such compounds are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

In the compounds of the invention, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of the invention. For example, different isotopic forms of hydrogen (H) include protium ($^1H$) and deuterium ($^2H$). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds of the invention can be prepared without undue experimentation by conventional techniques well known to those skilled in the art or by processes analogous to those described in the schemes and examples herein using appropriate isotopically-enriched reagents and/or intermediates.

Polymorphic forms of the compounds of the invention, and of the salts, solvates, esters and prodrugs of the compounds of the invention, are intended to be included in the present invention.

Another embodiment provides suitable dosages and dosage forms of the compounds of the invention. Suitable doses for administering compounds of the invention to patients may readily be determined by those skilled in the art, e.g., by an attending physician, pharmacist, or other skilled worker, and may vary according to patient health, age, weight, frequency of administration, use with other active ingredients, and/or indication for which the compounds are administered. Doses may range from about 0.001 to 500 mg/kg of body weight/day of the compound of the invention. In one embodiment, the dosage is from about 0.01 to about 25 mg/kg of body weight/day of a compound of the invention, or a pharmaceutically acceptable salt or solvate of said compound. In another embodiment, the quantity of active compound in a unit dose of preparation may be varied or adjusted from about 1 mg to about 100 mg, preferably from about 1 mg to about 50 mg, more preferably from about 1 mg to about 25 mg, according to the particular application. In another embodiment, a typical recommended daily dosage regimen for oral administration can range from about 1 mg/day to about 500 mg/day, preferably 1 mg/day to 200 mg/day, in two to four divided doses.

When used in combination with one or more additional therapeutic agents, the compounds of this invention may be administered together or sequentially. When administered sequentially, compounds of the invention may be administered before or after the one or more additional therapeutic agents, as determined by those skilled in the art or patient preference.

If formulated as a fixed dose, such combination products employ the compounds of this invention within the dosage range described herein and the other pharmaceutically active agent or treatment within its dosage range.

Accordingly, another embodiment provides combinations comprising an amount of at least one compound of the invention, or a pharmaceutically acceptable salt, solvate, ester or prodrug thereof, and an effective amount of one or more additional agents described above.

Another embodiment provides for pharmaceutically acceptable compositions comprising a compound of the invention, either as the neat chemical or optionally further comprising additional ingredients. For preparing pharmaceutical compositions from the compounds of the invention, inert, pharmaceutically acceptable carriers can be either solid or liquid. Solid form preparations include powders, tablets, dispersible granules, capsules, cachets and suppositories. The powders and tablets may be comprised of from about 5 to about 95 percent active ingredient. Suitable solid carriers are known in the art, e.g., magnesium carbonate, magnesium stearate, talc, sugar or lactose. Tablets, powders, cachets and capsules can be used as solid dosage forms suitable for oral administration. Examples of pharmaceutically acceptable carriers and methods of manufacture for various compositions may be found in A. Gennaro (ed.), *Remington's Pharmaceutical Sciences*, 18$^{th}$ Edition, (1990), Mack Publishing Co., Easton, Pa.

Liquid form preparations include solutions, suspensions and emulsions. Non-limiting examples which may be useful include water or water-propylene glycol solutions for parenteral injection or addition of sweeteners and opacifiers for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier, such as an inert compressed gas, e.g. nitrogen.

Also included are solid form preparations that are intended to be converted, shortly before use, to liquid form preparations for either oral or parenteral administration. Such liquid forms include solutions, suspensions and emulsions.

Another embodiment which may be useful includes compositions comprising a compound of the invention formulated for transdermal delivery. The transdermal compositions can take the form of creams, lotions, aerosols and/or emulsions and can be included in a transdermal patch of the matrix or reservoir type as are conventional in the art for this purpose.

Other embodiment which may be useful includes compositions comprising a compound of the invention formulated for subcutaneous delivery or for oral delivery. In some embodiments, it may be advantageous for the pharmaceutical preparation comparing one or more compounds of the invention be prepared in a unit dosage form. In such forms, the preparation may be subdivided into suitably sized unit doses containing appropriate quantities of the active component, e.g., an effective amount to achieve the desired purpose. Each of the foregoing alternatives, together with their corresponding methods of use, are considered as included in the various embodiments of the invention.

Preparative Examples

Compounds of the invention can be made using procedures known in the art. The following reaction schemes show typical procedures, but those skilled in the art will recognize that other procedures can also be suitable. Reactions may involve monitoring for consumption of starting material, and there are many methods for such monitoring, including but not limited to thin layer chromatography (TLC) and liquid chromatography mass spectrometry (LCMS), and those skilled in the art will recognize that where one method is specified, other non-limiting methods may be substituted.

Techniques, solvents and reagents may be referred to by their abbreviations as follow:
Acetic acid: AcOH
Acetonitrile: MeCN
Aqueous: aq.
[2-(Di-1-adamantylphosphino)-2',4',6'-triisopropyl-3,6-dimethoxybiphenyl][2-(2'-amino-1,1'-biphenyl)]palladium(II) methanesulfonate: AdBrettPhos Pd G3
4,5-Bis(diphenylphosphino)-9,9-dimethylxanthene: Xantphos
N-bromosuccinimide: NBS
tert-Butoxycarbonyl: t-Boc or Boc
tert-Butyl: t-Bu or tBu
n-Butyllithium: nBuLi or n-BuLi
1, 1'-Carbonyldiimidazole: CDI
Chloro[(tricyclohexylphosphine)-2-(2'-aminobiphenyl)]palladium(II), second generation: Tricyclohexylphosphine Pd G2, PCy$_3$ Pd G2
Dichloromethane: DCM
Diethylamine: DEA
Diethylaminosulfur trifluoride: DAST
Diisobutylaluminum hydride: DIBAL
Diisopropylethylamine: DIEA or iPr$_2$Net
Dimethylacetamide: DMA
Dimethylformamide: DMF
Dimethylsulfoxide: DMSO
Ethyl: Et
Diethylether: Et$_2$O
Ethanol: EtOH
Ethyl acetate: AcOEt, EtOAc, or EA
Example: Ex.
Grams: g
Hexanes: hex
High performance liquid chromatography: HPLC
Inhibition: Inh.
iso-propyl alcohol: IPA
Potassium bis(trimethylsilyl)amide: KHMDS
Liquid chromatography mass Spectrometry: LCMS
Liter: L
Methyl: Me
Methoxyethoxymethyl: MEM
Methanol: MeOH
N-methylpyrrolidinone: NMP
Microliters: μl or μL
Milligrams: mg
Milliliters: mL
Millimoles: mmol
Minutes: min
Molar: M
Nanomolar: nM
Normal (concentration): N
Nuclear magnetic resonance spectroscopy: NMR
Number: No. or no. or #
Observed: Obs.
Para-toluene sulfonyl: OTs
Para-methoxy benzyl: PMB
Petroleum ether: PE
Room temperature (ambient, about 25° C.): rt or RT
Supercritical Fluid Chromatography: SFC
Tetramethyl(tris(dimethylamino)phosphoranylidene)phosphorictriamid-Et-imin: Phosphazene base P2-Et
Temperature: temp.
Triethylamine: Et$_3$N, TEA
Trifluoroacetic acid: TFA
Tetrahydrofuran: THF Method A

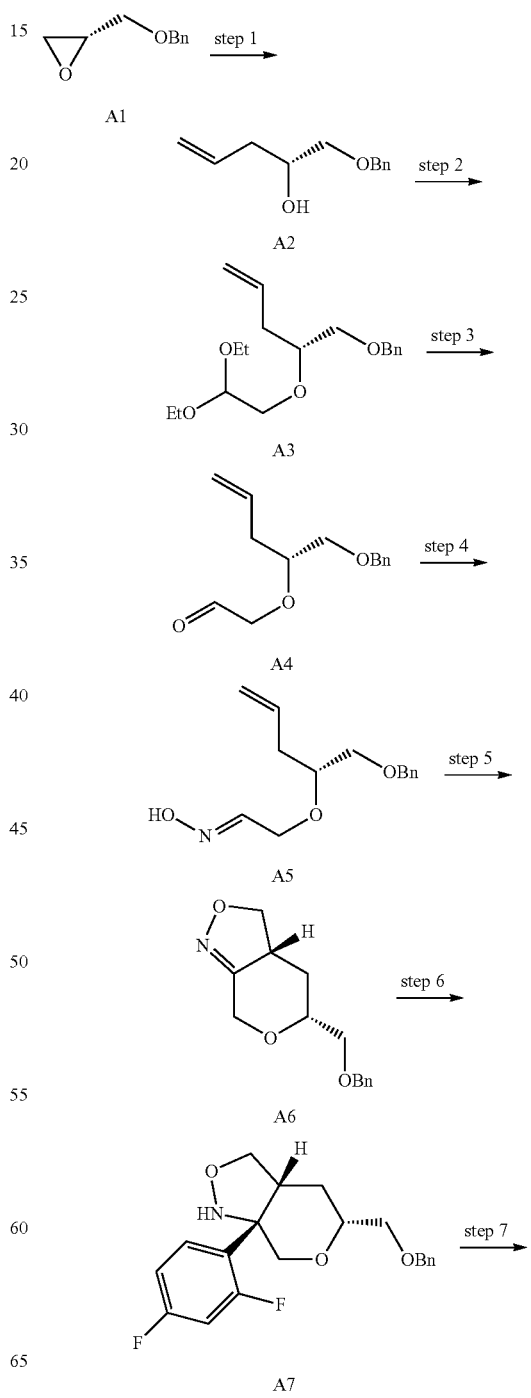

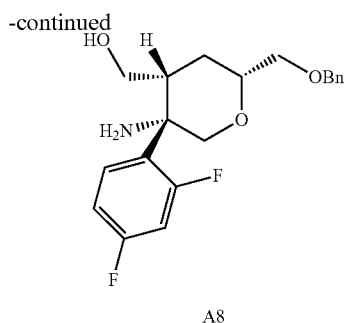

A8

Step 1

Into a 10-L 4-necked round-bottom flask purged and maintained with an inert atmosphere of nitrogen were placed a solution of (2R)-2-[(benzyloxy)methyl]oxirane A1 (300 g, 1.83 mol) in tetrahydrofuran (3.6 L) and copper(I) iodide (20.1 g, 105.54 mmol). The mixture was then cooled to −78° C. To the mixture was added dropwise over 1 h a solution of bromo(ethenyl)magnesium (2.01 L, 1M in THF). After the addition was complete, the resulting mixture was stirred at room temperature for 1 h. The reaction was then quenched by the addition of 360 mL of saturated aq. $NH_4Cl$. The mixture was then diluted with 2.5 L of aq $NH_4Cl$, and extracted with 3×1.5 L of ethyl acetate. The combined organic layers were washed with 2×1 L of brine, dried over anhydrous sodium sulfate, and concentrated under vacuum to afford A2 which was used without further purification.

Step 2

To a stirred solution of sodium hydride (190.3 g, 4.76 mol) in tetrahydrofuran (1.9 L) in a 10-L 4-necked round-bottom flask under a nitrogen atmosphere was added a solution of A2 (366 g, 1.90 mol) in tetrahydrofuran (1 L) dropwise at −30° C. After stirring at room temperature for 30 min, a solution of 2-bromo-1,1-diethoxyethane (750 g, 3.81 mol) in tetrahydrofuran (1 L) was added dropwise at room temperature. The resulting solution was stirred at room temperature for 1 h and 70° C. for 18 h. The reaction mixture was cooled to room temperature and then quenched by the addition of 400 mL of water while maintaining the temperature under 18° C. The resulting solution was diluted with 2 L of brine, and extracted with 3×1 L of ethyl acetate. The combined organic layers were washed with 2×2 L of brine, dried over anhydrous sodium sulfate and concentrated under vacuum. The residue was purified by silica gel chromatography eluting with ethyl acetate/petroleum ether (1:10) to afford A3.

Step 3

Into a 3-L 4-necked round-bottom flask purged and maintained with an inert atmosphere of nitrogen, were placed A3 (404 g, 1.31 mol), formic acid (808 mL), and water (202 mL). The resulting solution was stirred for 10 h at room temperature. The mixture was used in the next step without workup or purification.

Step 4

Into a 10-L 4-necked round-bottom flask purged and maintained with an inert atmosphere of nitrogen were placed the mixture containing A4 from step 3 (1414 mL), ethanol (2020 mL), water (808 mL), hydroxylamine sulfate (879 g, 5.36 mol), and sodium acetate (438.3 g, 5.34 mol). The resulting solution was stirred for 18 h at room temperature. After that time, the solids were removed by filtration and the filtrate was concentrated under vacuum. The residue was diluted with 3 L of $H_2O$ and extracted with 3×1.5 L of ethyl acetate. The combined organic layers were washed with 2×1 L of brine, dried over anhydrous sodium sulfate and concentrated under vacuum to afford A5.

Step 5

To a stirred solution of A5 (383 g, 1.54 mol) in dichloromethane (1.7 L) in a 5-L 4-necked round-bottom flask under atmosphere of nitrogen was added sodium hypochlorite (1025.7 g, 13.78 mol, 14.5% solution) dropwise at 0-15° C. The resulting solution was stirred at 0° C. for 1.5 h and quenched by the addition of 1.5 L of $H_2O$. The resulting mixture was extracted with 3×1 L of dichloromethane and the combined organic extracts were washed with 2×500 mL of brine, dried over sodium sulfate and concentrated under vacuum. The residue was purified by silica gel chromatography eluting with EA/PE (1:10) to afford A6.

Step 6

To a stirred solution of A6 (143.5 g, 580.3 mmol) in toluene/diisopropyl ether (2.7 L/2.7 L) in a 10-L 4-necked round-bottom flask at −76° C. was added $BF_3.Et_2O$ (443.6 g, 1.45 mol) dropwise. After stirring for 30 min at −76° C., to this mixture were added 2,4-difluoro-1-iodobenzene (209.3 g, 872.1 mmol) followed by and n-BuLi (842.5 mmol, 337 mL, 2.5 M in hexanes) dropwise at −76° C. The resulting solution was stirred for 1.5 h at −76° C. and then quenched by the addition of 2.5 L of aq. $NH_4Cl$. The resulting mixture was extracted with 3×1 L of ethyl acetate. the combined organic layers were washed with 2×1 L of brine, dried over anhydrous sodium sulfate and concentrated under vacuum. The residue was purified by silica gel chromatography eluting with ethyl acetate/petroleum ether (1:5) to afford A7.

Step 7

Into a 3-L 4-necked round-bottom flask purged and maintained with an inert atmosphere of nitrogen, were placed A7 (89.16 g, 246.7 mmol), acetic acid (1100 mL), and zinc (208.7 g, 3.19 mol). The resulting mixture was stirred for 10 h at room temperature. The mixture was then filtered and the filtrate was concentrated under vacuum. The residue was adjusted to pH 8 with sodium bicarbonate (5%) and extracted with 3×1 L of ethyl acetate. The combined organic layers were washed with 2×500 mL of brine, dried over anhydrous sodium sulfate, and concentrated. The residue was purified by silica gel chromatography eluting with ethyl acetate/petroleum ether (1:10) to afford A8.

Method B

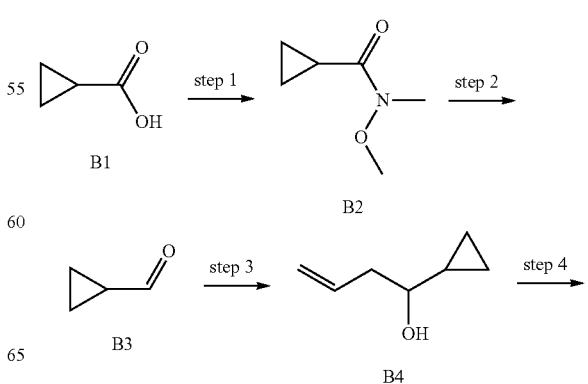

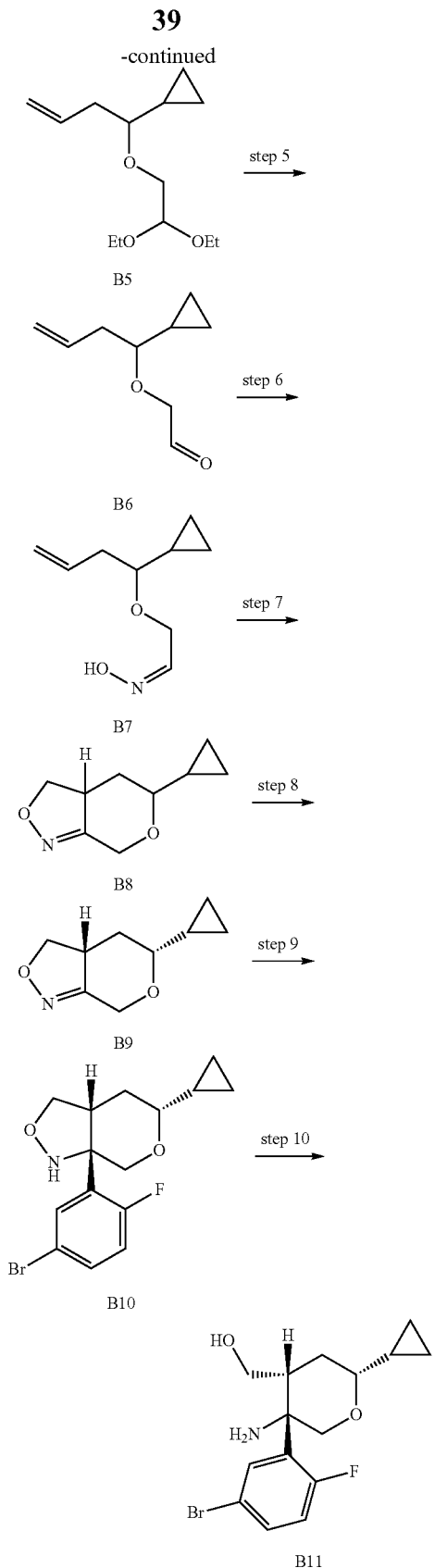

dichloromethane (5000 mL), methoxy(methyl)amine hydrochloride (620 g, 6.36 mol), TEA (1761 g, 17.40 mol), and CDI (1130 g, 6.97 mol). The resulting solution was stirred overnight at room temperature. The mixture was then diluted with 5000 mL of water and extracted with 2×2000 mL of dichloromethane. The combined organic layers were washed with 2000 mL of brine, dried over anhydrous sodium sulfate, and concentrated under vacuum to afford B2.

Step 2

To a stirred solution of B2 (450 g, 3.48 mol) in tetrahydrofuran (5000 mL) in a 10-L 4-necked round-bottom flask under nitrogen atmosphere was added DIBAL (5.32 mmol, 5232 mL, 1.0 M in THF) dropwise at −78° C. The resulting solution was stirred at room temperature for 3 h and quenched by the addition of 3000 mL of aqueous $NH_4Cl$. The mixture was filtered and the filtrate was extracted with 2×2000 mL of ethyl acetate. The combined organic extracts were washed with 2×2000 mL of brine, dried over anhydrous sodium sulfate, and concentrated under vacuum while maintaining the temperature below 30° C. to afford B3.

Step 3

To a stirred solution of B3 (195 g, 2.78 mol) in ether (2000 mL) in a 5-L 4-necked round-bottom flask was added a solution of bromo(prop-2-en-1-yl)magnesium (2785 mL) dropwise at −20° C. The resulting solution was stirred for 1 h from −20 to 0° C. The reaction was then quenched by the addition of 1000 mL of $NH_4Cl$ (20%) and extracted with 2×1000 mL of ether. The combined organic extracts were washed with 1×1000 mL of brine, dried over anhydrous sodium sulfate, and concentrated under vacuum to afford B4.

Step 4

To a stirred mixture of sodium hydride (343 g, 8.57 mol, 60%) in tetrahydrofuran (3000 mL) was added B4 (291.5 g, 2.60 mol) dropwise at 0° C. The mixture was stirred until the internal temperature reached 21° C. To this mixture were added 2-bromo-1,1-diethoxyethane (1071 g, 5.43 mol) dropwise and NaI (196 g) at 0-5° C. The resulting solution was stirred at reflux overnight. The reaction mixture was cooled and quenched by the addition of water. The resulting mixture was extracted with 2×2000 mL of ether. The combined organic extracts were washed with 2×2000 mL of brine, dried over anhydrous sodium sulfate, and filtered. The filtrate was concentrated under vacuum and the residue was purified by silica gel chromatography eluting with ethyl acetate/petroleum ether (1:10) to afford B5.

Step 5

Into a 10-L 4-necked round-bottom flask was placed a solution of B5 (420 g, 1.84 mol) in tetrahydrofuran (5526 mL) and followed by addition of HCl (1N, 5526 mL) dropwise with stirring at 0-10° C. The resulting solution was stirred overnight at 30° C. and diluted with 5000 mL of saturated aqueous sodium carbonate solution. The mixture was stirred for 10 min at r.t and extracted with 2×2000 mL of ether. The combined organic layers were washed with 1×2000 mL of brine, dried over anhydrous sodium sulfate and concentrated under vacuum to afford B6.

Step 6

Into a 5-L 4-necked round-bottom flask were placed a solution of B6 (260 g, 1.69 mol) in ethanol (2000 mL) water (1000 mL) and NaOAc (692 g). After stirring for 15 min, $NH_2OH \cdot HCl$ (350 g) was added. The mixture was stirred for 5 min at 60° C. and diluted with water until a clear solution formed. The resulting solution was stirred for 2 h at 60° C. The reaction mixture was cooled and concentrated under vacuum. The resulting solution was diluted with 1000 mL of water and extracted with 2×1000 mL of ether. The combined Step 1

Into a 10-L 4-necked round-bottom flask were placed a solution of cyclopropanecarboxylic acid (500 g, 5.81 mol) in organic layers were washed with 1×1000 mL of brine, dried over anhydrous sodium sulfate and concentrated under vacuum to afford B7.

Step 7

To a stirred solution of B7 (230 g, 1.36 mol) in dichloromethane (3500 mL) was added aqueous NaOCl solution (3766 mL, 3.12 mol, 6.15% solution) dropwise at 19-25° C. The resulting solution was stirred for 15 min at 19-25° C. and diluted with 1000 mL of water. The resulting solution was extracted with 2×1000 mL of dichloromethane. The combined organic extracts were washed with 1×1000 mL of brine, dried over anhydrous sodium sulfate and concentrated under vacuum. The residue was purified by silica gel chromatography eluting with ethyl acetate/petroleum ether (1:10) to afford B8.

Step 8

The crude product B8 (117 g, 699.74 mmol) was purified by preparative SFC under the following conditions (prep SFC 350-2: Column, Chiralpak AS-H, 5×25 cm, 5 μm; mobile phase, 65:35 $CO_2$:ethanol (w/0.2% DEA); Detector, uv 220 nm) to give B9.

Step 9

To a stirred solution of 4-bromo-1-fluoro-2-iodobenzene (188 g, 624.80 mmol) in toluene (2000 mL) and tetrahydrofuran (200 mL) in a 5-L 4-necked round-bottom flask at −78° C. under nitrogen atmosphere was added n-BuLi (250 mL) dropwise. After stirring for 30 min at −78° C., $BF_3 \cdot Et_2O$ (88 g) was added dropwise at −78° C. To the mixture was added a solution of B9 (52 g, 311.00 mmol) in toluene (50 mL) dropwise at −78° C. The resulting solution was stirred for 1 h at −78° C. and then quenched by the addition of 2000 mL of $NH_4Cl$. The resulting mixture was extracted with 2×1000 mL of ethyl acetate. The combined organic extracts were washed with 2×1000 mL of brine, dried over anhydrous sodium sulfate and concentrated under vacuum. The residue was washed with 500 mL of hexane and the solids were collected by filtration to afford B10.

Step 10

Into a 2-L 3-necked round-bottom flask purged and maintained with an inert atmosphere of nitrogen were placed a solution of B10 (71 g, 207.48 mmol) in acetic acid (700 mL) followed by the addition of zinc (133.3 g). The resulting mixture was stirred overnight at 20° C. After that time, the mixture was diluted with 1000 mL of water/ice. The solids were collected by filtration, washed with n-hexane and ether to afford B11.

Method C

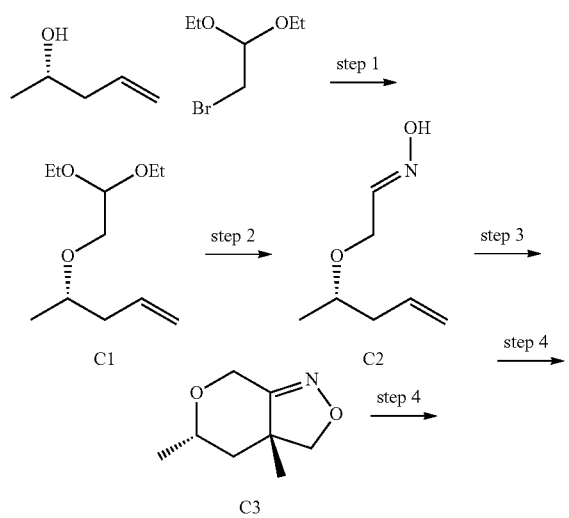

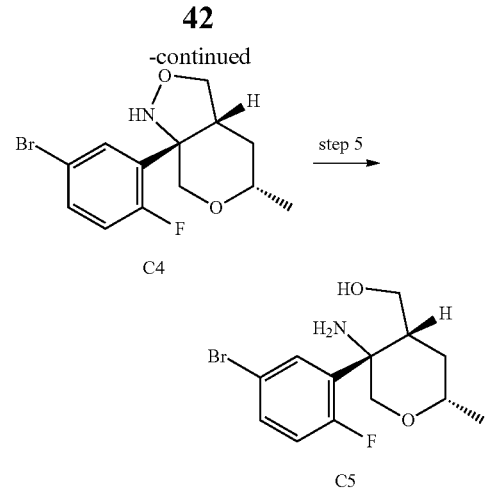

Step 1

To a suspension of NaH (13.9 g, 348 mmol, 60%) in tetrahydrofuran (350 mL) in a 1-L round bottom flask at 0° C. was added a solution of (S)-pent-4-en-2-ol (10 g, 116 mmol) in tetrahydrofuran (50 mL). The reaction mixture was warmed to room temperature and stirred for 30 minutes. After that time, 2-bromo-1,1-diethoxyethane (68.6 g, 348 mmol) was added at room temperature. The reaction mixture was then heated to reflux for 18 hours. The mixture was then, cooled to 0° C. and quenched with water (50 mL). The mixture was partitioned between ethyl acetate (300 mL) and water (200 mL) and the layers were separated. The organic phase was washed with brine (2×100 mL), dried, and concentrated in vacuo. The residue was purified by silica gel chromatography (hexanes/ethyl acetate=30:1) to afford C1.

Step 2

To a solution of C1 (17.56 g, 87 mmol) in tetrahydrofuran (100 mL) was added aqueous hydrochloric acid (2 M, 51.0 mL, 0.102 mol) at room temperature. The reaction mixture was heated at 75° C. for 1 h and concentrated in vacuo. To the residue were added ethanol (100 mL), water (20 mL), sodium acetate (35.17 g, 0.429 mol), and hydroxylamine hydrochloride (17.9 g, 0.257 mol). The reaction mixture was stirred at 60° C. for 18 h and then concentrated in vacuo. The residue was partitioned between water and dichloromethane and the layers were separated. The aqueous layer was extracted with dichloromethane (3×200 mL). The combined organic phases were dried over sodium sulfate, filtered, and concentrated in vacuo to give crude product C2.

Step 3

To a solution of C2 (7.6 g) and triethylamine (0.455 g, 4.50 mmol) in dichloromethane (150 mL) at room temperature was slowly added a 5% aqueous solution of sodium hypochlorite (90 mL) while maintaining the internal temperature between 20° C. and 25° C. After the addition, the organic phase was separated, dried, and concentrated in vacuo. The residue was purified by silica gel chromatography (hexanes/ethyl acetate=10:1) to afford C3.

Step 4

To a solution of C3 (3.30 g, 23.38 mmol) in toluene (100 mL) at −78° C. under $N_2$ atmosphere was added boron trifluoride diethyl etherate (6.38 mL, 23.38 mmol, 46.5%). The reaction mixture was stirred at this temperature for 30 min. After that time 4-bromo-1-fluoro-2-iodobenzene (3.24 mL, 24.55 mmol) and n-butyllithium (9.82 mL, 24.55 mmol) were introduced slowly. The mixture was stirred at this temperature for 3 h, quenched with saturated aqueous NH$_4$Cl (30 mL), and extracted with EtOAc (3×80 mL). The combined organic extracts were dried over Na$_2$SO$_4$ and concentrated to give C4.

Step 5

To a solution of C4 (2.13 g, 6.74 mmol) in acetic acid (45 mL) was added zinc (4.40 g, 67.4 mmol) at room temperature. The mixture was stirred at rt under nitrogen for 5 h and then filtered. The filtrate was concentrated and the residue was cooled in the ice bath and neutralized with sat. NaHCO$_3$ to pH 7 to 8. The mixture was then extracted with EtOAc three times. The organic extracts were combined and concentrated to give C5.

Method D

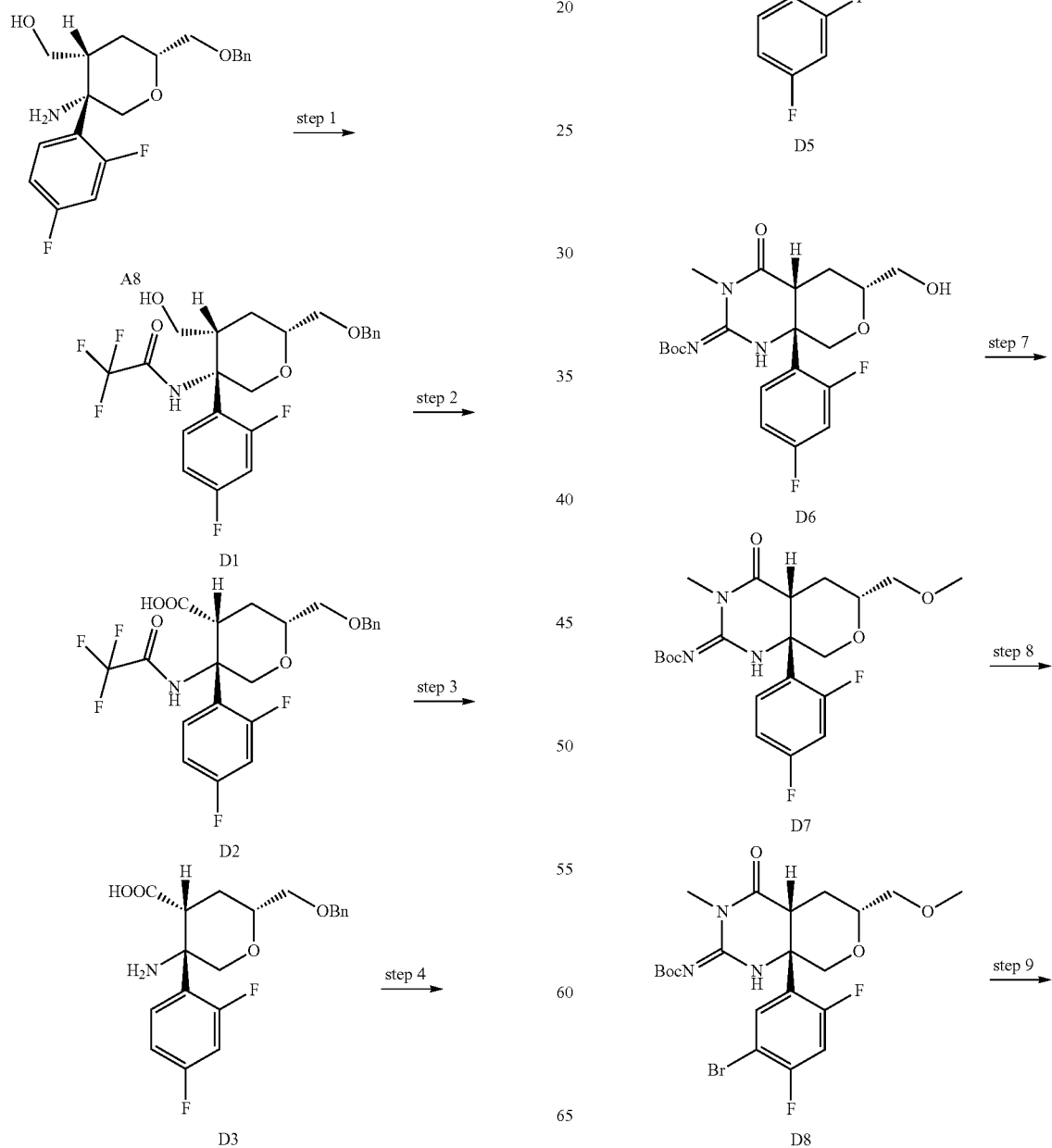

-continued

D9

Step 1

To a solution of A8 (6.6 g, 18.16 mmol) and Et$_3$N (3.80 mL, 27.2 mmol) in CH$_2$Cl$_2$ (40 mL) at 0° C. was added 2,2,2-trifluoroacetic anhydride (3.03 mL, 21.79 mmol). The mixture was stirred at 0° C. for 2 h and for an additional 2 h at RT. The mixture was then partitioned between DCM and H$_2$O, the organic layer was washed with brine, dried over Na$_2$SO$_4$, and filtered. The filtrate was concentrated to give D1.

Step 2

To a solution of D1 (8.34 g, 18.15 mmol) in acetonitrile (100 mL) were added 4-methylmorpholine N-oxide (8.51 g, 72.6 mmol) and tetrapropylammonium perruthenate (0.51 g, 1.45 mmol) in three portions. The resulting mixture was stirred at rt for 4 h. Then 2-propanol (20 mL) was added and the mixture was stirred overnight. The mixture was concentrated in vacuo and the residue was partitioned between 200 mL ethyl acetate and 80 mL 1 N HCl. The layers were separated and the organic layer was washed with brine, dried over Na$_2$SO$_4$, and filtered. The filtrate was concentrated to afford D2.

Step 3

To a solution of D2 (8.0 g, 16.90 mmol) in 1,4-dioxane (20 mL) was added a solution of LiOH (4.5 g, 188 mmol) in water (20 mL). The mixture was heated to 150° C. in a sealed tube for 16 h. The reaction mixture was then cooled to rt and adjusted pH 1 to 2 by addition of concentrated aqueous HCl. The mixture was extracted with isopropyl alcohol/CHCl$_3$ (1/3) until LC/MS showed no remaining product in aqueous layer. The organic layer was dried over Na$_2$SO$_4$, filtered, and concentrated to afford D3.

Step 4

To a solution of D3 (6.38 g, 16.91 mmol) in MeOH (30 mL) was added SOCl$_2$ (12.34 mL, 169 mmol) dropwise. The mixture was heated at reflux overnight, cooled to rt and concentrated in vacuo. The residue was partitioned between saturated aq. NaHCO$_3$ and ethyl acetate and the layers were separated. The organic layer was dried over Na$_2$SO$_4$, filtered, and concentrated in vacuo. The residue was purified by column chromatography on silica gel eluting with 0-5% MeOH/DCM to afford D4.

Step 5

To a solution of D4 (6.5 g, 16.61 mmol) in DMF (25 mL) were added DIPEA (11.60 mL, 66.4 mmol), 1-ethyl-3-β-dimethylaminopropyl) carbodiimide hydrochloride (6.37 g, 33.2 mmol) and N-Boc-N'-methyl thiourea (6.32 g, 33.2). The mixture was stirred at rt for 4 h, then 50° C. for an additional 5 h. The mixture was cooled, diluted with ethyl acetate (100 mL) washed with H$_2$O (3×30 mL). The organic layer was dried over Na$_2$SO$_4$ and filtered. The filtrate was concentrated and the residue was purified by column chromatography on silica gel eluting with 0-5% MeOH/DCM to afford D5.

Step 6

To a solution of D5 (5.5 g, 10.67 mmol) in CH$_2$Cl$_2$ (25 mL) at −10° C. was added BCl$_3$ (53.3 mL, 53.3 mmol, 1.0 M in DCM). The mixture was stirred at −10° C. for 3 h and concentrated in vacuo. The residue was partitioned between CHCl$_3$/IPA (3/1) and saturated NaHCO$_3$ and the layers were separated. The organic layer was dried over Na$_2$SO$_4$, filtered, and concentrated in vacuo. The residue was dissolved in MeOH (25 mL), Et$_3$N (2.23 mL, 16.00 mmol) and (Boc)$_2$O (3.47 mL, 14.94 mmol) were added. The mixture was stirred at rt overnight and concentrated in vacuo. The residue was purified by column chromatography on silica gel eluting with 0-20% ethyl acetate/hexane to afford D6.

Step 7

To a solution of D6 (2.3 g, 5.41 mmol) in THF (20 mL) was added NaH (0.54 g, 13.52 mmol). The mixture was stirred at rt for 20 min, followed by addition of MeI (0.37 mL, 5.95 mmol). The mixture was stirred at rt overnight. After that time, the mixture was partitioned between ethyl acetate and H$_2$O and the layers were separated. The organic layer was dried over Na$_2$SO$_4$, filtered and concentrated in vacuo. The residue was purified by column chromatography on silica gel eluting with 0-30% ethyl acetate/hexane to afford D7.

Step 8

To a solution of D7 (1200 mg, 2.73 mmol) in TFA (15 mL) at 0° C. were added H$_2$SO$_4$ (0.87 mL, 16.38 mmol) dropwise and NBS (3888 mg, 21.85 mmol). The mixture was heated at 65° C. for 7 h and concentrated in vacuo. The residue was partitioned between saturated Na$_2$CO$_3$ and ethyl acetate and the layers were separated. The organic layer was dried over Na$_2$SO$_4$, filtered and concentrated in vacuo. The residue was dissolved in CH$_2$Cl$_2$ (15 mL), to the solution were added Et$_3$N (0.76 mL, 5.46 mmol) and (Boc)$_2$O (0.95 mL, 4.10 mmol). The mixture was stirred at rt overnight and concentrated in vacuo. The residue was purified by column chromatography on silica gel eluting with 0-30% ethyl acetate/hexane to afford D8.

Step 9

To a solution of D8 (470 mg, 0.91 mmol) in tetrahydrofuran (10 mL) at −20° C. was added a solution of isopropylmagnesium chloride lithium chloride complex (1.05 mL, 1.36 mmol). The resulting mixture was stirred at −20° C. for 30 min, cooled to −78° C. and treated with a solution of n-BuLi (1.13 mL, 1.81 mmol). The mixture was stirred at −78° C. for 2 h and then tributyl borate (835 mg, 3.63 mmol) was introduced. The mixture was stirred at −78° C. for 2 h, then gradually warmed to rt and stirred for an additional 1 h. The mixture was then quenched with saturated NH$_4$Cl and extracted with ethyl acetate. The combined organic extracts were dried over Na$_2$SO$_4$, filtered and concentrated in vacuo. The residue was dissolved in CH$_2$Cl$_2$ (5 mL) and treated with H$_2$O$_2$ (2.31 mL, 22.67 mmol, 30% in H$_2$O). The mixture was stirred at rt for 4 h and partitioned between ethyl acetate and H$_2$O. The layers were separated, the organic layer was dried over Na$_2$SO$_4$, filtered and concentrated in vacuo. The residue was purified by column chromatography on silica gel eluting with 0-50% ethyl acetate/hexane to afford D9.

Method E

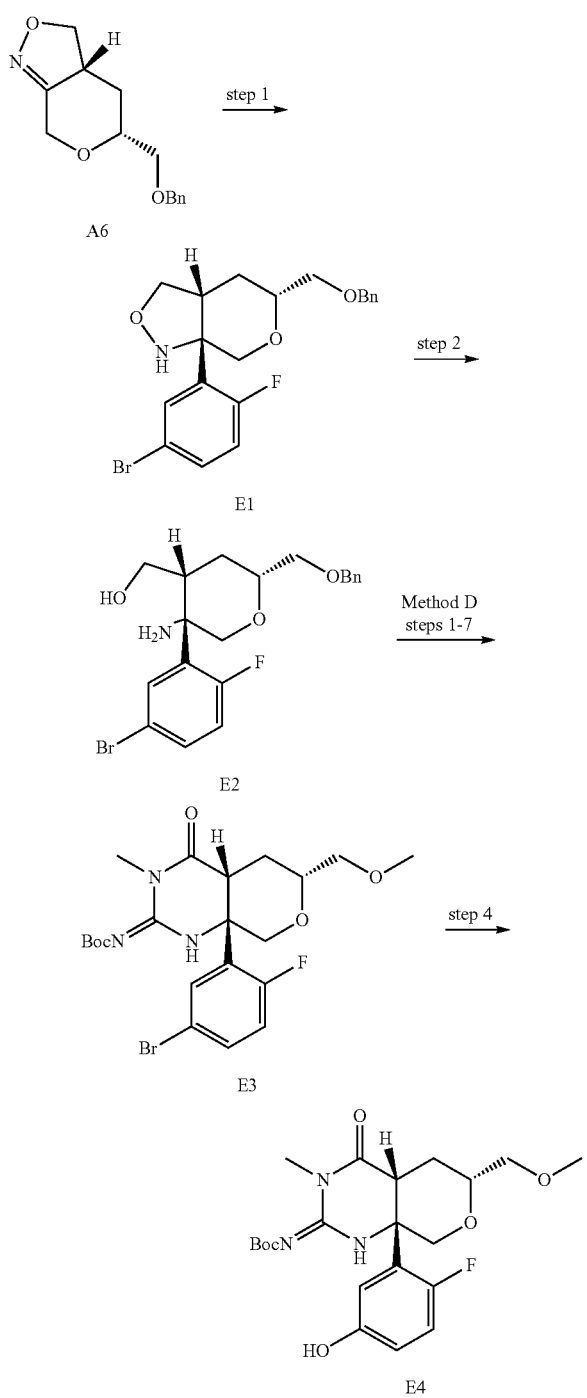

Step 1

A solution of A6 (12 g, 48.5 mmol) in toluene (150 mL) was cooled to −78° C. under N₂ and then boron trifluoride diethyl etherate (14 mL, 48.5 mmol) was added. The reaction mixture was stirred at this temperature for 30 min. To the mixture were added slowly 4-bromo-1-fluoro-2-iodobenzene (16.06 g, 53.4 mmol) and a solution of n-BuLi (21.35 mL, 53.4 mmol). The mixture was stirred at this temp for 3 h, quenched with saturated NH₄Cl (30 mL), and extracted with EtOAc (3×80 mL). The combined organic extracts were dried over Na₂SO₄ and concentrated to afford E1.

Step 2

To a solution of E1 (18 g, 42.6 mmol) in acetic acid (100 mL) was added zinc (27.9 g, 426 mmol) at 25° C. The mixture was stirred at 25° C. for 4 h and filtered. The filtrate was concentrated. The residue was diluted with EtOAc (50 mL) and neutralized with aq. NaHCO₃ to pH 7. The phases were separated, the aqueous phase was extracted with EtOAc (3×150 mL). The combined organic extracts were concentrated and the residue was purified by column chromatography (SiO₂, PE:EtOAc=5:1 to 2:1) to afford E2.

E3 was synthesized from E2 according to a method similar to Method D.

Step 4

To a solution of E3 (260 mg, 0.52 mmol) in MeOH (3 mL) were added DIPEA (0.27 mL, 1.56 mmol), tetrahydroxydiboron (93 mg, 1.04 mmol) and PCy₃ Pd G2 (30.7 mg, 0.052 mmol). The mixture was stirred at rt for 3 h and concentrated in vacuo. The residue was dissolved in CH₂Cl₂ (15 mL) and treated with H₂O₂ (0.45 mL, 5.20 mmol, 30% in H₂O). The mixture was stirred at rt for 3 h and then partitioned between ethyl acetate and H₂O and the layers were separated. The organic layer was dried over Na₂SO₄ and filtered. The filtrate was concentrated in vacuo and the residue was purified by column chromatography on silica gel eluting with 0-50% ethyl acetate/hexane to afford E4.

Method F

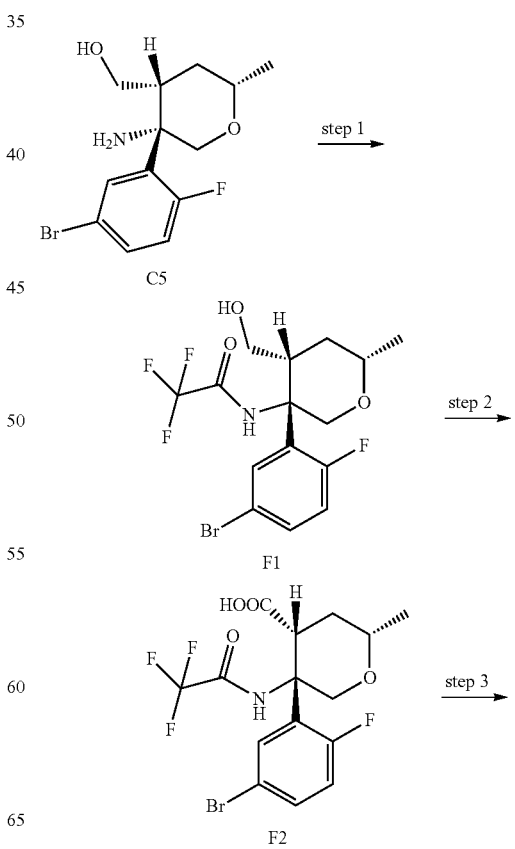

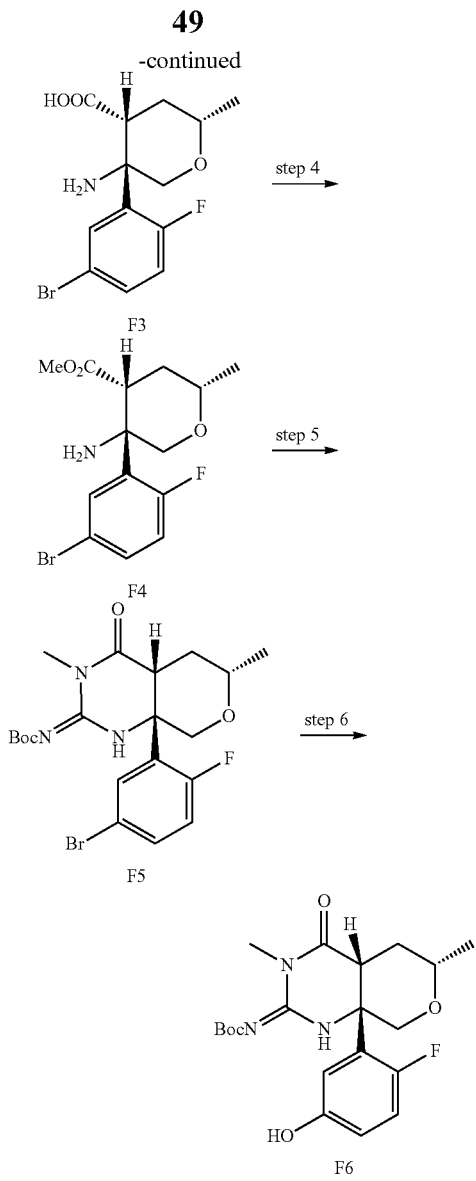

reaction mixture in a sealed tube was heated at 150° C. for 11 h and cooled to rt. The reaction mixture was acidified to pH 1 with concentrated HCl and concentrated to afford F3.

Step 4

To a solution of the above crude material F3 in MeOH (30 mL) at 0° C. was added SOCl$_2$ (4.02 mL, 55.1 mmol) dropwise. The resulting mixture was heated at 60° C. under nitrogen for 8 h and concentrated. The residue was cooled in the ice bath and quenched with water. It was basified with saturated NaHCO$_3$ to pH 7 and extracted with CHCl$_3$/2-propanol (3/1) (×5). The organic extracts were dried over MgSO$_4$, and concentrated. The residue was purified by flash chromatography (SiO$_2$, eluting with 0-4% [7N NH$_3$ in MeOH]/DCM) to afford F4.

Step 5

To a solution of F4 (880 mg, 2.54 mmol) in DMF (25 mL) were added DIPEA (1.77 mL, 10.17 mmol), N-Boc-N'-methyl thiourea (1.45 g, 7.63 mmol) and N1-((ethylimino)methylene)-N3,N3-dimethylpropane-1,3-diamine hydrochloride (1.46 g, 7.63 mmol). The reaction mixture was stirred at rt overnight. It was diluted with EtOAc and washed with water (×3). The organic layer was dried with MgSO$_4$, concentrated. The residue was purified by flash chromatography (SiO$_2$, eluting with 0-2% [7N NH$_3$ in MeOH]/DCM) to afford F5.

Step 6

To a microwave vial containing F5 (730 mg, 1.55 mmol) were added AdBrettPhos Pd G3 (235 mg, 233 μmol) and DMSO (16 mL). The mixture was bubbled with nitrogen for 5 min. After addition of water (168 μL, 9.31 mmol) and phosphazene base P2-Et (1844 mg, 5.43 mmol), the mixture was bubbled with nitrogen for additional 5 min. The mixture in a sealed tube was heated at 40° C. for 7 h and cooled to rt. It was partitioned between EtOAc and saturated NH$_4$Cl (aq.). The aqueous layer was extracted with EtOAc and the combined organic layers were washed successively with water (2×) and brine, then dried, filtered. The filtrate was concentrated; the residue was purified by preparative TLC eluting with 3% 7N NH$_3$ in MeOH/DCM to afford F6.

Method G

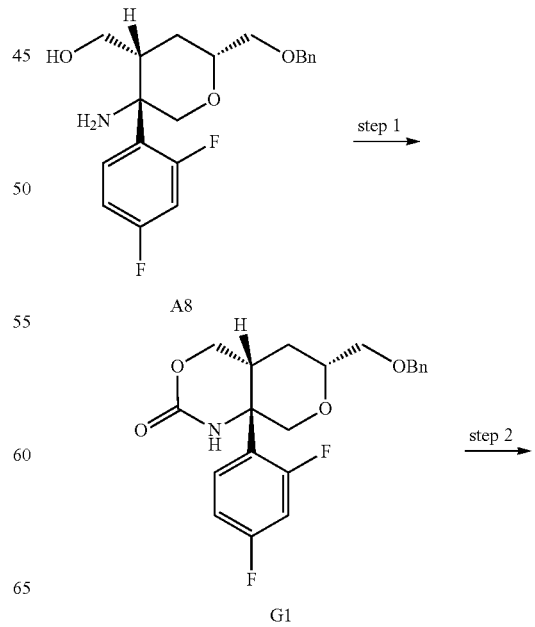

Step 1

To a solution of C5 (2.45 g) and TEA (1.61 mL, 11.55 mmol) in DCM (70 mL) at 0° C. under nitrogen was added trifluoroacetic anhydride (1.19 mL, 8.47 mmol). The reaction mixture was stirred at 0° C. for 30 min and rt for 1 hr. The mixture was concentrated and the residue was purified by chromatography (RediSep Rf40 g, eluting with 0-2% [7 N NH$_3$ in MeOH]/DCM) to afford F1.

Step 2

To a solution of F1 (1.49 g, 3.79 mmol) in acetonitrile (35 mL) was added 4-methylmorpholine N-oxide (1.686 g, 14.39 mmol) followed by tetrapropylammonium perruthenate (101 mg, 0.28 mmol). The reaction mixture was stirred at rt under nitrogen for 3 h and quenched with 2-propanol (15 mL). The mixture was stirred at rt for 2 h and concentrated. The residue was partitioned between EtOAc and 1 N HCl and the layers were separated. The organic layer was washed with brine, dried over MgSO$_4$, and concentrated to afford F2.

Step 3

To a solution of F2 (1.60 g, 3.74 mmol) in 1,4-dioxane (30 mL) was added lithium hydroxide (1.88 g, 44.8 mmol). The

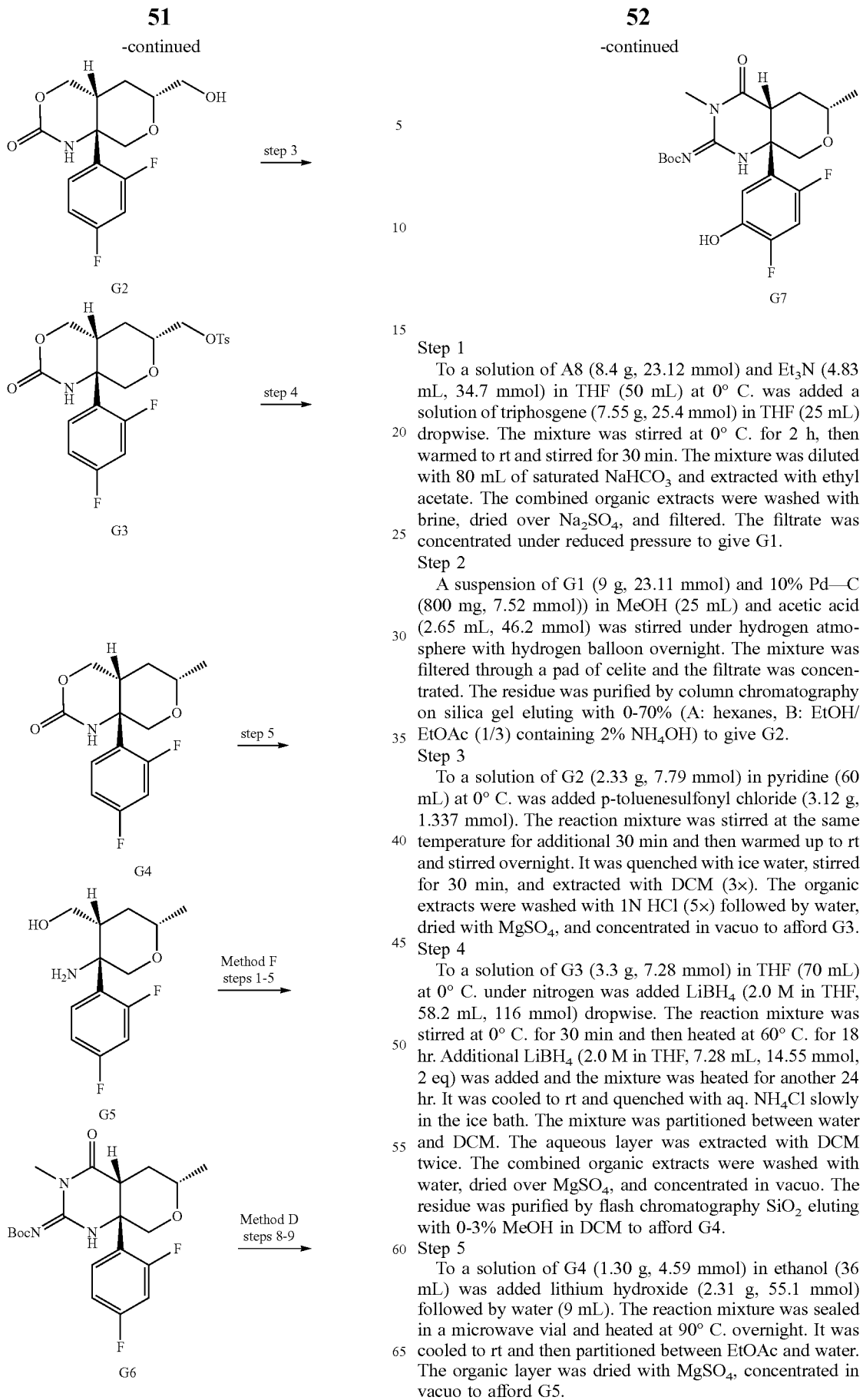

Step 1

To a solution of A8 (8.4 g, 23.12 mmol) and Et₃N (4.83 mL, 34.7 mmol) in THF (50 mL) at 0° C. was added a solution of triphosgene (7.55 g, 25.4 mmol) in THF (25 mL) dropwise. The mixture was stirred at 0° C. for 2 h, then warmed to rt and stirred for 30 min. The mixture was diluted with 80 mL of saturated NaHCO₃ and extracted with ethyl acetate. The combined organic extracts were washed with brine, dried over Na₂SO₄, and filtered. The filtrate was concentrated under reduced pressure to give G1.

Step 2

A suspension of G1 (9 g, 23.11 mmol) and 10% Pd—C (800 mg, 7.52 mmol)) in MeOH (25 mL) and acetic acid (2.65 mL, 46.2 mmol) was stirred under hydrogen atmosphere with hydrogen balloon overnight. The mixture was filtered through a pad of celite and the filtrate was concentrated. The residue was purified by column chromatography on silica gel eluting with 0-70% (A: hexanes, B: EtOH/EtOAc (1/3) containing 2% NH₄OH) to give G2.

Step 3

To a solution of G2 (2.33 g, 7.79 mmol) in pyridine (60 mL) at 0° C. was added p-toluenesulfonyl chloride (3.12 g, 1.337 mmol). The reaction mixture was stirred at the same temperature for additional 30 min and then warmed up to rt and stirred overnight. It was quenched with ice water, stirred for 30 min, and extracted with DCM (3x). The organic extracts were washed with 1N HCl (5x) followed by water, dried with MgSO₄, and concentrated in vacuo to afford G3.

Step 4

To a solution of G3 (3.3 g, 7.28 mmol) in THF (70 mL) at 0° C. under nitrogen was added LiBH₄ (2.0 M in THF, 58.2 mL, 116 mmol) dropwise. The reaction mixture was stirred at 0° C. for 30 min and then heated at 60° C. for 18 hr. Additional LiBH₄ (2.0 M in THF, 7.28 mL, 14.55 mmol, 2 eq) was added and the mixture was heated for another 24 hr. It was cooled to rt and quenched with aq. NH₄Cl slowly in the ice bath. The mixture was partitioned between water and DCM. The aqueous layer was extracted with DCM twice. The combined organic extracts were washed with water, dried over MgSO₄, and concentrated in vacuo. The residue was purified by flash chromatography SiO₂ eluting with 0-3% MeOH in DCM to afford G4.

Step 5

To a solution of G4 (1.30 g, 4.59 mmol) in ethanol (36 mL) was added lithium hydroxide (2.31 g, 55.1 mmol) followed by water (9 mL). The reaction mixture was sealed in a microwave vial and heated at 90° C. overnight. It was cooled to rt and then partitioned between EtOAc and water. The organic layer was dried with MgSO₄, concentrated in vacuo to afford G5.

G6 was synthesized from G5 according to a method similar to method F (steps 1-5). G7 was synthesized from G6 according to a method similar to method D (steps 8-9).

Method H

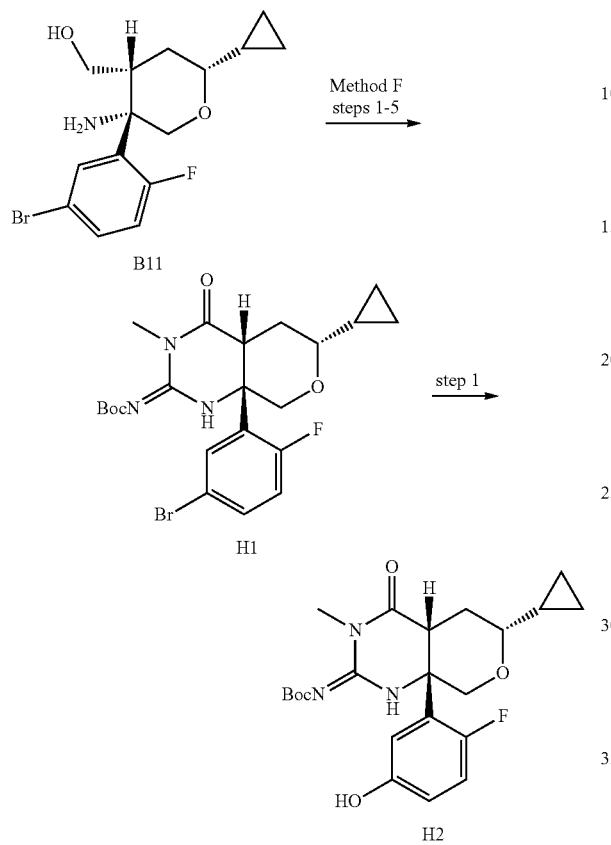

Compound H1 was prepared from B11 according to a method similar to method F.

Step 1

To a solution of H1 (1900 mg, 3.83 mmol) in MeOH (15 mL) were added DIPEA (2.01 mL, 11.48 mmol), tetrahydroxydiboron (686 mg, 7.66 mmol) and PCy₃ Pd G2 (226 mg, 0.38 mmol). The mixture was stirred at rt for 3 h and concentrated in vacuo. The residue was dissolved in CH₂Cl₂ (15 mL) and treated with H₂O₂ (3.35 mL, 38.3 mmol, 30% in H₂O). the mixture was stirred at rt for 3 h and then partitioned between ethyl acetate and H₂O. The organic layer was dried over Na₂SO₄ and filtered. The filtrate was concentrated in vacuo; the residue was purified by column chromatography on silica gel eluting with 0-50% ethyl acetate/hexane to afford H2.

Method I

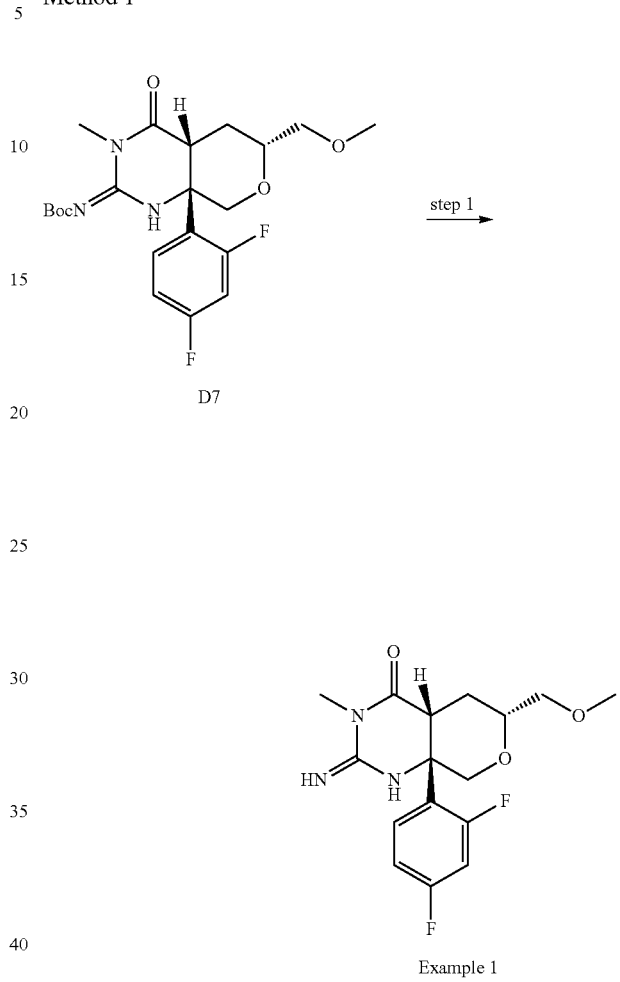

Step 1

To a solution of D7 (35 mg, 0.080 mmol) in CH₂Cl₂ (1 mL) was added TFA (500 μL, 6.49 mmol). The mixture was stirred at rt for 2 h and concentrated in vacuo. The residue was purified by preparative TLC eluting with 3% 7N NH₃ in MeOH/DCM to afford example 1.

Using the appropriate precursor, the following Examples were prepared using the conditions described in Method I.

| Entry | Precursor | Product | Example # |
|---|---|---|---|
| 1 | G6 | | 11 |

-continued
| Entry | Precursor | Product | Example # |
|---|---|---|---|
| 2 | F5 | | 12 |
| 3 | E3 | | 33 |
| 4 | F6 | | 64 |
Method J
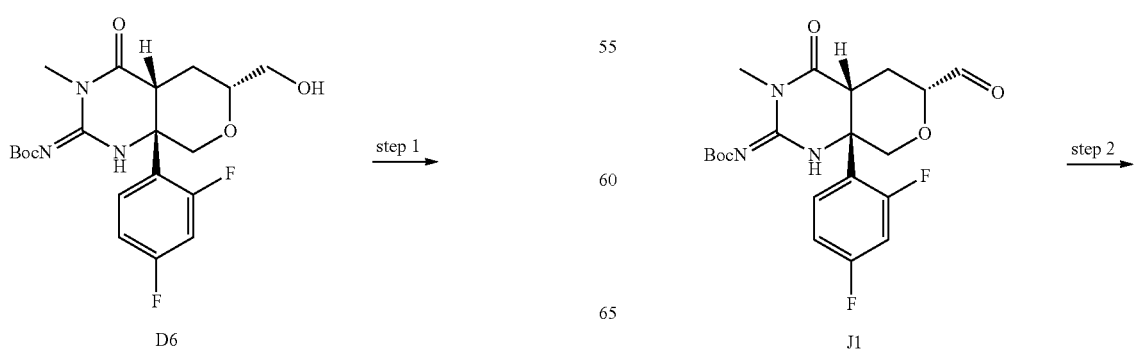

57

-continued

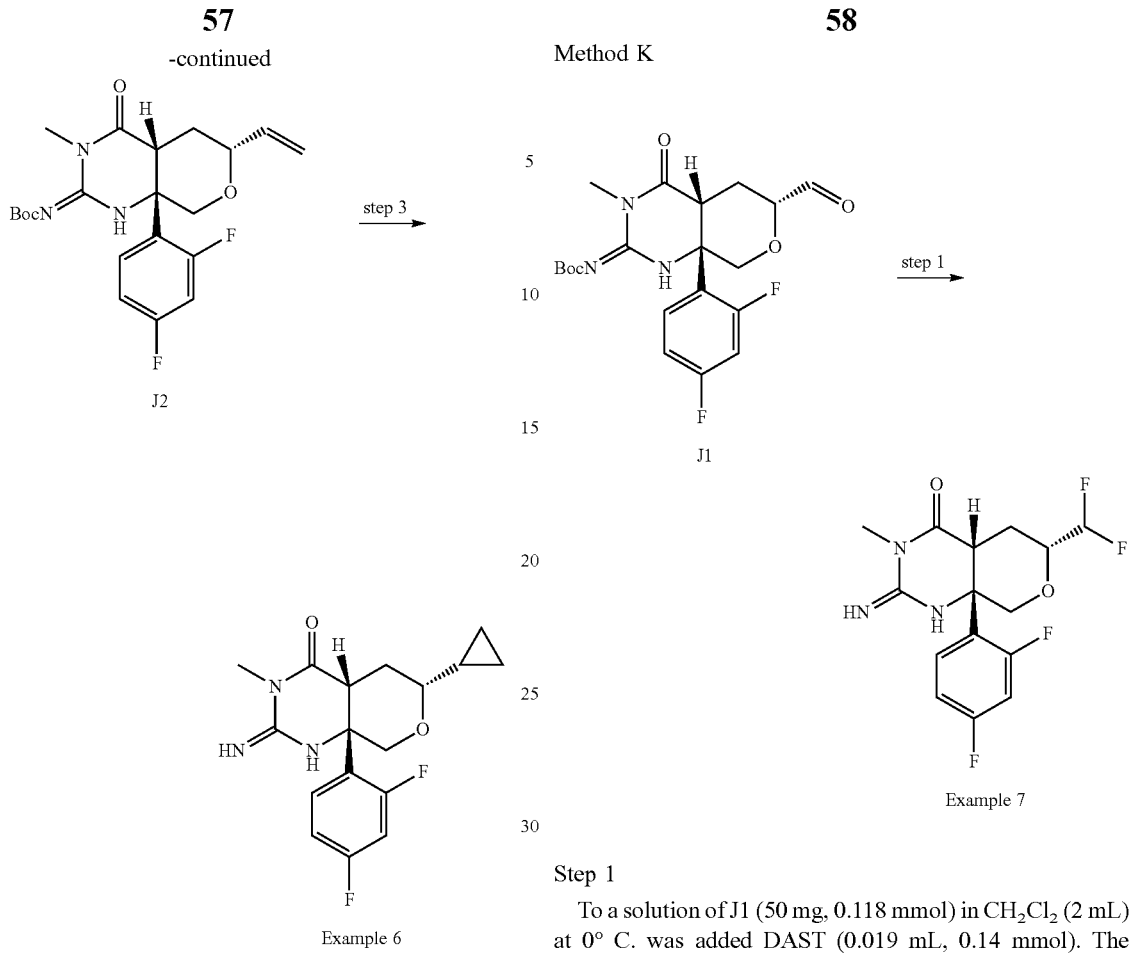

J2

Example 6

Step 1

To a solution of D6 (840 mg, 1.974 mmol) in DCM (10 mL) was added Dess-Martin periodinane (1256 mg, 2.96 mmol). The mixture was stirred at rt for 3 h, and then partitioned between DCM and saturated $NaHCO_3$. The organic phase was dried over $Na_2SO_4$, filtered, and concentrated in vacuo to afford J1.

Step 2

To a solution of KHMDS (6.24 ml, 6.24 mmol, 1.0 M in THF) in THF (10 mL) at 0° C. was added methyltriphenylphosphonium bromide (2227 mg, 6.24 mmol). The mixture was stirred at 0° C. for 40 min, J1 (660 mg, 1.56 mmol) was added. The mixture was stirred at 0° C. for 1 h and rt for 1 h. The reaction mixture was partitioned between saturated $NH_4Cl$ and ethyl acetate. The organic phase was dried over $Na_2SO_4$, filtered, and concentrated in vacuo. The residue was purified by column chromatography on silica gel eluting with 0-40% ethyl acetate to afford J2.

Step 3

To a solution of diiodomethane (0.19 mL, 2.37 mmol) and J2 (100 mg, 0.24 mmol) in $CH_2Cl_2$ (8 mL) at 0° C. was added $Et_2Zn$ (2.37 mL, 2.37 mmol, 1.0M in hexane). The mixture was stirred at 0° C. for 1 h and rt overnight. The reaction was partitioned between saturated $NH_4Cl$ and ethyl acetate; the organic phase was dried over $Na_2SO_4$, filtered, and concentrated in vacuo. The residue was purified by column chromatography on silica gel eluting with 0-5% MeOH/DCM to afford example 6.

58

Method K

Example 7

Step 1

To a solution of J1 (50 mg, 0.118 mmol) in $CH_2Cl_2$ (2 mL) at 0° C. was added DAST (0.019 mL, 0.14 mmol). The mixture was stirred at 0° C. for 2 h and concentrated in vacuo. The residue was dissolved in $CH_2Cl_2$ (2 mL) and treated with TFA (1 mL, 12.98 mmol). The mixture was stirred at rt for 3 h and then concentrated in vacuo. It was basified by addition of 1 ml of 7N $NH_3$ in MeOH and concentrated in vacuo. The residue was purified by preparative TLC to afford example 7.

Method L

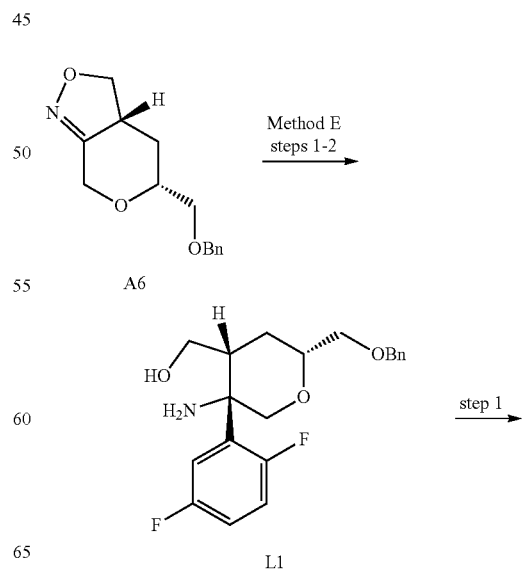

A6

L1

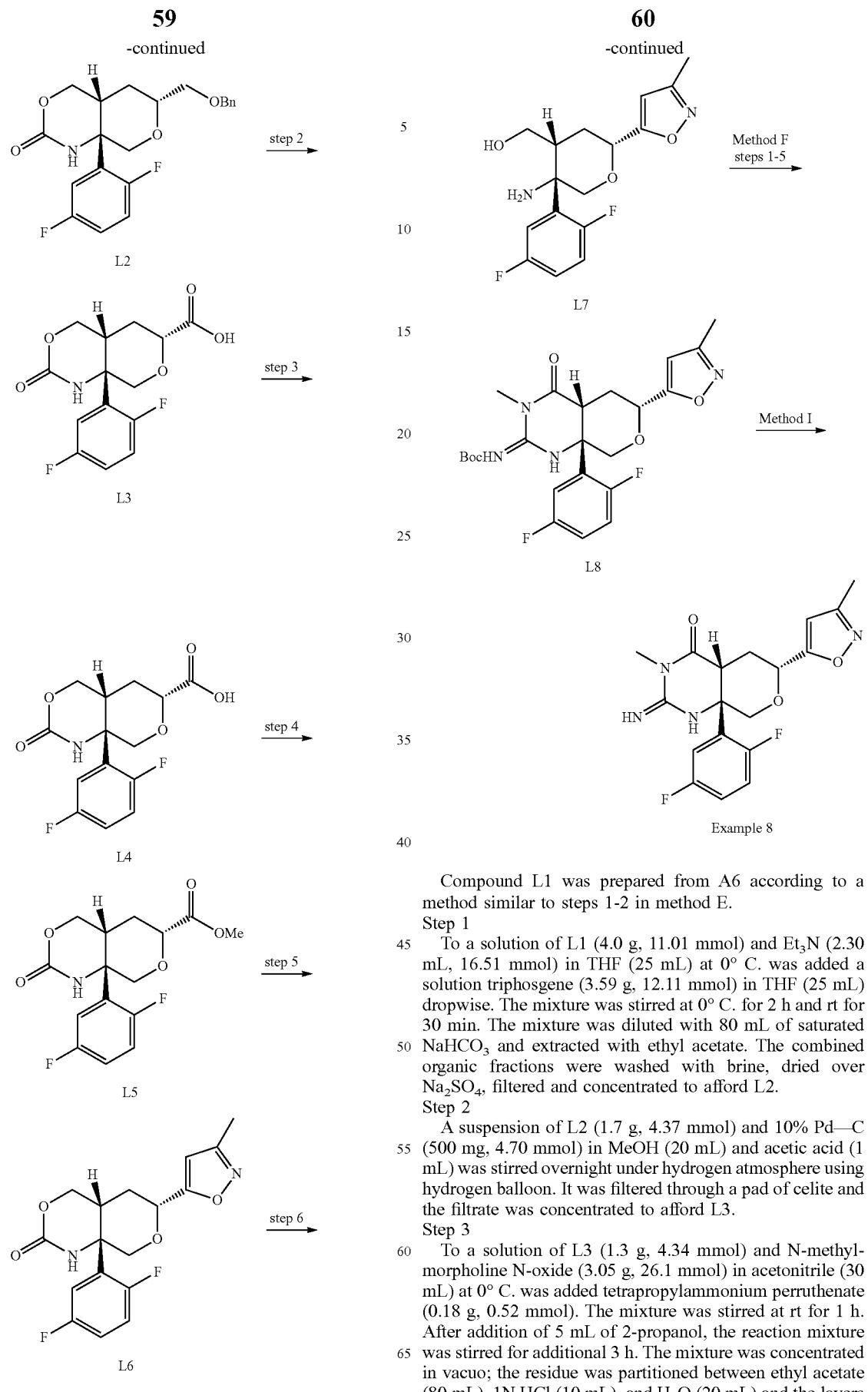

Compound L1 was prepared from A6 according to a method similar to steps 1-2 in method E.

Step 1

To a solution of L1 (4.0 g, 11.01 mmol) and Et$_3$N (2.30 mL, 16.51 mmol) in THF (25 mL) at 0° C. was added a solution triphosgene (3.59 g, 12.11 mmol) in THF (25 mL) dropwise. The mixture was stirred at 0° C. for 2 h and rt for 30 min. The mixture was diluted with 80 mL of saturated NaHCO$_3$ and extracted with ethyl acetate. The combined organic fractions were washed with brine, dried over Na$_2$SO$_4$, filtered and concentrated to afford L2.

Step 2

A suspension of L2 (1.7 g, 4.37 mmol) and 10% Pd—C (500 mg, 4.70 mmol) in MeOH (20 mL) and acetic acid (1 mL) was stirred overnight under hydrogen atmosphere using hydrogen balloon. It was filtered through a pad of celite and the filtrate was concentrated to afford L3.

Step 3

To a solution of L3 (1.3 g, 4.34 mmol) and N-methylmorpholine N-oxide (3.05 g, 26.1 mmol) in acetonitrile (30 mL) at 0° C. was added tetrapropylammonium perruthenate (0.18 g, 0.52 mmol). The mixture was stirred at rt for 1 h. After addition of 5 mL of 2-propanol, the reaction mixture was stirred for additional 3 h. The mixture was concentrated in vacuo; the residue was partitioned between ethyl acetate (80 mL), 1N HCl (10 mL), and H$_2$O (20 mL) and the layers were separated. The organic phase was dried over Na$_2$SO$_4$, filtered and concentrated in vacuo to afford L4.

Step 4

To a solution of L4 (1.20 g, 3.83 mmol) in THF (20 mL) at 0° C. was added trimethylsilyldiazomethane (2.87 ml, 5.75 mmol, 2.0 M in diethyl ether). The resulting mixture was stirred at 0° C. for 3 h, then 10 mL MeOH was added. The mixture was stirred for another 10 min and concentrated in vacuo. The residue was purified by column chromatography on silica gel eluting with 0-4% MeOH/DCM to afford L5.

Step 5

To a solution of acetone oxime (0.61 g, 8.40 mmol) in THF (35 mL) was added n-BuLi (9.45 mL, 15.12 mmol, 1.6M in hexane) at 0° C. The mixture was stirred at 0° C. for 1 h, and followed by addition of L5 (1.10 g, 3.36 mmol). The reaction mixture was stirred at 15° C. for additional 1 h, then cooled again in an ice bath. After addition of H$_2$SO$_4$ (0.89 mL, 16.81 mmol), the mixture was stirred at 15° C. for 4 h and cooled again to 0° C. It was neutralized with 5 M NaOH, extracted with ethyl acetate. The organic phase was concentrated and the residue was purified by preparative TLC eluting with 4% MeOH in DCM to give L6.

Step 6

A solution of L6 (600 mg, 1.71 mmol), LiOH (200 mg, 8.35 mmol), EtOH (4 mL) and water (1.0 mL) in a sealed microwave tube was heated at 80° C. overnight. The mixture was cooled, diluted with ethyl acetate; the organic phase was washed with brine, dried over Na$_2$SO$_4$, and filtered. The filtrate was concentrated to afford L7.

L8 was prepared from L7 according to a method similar to method F (steps 1-5).

Example 8 was prepared from L8 according to a method similar to method I.

Method M

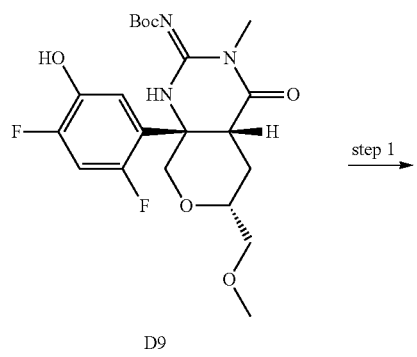

D9

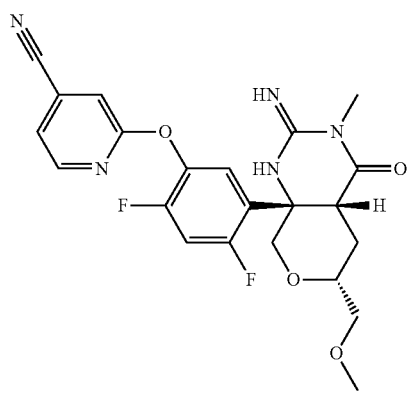

Example 2

Step 1

To a solution of D9 (50 mg, 0.11 mmol) in DMSO (2 mL) were added 2-fluoroisonicotinonitrile (40.2 mg, 0.33 mmol) and Cs$_2$CO$_3$ (107 mg, 0.33 mmol). The mixture was stirred at 80° C. for 1 h. The reaction mixture was cooled to rt and partitioned between ethyl acetate and H$_2$O. The organic phase was dried over Na$_2$SO$_4$, filtered, and concentrated in vacuo. The residue was dissolved in 1 mL of DCM and treated with 1 mL of TFA. The mixture was stirred at rt for 4 h and concentrated in vacuo; the residue was purified by preparative TLC eluting with 3% of 7N NH$_3$ in MeOH/DCM to afford example 2.

Using the appropriate core and reagent, the following Examples were prepared using the conditions described in Method M.

| Entry | Core | Reagent | Product | Example # |
|---|---|---|---|---|
| 1 | ![D9 structure] D9 | ![reagent structure] | ![product structure] | 3 |

-continued
| Entry | Core | Reagent | Product | Example # |
|---|---|---|---|---|
| 2 | | 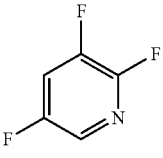 | 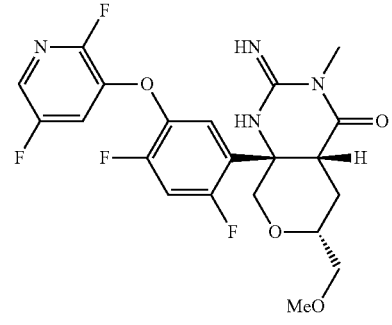 [SMILES: COC[C@H]1C[C@H]2C(=O)N(C)C(=N)N[C@@]2(c2cc(Oc3cc(F)cnc3F)c(F)cc2F)CO1] | 59 |
| 3 | |  | 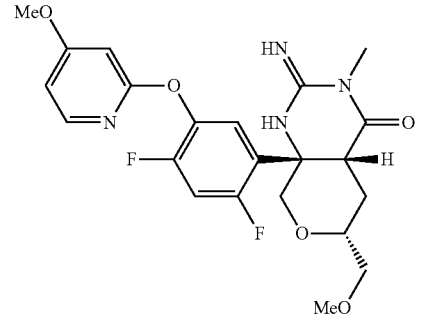 [SMILES: COC[C@H]1C[C@H]2C(=O)N(C)C(=N)N[C@@]2(c2cc(Oc3cc(OC)ccn3)c(F)cc2F)CO1] | 4 |
| 4 | 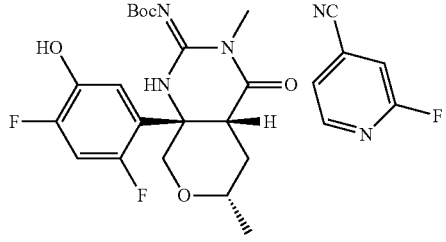<br>G7 | 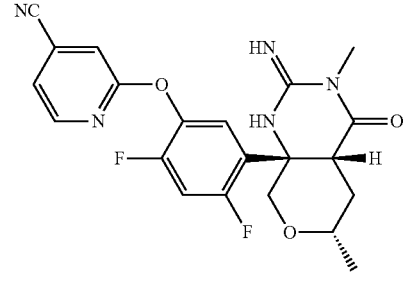 [SMILES: C[C@H]1C[C@H]2C(=O)N(C)C(=N)N[C@@]2(c2cc(Oc3cc(C#N)ccn3)c(F)cc2F)CO1] |  | 9 |
| 5 | | 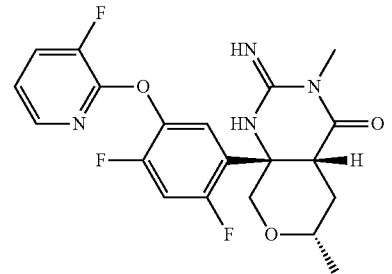 | 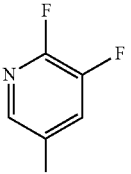 | 10 |
| 6 | | 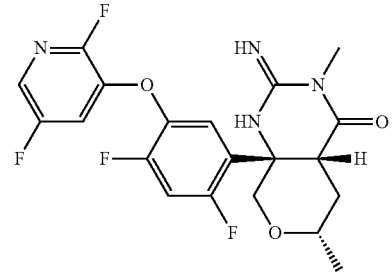 [SMILES: C[C@H]1C[C@H]2C(=O)N(C)C(=N)N[C@@]2(c2cc(Oc3cc(F)cnc3F)c(F)cc2F)CO1] | | 62 |

-continued
| Entry | Core | Reagent | Product | Example # |
|---|---|---|---|---|
| 7 | | 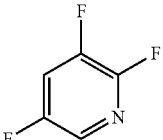 | 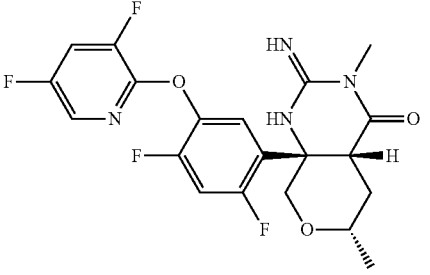 [SMILES: C[C@H]1C[C@H]2C(=O)N(C)C(=N)N[C@@]2(c2cc(Oc3ncc(F)cc3F)c(F)cc2F)CO1] | 63 |
| 8 | 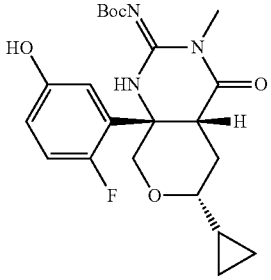 H2 | 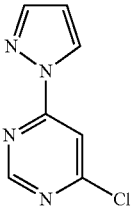 [SMILES: Clc1cc(-n2cccn2)ncn1] | 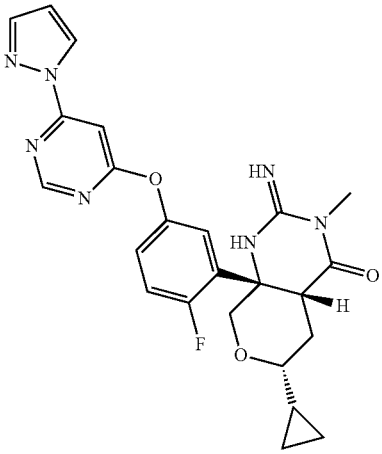 [SMILES: CN1C(=N)N[C@@]2(c3cc(Oc4cc(-n5cccn5)ncn4)ccc3F)CO[C@@H](C3CC3)C[C@H]2C1=O] | 13 |
| 9 | | 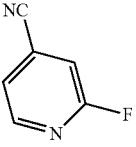 | 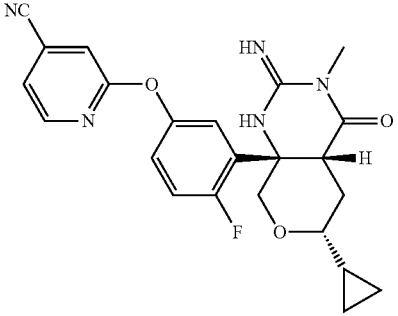 | 14 |
| 10 | | 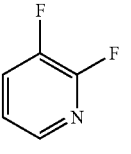 | 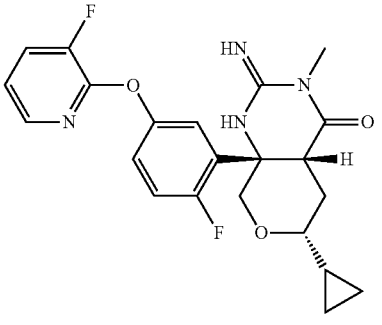 [SMILES: CN1C(=N)N[C@@]2(c3cc(Oc4ncccc4F)ccc3F)CO[C@@H](C3CC3)C[C@H]2C1=O] | 15 |

-continued
| Entry | Core | Reagent | Product | Example # |
|---|---|---|---|---|
| 11 | | 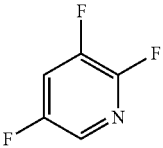 | 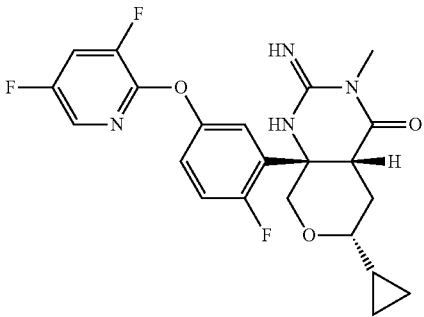 [SMILES: CN1C(=N)N[C@@]2(c3cc(Oc4ncc(F)cc4F)ccc3F)CO[C@@H](C3CC3)C[C@H]2C1=O] | 18 |
| 12 | |  | 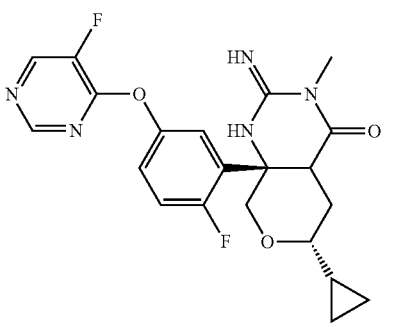 [SMILES: CN1C(=N)N[C@@]2(c3cc(Oc4ncncc4F)ccc3F)CO[C@@H](C3CC3)CC2C1=O] | 58 |
| 13 | | 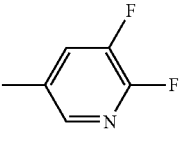 | 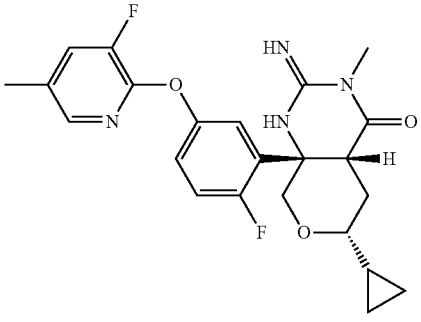 [SMILES: Cc1cnc(Oc2ccc(F)c([C@]34CO[C@@H](C5CC5)C[C@H]3C(=O)N(C)C(=N)N4)c2)c(F)c1] | 60 |
| 14 | 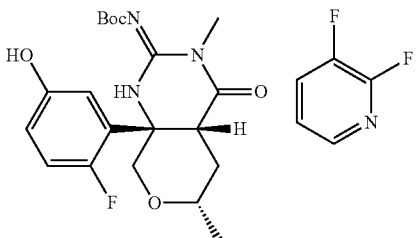 F6 |  | 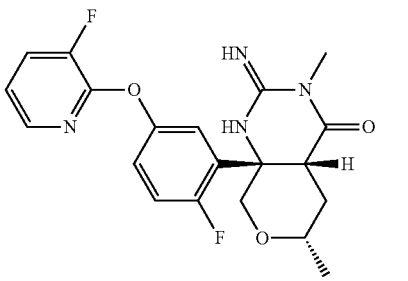 [SMILES: C[C@H]1C[C@H]2C(=O)N(C)C(=N)N[C@@]2(c2cc(Oc3ncccc3F)ccc2F)CO1] | 19 |
| 15 | | 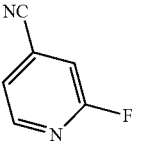 | 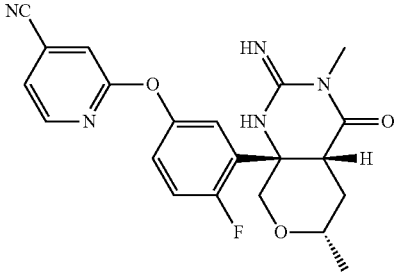 [SMILES: C[C@H]1C[C@H]2C(=O)N(C)C(=N)N[C@@]2(c2cc(Oc3cc(C#N)ccn3)ccc2F)CO1] | 21 |

-continued
| Entry | Core | Reagent | Product | Example # |
|---|---|---|---|---|
| 16 | |  | 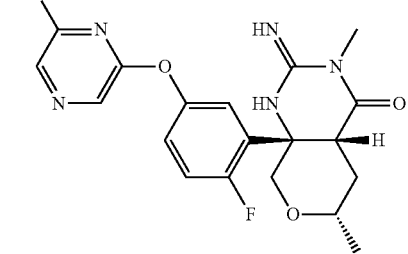 | 65 |
| 17 | | 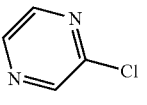 | 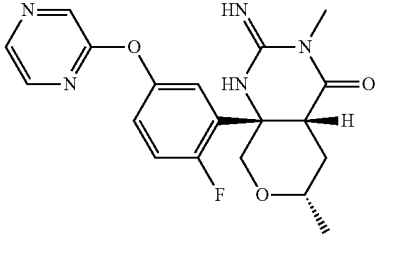 [SMILES: C[C@H]1C[C@H]2C(=O)N(C)C(=N)N[C@@]2(c2cc(Oc3cnccn3)ccc2F)CO1] | 66 |
| 18 | |  | 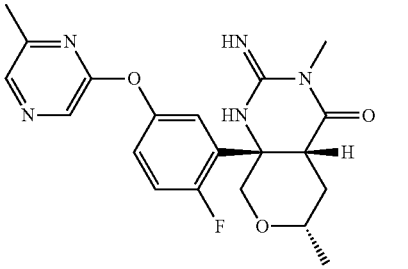 [SMILES: Cc1cncc(Oc2ccc(F)c([C@]34CO[C@@H](C)C[C@H]3C(=O)N(C)C(=N)N4)c2)n1] | 67 |
| 19 | | 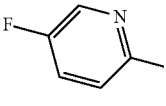 | 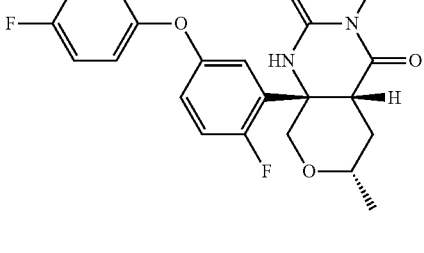 | 68 |
| 20 | | 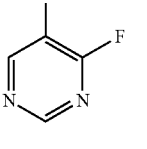 | 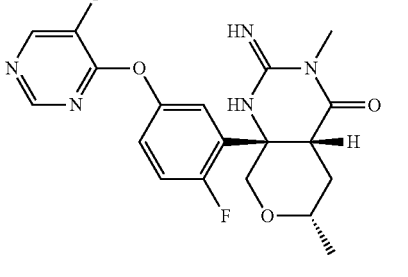 | 69 |

-continued

| Entry | Core | Reagent | Product | Example # |
|---|---|---|---|---|
| 21 | | | | 70 |
| 22 | | | | 79 |
| 23 | | | | 80 |
| 24 | H2 | | | 22 |
| 25 | E4 | | | 30 |

-continued
| Entry | Core | Reagent | Product | Example # |
|---|---|---|---|---|
| 26 | | 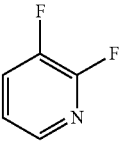 | 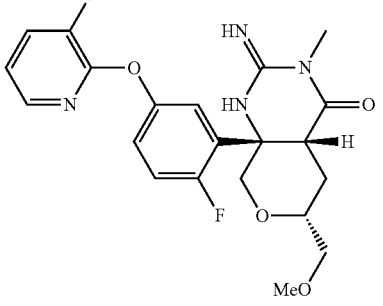 | 31 |
| 27 | 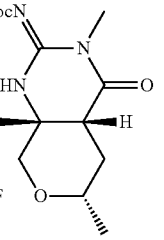<br>F6 | 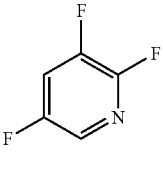 | 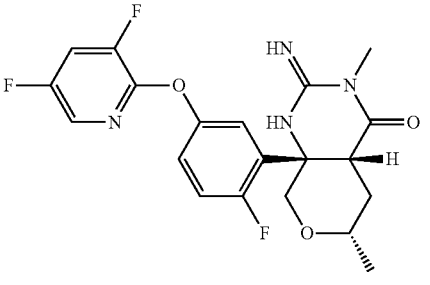 [SMILES: C[C@H]1C[C@H]2C(=O)N(C)C(=N)N[C@@]2(c2cc(Oc3ncc(F)cc3F)ccc2F)CO1] | 36 |
| 28 | 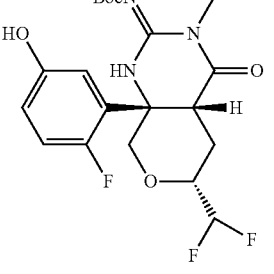 |  | 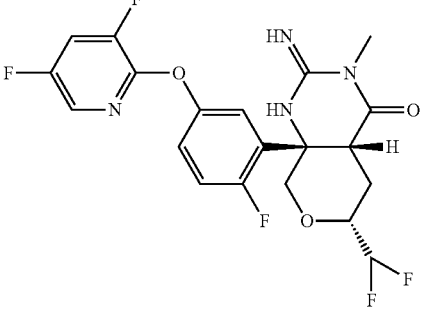 | 61 |
| 29 | 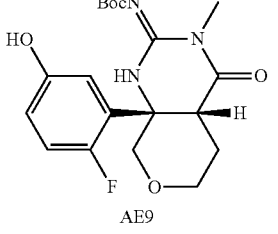<br>AE9 | 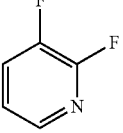 | 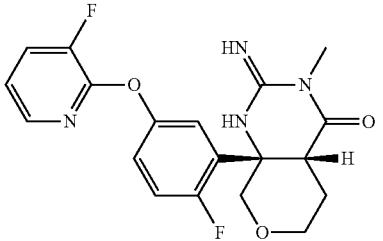 [SMILES: CN1C(=N)N[C@@]2(c3cc(Oc4ncccc4F)ccc3F)COCC[C@H]2C1=O] | 87 |
| 30 | 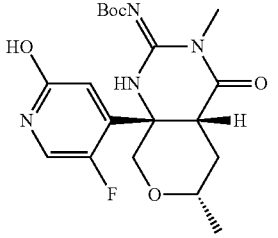<br>AH2 | 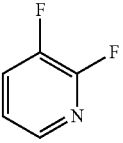 | 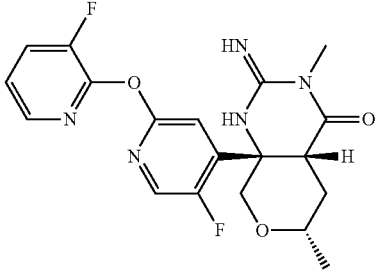 [SMILES: C[C@H]1C[C@H]2C(=O)N(C)C(=N)N[C@@]2(c2cc(Oc3ncccc3F)ncc2F)CO1] | 96 |

Method N

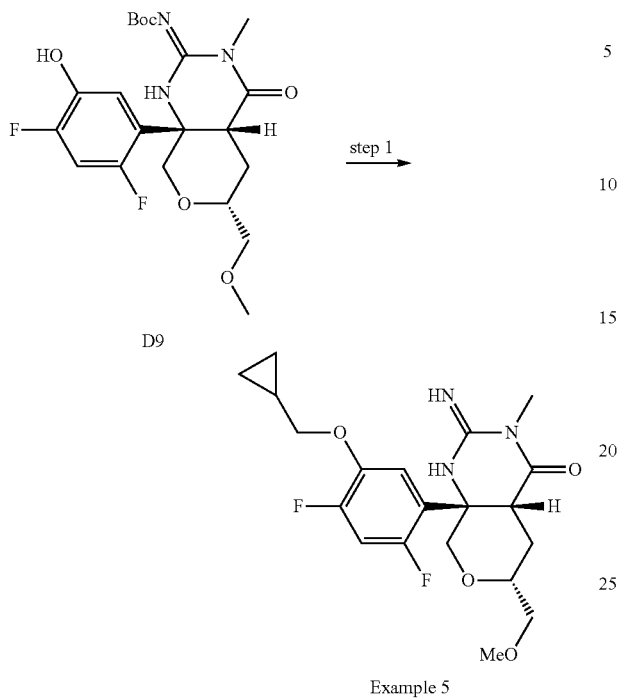

D9

Example 5

Step 1

To a solution of D9 (20 mg, 0.044 mmol) in DMSO (2 mL) were added K$_2$CO$_3$ (6.07 mg, 0.044 mmol) and (bromomethyl)cyclopropane (7.71 mg, 0.057 mmol). The mixture was stirred at 50° C. for 2 h and cooled to rt. It was partitioned between ethyl acetate and H$_2$O; the organic phase was dried over Na$_2$SO$_4$, filtered and concentrated in vacuo. The residue was dissolved in 1 mL DCM and treated with 1 mL of TFA. The mixture was stirred at rt for 4 h and concentrated in vacuo. The residue was purified by preparative TLC eluting with 3% of 7N NH$_3$ in MeOH/DCM to afford example 5.

Using the appropriate core and reagent, the following Examples were prepared using the conditions described in Method N.

| Entry | Core | Reagent | Product | Example # |
|---|---|---|---|---|
| 1 | F6 | cyclopropylmethyl bromide | | 23 |
| 2 | H2 | cyclopropylmethyl bromide | | 24 |

-continued

| Entry | Core | Reagent | Product | Example # |
|---|---|---|---|---|
| 3 | E4 | cyclopropylmethyl bromide | | 32 |
| 4 | H2 | F₃C-CH₂-OTf | | 55 |
| 5 | AD18 | cyclopropylmethyl bromide | | 85 |
| 6 | AE9 | cyclopropylmethyl bromide | | 88 |

| Entry | Core | Reagent | Product | Example # |
|---|---|---|---|---|
| 7 | AF8 | 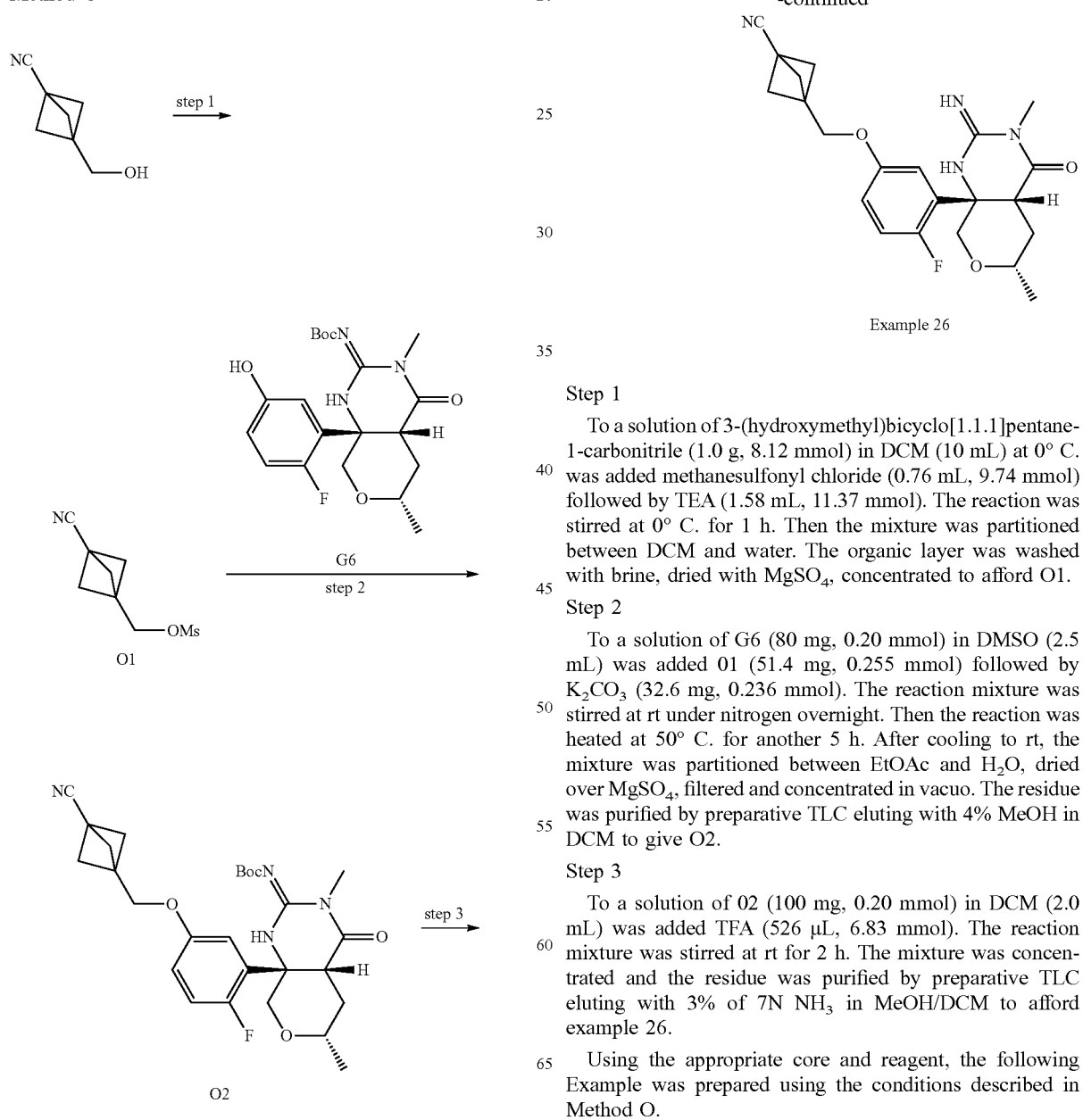 | | 90 |

Method O

Step 1

To a solution of 3-(hydroxymethyl)bicyclo[1.1.1]pentane-1-carbonitrile (1.0 g, 8.12 mmol) in DCM (10 mL) at 0° C. was added methanesulfonyl chloride (0.76 mL, 9.74 mmol) followed by TEA (1.58 mL, 11.37 mmol). The reaction was stirred at 0° C. for 1 h. Then the mixture was partitioned between DCM and water. The organic layer was washed with brine, dried with MgSO$_4$, concentrated to afford O1.

Step 2

To a solution of G6 (80 mg, 0.20 mmol) in DMSO (2.5 mL) was added O1 (51.4 mg, 0.255 mmol) followed by K$_2$CO$_3$ (32.6 mg, 0.236 mmol). The reaction mixture was stirred at rt under nitrogen overnight. Then the reaction was heated at 50° C. for another 5 h. After cooling to rt, the mixture was partitioned between EtOAc and H$_2$O, dried over MgSO$_4$, filtered and concentrated in vacuo. The residue was purified by preparative TLC eluting with 4% MeOH in DCM to give O2.

Step 3

To a solution of O2 (100 mg, 0.20 mmol) in DCM (2.0 mL) was added TFA (526 μL, 6.83 mmol). The reaction mixture was stirred at rt for 2 h. The mixture was concentrated and the residue was purified by preparative TLC eluting with 3% of 7N NH$_3$ in MeOH/DCM to afford example 26.

Using the appropriate core and reagent, the following Example was prepared using the conditions described in Method O.

| Entry | Core | Reagent | Product | Example # |
|---|---|---|---|---|
| 1 | H2 | O1 | | 37 |

Method P

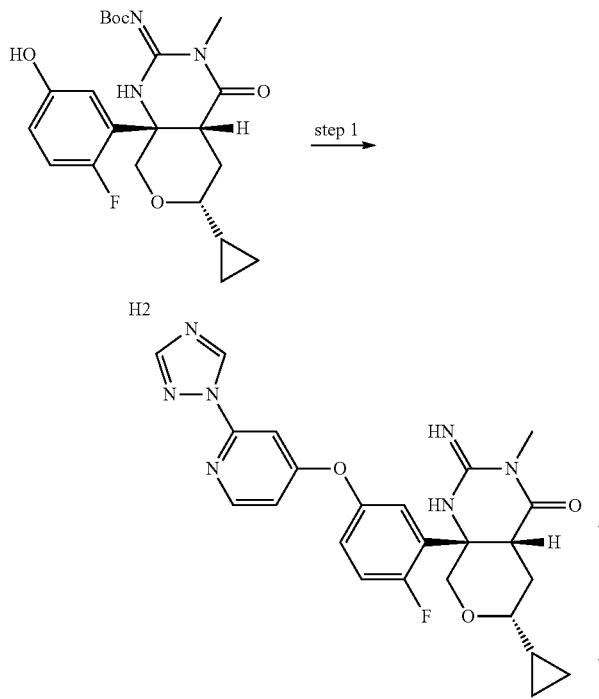

Example 16

Step 1

To a solution of H2 (110 mg, 0.254 mmol) in DMA (2 mL) were added 4-bromo-2-(1H-1,2,4-triazol-1-yl)pyridine (143 mg, 0.63 mmol), 2-picolinic acid (15.62 mg, 0.13 mmol), CuI (24.16 mg, 0.13 mmol) and $Cs_2CO_3$ (331 mg, 1.02 mmol). The mixture was stirred at 80° C. overnight. The reaction mixture was cooled to rt and partitioned between ethyl acetate and $H_2O$. The organic phase was dried over $Na_2SO_4$, filtered and concentrated in vacuo. The residue was dissolved in 1 mL DCM and treated with 1 mL of TFA. The mixture was stirred at rt for 2 h and concentrated in vacuo. The residue was purified by preparative TLC eluting with 3% 7N $NH_3$ in MeOH/DCM to afford example 16.

Using the appropriate core and reagent, the following Examples were prepared using the conditions described in Method P.

| Entry | Core | Reagent | Product | Example # |
|---|---|---|---|---|
| 1 | H2 | | | 17 |

-continued

| Entry | Core | Reagent | Product | Example # |
|---|---|---|---|---|
| 2 | | 5-bromo-2-(difluoromethyl)pyridine | (product structure) | 20 |
| 3 | | 3-iodobenzonitrile | (product structure) | 25 |
| 4 | | 5-bromonicotinonitrile | (product structure) | 27 |
| 5 | | 2-chloro-6-(difluoromethyl)pyrazine | (product structure) | 29 |

-continued
| Entry | Core | Reagent | Product | Example # |
|---|---|---|---|---|
| 6 | | 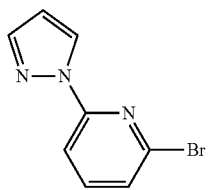 [SMILES: Brc1cccc(-n2cccn2)n1] | 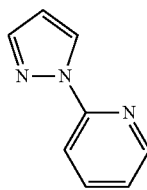 | 34 |
| 7 | | 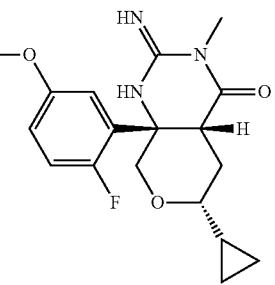 | 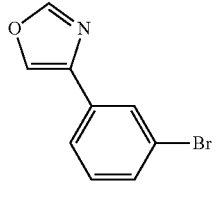 | 35 |
| 8 | | 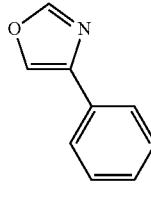 | 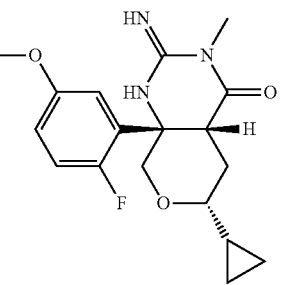 | 56 |

Method Q

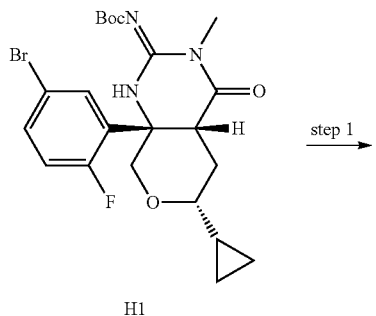

H1

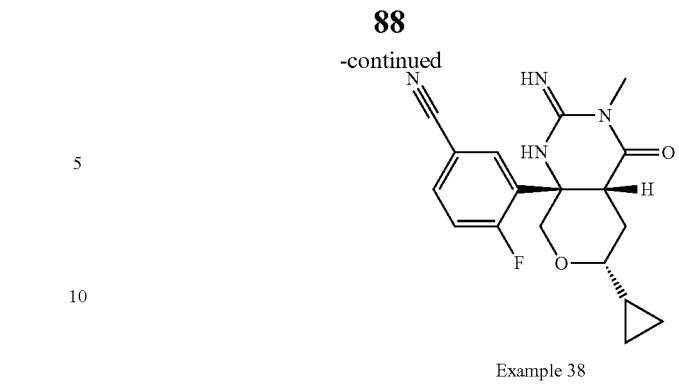

Example 38

Step 1

A microwave tube was charged with H1 (500 mg, 1.007 mmol), zinc cyanide (177 mg, 1.51 mmol), Xantphos (87 mg, 0.15 mmol), $Pd_2(dba)_3$ (92 mg, 0.101 mmol) and DMF (4 mL). The reaction was heated at 100° C. for 1 h and then cooled to rt. The resulted mixture was partitioned between ethyl acetate and $H_2O$. The organic phase was dried over $Na_2SO_4$, filtered and concentrated in vacuo. The residue was purified by column chromatography on silica gel, eluting with 0-5% MeOH/DCM to afford example 38.

Method S

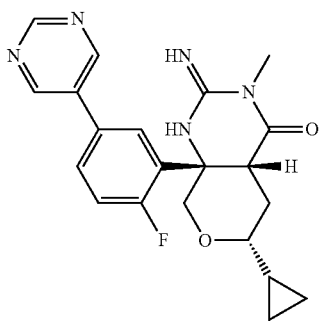

Example 28

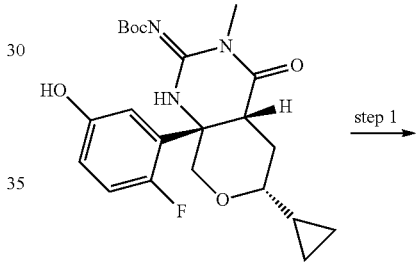

H2

Step 1

To a solution of H1 (50 mg, 0.10 mmol) in 1,4-dioxane (2 mL) and water (100 μL), was added pyrimidin-5-ylboronic acid (24.96 mg, 0.20 mmol), [1,1'-bis(di-tert-butylphosphino) ferrocene]dichloropalladium(II) (6.57 mg, 10.07 μmol) and $Cs_2CO_3$ (98 mg, 0.30 mmol). The mixture was heated to 90° C. and stirred overnight. Then the reaction was cooled to rt and partitioned between ethyl acetate and $H_2O$. The organic phase was dried over $Na_2SO_4$, filtered and concentrated in vacuo. The residue was purified by preparative TLC eluting with 3% 7N $NH_3$ in MeOH/DCM to afford example 28.

Method R

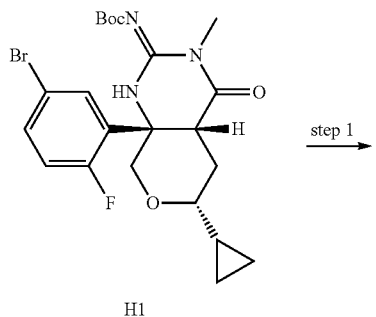

H1

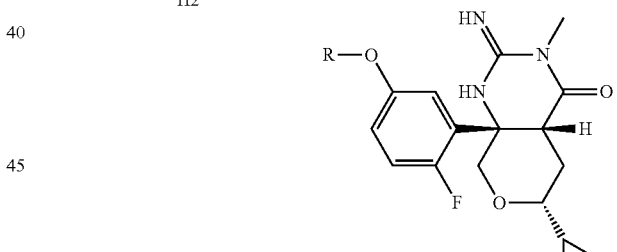

Examples 39-40

Parallel preparation of Examples 39-40: To a set of vials containing the requisite aryl bromide (0.12 mmol) was added bis[(tetrabutylammonium iodide)copper(I) iodide] (3.9 mg, 0.0034 mmol), 1,10 phenanthroline (2.5 mg, 0.014 mmol) followed by $Cs_2CO_3$ (68 mg, 0.21 mmol). The vials were capped and transferred into a glove box under an atmosphere of nitrogen. To each vial was added a solution of H2 (30 mg, 0.069 mmol) in dioxane (1.0 mL). The vials were capped and the mixtures were heated at 100° C. with stirring overnight. After that time, the mixtures were allowed to cool to RT. To each vial was added water (2 mL) and DCM (2 mL). The mixtures were transferred to a set of fritted barrel filters. The organic layer from each mixture was drained into a clean vial. Additional DCM (1 mL) was added to each aqueous layer and the organic layer was again drained and combined with the previous organic extract. The solvent from the combined organic layers was removed in vacuo. The crude residues were dissolved in DMSO (1 mL) and filtered. The crude products were purified by mass triggered reverse phase HPLC using the following conditions: [column: Waters XBridge C18, 5 μm, 19×100 mm; solvent gradient: 19-21% initial to 49-51% final MeCN (0.1% NH₄OH) in water (0.1% NH₄OH) 25 mL/min; 8 min run time] to afford Examples 39-40.

| Entry | Core | Reagent | Product | Example # |
|---|---|---|---|---|
| 1 | H2 | | | 39 |
| 2 | | (HCl) | | 40 |

Method T

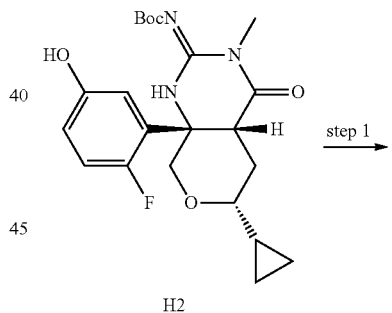

H2

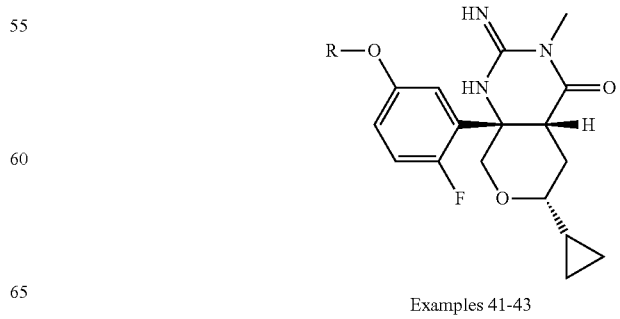

Examples 41-43

Parallel preparation of Examples 41-43: To a set of vials containing the requisite aryl chloride (0.12 mmol) was added a solution of H2 (30 mg, 0.069 mmol) in DMF (0.5 mL) followed by Cs$_2$CO$_3$ (68 mg, 0.21 mmol). The vials were capped and the mixtures were heated at 120° C. with stirring for 5 hours. After that time, the mixtures were allowed to cool to RT. To each vial was added water (2 mL) and DCM (2 mL). The mixtures were transferred to a set of fritted barrel filters. The organic layer from each mixture was drained into a clean vial. Additional DCM (1 mL) was added to each aqueous layer and the organic layer was again drained and combined with the previous organic extract. The solvent from the combined organic layers was removed in vacuo. The crude residues were dissolved in DMSO (1 mL) and filtered. The crude products were purified by mass triggered reverse phase HPLC using the following conditions: [column: Waters XBridge C18 5 µm, 19×100 mm; solvent gradient range: 15-18% initial to 45-53% final MeCN (0.1% NH$_4$OH) in water (0.1% NH$_4$OH) 25 mL/min; 8 min run time] to afford Examples 41-43.

Method U

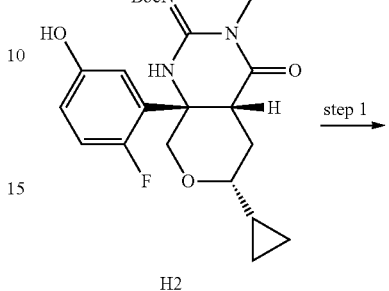

H2

| Entry | Core | Reagent | Product | Example # |
|-------|------|---------|---------|-----------|
| 1 | H2 | | | 41 |
| 2 | | | | 42 |
| 3 | | | | 43 |

-continued

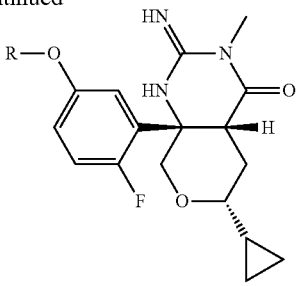

Examples 44-46

Parallel preparation of Examples 44-46: To a set of vials containing the requisite alkyl bromide (0.12 mmol) was added a solution of H2 (30 mg, 0.069 mmol) in DMF (0.5 mL) followed by Cs$_2$CO$_3$ (68 mg, 0.21 mmol). The vials were capped and the mixtures were stirred at RT overnight. To each vial was added water (2 mL). The mixtures were extracted with DCM (2×2 mL). The combined organic layers from each extraction was removed in vacuo. To each residue was added DCM (1 mL) and TFA (0.5 mL). The mixtures were shaken at RT for 2 hours. After that time, the mixtures were concentrated in vacuo. The crude residues were dissolved in DMSO (1 mL) and filtered. The crude products were purified by mass triggered reverse phase HPLC using the following conditions: [Waters Sunfire C18 column, 5 μm, 30×100 mm, gradient range of 12-20% initial to a range of 42-50% final MeCN (0.1% TFA) in water (0.1% TFA) 25 mL/min, 9-12 min run time] to afford Examples 44-46.

| Entry | Core | Reagent | Product | Example # |
|---|---|---|---|---|
| 1 | H2 | | | 44 |
| 2 | | | | 45 |
| 3 | | | | 46 |

Method V

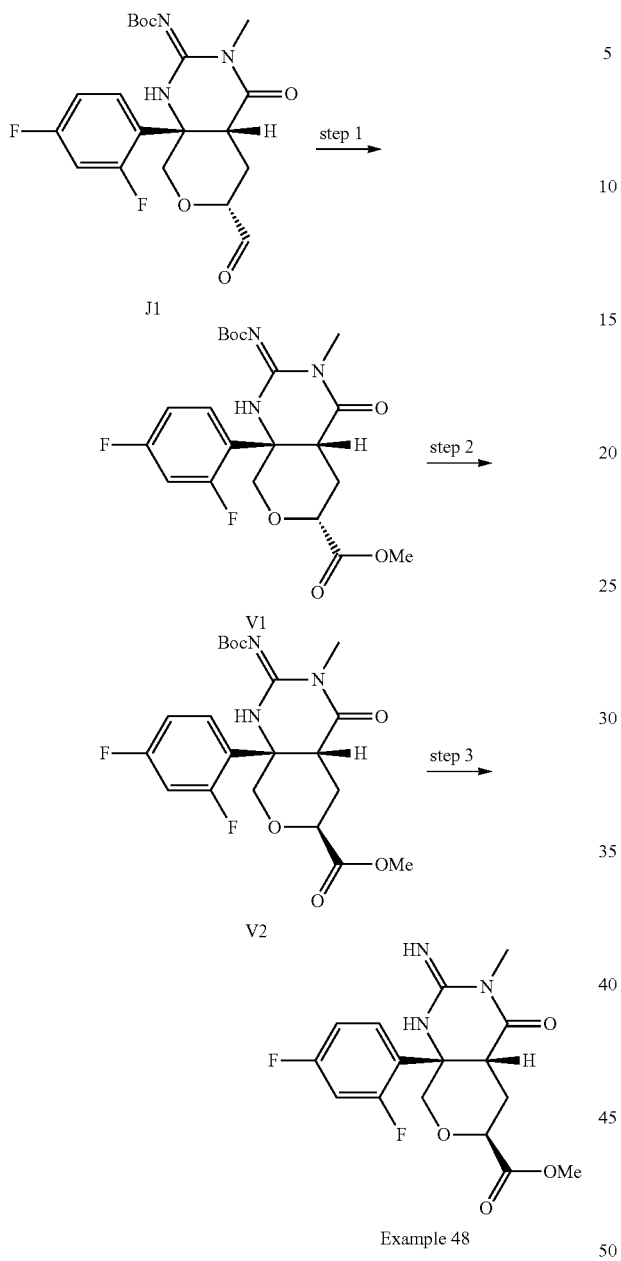

Step 1

To a solution of J1 (700 mg, 1.65 mmol) in acetonitrile (5 mL), was added 4-methylmorpholine N-oxide monohydrate (22 mg, 0.16 mmol) and tetrapropylammonium perruthenate (2324 mg, 6.61 mmol). The mixture was stirred at rt for 2 h. The reaction was quenched by adding 1 mL isopropanol and then stirred at rt for 1 h. The resulted mixture was partitioned between diethyl ether (40 mL) and aqueous 1N HCl (15 mL). The organic phase was washed with brine, dried over Na$_2$SO$_4$, filtered and concentrated in vacuo. The residue was dissolved in CH$_2$Cl$_2$ (5 mL), followed by the addition of trimethylsilyldiazomethane (1.24 mL, 2.48 mmol). The mixture was stirred at rt for 2 h and then concentrated in vacuo. The residue was purified by column chromatography on silica gel, eluting with 0-20% ethyl acetate/hexane to afford V1.

Step 2

To a solution of V1 (250 mg, 0.55 mmol) in THF (2 mL) at −78° C., was added LiHDMS (2.76 mL, 2.76 mmol, 1.0 M in THF). The reaction was stirred at −78° C. for 1 h and warmed to 0° C. The reaction was quenched by the addition of 5 mL saturated NH$_4$Cl. The mixture was partitioned between ethyl acetate and H$_2$O. The organic phase was dried over Na$_2$SO$_4$, filtered and concentrated in vacuo. The residue was purified by preparative TLC, eluting with 25% ethyl acetate/hexane, to afford V2.

Step 3

To a solution of V2 (4 mg, 8.82 μmol) in CH$_2$Cl$_2$ (500 μL) was added TFA (500 μL, 6.49 mmol). The mixture was stirred at rt for 2 h and then concentrated in vacuo. The residue was purified by preparative TLC, eluting with 4% of 7N NH$_3$ in MeOH/DCM to afford example 48.

Method W

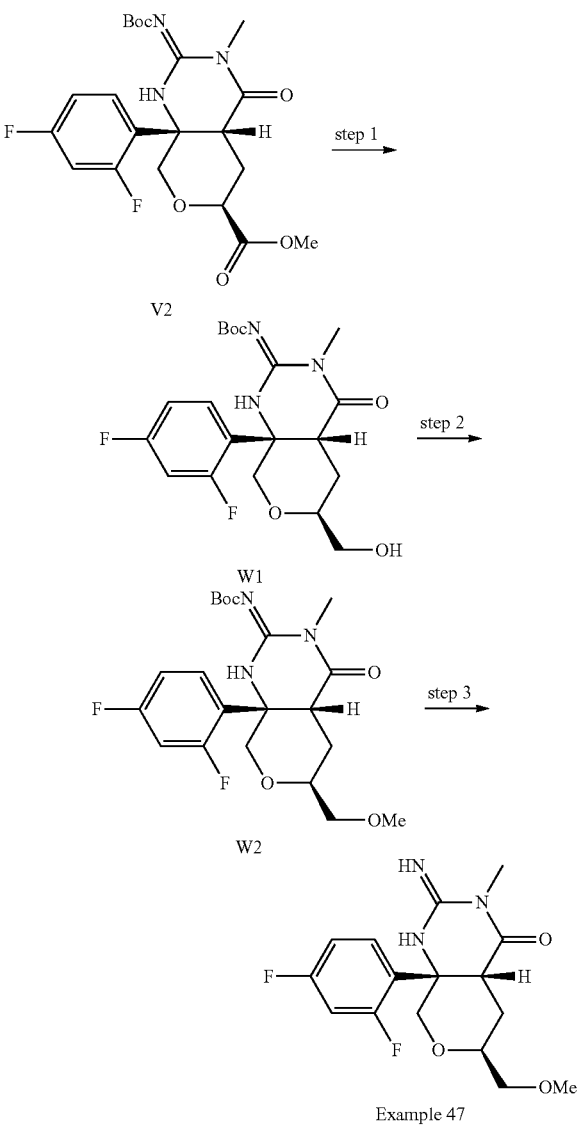

Step 1

To a solution of V2 (50 mg, 0.11 mmol) in THF (1.5 mL) at −10° C., was added LiBH$_4$ (12 mg, 0.55 mmol). The mixture was gradually warmed to 0° C. and stirred at 0° C.

for 1 h. The reaction was partitioned between ethyl acetate and H₂O. The organic phase was dried over Na₂SO₄, filtered and concentrated in vacuo. The residue was purified by preparative TLC, eluting with 50% ethyl acetate/hexane, to afford W1.

Step 2

To a solution of W1 (24 mg, 0.056 mmol) in THF (1 mL), was added NaH (5.64 mg, 0.14 mmol), followed by addition of MeI (4.23 µl, 0.068 mmol). The mixture was stirred at rt overnight and concentrated in vacuo. The residue was purified by preparative TLC, eluting with 30% ethyl acetate/hexane, to afford W2.

Step 3

To a solution of W2 (10 mg, 0.023 mmol) in CH₂Cl₂ (300 µL), was added TFA (500 µl, 6.49 mmol). The mixture was stirred at rt for 2 h and concentrated in vacuo. The residue was purified by preparative TLC, eluting with 4% of 7N NH₃ in MeOH/DCM, to afford example 47.

Method X

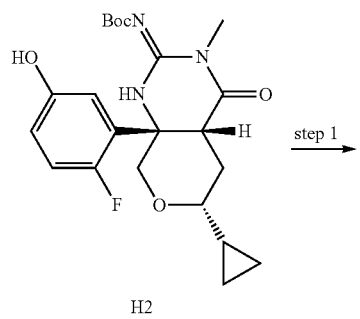

H2

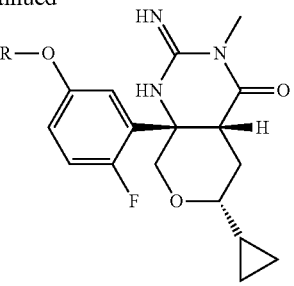

Examples 49-54

Parallel preparation of Examples 49-54: To a set of vials containing the requisite alcohols (0.087 mmol) was added a solution of H2 (25 mg, 0.058 mmol) in THF (0.5 mL) followed by a solution of 2-(tributylphosphoranylidene) acetonitrile (1 M in toluene, 0.17 mL, 0.17 mmol). The vials were capped and the mixtures were stirred at 50° C. overnight. After that time, the mixtures were concentrated in vacuo. To each residue was then added DCM (1 mL) and TFA (0.5 mL). The mixtures were shaken at RT for 1.5 hours. After that time, the mixtures were concentrated in vacuo. The crude residues were dissolved in DMSO (1 mL) and filtered. The crude products for entry 1 was purified by mass triggered reverse phase HPLC using the following conditions: [Waters Sunfire C18 column, 5 µm, 30×100 mm, gradient range of 15% initial to 50% final MeCN (0.1% formic acid) in water (0.1% formic acid) 25 mL/min, 8 min run time] to afford Example 49. The crude products from entries 2-6 were purified by mass triggered reverse phase HPLC using the following conditions: [column: Waters XBridge C18 5 µm, 19×100 mm; solvent gradient range: 23-39% initial to 54-69% final MeCN (0.1% NH₄OH) in water (0.1% NH₄OH) 25 mL/min; 8 min run time] to afford Examples 50-54.

| Entry | Core | Reagent | Product | Example # |
|---|---|---|---|---|
| 1 | H2 | ⌒⌒OH | | 49 |
| 2 | | MeO⌒⌒OH | | 50 |

| Entry | Core | Reagent | Product | Example # |
|---|---|---|---|---|
| 3 | | 3,3-difluorocyclobutyl-CH2OH | (structure) | 51 |
| 4 | | 2,2-difluorocyclopropyl-CH2OH | (structure) | 52 |
| 5 | | 3-methoxycyclobutyl-CH2OH | (structure) | 53 |
| 6 | | bicyclo[1.1.1]pentyl-CH2OH | (structure) | 54 |

Method Y

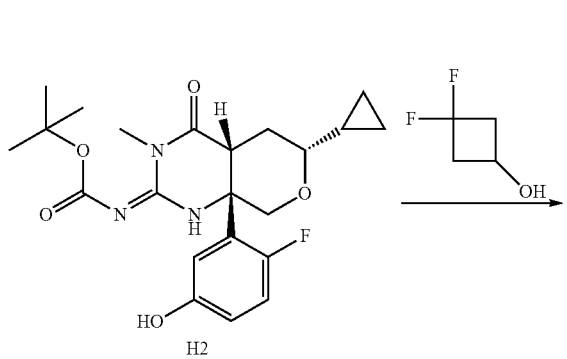

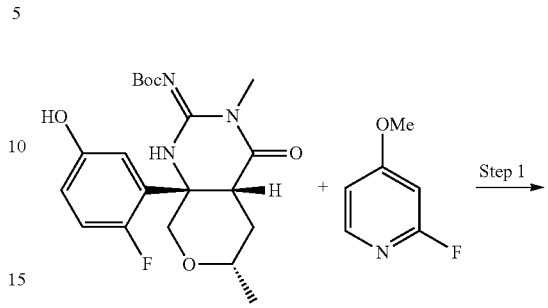

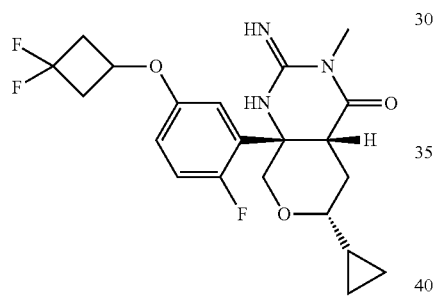

Example 57

Method Z

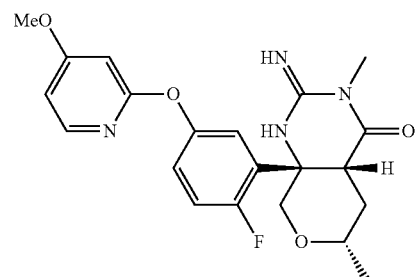

Example 71

To a solution of 3,3-difluorocyclobutanol (74.8 mg, 0.69 mmol) in CH$_2$Cl$_2$ (2 mL) in a microwave tube at −78° C. were added Et$_3$N (0.096 ml, 0.69 mmol) and trifluoromethanesulfonic anhydride (0.692 ml, 0.692 mmol). The mixture was stirred at −78° C. for 30 min, then warmed to RT and stirred for 1 h. (Z)-tert-butyl ((4aR,6R,8aS)-6-cyclopropyl-8a-(2-fluoro-5-hydroxyphenyl)-3-methyl-4-oxohexahydro-1H-pyrano[3,4-d]pyrimidin-2(3H)-ylidene)carbamate H2 (100 mg, 0.231 mmol) and DBU (0.070 ml, 0.461 mmol) were added. It was stirred at 50° C. overnight and cooled to RT. After addition of 2 mL of TFA, the mixture was stirred at RT for 3 h and concentrated in vacuo. The residue was purified by preparative TLC, eluting with 4% 7N NH$_3$ in MeOH/DCM, to give (4aR,6R,8aS)-6-cyclopropyl-8a-(5-(3,3-difluorocyclobutoxy)-2-fluorophenyl)-2-imino-3-methyl-hexahydro-1H-pyrano[3,4-d]pyrimidin-4(4aH)-one example 57.

Step 1

To a solution of F6 (40.0 mg, 0.098 mmol) and 2-fluoro-4-methoxypyridine (25.0 mg, 0.197 mmol) in DMSO (2 mL) was added Cs$_2$CO$_3$ (96.0 mg, 0.295 mmol). The mixture was stirred at 110° C. for 1 h under microwave condition, and then quenched with water, extracted with EtOAc (25 mL×4). The combined extracts were washed with brine, dried over Na$_2$SO$_4$ and concentrated in vacuo. The residue was further purified by p-HPLC (TFA) to give Example 71.

Using the appropriate precursor, the following Examples were prepared using the conditions described in the above method.

| Entry | Core | Reagent | Product | Example # |
|---|---|---|---|---|
| 1 | F6 | 4-methoxy-2-fluoropyridine | | 71 |
| 2 | | 3-chloro-2-fluoropyridine | | 72 |
| 3 | | 3-methyl-2-fluoropyridine | | 73 |
| 4 | | 3,4-difluoropyridine | | 74 |
| 5 | | 3-chloro-4-fluoropyridine | | 75 |

| Entry | Core | Reagent | Product | Example # |
|---|---|---|---|---|
| 6 | | 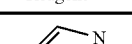 |  | 76 |

Method AA

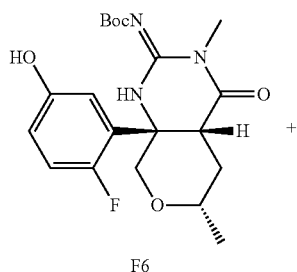

F6

+

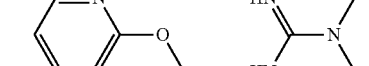

Step 1

A mixture of F6 (20.0 mg, 0.049 mmol), CuI (3.7 mg, 0.019 mmol), 3-chloroisoquinoline (16.1 mg, 0.098 mmol), N,N-dimethylglycine (4.1 mg, 0.039 mmol) and $Cs_2CO_3$ (35.2 mg, 0.108 mmol) in dioxane (3 mL) was stirred at 100° C. for 14 h. The reaction mixture was quenched with water and extracted with EtOAc (15 mL×4). The combined extracts were washed with brine (10 mL), dried over $Na_2SO_4$, filtered and the filtrate was concentrated in vacuo. The residue was purified by p-HPLC (TFA condition) to give Example 77.

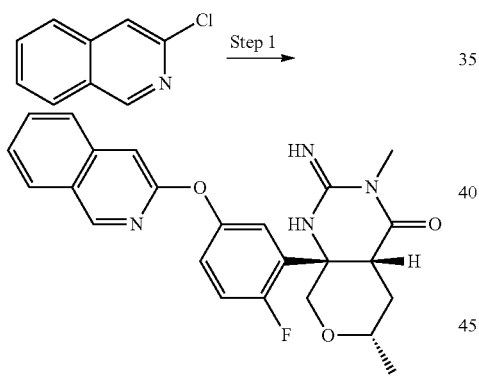

Example 77

| Entry | Core | Reagent | Product | Example # |
|---|---|---|---|---|
| 1 | 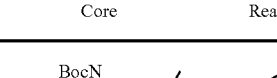<br>F6 | 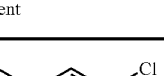 | 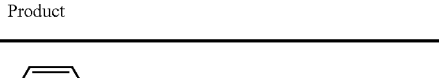 | 77 |

| Entry | Core | Reagent | Product | Example # |
|---|---|---|---|---|
| 2 | | F, Cl pyridine | Example 78 structure | 78 |

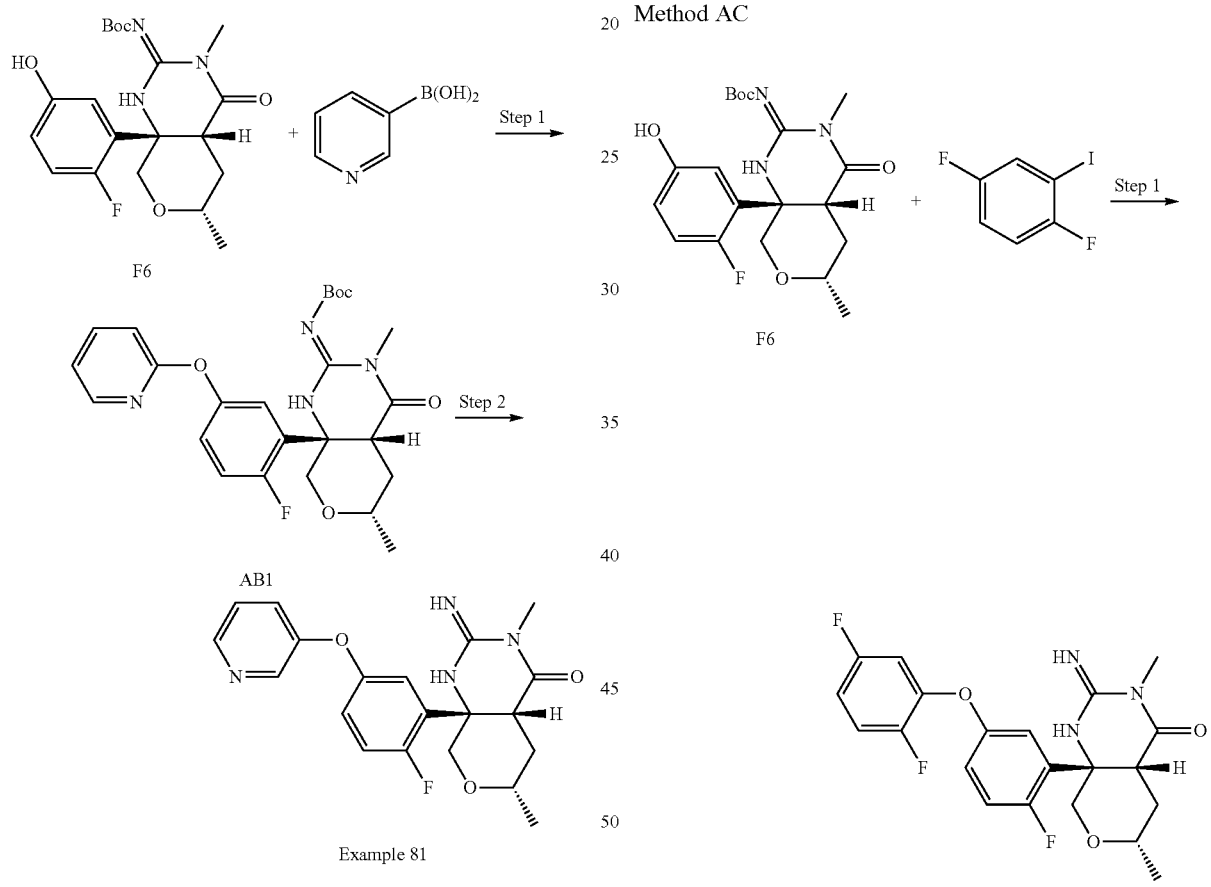

Method AB

Step 1
A flask was charged with F6 (40.0 mg, 0.098 mmol), copper(II) acetate (35.7 mg, 0.196 mmol), pyridin-3-ylboronic acid (36.2 mg, 0.295 mmol) and molecular sieves (300 mg). The mixture was diluted with DCM (5 mL), followed by the addition of Et$_3$N (0.068 mL, 0.491 mmol). The reaction mixture was stirred at 17° C. for 20 h under O$_2$ balloon (15 psi). The reaction mixture was stirred at 30° C. for another 72 h. and filtered. The filtrate was concentrated. The residue was purified by p-TLC (PE:EtOAc=1.5:1) to give AB1.

Step 2
To a solution of AB1 (5.0 mg, 10.32 μmol) in DCM (1 mL) was added TFA (0.3 mL, 3.89 mmol). The mixture was stirred at 17° C. for 1.5 h, concentrated in vacuo. The residue was purified by p-HPLC (TFA) to give Example 81.

Method AC

Step 1
A flask was charged with F6 (40.0 mg, 0.098 mmol), copper(I) chloride (9.7 mg, 0.098 mmol), 1,4-difluoro-2-iodobenzene (47.1 mg, 0.196 mmol), 2,2,6,6-tetramethyl-3,5-heptanedione (18.1 mg, 0.098 mmol) and Cs$_2$CO$_3$ (70.4 mg, 0.216 mmol). The mixture was diluted with NMP (3 mL) and stirred at 90° C. for 16 h, quenched with water and extracted with EtOAc (15 mL×4). The combined extracts were washed with brine, dried over Na$_2$SO$_4$ and concentrated in vacuo. The residue was purified by p-HPLC (TFA) to give Example 82.

Method AD
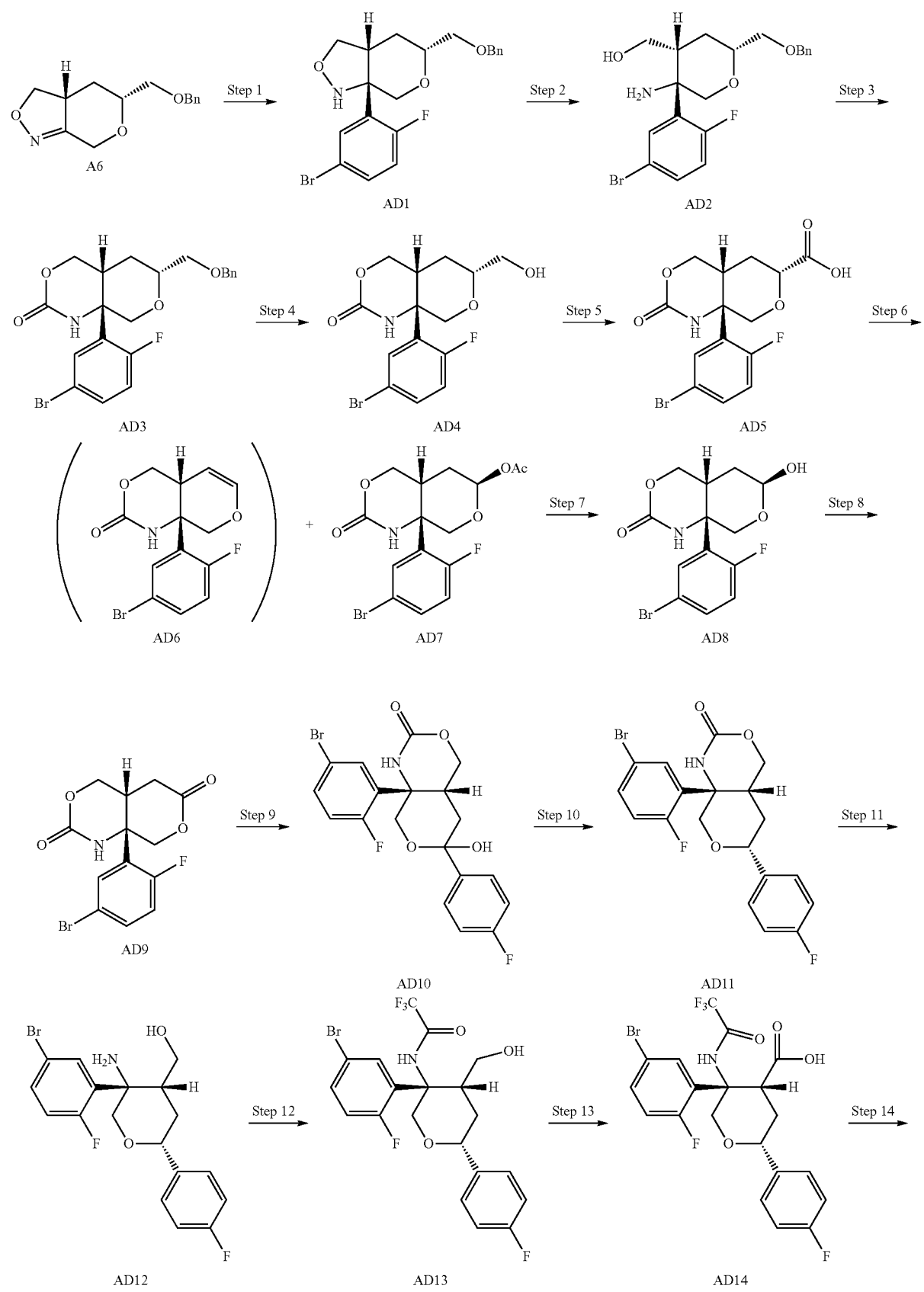

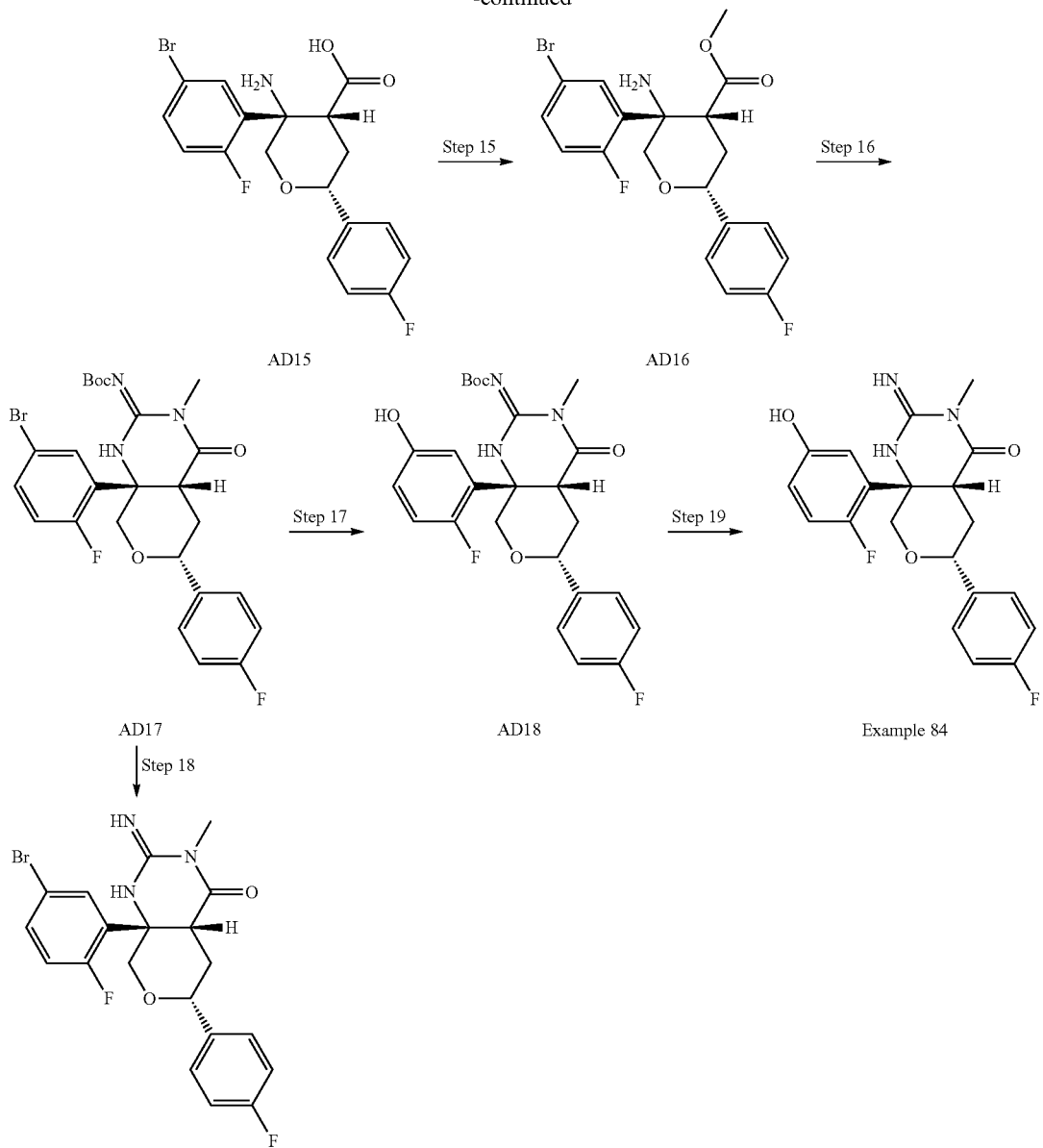

Step 1

To a solution of A6 (26 g, 105 mmol) in toluene (400 mL) at −78° C. under N$_2$ was added boron trifluoride diethyl etherate (30 mL, 105 mmol). The mixture was stirred at −78° C. for 30 min., then 4-bromo-1-fluoro-2-iodobenzene (34.8 g, 116 mmol) was added followed by the slow addition of n-butyllithium (46.3 mL, 116 mmol, 2.5 M in hexane). The mixture was stirred at −78° C. for 3 h, and quenched with saturated NH$_4$Cl, extracted with EtOAc (3×150 mL). The combined extracts were washed with brine, dried over Na$_2$SO$_4$ and concentrated in vacuo. The residue was purified by silica gel chromatography (PE:EtOAc=20:1 to 5:1) to give AD1.

Step 2

To a solution of AD1 (51 g, 121 mmol) in AcOH (600 mL) was added zinc (79 g, 1208 mmol) at 25° C. The mixture was stirred at 25° C. for 13 h, filtered. The filtrate was neutralized with saturated NaHCO$_3$, and then extracted with EtOAc (3×200 mL). The combined extracts were washed with brine, dried over Na$_2$SO$_4$ and concentrated in vacuo. The residue was purified by silica gel chromatography (PE: EtOAc=10:1 to 3:1) to give AD2.

Step 3

To a solution of AD2 and TEA (0.985 ml, 7.07 mmol) in THF (15 mL) at 0° C. was added a solution of triphosgene (1.539 g, 5.18 mmol) in THF (5 mL). The resulting mixture was stirred at 0° C. for 2 h, then at 25° C. for 1 h. The mixture was poured into ice-water and neutralized with saturated aqueous NaHCO$_3$, then extracted with EtOAc (30 mL×3). The combined extracts were washed with brine, dried over Na$_2$SO$_4$ and concentrated in vacuo to give AD3.

Step 4

To a solution of AD3 (1 g, 2.221 mmol) in CH$_2$Cl$_2$ (10 mL) was added boron trichloride (11.1 mL, 11.1 mmol, 1M in CH$_2$Cl$_2$) at −10° C. under N$_2$. The mixture was stirred at −10° C. for 3 h, and then poured into ice-water. The solution was neutralized with saturated NaHCO$_3$, and then extracted with DCM (20 mL×3). The combined extracts were washed with brine, dried over Na$_2$SO$_4$ and concentrated in vacuo to give AD4.

Step 5

To a solution of AD4 (650 mg, 1.805 mmol) in acetonitrile (6 mL) was added 4-methylmorpholine N-oxide monohydrate (976 mg, 7.22 mmol), then added TPAP (50.7 mg, 0.144 mmol). The mixture was stirred at 25° C. for 4 h, quenched with 2-propanol (2 mL) and stirred for 1 h. The mixture was concentrated, diluted with EtOAc (10 mL) and filtered through celite. The filtrate partitioned between 1N HCl (10 mL) and EtOAc (20 mL). The organic layer was separated and washed with brine (20 mL), dried over Na$_2$SO$_4$ and concentrated in vacuo. The residue was purified by p-HPLC (TFA) to give AD5.

Step 6

To a solution of AD6 (25 g, 66.8 mmol) in pyridine (300 mL) was added Pb(OAc)$_4$ (89 g, 200 mmol). The mixture was stirred at 55° C. for 2 h, quenched with ice and HCl (2 N, 300 mL). The mixture was extracted with EtOAc (200 mL×3). The combined extracts were washed with HCl (2 N, 100 mL×3), brine, dried over Na$_2$SO$_4$ and concentrated in vacuo. The residue was purified by silica gel chromatography (PE:EtOAc=1:1) to give AD6 and AD7.

Step 7

To a solution of AD7 (30 mg, 0.077 mmol) in MeOH (3 mL) was added K$_2$CO$_3$ (2.67 mg, 0.019 mmol) at 25° C. The mixture was stirred at 25° C. for 1 h, concentrated. The residue was neutralized with HCl (2 N, 10 mL), and extracted with EtOAc (15 mL×3). The combined extracts were washed with brine, dried over Na$_2$SO$_4$ and concentrated in vacuo to give AD8.

Step 8

To a solution of AD8 (2.1 g, 6.07 mmol) in CH$_2$Cl$_2$ (20 mL) was added 4-methylmorpholine N-oxide monohydrate (2.46 g, 18.2 mmol) and TPAP (0.107 g, 0.303 mmol). The mixture was stirred at 20° C. for 1 h, diluted with DCM and filtered. The filtrate was concentrated in vacuo at 20° C. The residue was purified by silica gel chromatography (PE:EtOAc=1:1) to give AD9.

Step 9

A suspension of magnesium (0.312 g, 12.86 mmol) and 1-bromo-4-fluorobenzene (1.5 g, 8.57 mmol) in THF (9 mL) was heated at 60° C. until most of magnesium chips disappeared.

To a solution of AD9 (206 mg, 0.599 mmol) in THF (2 mL) at −78° C. was added above prepared (4-fluorophenyl)magnesium bromide (4.66 mL, 4.19 mmol) slowly. The solution was stirred at −78° C. for 60 min., quenched by addition of saturated NH$_4$Cl at 0° C. and extracted with EtOAc (20 mL×3). The combined extracts were washed with brine, dried over Na$_2$SO$_4$ and concentrated in vacuo. The residue was purified by p-HPLC (TFA) to give AD10.

Step 10

To a solution of AD10 (15 mg, 0.034 mmol) in 1,2-dichloroethane (0.25 mL) at 0° C. was added triethylsilane (59.4 mg, 0.511 mmol) and TFA (0.25 mL, 3.24 mmol). The mixture was stirred at 15° C. for 5 min, concentrated and neutralized with saturated NaHCO$_3$. The mixture was extracted with EtOAc (10 mL×3). The combined extracts were washed with brine, dried over Na$_2$SO$_4$ and concentrated in vacuo. The residue was purified by p-TLC (PE:EA=2:1) to give AD11.

Step 11

To a solution of AD11 (33 mg, 0.078 mmol) in EtOH (1 mL) and water (3 mL) was added LiOH.H$_2$O (32.6 mg, 0.778 mmol). The reaction mixture was stirred at 100° C. for 2 days, and poured into ice water, extracted with EtOAc (15 mL×3). The combined extracts were washed with brine (5 mL), dried over Na$_2$SO$_4$ and concentrated in vacuo to give AD12.

Step 12

To a solution of AD12 (190 mg, 0.477 mmol) in DCM (3 mL) was added TEA (0.100 ml, 0.716 mmol) and TFAA (0.081 mL, 0.573 mmol) at 0° C. The reaction mixture was stirred at 15° C. for 3.5 h, quenched with H$_2$O and extracted with DCM (40 mL×3). The combined extracts were washed with brine, dried over Na$_2$SO$_4$ and concentrated in vacuo to give AD13.

Step 13

To a solution of AD13 (220 mg, 0.445 mmol) in acetonitrile (3 mL) was added NMO (209 mg, 1.780 mmol) and TPAP (12.51 mg, 0.036 mmol) at 0° C. The mixture was stirred at 20° C. for 2.5 h, quenched with 2-propanol (5 mL) and stirred for 1 h. The mixture was concentrated, diluted with EtOAc (20 mL) and filtered through celite. The filtrate was partitioned between 1N HCl (30 mL). The organic layer was separated and the aqueous phase was extracted with EtOAc (30 mL×3). The combined organic layers were washed with brine (50 mL), dried over Na$_2$SO$_4$ and concentrated to give AD14.

Step 14

To a solution of AD14 (300 mg, 0.707 mmol) in dioxane (2 mL) and water (6 mL) was added LiOH.H$_2$O (297 mg, 7.07 mmol). The reaction mixture was stirred at 150° C. for 16 h, poured into ice water (5 mL), added brine (5 mL) and extracted with EtOAc (35 mL×3). The combined extracts were washed with brine, dried over Na$_2$SO$_4$ and concentrated in vacuo to give AD15.

Step 15

To a solution of AD15 (810 mg, 1.965 mmol) in MeOH (8 mL) was added SOCl$_2$ (1.434 mL, 19.65 mmol) dropwise. After addition, the mixture was stirred at reflux for 4 h. The mixture was concentrated in vacuo. The residue was partitioned between saturated NaHCO$_3$ (40 mL) and ethyl acetate (20 mL). The organic layer was separated and the aqueous phase was extracted with EtOAc (20 mL×3). The combined organic layers were washed with brine, dried over Na$_2$SO$_4$ and concentrated in vacuo. The residue was purified by silica gel chromatography (EtOAc/PE=85%) to give AD16.

Step 16

A mixture of N-Boc-N'-methyl thiourea (161 mg, 0.845 mmol), AD16 (180 mg, 0.422 mmol), EDCI (162 mg, 0.845 mmol) and DIPEA (218 mg, 1.689 mmol) in DMF (12 mL) was stirred at 50° C. for 21 h, diluted with water (10 mL) and extracted with EtOAc (35 mL×3). The combined extracts were washed with brine, dried over Na$_2$SO$_4$ and concentrated. The residue was purified by silica gel chromatography (PE:EtOAc=40:1) to give AD17.

Step 17

To a microwave vial containing AD17 (120 mg, 0.218 mmol) was added Ad-Brett phos G3 (33.1 mg, 0.033 mmol) and DMSO (3 mL). Nitrogen was bubbled through for 5 min. Then H$_2$O (0.024 mL, 1.308 mmol) was added followed by phosphazene base P2-ET (259 mg, 0.763 mmol). Nitrogen was bubbled through for another 5 min. The mixture was sealed in the microwave vial and stirred at 25° C. for 16 h. The mixture was partitioned between EtOAc (30 mL) and saturated NH$_4$Cl (10 mL). The aqueous layer was extracted with EtOAc (30 mL×2). The combined organic layers were washed with water, brine (10 mL), dried over Na$_2$SO$_4$ and concentrated in vacuo. The residue was purified by p-TLC (PE:EA=2:1) to give AD18.

Step 18

To a solution of AD17 (20 mg, 0.022 mmol) in DCM (1.2 mL) was added TFA (0.4 mL, 5.19 mmol). The solution was stirred at 20° C. for 1.5 h, concentrated. The residue was purified by p-HPLC (TFA) to give Example 83.

Step 19

To a solution of AD18 (10 mg, 0.021 mmol) in DCM (1.2 mL) was added TFA (0.4 mL, 5.19 mmol). The solution was stirred at 20° C. for 0.5 h, concentrated. The residue was purified by p-HPLC (TFA) to give Example 84.

Method AE mixture was stirred at 15° C. for 2 h, concentrated and neutralized with saturated NaHCO$_3$. The mixture was extracted with EtOAc (10 mL×3). The combined extracts were washed with brine, dried over Na$_2$SO$_4$ and concentrated in vacuo. The residue was purified by p-TLC (PE:EtOAc=1:1) to give AE1.

Step 2

To a solution of AE1 (540 mg, 1.636 mmol) in EtOH (2 mL) and water (6 mL) was added LiOH.H$_2$O (392 mg, 16.36 mmol). The reaction mixture was stirred at 100° C. for 12 h, and then extracted with EtOAc (30 mL×3). The combined extracts were washed with brine, dried over Na$_2$SO$_4$ and concentrated in vacuo to give AE2.

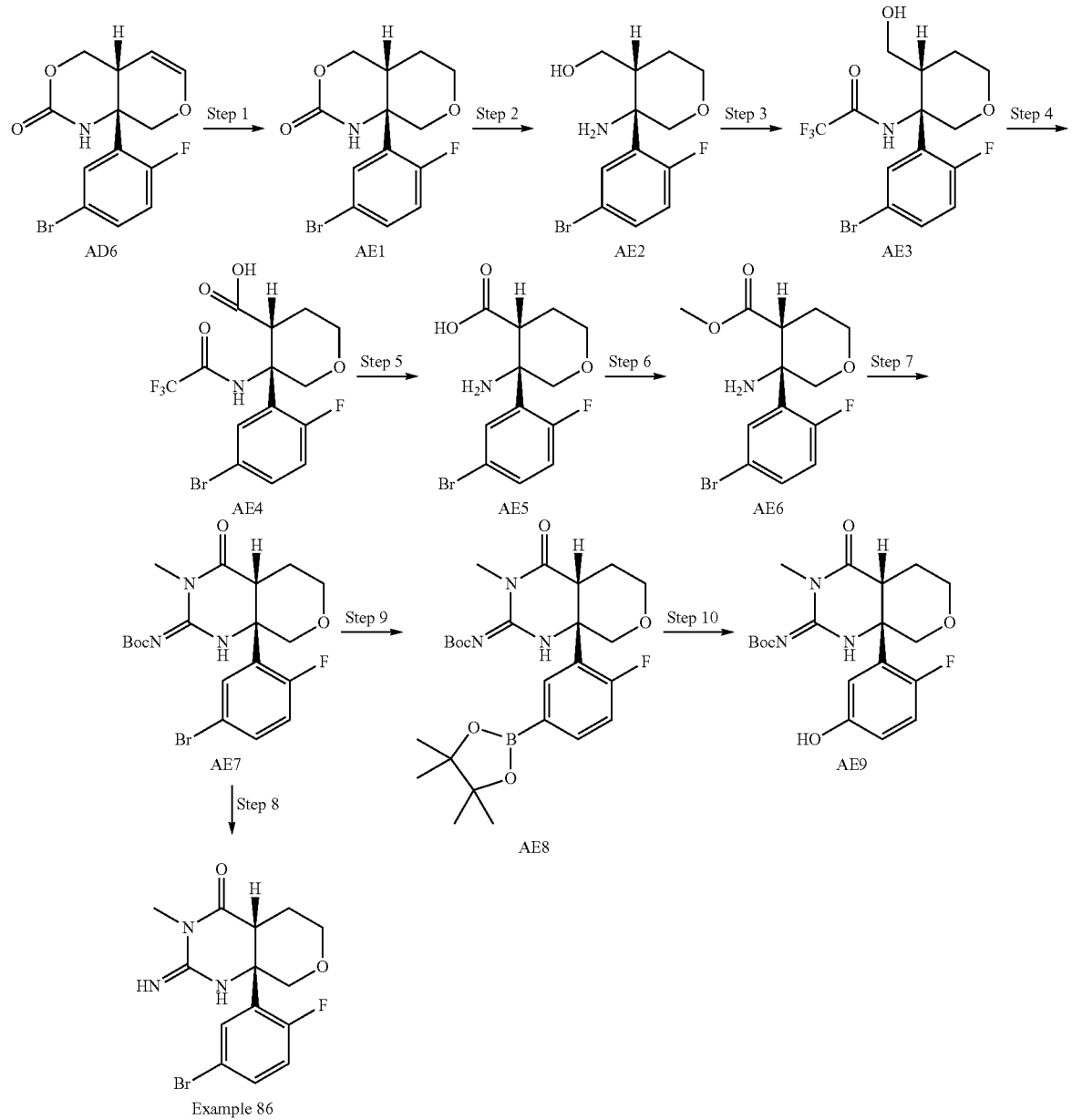

Step 1

To a solution of AD6 (80 mg, 0.244 mmol) in 1,2-dichloroethane (0.7 mL) at 0° C. were added triethylsilane (425 mg, 3.66 mmol) and TFA (0.7 mL, 9.09 mmol). The Step 3

To a mixture of AE2 (500 mg, 1.644 mmol) in DCM (3 mL) were added TEA (0.458 mL, 3.29 mmol) and TFAA (0.279 mL, 1.973 mmol) at 0° C. The reaction mixture was stirred at 15° C. for 3.5 h, quenched with H₂O and extracted with DCM (40 mL×3). The combined extracts were washed with brine, dried over Na₂SO₄ and concentrated in vacuo. The residue was purified by silica gel chromatography (PE:EtOAc=4:1 to 3:1) to give AE3.

Step 4

To a solution of AE3 (540 mg, 1.349 mmol) in acetonitrile (3 mL) were added NMO (632 mg, 5.40 mmol) and TPAP (37.9 mg, 0.108 mmol) at 0° C. The mixture was stirred at 20° C. for 2.5 h, quenched with 2-propanol (5 mL) and stirred for 1 h. The mixture was concentrated, diluted with EtOAc (20 mL) and filtered through celite. The filtrate was partitioned between 1N HCl (30 mL) and extracted with EtOAc (30 mL×3). The combined extracts were washed with brine, dried over Na₂SO₄ and concentrated to give AE4.

Step 5

To a mixture of AE4 (500 mg, 1.207 mmol) in 1,4-dioxane (2 mL) and H₂O (2 mL) was added LiOH.H₂O (289 mg, 12.07 mmol). The reaction mixture was stirred at 150° C. for 3 h, cooled to rt and acidified by HCl (2 N) to pH 2. The solution was extracted with i-PrOH/CHCl₃ (1:3, 30 mL×3). The combined extracts were washed with brine, dried over Na₂SO₄ and concentrated in vacuo to give AE5.

Step 6

To a mixture of AE5 (420 mg, 1.320 mmol) in MeOH (3 mL) at 0° C. was added SOCl₂ (0.964 mL, 13.20 mmol) slowly, and the reaction mixture was then stirred at 60° C. for 2 h. The reaction mixture was concentrated. The residue was dissolved in DCM and washed with water, brine and dried over Na₂SO₄, concentrated. The residue was purified by silica gel chromatography (SiO₂, PE:EtOAc=10:1 to 5:1) to give AE6.

Step 7

To a mixture of AE6 (266 mg, 0.801 mmol) in DMF (5 mL) were added EDCI (307 mg, 1.602 mmol), DIPEA (0.559 mL, 3.20 mmol), and N-Boc-N'-methylthiourea (305 mg, 1.602 mmol). The mixture was stirred at 15° C. for 18 h, and then stirred at 40° C. for additional 24 h. The reaction mixture was quenched with water and extracted with EtOAc (30 mL×3). The organic layer was washed with brine, dried over Na₂SO₄ and concentrated in vacuo. The residue was purified by silica gel chromatography (PE:EtOAc=10:1) to give AE7.

Step 8

To a solution of AE7 (10 mg, 0.022 mmol) in DCM (1.2 mL) was added TFA (0.4 mL, 5.19 mmol). The solution was stirred at 20° C. for 1.5 h and concentrated in vacuo. The residue was purified by p-HPLC (TFA) to give Example 86.

Step 9

A mixture of 4,4,4',4',5,5,5',5'-octamethyl-2,2'-bi(1,3,2-dioxaborolane) (44.5 mg, 0.175 mmol), AE7 (40 mg, 0.088 mmol), potassium acetate (25.8 mg, 0.263 mmol) and PdCl₂(dppf) (12.83 mg, 0.018 mmol) in 1,4-dioxane (1 mL) was stirred at 60° C. overnight. The reaction mixture was quenched with water and extracted with EtOAc (20 mL×3). The combined extracts were washed with brine, dried over Na₂SO₄ and concentrated to give AE8.

Step 10

To a solution of AE (400 mg, 0.795 mmol) in DCM (3 mL) was added H₂O₂ (0.696 mL, 7.95 mmol). The mixture was stirred at 15° C. for 2.5 h, quenched with water and extracted with EtOAc (20 mL×3). The combined extracts were washed with brine, dried over Na₂SO₄ and concentrated in vacuo. The residue was purified by silica gel chromatography (PE:EtOAc=5:1) to give AE9.

Method AF

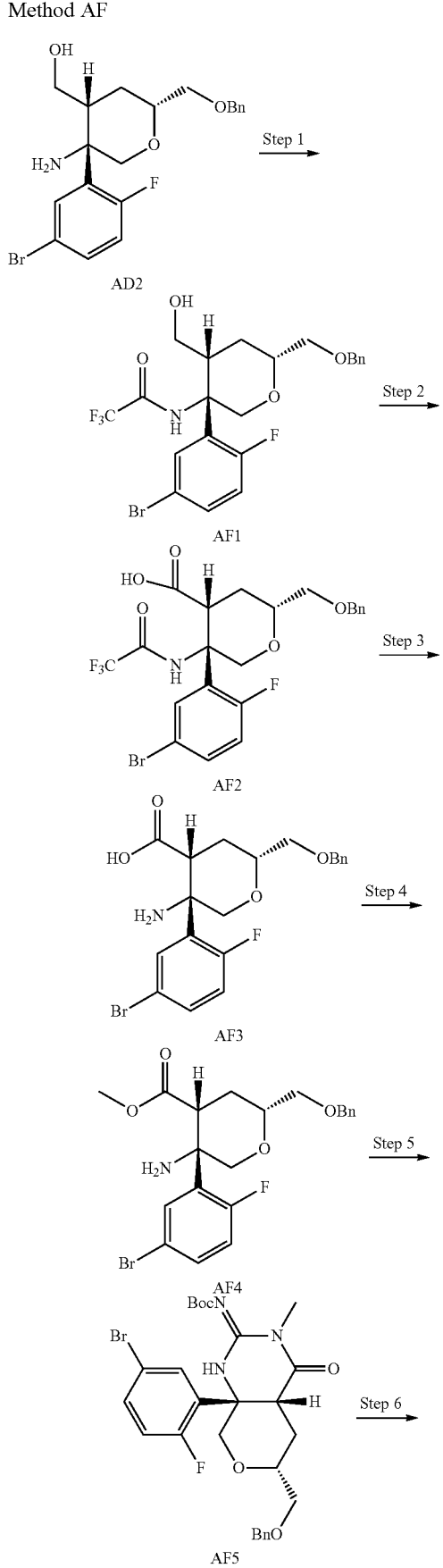

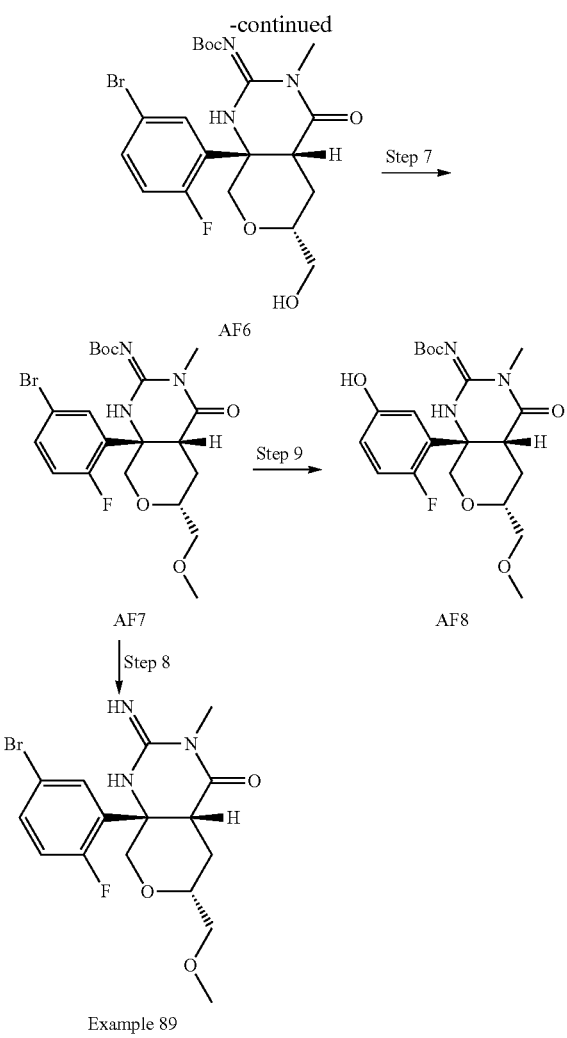

AF6

AF7

AF8

Example 89

Step 1

To a solution of AD2 (3.5 g, 8.25 mmol) and TEA (1.725 mL, 12.37 mmol) in DCM (14 mL) at 0° C. was added 2,2,2-trifluoroacetic anhydride (1.38 mL, 9.90 mmol). The mixture was stirred at 0° C. for 1 h, then at 25° C. for 2 h. The mixture was quenched with water. The organic phase was separated and washed with brine, dried over $Na_2SO_4$ and concentrated in vacuo to afford AF1.

Step 2

To a solution of AF1 (4.5 g, 8.22 mmol) in acetonitrile (46 mL) was added NMO (4.44 g, 32.9 mmol) and TPAP (0.231 g, 0.657 mmol). The mixture was stirred at 25° C. for 4 h, quenched with 2-propanol (7.5 mL) and stirred for 1 h. The mixture was concentrated, diluted with EtOAc (40 mL) and filtered through celite. The filtrate was partitioned between 1N HCl (100 mL) and EtOAc (100 mL). The organic layer was separated and washed with brine, dried over $Na_2SO_4$ and concentrated in vacuo to afford AF2.

Step 3

To a solution of AF2 (4.7 g, 7.74 mmol) in 1,4-dioxane (17 mL) in a sealed tube was added a solution of lithium hydroxide hydrate (3.25 g, 77 mmol) in water (17 mL). The mixture was heated to 150° C. and stirred for 7 h, cooled to RT and neutralized with conc. HCl to pH 1-2. The solution was extracted with isopropyl alcohol/$CHCl_3$ (v/v=1/3, 40 mL×3). The combined extracts were dried over $Na_2SO_4$ and concentrated in vacuo to give AF3.

Step 4

To a solution of AF3 (4.5 g, 7.19 mmol) in MeOH (15 mL) was added $SOCl_2$ (5.25 mL, 71.9 mmol) dropwise. After addition, the mixture was stirred at reflux for 3 h, concentrated in vacuo. The residue was neutralized with saturated $NaHCO_3$ and extracted with ethyl acetate (40 mL×3). The combined extracts were washed with brine, dried over $Na_2SO_4$ and concentrated in vacuo. The residue was purified by silica gel chromatography (PE:EtOAc=7:1) to give AF4.

Step 5

A mixture of N-Boc-N'-methyl thiourea (1.262 g, 6.63 mmol), AF4 (1.5 g, 3.32 mmol), EDCI (1.271 g, 6.63 mmol) and DIEA (1.714 g, 13.27 mmol) in DMF (6 mL) was stirred at 50° C. for 5 h. Additional EDCI (1.27 g, 6.63 mmol) and N-Boc-N'-methyl thiourea (1.26 g, 6.63 mmol) were added to the mixture and the mixture was stirred at 50° C. for 16 h. The mixture was quenched with water and extracted with EtOAc (35 mL×3). The combined extracts were washed with brine, dried over $Na_2SO_4$ and concentrated in vacuo. The residue was purified by silica gel chromatography (PE:EtOAc=40:1 to 15:1) to give AF5.

Step 6

To a solution of AF5 (2.46 g, 3.63 mmol) in $CH_2Cl_2$ (15 mL) at −10° C. was added $BCl_3$ (18.14 mL, 18.14 mmol). The mixture was stirred at −10° C. for 2 h, and concentrated in vacuo. The residue was neutralized with saturated $NaHCO_3$ and extracted with $CHCl_3$/IPA (v/v=3/1, 50 mL×4). The combined extracts were dried over $Na_2SO_4$ and concentrated in vacuo to afford free base (1.26 g). The free base (1.26 g, 2.94 mmol) was dissolved in MeOH (15 mL) followed by addition of TEA (0.89 mL, 6.39 mmol) and $(Boc)_2O$ (1.38 mL, 5.96 mmol). The mixture was stirred at 25° C. for 16 h, and concentrated in vacuo. The residue was purified by silica gel chromatography (PE:EtOAc=1:1) to give AF6.

Step 7

To a solution of AF6 (1 g, 1.953 mmol) in THF (20 mL) was added NaH (0.195 g, 4.88 mmol). The mixture was stirred at 25° C. for 20 min, followed by addition of iodomethane (0.305 g, 2.15 mmol). The mixture was stirred at 25° C. for 16 h, quenched with water and extracted with EtOAc (50 mL×3). The combined extracts were washed with brine, dried over $Na_2SO_4$ and concentrate in vacuo. The residue was purified by silica gel chromatography (PE: EtOAc=1:1) to give AF7.

Step 8

To a solution of AF7 (30 mg, 0.060 mmol) in DCM (3 mL) was added TFA (0.5 mL, 6.49 mmol). The mixture was stirred at 25° C. for 2 h, concentrated and purified by p-HPLC (TFA) to give Example 89.

Step 9

To a solution of AF7 (300 mg, 0.600 mmol)) in MeOH (3 mL) were added DIEA (0.314 mL, 1.799 mmol), hypodiboric acid (108 mg, 1.199 mmol) and $PCy_3$ precatalyst (35.4 mg, 0.060 mmol). The mixture was stirred at 25° C. for 1 h and concentrated in vacuo. The residue was dissolved in $CH_2Cl_2$ (3 mL), followed by addition of hydrogen peroxide (680 mg, 6.00 mmol) (30% in $H_2O$) and stirred at 25° C. for 0.5 h. The mixture was diluted with water and extracted with EtOAc (30 mL×2). The combined extracts were washed with brine, dried over $Na_2SO_4$ and concentrated in vacuo. The residue was purified by silica gel chromatography (PE:EtOAc=4:1 to 5:2) to give AF8.

Method AG

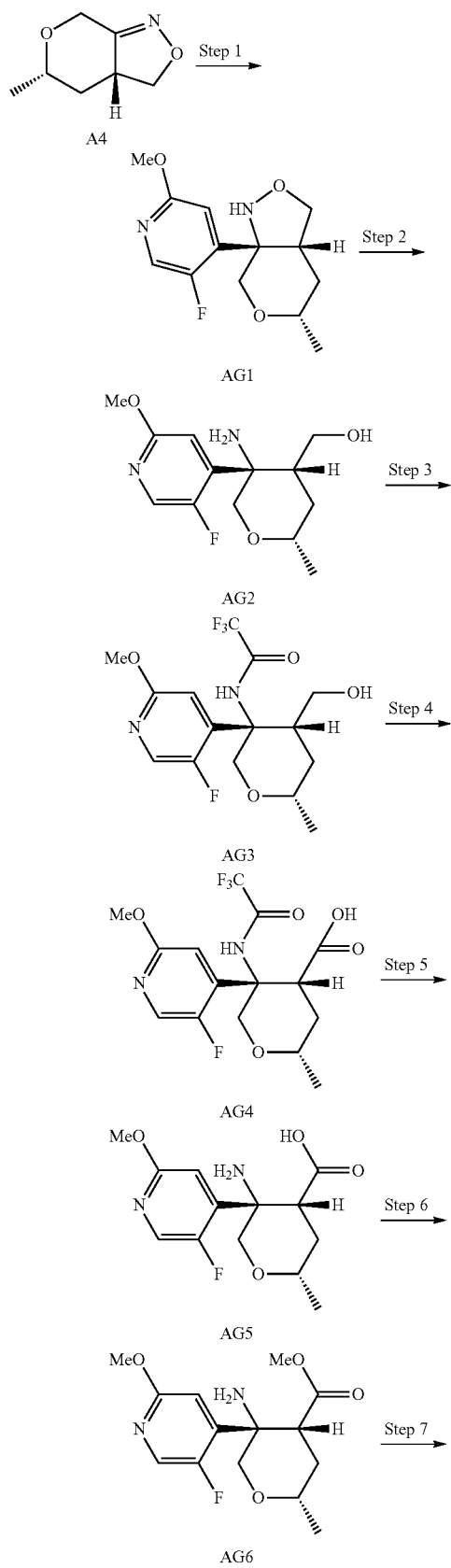

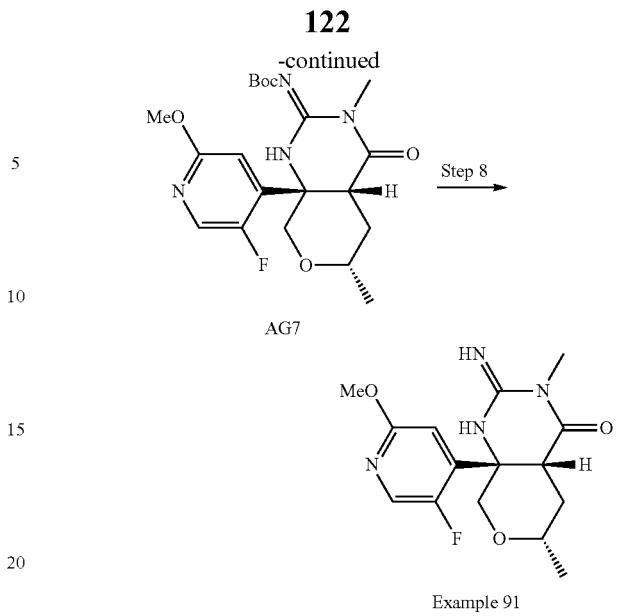

Step 1

To a solution of A4 (3.5 g, 24.79 mmol) in toluene (100 mL) was added BF$_3$.OEt$_2$ (16.0 mL, 59.5 mmol) under N$_2$ at −78° C. After stirring for 30 min, 5-fluoro-4-iodo-2-methoxypyridine (29.8 mmol) and n-butyllithium (11.9 mL, 29.8 mmol, 2.5 M in THF) were added. Then the mixture was stirred at −78° C. for 2 h under N$_2$. The mixture was quenched with saturated NH$_4$Cl and extracted with EtOAc (150 mL×3). The combined extracts were washed with brine, dried over Na$_2$SO$_4$ and concentrated. The residue was purified by silica gel chromatography (PE:EtOAc=20:1) to give AG1.

Step 2

To a solution of AG1 (1.05 g, 3.91 mmol) in AcOH (15 mL) was added zinc (2.56 g, 39.1 mmol) slowly at 15° C. The mixture was stirred at 15° C. for 18 h, concentrated. The residue was neutralized with saturated Na$_2$CO$_3$ and extracted with EtOAc (30 mL×3). The combined extracts were washed with brine, dried over Na$_2$SO$_4$ and concentrated to give AG2.

Step 3

To a solution of AG2 (1.0 g, 3.70 mmol) in DCM (15 mL) were added TFAA (0.784 mL, 5.55 mmol) and Et$_3$N (1.289 mL, 9.25 mmol). Then the mixture was stirred at 15° C. for 18 h, and then concentrated in vacuo. The residue was dissolved in EtOAc (50 mL) and washed with saturated Na$_2$CO$_3$, brine, dried over Na$_2$SO$_4$ and concentrated in vacuo. The residue was purified by silica gel chromatography (PE:EtOAc=10:1 to 2:1) to give AG3.

Step 4

To a solution of AG3 (1.2 g, 3.28 mmol) in acetonitrile (15 mL) were added NMO (1.535 g, 13.10 mmol) and TPAP (0.058 g, 0.164 mmol). The mixture was stirred at 15° C. for 2 h, quenched with i-PrOH (20 mL) and stirred for 2 h. The solvent was removed. The residue was diluted with water (30 mL) and acidified to pH 3~4 with aqueous HCl (3 M). The mixture was extracted with EtOAc (20 mL×3) and the combined extracts were washed with brine, dried over Na$_2$SO$_4$ and concentrated to give AG4.

Step 5

To a solution of AG4 (1.42 g, 3.73 mmol) in dioxane (10 mL) and water (10 mL) was added LiOH.H$_2$O (1.567 g, 37.3 mmol). The mixture in a seal tube was heated at 150° C. for 5 h, cooled to rt. The mixture was acidified to pH 3~4 with aqueous HCl (6 N) and extracted with CH$_3$Cl/i-PrOH (3/1, 20 mL×3). The combined extracts were washed with brine, dried over Na$_2$SO$_4$ and concentrated to give AG5.

Step 6

To a solution of AG5 (850 mg, 2.99 mmol) in MeOH (20 mL) cooled to 0° C. was added SOCl$_2$ (2.18 mL, 29.9 mmol) under N$_2$. Then the mixture was stirred at 60° C. for 2 h, and then concentrated in vacuo. The residue was neutralized with saturated NaHCO$_3$ and extracted with EtOAc (30 mL×3). The combined extracts were washed with brine, dried over Na$_2$SO$_4$ and concentrated to give AG6.

Step 7

To a solution of AG6 (510 mg, 1.710 mmol) in DMF (10.0 mL) were added N-Boc-N'-methyl thiourea (390 mg, 2.052 mmol), EDCI (655 mg, 3.42 mmol) and DIPEA (1.194 mL, 6.84 mmol) at 15° C. The mixture was stirred at 15° C. for 24 h. Additional N-Boc-N'-methyl thiourea (390 mg, 2.05 mmol), EDCI (655 mg, 3.42 mmol) and DIPEA (884 mg, 6.84 mmol) were added and the mixture was stirred at 15° C. for additional 24 h, quenched with water (50 mL) and extracted with EtOAc (30 mL×3). The combined organic layers were dried over Na$_2$SO$_4$, filtered and concentrated in vacuo. The residue was purified by silica gel chromatography (PE:EtOAc=50:1 to 20:1) to give AG7.

Step 8

To a solution of AG7 (20 mg, 0.047 mmol) in DCM (1.0 mL) was added TFA (0.18 mL, 2.37 mmol). The solution was stirred at 15° C. for 1 h, concentrated in vacuo and purified by p-HPLC (TFA) to give Example 91.

Method AH

Step 1

A mixture of AG7 (500 mg, 1.184 mmol), NaI (532 mg, 3.55 mmol) and TMSCl (0.756 mL, 5.92 mmol) in CH$_3$CN (2.0 mL) was stirred at 80° C. for 1.5 h, and concentrated in vacuo to give AH1.

Step 2

To a solution of AH1 (800 mg, 0.960 mmol) in MeOH (1.0 mL) was added Boc$_2$O (0.22 mL, 0.96 mmol) and Et$_3$N (0.13 mL, 0.96 mmol). The resulting mixture was stirred at 20° C. for 15 h, concentrated in vacuo to give AH2.

Step 3

A mixture of AH2 (100 mg, 0.245 mmol), K$_2$CO$_3$ (102 mg, 0.735 mmol) and (bromomethyl)cyclopropane (99 mg, 0.735 mmol) in DMSO (0.5 mL) was stirred at 50° C. for 2 h. The mixture was diluted with water and extracted EtOAc. The combined extracts were dried over Na$_2$SO$_4$ and concentrated in vacuo. The residue was purified by p-TLC (PE:EtOAc=1:1) to give AH3 and AH4.

Step 4

A solution of AH3 (20 mg, 0.018 mmol) in DMF (1 mL) and water (0.5 mL) was stirred at 80° C. for 2 h and at 100° C. for another 2 h. The mixture was purified directly by p-HPLC (neutral) to give Example 92 and Example 93.

Step 5

A solution of AH4 (50 mg, 0.037 mmol) in DMF (1.5 mL) and water (0.5 mL) was stirred at 80° C. for 2 h and at 100° C. for another 2 h. The mixture was purified directly by p-HPLC (neutral), and then separated by SFC to give Example 94 and Example 95.

SFC separation condition: Column: Chiralpak AD-3, 150×4.6 mm I.D., 3 um. Mobile phase: A: CO2, B: ethanol (0.05% DEA). Gradient: from 5% to 40% of B in 5.5 min

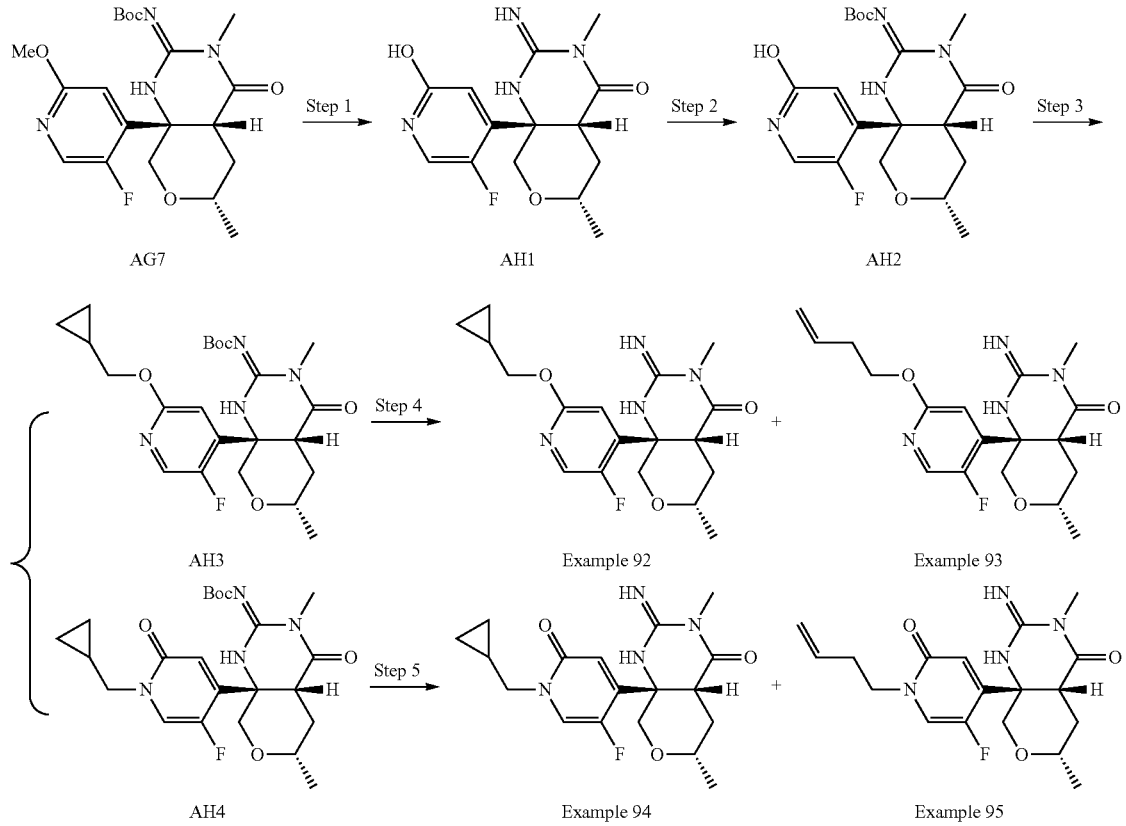

and hold 40% for 2 min, then 5% of B for 2.5 min. Flow rate: 2.5 mL/min. Column temp.: 35° C. Wavelength: 220 nm.

Table 1 below further depicts non-limiting example compounds of the invention and selected data therefor.

TABLE 1

| Ex | Structure<br>HNMR<br>IUPAC Name | LCMS<br>m/z | BACE-1<br>$K_i$ (nM) | BACE-2<br>$K_i$ (nM) |
|---|---|---|---|---|
| 1 | 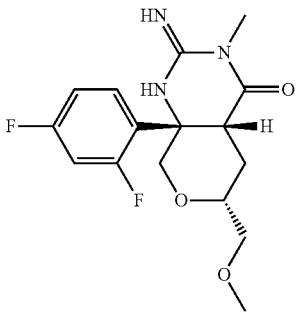<br>δ (400 MHz, CDCl$_3$): 1.81-1.74 (1 H, m), 1.86 (2 H, br s), 3.12 (3 H, s), 3.39 (3 H, s), 3.55-3.48 (3 H, m), 3.90 (2 H, q, J = 11.48 Hz), 6.85-6.78 (2 H, m), 7.47-7.42 (1 H, m).<br>(4aR,6R,8aS)-8a-(2,4-difluorophenyl)-2-imino-6-(methoxymethyl)-3-methylhexahydro-1H-pyrano[3,4-d]pyrimidin-4(4aH)-one | 340.3 | 629 | 237 |
| 2 | 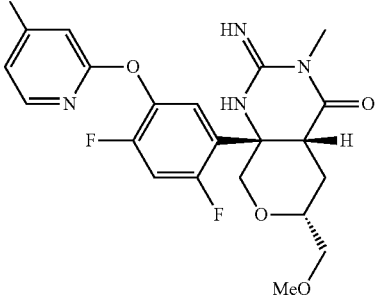<br>δ (400 MHz, CDCl$_3$): 1.75 (1 H, d, J = 13.04 Hz), 1.87 (1 H d, J = 12.72 Hz), 3.12 (3 H, s), 3.41 (3 H, s), 3.55-3.47 (4 H, m), 3.92 (2 H, s), 6.95 (1 H, t, J = 10.37 Hz), 7.23-7.22 (1 H, m), 7.34-7.30 (2 H, m), 8.23 (1 H, d, J = 5.31 Hz)<br>2-(2,4-difluoro-5-((4aR,6R,8aS)-2-imino-6-(methoxymethyl)-3-methyl-4-oxohexahydro-1H-pyrano[3,4-d]pyrimidin-8a(8H)-yl)phenoxy)isonicotinonitrile | 458.4 | 3 | 11 |
| 3 | 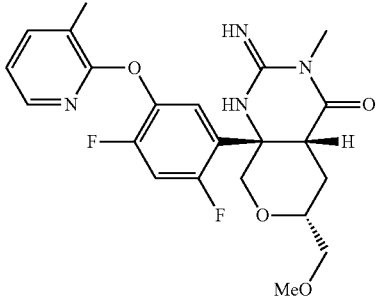<br>δ (400 ppm, CHCl$_3$-d(400 MHz, CDCl$_3$): 09 Hz), 3.60-3.52 (2 H, m), 3 72-3.69 (1 H, m), 3.95-3.89 (2 H, m), 6.92 (1 H, dd, J = 11.32, 9.57 Hz), 6.99 (1 H, ddd, J = 7.92, 4.88, 3.12 Hz), 7.38 (1 H, t, J = 8.15 Hz), 7.47 (1 H, ddd, J = 9.89, 7.89, 1.53 Hz), 7.82 (1 H, dd, J = 4.88, 1.51 Hz).<br>(4aR,6R,8aS)-8a-(2,4-difluoro-5-((3-fluoropyridin-2-yl)oxy)phenyl)-2-imino-6-(methoxymethyl)-3-methylhexahydro-1H-pyrano[3,4-d]pyrimidin-4(4aH)-one | 451.4 | 1 | 3 |

TABLE 1-continued

| Ex | Structure HNMR IUPAC Name | LCMS m/z | BACE-1 $K_i$ (nM) | BACE-2 $K_i$ (nM) |
| --- | --- | --- | --- | --- |
| 4 | 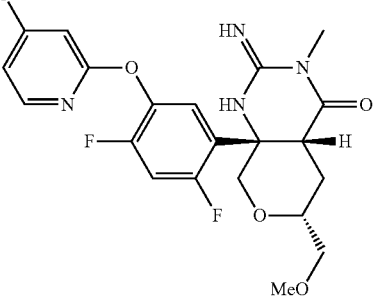 δ (400 MHz, CDCl$_3$): 1.76-1.69 (1 H, m), 1.90-1.86 (1 H, m), 3.13 (3 H, s), 3.40 (3 H, s), 3.55-3.49 (3 H, m), 3.74-3.71 (1 H, m), 3.93-3.88 (5 H, m), 6.44 (1 H, d, J = 2.14 Hz), 6.58 (1 H, dd, J = 5.87, 2.16 Hz), 6.92 (1 H, t, J = 10.48 Hz), 7.30 (1 H, s), 7.89 (1 H, d, J = 5.86 Hz). (4aR,6R,8aS)-8a-(2,4-difluoro-5-((4-methoxypyridin-2-yl)oxy)phenyl)-2-imino-6-(methoxymethyl)-3-methylhexahydro-1H-pyrano[3,4-d]pyrimidin-4(4aH)-one | 463.4 | 20 | 61 |
| 5 | 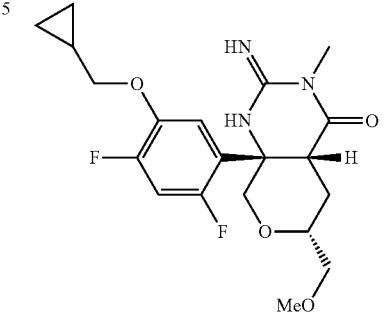 δ (400 MHz, CDCl$_3$): 0.30-0.26 (2 H, m), 0.32 (1 H, s), 0.60 (2 H, d, J = 8.04 Hz), 1.77-1.70 (1 H, m), 1.90-1.86 (1 H, m), 3.12 (3 H, s), 3.41 (3 H, s), 3.55-3.49 (3 H, m), 3.89-3.71 (5 H, m), 6.84 (1 H, t, J = 10.88 Hz), 7.07 (1 H, t, J = 8.35 Hz) (4aR,6R,8aS)-8a-(5-(cyclopropylmethoxy)-2,4-difluorophenyl)-2-imino-6-(methoxymethyl)-3-methylhexahydro-1H-pyrano[3,4-d]pyrimidin-4(4aH)-one | 410.4 | 68 | 82 |
| 6 | 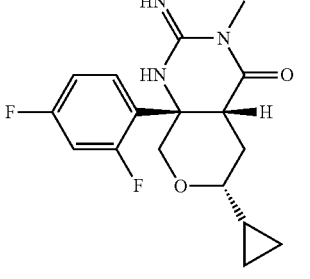 δ (400 MHz, CDCl$_3$): 0.28 (1 H, dq, J = 9.52, 4.60 Hz), 0.44 (1 H, dq, J = 9.55, 4.58 Hz), 0.62-0.52 (2 H, m), 0.98-0.93 (1 H, m), 1.84-1.77 (1 H, m), 2.03 (1 H, dd, J = 12.77, 4.51 Hz), 2.82 (1 H, t, J = 9.57 Hz), 3.13 (3 H, s), 3.47 (1 H, dd, J = 12.44, 4.89 Hz), 3.78 (1 H, d, J = 11.92 Hz), 3.87 (1 H, d, J = 11.91 Hz), 6.85-6.77 (2 H, m), 7.44-7.39 (1 H, m) (4aR,6R,8aS)-6-cyclopropyl-8a-(2,4-difluorophenyl)-2-imino-3-methylhexahydro-1H-pyrano[3,4-d]pyrimidin-4(4aH)-one | 336.3 | 99 | 265 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 7 | δ (400 MHz, CDCl$_3$): 1.83 (1 H, q, J = 12.49 Hz), 2.02 (1 H, dd, J = 13.21, 4.71 Hz), 3.12 (3 H, s), 3.54 (1 H, dd, J = 12.61, 4.94 Hz), 3.79 (1 H, q, J = 10.82 Hz), 3.96-3.88 (2 H, m), 5.81 (1 H, td, J = 55.37, 3.47 Hz), 6.87-6.80 (2 H, m), 7.45-7.40 (1 H, m) (4aR,6R,8aS)-6-(difluoromethyl)-8a-(2,4-difluorophenyl)-2-imino-3-methylhexahydro-1H-pyrano[3,4-d]pyrimidin-4(4aH)-one | 346.3 | 312 | 254 |
| 8 | δ (400 MHz, CDCl$_3$): 2.04 (1 H, d, J = 13.67 Hz), 2.30 (3 H, s), 3.18 (3 H, S), 3.71 (1 H, dd, J = 13.34, 5.00 Hz), 4.04 (2 H, t, J = 13.90 Hz), 4.74 (1 H, d, J = 11.61 Hz), 6.11 (1 H, S), 7.07-6.97 (3 H, m), 7.18 (1H, S) (4aR,6R,8aS)-8a-(2,5-difluorophenyl)-2-imino-3-methyl-6-(3-methylisoxazol-5-yl)hexahydro-1H-pyrano[3,4-d]pyrimidin-4(4aH)-one | 377.4 | 131 | 34 |
| 9 | δ (400 MHz, CDCl$_3$): 1.28 (3 H, d, J = 6.06 Hz), 1.60 (1 H, q, J = 12.20 Hz), 1.90 (1 H, dd, J = 13.01, 4.76 Hz), 3.13 (3 H, s), 3.50-3.54 (1 H, m), 3.65 (1 H, dd, J = 11.22, 6.21 Hz), 3.85 (2 H, s), 6.95 (1 H, t, J = 10.39 Hz), 7.24 (2H, d, J = 3.40 Hz), 7.27-7.30 (1H, m), 8.23 (1 H, d, J = 5.34 Hz). 2-(2,4-difluoro-5-((4aR,6S,8aS)-2-imino-3,6-dimethyl-4-oxohexahydro-1H-pyrano[3,4-d]pyrimidin-8a(8H)-yl)phenoxy)isonicotinonitrile | 428.4 | 2 | 4 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 10 | | 421.4 | 4 | 2 |

δ (400 MHz, CDCl$_3$): 1.27 (3 H, d, J = 6.04 Hz), 1.60 (1 H, q, J = 12.23 Hz), 1.89 (1 H, dd, J = 13.05, 4.78 Hz), 3.13 (3 H, s), 3.49-3.54 (1 H, m), 3.64 (1 H, dd, J = 11.25, 6.39 Hz), 3.89-3.83 (2 H, m), 6.94 (1 H, t, J = 10.43 Hz), 6.99-7.02 (1 H, m), 7.33 (1H, t, J = 8.07 Hz), 7.48 (1 H, t, J = 8.87 Hz), 7.83 (1 H, d, J = 4.87 Hz)
(4aR,6S,8aS)-8a-(2,4-difluoro-5-((3-fluoropyridin-2-yl)oxy)phenyl)-2-imino-3,6-dimethylhexahydro-1H-pyrano[3,4-d]pyrimidin-4(4aH)-one

| 11 | | 310.3 | 110 | 105 |

δ (400 MHz, CDCl$_3$): 1.30 (3 H, d, J = 6.14 Hz), 1.68-1.60 (1 H, m), 1.91 (1 H, ddd, J = 13.10, 4.93, 2.07 Hz), 3.14 (3 H, s), 3.53 (1 H, dd, J = 12.46, 4.97 Hz), 3.70-3.64 (1 H, m), 3.85 (2 H, s), 6.87-6.79 (2 H, m), 7.41 (1 H, td, J = 8.94, 6.38 Hz)
(4aR,6S,8aS)-8a-(2,4-difluorophenyl)-2-imino-3,6-dimethylhexahydro-1H-pyrano[3,4-d]pyrimidin-4(4aH)-one

| 12 | | 371.2 | 562 | 125 |

δ (400 MHz, CDCl$_3$): 1.29 (3 H, d, J = 6.15 Hz), 1.61 (1 H, q, J = 12.24 Hz), 1.90 (1 H, dd, J = 13.09, 4.68 Hz), 3.15 (3 H, s), 3.54 (1 H, dd, J = 12.45, 4.92 Hz), 3.67-3.62 (1 H, m), 3.85 (2 H, s), 6.94 (1 H, dd, J = 11.63, 8.66 Hz), 7.38 (1 H, dt, J = 8.51, 3.33 Hz), 7.54 (1 H, dd, J = 6.91, 2.55 Hz)
(4aR,6S,8aS)-8a-(5-bromo-2-fluorophenyl)-2-imino-3,6-dimethylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 13 | | 478.5 | 52 | 23 |

δ (400 MHz, CDCl₃): 0.28 (1 H, dq, J = 9.38, 4.72 Hz), 0.44 (1 H, dd, J = 9.42, 4.93 Hz), 0.54 (1 H, s), 0.58 (1 H, s), 0.92 (1 H, t, J = 7.24 Hz), 1.79 (1 H, d, J = 13.42 Hz), 2.06 (1 H, s), 2.84 (1 H, t, J = 9.48 Hz), 3.14 (3 H, s), 3.56-3.51 (1 H, m), 3.84 (2 H, d, J = 11.89 Hz), 6.52 (1 H, t, J = 2.08 Hz), 7.11 (2 H, d, J = 7.98 Hz), 7.25 (1 H, dd, J = 6.34, 2.13 Hz), 7.38 (1 H, s), 7.79 (1 H, s), 8.57 (2 H, d, J = 3.19 Hz).
(4aR,6R,8aS)-8a-(5-((6-(1H-pyrazol-1-yl)pyrimidin-4-yl)oxy)-2-fluorophenyl)-6-cyclopropyl-2-imino-3-methylhexahydro-1H-pyrano[3,4-d]pyrimidin-4(4aH)-one

| 14 | | 436.5 | 2 | 13 |

δ (400 MHz, CDCl₃): 0.27 (1 H, dq, J = 9.43, 4.69 Hz), 0.44 (1 H, dd, J = 9.53, 5.02 Hz), 0.54 (1 H, dd, J = 10.58, 5.83 Hz), 0.58 (1 H, s), 0.90 (1 H, t, J = 7.24 Hz), 1.78 (1 H, q, J = 12.19 Hz), 2.04-2.01 (1 H, m), 2.83 (1 H, t, J = 9.47 Hz), 3.13 (3 H, s), 3.53 (1 H, d, J = 12.00 Hz), 3.84 (2 H, t, J = 13.01 Hz), 7.11-7.04 (3 H, m), 7.21 (2 H, d, J = 5.07 Hz), 8.26 (1 H, d, J = 5.11 Hz).
2-(3-((4aR,6R,8aS)-6-cyclopropyl-2-imino-3-methyl-4-oxohexahydro-1H-pyrano[3,4-d]pyrimidin-8a(8H)-yl)-4-fluorophenoxy)isonicotinonitrile

| 15 | | 429.4 | 2 | 8 |

δ (400 MHz, CDCl₃): 0.27 (1 H, d, J = 8.02 Hz), 0.43 (1 H, s), 0.55-0.52 (1 H, m), 0.58 (1 H, s), 0.97 (1 H, s), 1.81 (1 H, s), 2.03 (1 H, s), 2.82 (1 H, t, J = 9.46 Hz), 3.14 (3 H, d, J = 4.13 Hz), 3.54-3.50 (1 H, m), 3.84-3.81 (1 H, m), 3.90 (1 H, d, J = 12.14 Hz), 7.01 (1 H, s), 7.09-7.07 (2 H, m), 7.24 (1 H, d, J = 6.51 Hz), 7.48 (1 H, t, J = 8.33 Hz), 7.88-7.87 (1 H, m).
(4aR,6R,8aS)-6-cyclopropyl-8a-(2-fluoro-5-((3-fluoropyridin-2-yl)oxy)phenyl)-2-imino-3-methylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 16 | 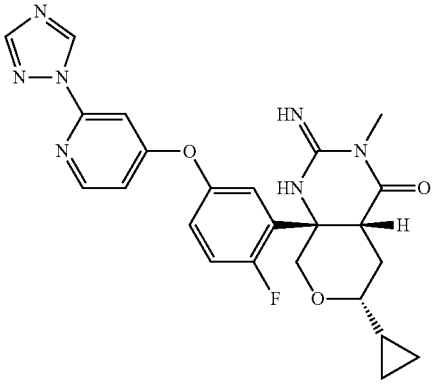 δ (400 MHz, CDCl$_3$): 0.27 (1 H, dd, J = 9.36, 4.95 Hz), 0.43 (1 H, d, J = 8.12 Hz), 0.55 (2 H, br s), 0.90 (1 H, t, J = 9.13 Hz), 1.76 (1 H, q, J = 12.18 Hz), 2.03 (1 H, d, J = 13.09 Hz), 2.83 (1 H, t, J = 9.30 Hz), 3.10 (3 H, s), 3.55 (1 H, d, J = 12.18 Hz), 3.82 (1 H, d, J = 11.40 Hz), 3.86 (1 H, s), 6.73 (1 H, s), 7.04 (1 H, d, J = 8.28 Hz), 7.13 (1 H, t, J = 10.04 Hz), 7.21 (1 H, s), 7.55 (1 H, s), 8.05 (1 H, s), 8.28 (1 H, d, J = 5.66 Hz), 9.15 (1 H, s). (4aR,6R,8aS)-8a-(5-((2-(1H-1,2,4-triazol-1-yl)pyridin-4-yl)oxy)-2-fluorophenyl)-6-cyclopropyl-2-imino-3-methylhexahydro-1H-pyrano[3,4-d]pyrimidin-4(4aH)-one | 478.5 | 43 | 42 |
| 17 | 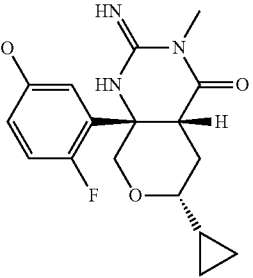 δ (400 MHz, CDCl$_3$): 0.28 (1 H, dt, J = 9.26, 4.80 Hz), 0.43 (1 H, dq, J = 9.51, 4.59 Hz), 0.59-0.53 (2 H, m), 0.90 (1 H, t, J = 7.03 Hz), 1.78 (1 H, q, J = 12.22 Hz), 2.03 (1 H, dd, J = 13.04, 4.63 Hz), 2.41 (3 H, s), 2.83 (1 H, t, J = 9.47 Hz), 3.14 (3 H, s), 3.55 (1 H, dd, J = 12.36, 4.81 Hz), 3.72 (1 H, s), 3.81 (1 H, d, J = 11.96 Hz), 7.07 (2H, d, J = 8.16 Hz), 7.21 (1 H, d, J = 6.28 Hz), 8.09 (1 H, s), 8.16 (1 H, s) (4aR,6R,8aS)-6-cyclopropyl-8a-(2-fluoro-5-((6-methylpyrazin-2-yl)oxy)phenyl)-2-imino-3-methylhexahydro-1H-pyrano[3,4-d]pyrimidin-4(4aH)-one | 426.5 | 12 | 102 |
| 18 | 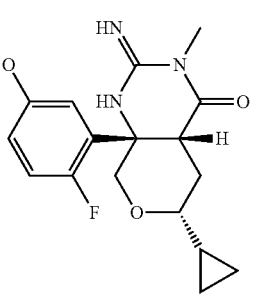 δ (400 MHz, CDCl$_3$): 0.27 (1 H, dd, J = 9.44, 4.91 Hz), 0.45-0.42 (1 H, m), 0.60-0.51 (2 H, m), 0.95 (1 H, d, J = 8.36 Hz), 1.79-1.72 (1 H, m), 2.06-2.00 (1 H, m), 2.83 (1 H, t, J = 9.60 Hz), 3.14 (3 H, s), 3.53 (1 H, td, J = 12.34, 4.84 Hz), 3.93-3.81 (2 H, m), 6.98-6.96 (1 H, m), 7.09-7.05 (3 H, m), 7.80-7.79 (1 H, m). (4aR,6R,8aS)-6-cyclopropyl-8a-(5-((3,5-difluoropyridin-2-yl)oxy)-2-fluorophenyl)-2-imino-3-methylhexahydro-1H-pyrano[3,4-d]pyrimidin-4(4aH)-one | 447.4 | 11 | 109 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 19 | 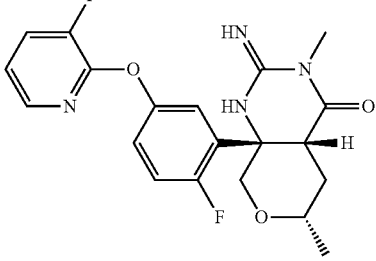<br>δ (400 MHz, CDCl₃): 1.27 (3 H, d, J = 6.07 Hz), 1.62 (1 H, q, J = 12.23 Hz), 1.90 (1 H, dd, J = 13.11, 4.68 Hz), 3.13 (3 H, s), 3.56 (1 H, dd, J = 12.44, 4.92 Hz), 3.65 (1 H, dd, J = 11.34, 6.29 Hz), 3.87 (2 H, s), 7.00 (1 H, dt, J = 7.97, 3.97 Hz), 7.08-7.06 (2 H, m), 7.24-7.22 (1 H, m), 7.47 (1 H, t, J = 8.93 Hz), 7.87 (1 H, d, J = 4.84 Hz).<br>(4aR,6S,8aS)-8a-(2-fluoro-5-((3-fluoropyridin-2-yl)oxy)phenyl)-2-imino-3,6-dimethylhexahydro-1H-pyrano[3,4-d]pyrimidin-4(4aH)-one | 403.4 | 7 | 5 |
| 20 | 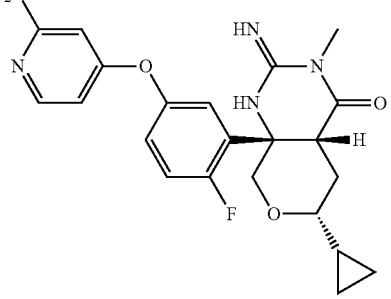<br>δ (400 MHz, CDCl₃): 0.28 (1 H, dd, J = 9.42, 4.85 Hz), 0.45 (1 H, dd, J = 9.53, 4.88 Hz), 0.59-0.55 (2 H, m), 0.98 (1 H, d, J = 8.45 Hz), 1.79 (1 H, d, J = 12.42 Hz), 2.06-2.04 (1 H, m), 2.84 (1 H, t, J = 8.55 Hz), 3.15 (3 H, s), 3.56 (1 H, dd, J = 12.46, 4.94 Hz), 3.90-3.84 (2 H, m), 6.60 (1 H, t, J = 55.46 Hz), 6.86 (1 H, d, J = 5.53 Hz), 7.07-7.02 (2 H, m), 7.21-7.13 (2 H, m), 8.50 (1 H, d, J = 5.66 Hz).<br>(4aR,6R,8aS)-6-cyclopropyl-8a-(5-((2-(difluoromethyl)pyridin-4-yl0oxy)-2-fluorophenyl)-2-imino-3-methylhexahydro-1H-pyrano[3,4-d]pyrimidin-4(4aH)-one | 461.5 | 60 | 228 |
| 21 | 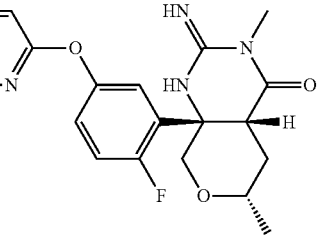<br>δ (400 MHz, CDCl₃): 1.29 (3 H, d, J = 6.22 Hz), 1.62 (1 H, q, J = 12.24 Hz), 1.91 (1 H, dd, J = 13.12, 4.66 Hz), 3.14 (3 H, s), 3.58 (1 H, dd, J = 12.45, 4.91 Hz), 3.67 (1 H, dd, J = 11.05, 6.21 Hz), 3.91-3.85 (2 H, m), 7.12-7.05 (2 H, m), 7.15 (1 H, s), 7.22-7.19 (2 H, m), 8.27 (1 H, d, J = 5.10 Hz).<br>2-(4-fluoro-3-((4aR,6S,8aS)-2-imino-3,6-dimethyl-4-oxohexahydro-1H-pyrano[3,4-d]pyrimidin-8a(8H)-yl)phenoxy)isonicotinonitrile | 410.4 | 6 | 6 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 22 | 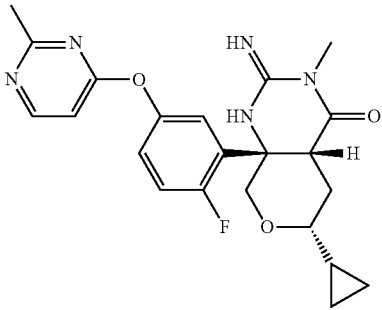 | 426.5 | 57 | 182 |

δ (400 MHz, CDCl$_3$): 0.28 (1 H, s), 0.43 (1 H, s), 0.55 (2 H, br s), 0.90 (1 H, s), 1.78 (1 H, d, J = 12.95 Hz), 2.05-2.02 (1 H, m), 2.56 (3 H, s), 2.84 (1 H, s), 3.13 (3 H, s), 3.55 (1 H, br s), 3.82 (1 H, d, J = 11.84 Hz), 4.14 (1 H, d, J = 8.21 Hz), 6.57 (1 H, s), 7.08 (2 H, d, J = 7.63 Hz), 7.20 (1 H, s), 8.45 (1 H, s).
(4aR,6R,8aS)-6-cyclopropyl-8a-(2-fluoro-5-((2-methylpyrimidin-4-yl)oxy)phenyl)-2-imino-3-methylhexahydro-1H-pyrano[3,4-d]pyrimidin-4(4aH)-one

| 23 | 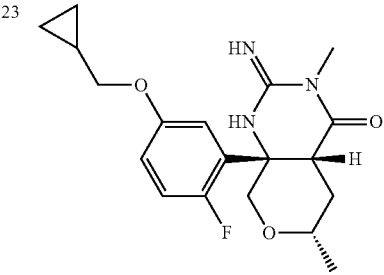 | 362.4 | 13 | 8 |

δ (400 MHz, CDCl$_3$): 0.32-0.29 (2 H, m), 0.63-0.61 (2 H, m), 1.25-1.18 (1 H, m), 1.29 (3 H, d, J = 6.13 Hz), 1.64 (1 H, q, J = 12.23 Hz), 1.93-1.89 (1 H, m), 3.14 (3 H, s), 3.56 (1 H, dd, J = 12.41, 4.94 Hz), 3.74-3.65 (3 H, m), 3.88-3.82 (2 H, m), 6.75 (1 H, dt, J = 8.88, 3.37 Hz), 6.96-6.93 (2 H, m).
(4aR,6S,8aS)-8a-(5-(cyclopropylmethoxy)-2-fluorophenyl)-2-imino-3,6-dimethylhexahydro-1H-pyrano[3,4-d]pyrimidin-4(4aH)-one

| 24 | 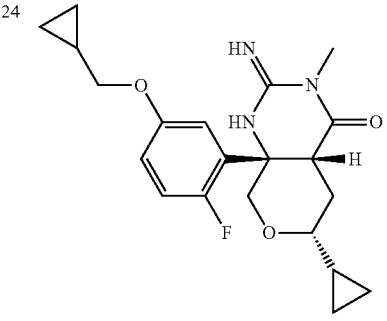 | 388.5 | 11 | 10 |

δ (400 MHz, CDCl$_3$): 0.30-0.27 (3 H, m), 0.46-0.41 (1 H, m), 0.61-0.52 (4 H, m), 1.00-0.96 (1 H, m), 1.21 (1 H, d, J = 9.07 Hz), 1.84-1.77 (1 H, m), 2.06-2.02 (1 H, m), 2.82 (1 H, t, J = 9.56 Hz), 3.14 (3 H, s), 3.52 (1 H, dd, J = 12.42, 5.16 Hz), 3.73-3.70 (2 H, m), 3.86-3.79 (2 H, m), 6.77-6.74 (1 H, m), 6.98-6.92 (2 H, m).
(4aR,6R,8aS)-6-cyclopropyl-8a-(5-(cyclopropylmethoxy)-2-fluorophenyl)-2-imino-3-methylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 25 | 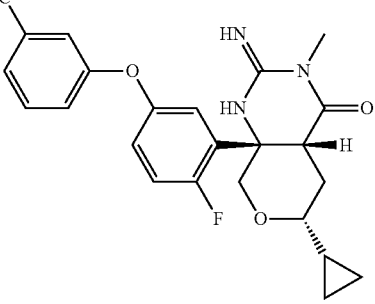 δ (400 MHz, CDCl₃): 0.32-0.23 (1 H, m), 0.45-0.40 (1 H, m), 0.61-0.51 (2 H, m), 1.00-0.87 (2 H, m), 2.01 (1 H, dd, J = 13.52, 4.89 Hz), 2.90-2.79 (1 H, m), 3.18-3.13 (3 H, m), 3.51 (1 H, dd, J = 12.50, 4.90 Hz), 3.83-3.76 (2 H, m), 6.94 (1 H, dt, J = 8.78, 3.36 Hz), 7.11-7.05 (4 14, m), 7.38-7.35 (2 H, m). 3-(3-((4aR,6R,8aS)-6-cyclopropyl-2-imino-3-methyl-4-oxohexahydro-1H-pyrano[3,4-d]pyrimidin-8a(8H)-yl)-4-fluorophenoxy)benzonitrile | 435.5 | 27 | 46 |
| 26 | 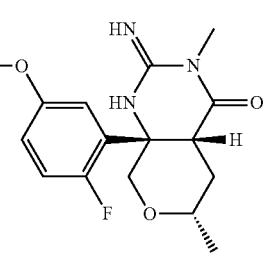 δ (400 MHz, CDCl₃): 1.29 (3 H, d, J = 6.30 Hz), 1.66-1.59 (1 H, m), 1.92 (1 H, d, J = 12.95 Hz), 2.27 (6 H, s), 3.15 (3 H, s), 3.57 (1 H, dd, J = 12.78, 5.42 Hz), 3.68-3.66 (1 H, m), 3.89-3.83 (4 H, m), 6.74-6.72 (1 H, m), 6.97-6.89 (2 H, m). 3-((4-fluoro-3-((4aR,6S,8aS)-2-imino-3,6-dimethyl-4-oxohexahydro-1H-pyrano[3,4-d]pyrimidin-8a(8H)-yl)phenoxy)methyl)bicyclo[1.1.1]pentane-1-carbonitrile | 413.5 | 8 | 98 |
| 27 | 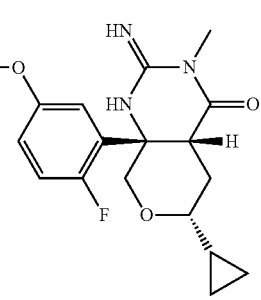 δ (400 MHz, CDCl₃): 0.27 (1 H, dd, J = 9.51, 5.07 Hz), 0.44 (1 H, d, J = 8.38 Hz), 0.54 (2 H, br s), 0.90 (1 H, t, J = 7.37 Hz), 1.75 (1 H, q, J = 12.23 Hz), 2.03 (1 H, d, J = 13.89 Hz), 2.83 (1 H, t, J = 9.35 Hz), 3.16 (3 H, s), 3.53 (1 H, d, J = 11.79 Hz), 3.83 (2 H, s), 6.99 (1 H, d, J = 8.42 Hz), 7.13 (2 H, t, J = 9.07 Hz), 7.35 (1 H, s), 8.47 (1 H, d, J = 2.72 Hz), 8.60 (1 H, s). 5-(3-((4aR,6R,8aS)-6-cyclopropyl-2-imino-3-methyl-4-oxohexahydro-1H-pyrano[3,4-d]pyrimidin-8a(8H)-yl)-4-fluorophenoxy)nicotinonitrile | 436.5 | 10 | 51 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 28 | | 396.4 | 136 | 627 |

δ (400 MHz, CDCl$_3$): 0.31-0.29 (1 H, m), 0.45 (1 H, s), 0.57 (2 H, br s), 0.90 (1 H, t, J = 6.84 Hz), 1.84 (1 H, br s), 2.08 (1 H, d, J = 13.16 Hz), 2.88 (1 H, t, J = 8.58 Hz), 3.22 (3 H, s), 3.69-3.66 (1 H, m), 3.84 (1 H, d, J = 12.27 Hz), 4.04 (1 H, d, J = 12.21 Hz), 7.22 (1 H, dd, J = 11.62, 8.42 Hz), 7.53 (1 H, s), 7.72 (1 H, s), 8.91 (2 H, s), 9.12 (1 H, s).
(4aR,6R,8aS)-6-cyclopropyl-8a-(2-fluoro-5-(pyrimidin-5-yl)phenyl)-2-imino-3-methylhexahydro-1H-pyrano[3,4-d]pyrimidin-4(4aH)-one

| 29 | | 462.4 | 16 | 54 |

δ (400 MHz, CDCl$_3$): 0.28-0.25 (1 H, m), 0.42 (1 H, d, J = 8.37 Hz), 0.55 (3 H, br s), 0.92-0.89 (1 H, m), 1.77 (1 H, q, J = 12.22 Hz), 2.03 (1 H, d, J = 13.05 Hz), 2.83 (1 H, t, J = 9.37 Hz), 3.12 (3 H, s), 3.55 (1 H, d, J = 11.84 Hz), 3.79 (1 H, d, J = 11.81 Hz), 3.89 (1 H, br s), 6.48 (1 H, t, J = 54.64 Hz), 7.08 (2 H, d, J = 7.68 Hz), 8.45 (1 H, s), 8.59 (1 H, s).
(4aR,6R,8aS)-6-cyclopropyl-8a-(5-((6-(difluoromethyl)pyrazin-2-yl)oxy)-2-fluorophenyl)-2-imino-3-methylhexahydro-1H-pyrano[3,4-d]pyrimidin-4(4aH)-one

| 30 | | 440.5 | 3 | 25 |

δ (400 MHz, CDCl$_3$): 1.76 (q, J = 12.13 Hz, 1 H), 1.98-2.11 (m, 1 H), 325 (s, 3 H), 3.41 (s, 3 H), 3.44-3.51 (m, 1 H), 3.53-3.62 (m, 1 H), 3.72-3.84 (m, 2 H), 3.87 (d, J = 12.91 Hz, 1 H), 4.23 (d, J = 12.91 Hz, 1 H), 7.07 (d, J = 5.87 Hz, 1 H), 7.19 (d, J = 8.22 Hz, 2 H), 7.21-7.26 (m, 2 H), 8.25 (d, J = 4.70 Hz, 1 H).
2-(4-fluoro-3-((4aR,6R,8aS)-2-imino-6-(methoxymethyl)-3-methyl-4-oxohexahydro-1H-pyrano[3,4-d]pyrimidin-8a(8H)-yl)phenoxy)isonicotinonitrile TABLE 1-continued

| Ex | Structure HNMR IUPAC Name | LCMS m/z | BACE-1 $K_i$ (nM) | BACE-2 $K_i$ (nM) |
|---|---|---|---|---|
| 31 | 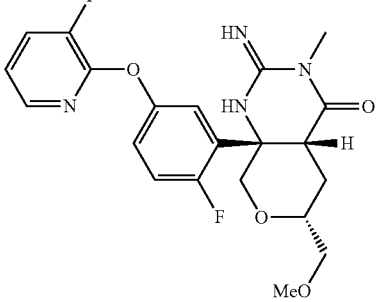 δ (400 MHz, CDCl$_3$): 1.75 (q, J = 12.39 Hz, 1 H), 1.99-2.09 (m, 1 H), 3.25 (s, 3 H), 3.41 (s, 3 H), 3.46 (dd, J = 10.17, 3.91 Hz, 1 H), 3.57 (dd, J = 9.98, 5.67 Hz, 1 H), 3.70-3.84 (m, 2 H), 3.88 (d, J = 12.52 Hz, 1 H), 4.24 (d, J = 12.91 Hz, 1 H), 6.99-7.07 (m, 1 H), 7.08-7.13 (m, 1 H), 7.14-7.25 (m, 2 H), 7.43-7.53 (m, 1 H), 7.88 (d, J = 4.30 Hz, 1 H). (4aR,6R,8aS)-8a-(2-fluoro-5-((3-fluoropyridin-2-yl)oxy)phenyl)-2-imino-6-(methoxymethyl)-3-methylhexahydro-1H-pyrano[3,4-d]pyrimidin-4(4aH)-one | 433.4 | 4 | 8 |
| 32 | 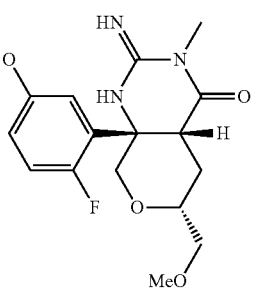 δ (400 MHz, CDCl$_3$): 0.26-0.39 (m, 2 H), 0.53-0.69 (m, 2 H), 1.14-1.27 (m, 1 H), 1.69-1.80 (m, 1 H), 2.04 (dd, J = 13.18, 3.39 Hz, 1 H), 3.28 (s, 3 H), 3.41 (s, 3 H), 3.43-3.49 (m, 1 H), 3.55-3.61 (m, 1 H), 3.67-3.89 (m, 5 H), 4.17 (d, J = 12.80 Hz, 1 H), 6.80-6.87 (m, 2 H), 7.01 (dd, J = 11.80, 8.78 Hz, 1 H). (4aR,6R,8aS)-8a-(5-(cyclopropylmethoxy)-2-fluorophenyl)-2-imino-6-(methoxymethyl)-3-methylhexahydro-1H-pyrano[3,4-d]pyrimidin-4(4aH)-one | 392.4 | 21 | 9 |
| 33 | 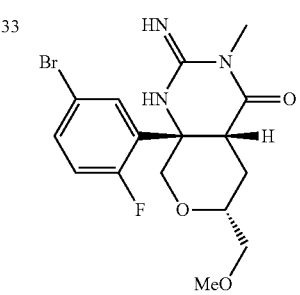 δ (400 MHz, CDCl$_3$): 1.79-1.86 (m, 1 H), 2.00-2.10 (m, 1 H), 3.30 (s, 3 H), 3.42 (s, 3 H), 3.46 (dd, J = 10.17, 3.91 Hz, 1 H), 3.58 (dd, J = 10.17, 5.48 Hz, 1 H), 3.71-3.88 (m, 3 H), 4.20 (d, J = 12.52 Hz, 1 H), 7.02 (dd, J = 11.54, 8.80 Hz, 1 H), 7.38 (d, J = 5.09 Hz, 1 H), 7.50 (d, J = 7.04 Hz, 1H). (4aR,6R,8aS)-8a-(5-bromo-2-fluorophenyl)-2-imino-6-(methoxymethyl)-3-methylhexahydro-1H-pyrano[3,4-d]pyrimidin-4(4aH)-one | 401.3 | 909 | 304 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 34 | δ (400 MHz, CDCl$_3$): 0.28 (1 H, s), 0.43 (1 H, s), 0.55 (2 H, br s), 0.90 (1 H, t, J = 6.76 Hz), 1.77 (1 H, br s), 2.03 (1 H, d, J = 12.83 Hz), 2.85 (1 H, br s), 3.03 (3 H, s), 3.56 (1 H, br s), 3.88 (2 H, s), 6.38 (1 H, s), 7.08 (2 H, s), 7.21 (1 H, s), 7.28 (2 H, s), 7.65 (1 H, s), 7.69 (1 H, s), 7.77 (1 H, br s). (4aR,6R,8aS)-8a-(5-(((6-(1H-pyrazol-1-yl)pyridin-2-yl)oxy)-2-fluorophenyl)-6-cyclopropyl-2-imino-3-methylhexahydro-1H-pyrano[3,4-d]pyrimidin-4(4aH)-one | 477.5 | 2.2 | 13.5 |
| 35 | δ (400 MHz, CDCl$_3$): 0.28-0.26 (1 H, m), 0.44 (1 H, s), 0.57 (2 H, br s) 0.90 (1 H, t, J = 6.76 Hz), 1.78 (1 H, d, J = 13.58 Hz), 2.02 (1 H, d, J = 12.83 Hz), 2.82 (1 H, br s), 3.09 (3 H, s), 3.52 (1 H, br s), 3.86 (2 H, s), 6.89 (2 H, br s), 7.00 (1 H, br s), 7.12 (1 H, s), 7.36 (2 H, t, J = 8.88 Hz), 7.50 (1 H, d, J = 7.63 Hz), 7.94 (2 H, d, J = 4.67 Hz). (4aR,6R,8aS)-6-cyclopropyl-8a-(2-fluoro-5-(3-(oxazol-4-yephenoxy)phenyl)-2-imino-3-methylhexahydro-1H-pyrano[3,4-d]pyrimidin-4(4aH)-one | 477.5 | 13 | 86 |
| 36 | δ (400 MHz, CDCl$_3$): 1.29 (3 H, d, J = 6.17 Hz), 1.90 (1 H, dd, J = 13.01, 4.79 Hz), 3.14 (3 H, s), 3.51 (1 H, s), 3.56 (1 H, dd, J = 12.50, 4.97 Hz), 3.67 (1 H, dd, J = 11.28,6.23 Hz), 3.82 (1 H, d, J = 11.77 Hz), 3.91 (1 H, dd, J = 11.80, 1.93 Hz), 6.98 (1 H, dt, J = 8.82, 3.37 Hz), 7.11-7.02 (3 H, m), 7.80 (1 H, t, J = 2.39 Hz). (4aR,6S,8aS)-8a-(5-(((3,5-difluoropyridin-2-yl)oxy)-2-fluorophenyl)-2-imino-3,6-dimethylhexahydro-1H-pyrano[3,4-d]pyrimidin-4(4aH)-one | 421.4 | 8.9 | 24 |

| Ex | Structure HNMR IUPAC Name | LCMS m/z | BACE-1 $K_i$ (nM) | BACE-2 $K_i$ (nM) |
|---|---|---|---|---|
| 37 | 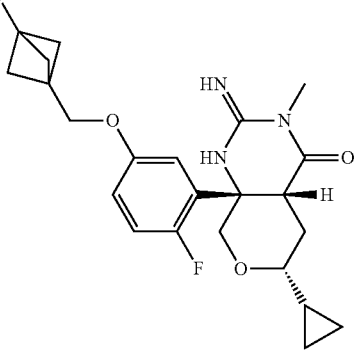 δ (400 MHz, CDCl₃): 0.27 (1 H, dq, J = 9.54, 4.64 Hz), 0.45-0.40 (1 H, m), 0.61-0.52 (2 H, m), 0.98-0.94 (1 H, m), 1.80 (1 H, q, J = 12.29 Hz), 2.02 (1 H, s), 2.21 (6 H, s), 2.81 (1 H, t, J = 9.78 Hz), 3.13 (3 H, s), 3.51 (1 H, dd, J = 12.46, 4.86 Hz), 3.84-3.78 (4 H, m), 6.71 (1 H, dt, J = 8.88, 3.30 Hz), 6.96-6.90 (2 H, m). 3-((3-((4aR,6R,8aS)-6-cyclopropyl-2-imino-3-methyl-4-oxohexahydro-1H-pyrano[3,4-d]pyrimidin-8a(8H)-yl)-4-fluorophenoxy)methyl)bicyclo[1.1.1]pentane-1-carbonitrile | 439.5 | 9 | 127 |
| 38 | 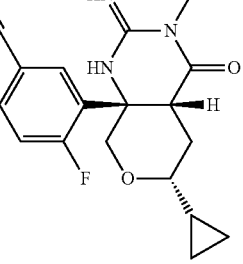 δ (400 MHz, CDCl₃): 0.28 (1 H, dq, J = 9.43, 4.83 Hz), 0.44 (1 H, dq, J = 9.48, 4.74 Hz), 0.63-0.52 (2 H, m), 0.99-0.95 (1 H, m), 1.77 (1 H, q, J = 12.32 Hz), 2.02 (1 H, dd, J = 13.21, 4.62 Hz), 2.81 (1 H, t, J = 9.59 Hz), 3.13 (3 H, s), 3.48 (1 H, dd, J = 12.48, 4.86 Hz), 3.80 (1 H, dd, J = 11.47, 2.07 Hz), 3.88 (1 H, d, J = 11.60 Hz), 7.17 (1 H, dd, J = 11.47, 8.45 Hz), 7.61 (1 H, ddd, J = 8.42, 4.27, 2.12 Hz), 7.81 (1 H, dd, J = 7.06, 2.14 Hz). 3-((4aR,6R,8aS)-6-cyclopropyl-2-imino-3-methyl-4-oxohexahydro-1H-pyrano[3,4-d]pyrimidin-8a(8H)-yl)-4-fluorobenzonitrile | 343.4 | 206 | 398 |
| 39 | 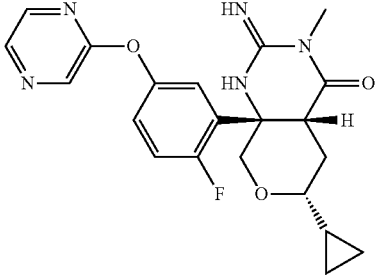 [SMILES: CN1C(=N)N[C@@]2(c3cc(Oc4cnccn4)ccc3F)CO[C@@H](C3CC3)C[C@H]2C1=O] (4aR,6R,8aS)-6-cyclopropyl-8a-(2-fluoro-5-(pyrazin-2-yloxy)phenyl)-2-imino-3-methylhexahydro-1H-pyrano[3,4-d]pyrimidin-4(4aH)-one | 412.2 | 13 | 73 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 40 | (4aR,6R,8aS)-6-cyclopropyl-8a-(2-fluoro-5-(pyridin-4-yloxy)phenyl)-2-imino-3-methylhexahydro-1H-pyrano[3,4-d]pyrimidin-4(4aH)-one | 411.2 | 54 | 11 |
| 41 | (4aR,6R,8aS)-6-cyclopropyl-8a-(2-fluoro-5-(pyridazin-4-yloxy)phenyl)-2-imino-3-methylhexahydro-1H-pyrano[3,4-d]pyrimidin-4(4aH)-one | 412.2 | 106 | 65 |
| 42 | (4aR,6R,8aS)-6-cyclopropyl-8a-(2-fluoro-5-((6-methoxypyrazin-2-yl)oxy)phenyl)-2-imino-3-methylhexahydro-1H-pyrano[3,4-d]pyrimidin-4(4aH)-one | 442.2 | 7 | 51 |
| 43 | (4aR,6R,8aS)-6-cyclopropyl-8a-(2-fluoro-5-(pyrimidin-2-yloxy)phenyl)-2-imino-3-methylhexahydro-1H-pyrano[3,4-d]pyrimidin-4(4aH)-one | 412.2 | 52 | 191 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 44 | 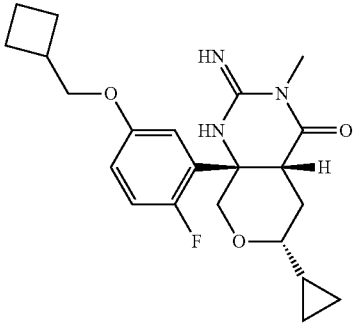 [SMILES: CN1C(=N)N[C@@]2(c3cc(OCC4CCC4)ccc3F)CO[C@@H](C3CC3)C[C@H]2C1=O]<br>—<br>(4aR,6R,8aS)-8a-(5-(cyclobutylmethoxy)-2-fluorophenyl)-6-cyclopropyl-2-imino-3-methylhexahydro-1H-pyrano[3,4-d]pyrimidin-4(4aH)-one | 402.2 | 30 | 20 |
| 45 | 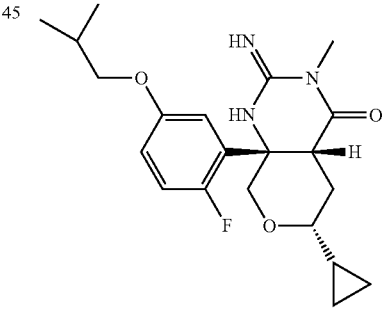<br>—<br>(4aR,6R,8aS)-6-cyclopropyl-8a-(2-fluoro-5-isobutoxyphenyl)-2-imino-3-methylhexahydro-1H-pyrano[3,4-d]pyrimidin-4(4aH)-one | 390.2 | 45 | 25 |
| 46 | 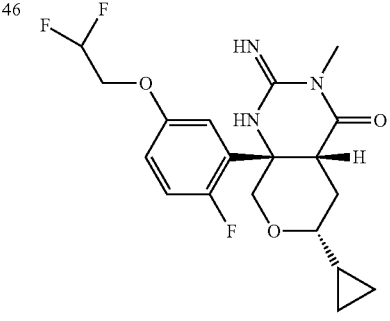<br>—<br>(4aR,6R,8aS)-6-cyclopropyl-8a-(5-(2,2-difluoroethoxy)-2-fluorophenyl)-2-imino-3-methylhexahydro-1H-pyrano[3,4-d]pyrimidin-4(4aH)-one | 398.2 | 40 | 41 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 47 | | 340.3 | 5722 | 9299 |

δ (400 MHz, CDCl₃): 1.29-1.26 (1 H, m), 1.43-1.37 (1 H m), 2.28 (1 H, ddd, J = 13.74, 4.77, 2.82 Hz), 3.32 (3 H, s), 3.40 (3 H, s), 3.47-3.45 (2 H, m), 3.51 (1 H, d, J = 12.66 Hz), 3.82-3.78 (1 H, m), 4.28 (1 H, dd, J = 12.63, 1.84 Hz), 6.92-6.82 (2 H, m), 7.74 (1 H, td, J = 9.09, 6.41 Hz).

(4aR,6S,8aS)-8a-(2,4-difluorophenyl)-2-imino-6-(methoxymethyl)-3-methylhexahydro-1H-pyrano[3,4-d]pyrimidin-4(4aH)-one

| 48 | | 354.3 | 1106 | 1385 |

δ (400 MHz, CDCl₃): 2.24 (1 H, br s), 2.38 (1 H, br s), 3.31 (3 H, s), 3.64 (1 H, d, J = 9.67 Hz), 3.79 (1 H, d, J = 12.74 Hz), 3.85 (3 H, s), 4.27-4.24 (1 H, m), 4.53 (1 H, s), 6.86 (1 H, t, J = 10.31 Hz), 6.94 (1 H, d, J = 8.98 Hz), 7.48 (1 H, d, J = 8.37 Hz).

methyl (4aR,6S,8aS)-8a-(2,4-difluorophenyl)-2-imino-3-methyl-4-oxooctahydro-1H-pyrano[3,4-d]pyrimidine-6-carboxylate

| 49 | | 376.2 | 66 | 64 |

(4aR,6R,8aS)-6-cyclopropyl-8a-(2-fluoro-5-propoxyphenyl)-2-imino-3-methylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 50 | 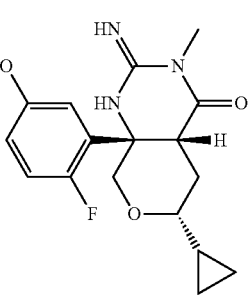 (4aR,6R,8aS)-6-cyclopropyl-8a-(2-fluoro-5-(2-methoxyethoxy)phenyl)-2-imino-3-methylhexahydro-1H-pyrano[3,4-d]pyrimidin-4(4aH)-one | 392.2 | 92 | 68 |
| 51 | 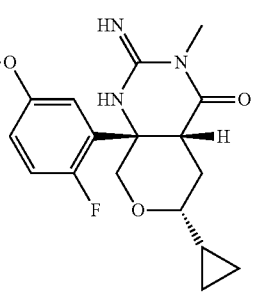 (4aR,6R,8aS)-6-cyclopropyl-8a-(5-((3,3-difluorocyclobutyl)methoxy)-2-fluorophenyl)-2-imino-3-methylhexahydro-1H-pyrano[3,4-d]pyrimidin-4(4aH)-one | 438.2 | 55 | 42 |
| 52 | 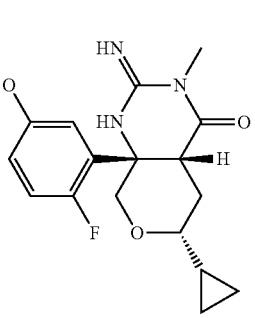 (4aR,6R,8aS)-6-cyclopropyl-8a-(5-((2,2-difluorocyclopropyl)methoxy)-2-fluorophenyl)-2-imino-3-methylhexahydro-1H-pyrano[3,4-d]pyrimidin-4(4aH)-one | 424.2 | 31 | 18 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 53 | 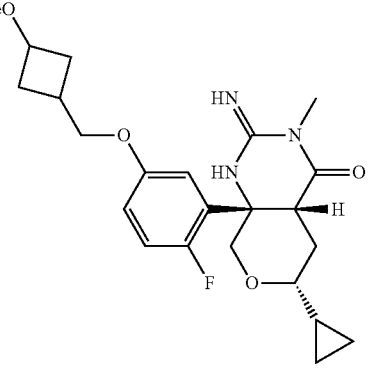<br>(4aR,6R,8aS)-6-cyclopropyl-8a-(2-fluoro-5-((3-methoxycyclobutyl)methoxy)phenyl)-2-imino-3-methylhexahydro-1H-pyrano[3,4-d]pyrimidin-4(4aH)-one | 432.2 | 180 | 117 |
| 54 | 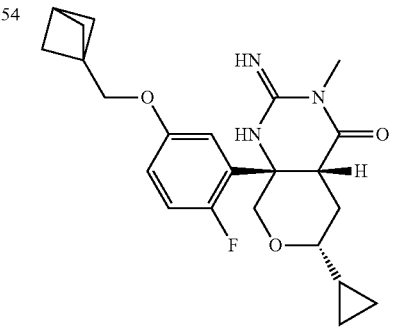<br>(4aR,6R,8aS)-8a-(5-(bicyclo[1.1.1]pentan-1-ylmethoxy)-2-fluorophenyl)-6-cyclopropyl-2-imino-3-methylhexahydro-1H-pyrano[3,4-d]pyrimidin-4(4aH)-one | 414.2 | 21 | 4 |
| 55 | 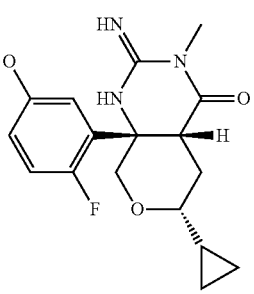<br>δ (400 MHz, CDCl$_3$): 0.31-0.28 (1 H, m), 0.46 (1 H, dt, J = 10.00, 4.65 Hz), 0.62-0.55 (2 H, m), 1.04-0.98 (1 H, m), 1.84 (1 H, q, J = 12.37 Hz), 2.13 (1 H, dd, J = 13.13, 4.76 Hz), 2.84 (1 H, t, J = 9.54 Hz), 3.27 (3 H, s), 3.78-3.73 (2 H, m), 4.06 (1 H, d, J = 12.59 Hz), 4.36-4.28 (2 H, m), 6.97-6.91 (2 H, m), 7.05 (1 H, dd, J = 11.32, 8.89 Hz).<br>(4aR,6R,8aS)-6-cyclopropyl-8a-(2-fluoro-5-(2,2,2-trifluoroethoxy)phenyl)-2-imino-3-methylhexahydro-1H-pyrano[3,4-d]pyrimidin-4(4aH)-one | 416.4 | 636 | 4612 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 56 | | 477.3 | 9 | 51 |

δ (400 MHz, CDCl$_3$): 0.27 (1 H, dd, J = 9.51, 5.01 Hz), 0.44 (1 H, dd, J = 9.50, 5.01 Hz), 0.58-0.53 (2 H, m), 0.97 (1 H, br s), 1.80 (1 H, q, J = 12.16 Hz), 2.03 (1 H, d, J = 11.87 Hz), 2.81 (1 H, t, J = 9.52 Hz), 3.12 (3 H, s), 3.52 (1 H, dd, J = 12.40, 4.86 Hz), 3.89-3.82 (2 H, m), 6.55 (1 H, s), 7.08-7.07 (2 H, m), 7.22 (2 H, d, J = 7.76 Hz), 7.37 (1 H, d, J = 5.60 Hz), 7.79 (1 H, s), 8.01 (1 H, s), 8.16 (1 H, d, J = 5.63 Hz).
(4aR,6R,8aS)-8a-(5-((4-(1H-pyrazol-1-yl)pyridin-2-yl)oxy)-2-fluorophenyl)-6-cyclopropyl-2-imino-3-methylhexahydro-1H-pyrano[3,4-d]pyrimidin-4(4aH)-one

| 57 | | 424.3 | 43 | 41 |

$^1$H NMR δ (400 MHz, CDCl$_3$): 0.27 (1 H, dd, J = 9.44, 5.02 Hz), 0.42 (1 H, s), 0.53 (2 H, br s), 0.90 (1 H, t, J = 6.83 Hz), 1.78 (1 H, br s), 2.03 (1 H, d, J = 12.87 Hz), 2.60 (1 H, br s), 2.69 (1 H, br s), 2.82 (1 H, t, J = 9.54 Hz), 3.10-3.02 (2 H, m), 3.17 (3 H, s), 3.55-3.51 (1 H, m), 3.82 (1 H, d, J = 11.95 Hz), 3.92 (1 H, br s), 4.53 (1 H, s), 6.69-6.67 (1 H, m), 6.83 (1 H, s), 6.97 (1 H, dd, J = 11.36, 8.87 Hz)
(6R,8aS)-6-cyclopropyl-8a-(5-(3,3-difluorocyclobutoxy)-2-fluorophenyl)-2-imino-3-methylhexahydro-1H-pyrano[3,4-d]pyrimidin-4(4aH)-one

| 58 | | 430.3 | 13 | 35 |

$^1$H NMR δ (400 MHz, CDCl$_3$): 0.27 (1 H, dq, J = 9.50, 4.70 Hz), 0.44 (1 H, dq, J = 9.54, 4.65 Hz), 0.62-0.52 (2 H, m), 1.00-0.94 (1 H, m), 1.28 (1 H, t, J = 7.13 Hz), 1.80 (1 H, q, J = 12.28 Hz), 2.04 (1 H, s), 2.82 (1 H, t, J = 9.67 Hz), 3.15 (3 H, s), 3.55-3.48 (1 H, m), 3.90-3.82 (2 H, m), 7.12 (2 H, d, J = 7.97 Hz), 8.47 (1 H, d, J = 1.40 Hz), 8.50 (1 H, d, J = 2.56 Hz)
(6R,8aS)-6-cyclopropyl-8a-(2-fluoro-5-((5-fluoropyrimidin-4-yl)oxy)phenyl)-2-imino-3-methylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 59 | 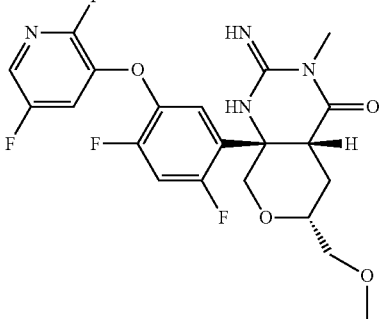<br>$^1$H NMR δ (400 MHz, CDCl$_3$): 1.27 (2 H, s), 1.73 (1 H, q, J = 12.45 Hz), 1.86 (1 H, d, J = 12.53 Hz), 3.13 (3 H, s), 3.40 (3 H, s), 3.49 (1 H, s), 3.73 (1 H, d, J = 10.75 Hz), 3.90 (2 H, s), 6.99 (2 H, t, J = 9.63 Hz), 7.18 (1 H, s), 7.80 (1 H, s).<br>(4aR,6R,8aS)-8a-(5-((2,5-difluoropyridin-3-yl)oxy)-2,4-difluorophenyl)-2-imino-6-(methoxymethyl)-3-methylhexahydro-1H-pyrano[3,4-d]pyrimidin-4(4aH)-one | 469.7 | 3 | 20 |
| 60 | 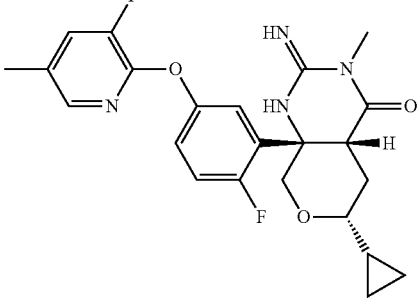<br>$^1$H NMR δ (400 MHz, CDCl$_3$): 0.27 (1 H, s), 0.44 (1 H, s), 0.57 (2 H, br s), 0.98 (1 H, s), 1.28 (2 H, s), 2.32 (3 H, s), 2.81 (1 H, s), 3.15 (3 H, s), 3.53 (1 H, d, J = 12.09 Hz), 3.87 (2 H, d, 1 = 22.29 Hz), 7.05 (2 H, d, J = 7.71 Hz), 7.22 (1 H, s), 7.32 (1 H, d, J = 10.63 Hz), 7.71 (1 H, s)<br>(4aR,6R,8aS)-6-cyclopropyl-8a-(2-fluoro-5-((3-fluoro-5-methylpyridin-2-yl)oxy)phenyl)-2-imino-3-methylhexahydro-1H-pyrano[3,4-d]pyrimidin-4(4aH)-one | 443.3 | 121 | 125 |
| 61 | 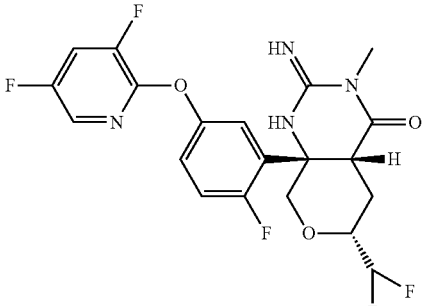<br>$^1$H NMR δ (400 MHz, CDCl$_3$): 1.84-1.77 (1 H, m), 2.02 (1 H, dd, J = 12.94, 4.58 Hz), 3.12 (3 H, s), 3.59 (1 H, dd, J = 12.62, 4.92 Hz), 3.84-3.78 (1 H, m), 3.95 (2 H, s), 5.81 (1 H, td, J = 55.35, 3.31 Hz), 7.10-7.07 (2 H, m), 7.18 (1H, m), 7.36-7.32 (1 H, m), 7.79 (1 H, d, J = 2.56 Hz).<br>(4aR,6R,8aS)-6-(difluoromethyl)-8a-(5-((3,5-difluoropyridin-2-yl)oxy)-2-fluorophenyl)-2-imino-3-methylhexahydro-1H-pyrano[3,4-d]pyrimidin-4(4aH)-one | 467.2 | 41 | 44 |

TABLE 1-continued

| Ex | Structure HNMR IUPAC Name | LCMS m/z | BACE-1 $K_i$ (nM) | BACE-2 $K_i$ (nM) |
|----|---|---|---|---|

62

¹H NMR δ (400 MHz, CDCl₃): 1.28-1.25 (4 H, m), 1.87 (1 H, d, J = 12.57 Hz), 3.11 (3 H, s), 3.48 (1 H, dd, J = 12.38, 4.93 Hz), 3.64 (1 H, dd, J = 11.00, 6.32 Hz), 3.74 (1 H, d, J = 11.59 Hz), 3.84 (1 H, d, J = 11.62 Hz), 6.98 (2 H, t, J = 9.77 Hz), 7.21 (1 H, t, J = 8.09 Hz), 7.77 (1 H, s)

(4aR,6S,8aS)-8a-(5-((2,5-difluoropyridin-3-yl)oxy)-2,4-difluorophenyl)-2-imino-3,6-dimethylhexahydro-1H-pyrano[3,4-d]pyrimidin-4(4aH)-one

63

¹H NMR δ (400 MHz, CDCl₃): 0.90 (1 H, t, J = 6.80 Hz), 1.11 (1 H, t, J = 7.23 Hz), 1.56 (1H, m), 1.90 (1 H, dd, J = 13.07, 4.80 Hz), 3.13 (3 H, s), 3.55-3.52 (1 H, m), 3.65 (1 H, dd, J = 11.14, 6.12 Hz), 3.86 (2 H, t, J = 11.18 Hz), 6.95 (1 H, t, J = 10.42 Hz), 7.36-7.32 (1 H, m), 7.36-7.37 (2 H, m), 7.74 (1 H, d, J = 2.52 Hz).

(4aR,6S,8aS)-8a-(5-((3,5-difluoropyridin-2-yl)oxy)-2,4-difluorophenyl)-2-imino-3,6-dimethylhexahydro-1H-pyrano[3,4-d]pyrimidin-4(4aH)-one

64 | | 308.1 | 357.9 | 82.74 |

δ (400 MHz, CD₃OD): 1.25 (3 H, d, J = 6.0 Hz), 1.65 (1 H, q, J = 12.1 Hz), 1.98 (1 H, d, J = 13.2 Hz), 3.17 (3 H, s), 3.61-3.84 (3 H, m), 4.10 (1 H, d, J = 12.8 Hz), 6.63-6.72 (1 H, m), 6.73-6.82 (1 H, m), 7.01 (1 H, dd, J = 9.2, 11.8 Hz).

(4aR,6S,8aS)-8a-(2-fluoro-5-hydroxyphenyl)-2-imino-3,6-dimethylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 65 | 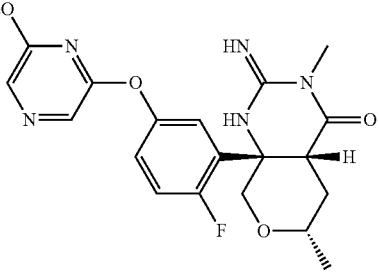 | 416.1 | 6.60 | 15.84 |

δ (400 MHz, CD$_3$OD): 1.26 (3 H, d, J = 6.0 Hz), 1.67 (1 H, d, J = 12.3 Hz), 1.89-2.13 (1 H, m), 3.17 (3 H, s), 3.66-3.80 (5 H, m), 3.82-3.91 (1 H, m), 4.15 (1 H, d, J = 12.8 Hz), 7.16 (1 H, d, J = 5.5 Hz), 7.30 (2 H, d, J = 8.4 Hz), 7.91 (2 H, d, J = 18.3 Hz).
(4aR,6S,8aS)-8a-(2-fluoro-5-((6-methoxypyrazin-2-yl)oxy)phenyl)-2-imino-3,6-dimethylhexahydro-1H-pyrano[3,4-d]pyrimidin-4(4aH)-one

| 66 | 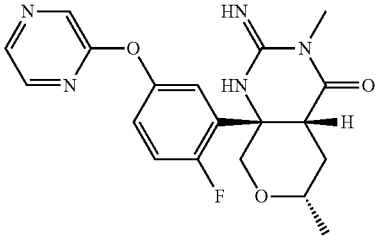 | 386.1 | 11.83 | 30.33 |

δ (400 MHz, CD$_3$OD): 1.25 (3 H, d, J = 6.0 Hz), 1.67 (1 H, q, J = 12.2 Hz), 1.93-2.01 (1 H, m), 3.17 (3 H, s), 3.63-3.73 (1 H, m), 3.76 (1 H, d, J = 12.8 Hz), 3.82 (1 H, dd, J = 4.7, 12.0 Hz), 4.17 (1 H, d, J = 12.6 Hz), 7.14-7.22 (1 H, m), 7.23-7.34 (2 H, m), 8.09 (1 H, br s), 8.30 (1 H, d, J = 2.2 Hz), 8.45 (1 H, s).
(4aR,6S,8aS)-8a-(2-fluoro-5-(pyrazin-2-yloxy)phenyl)-2-imino-3,6-dimethylhexahydro-1H-pyrano[3,4-d]pyrimidin-4(4aH)-one

| 67 | 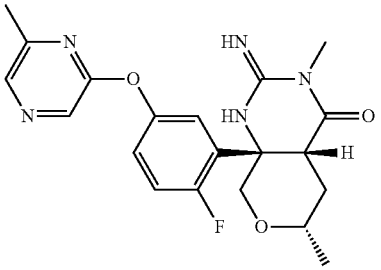 | 400.2 | 13.26 | 25.17 |

δ (400 MHz, CD$_3$OD): 1.24 (3 H, d, J = 6.2 Hz), 1.58-1.74 (1 H, m), 1.95 (1 H, br s), 2.37 (3 H, s), 3.17 (3 H, s), 3.61-3.75 (2 H, m), 3.84 (1 H, dd, J = 4.9, 12.1 Hz), 4.18 (1 H, d, J = 12.8 Hz), 7.12-7.19 (1 H, m), 7.33-7.21 (2 H, m), 8.19 (2 H, s).
(4aR,6S,8aS)-8a-(2-fluoro-5-((6-methylpyrazin-2-yl)oxy)phenyl)-2-imino-3,6-dimethylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 68 | | 403.1 | 157.3 | 71.29 |

δ (400 MHz, CD$_3$OD): 1.24 (3 H, d, J = 6.2 Hz), 1.58-1.75 (H, m), 1.90-2.04 (1 H, m), 3.16 (3 H, s), 3.75 (3 H, d, J = 12.8 Hz), 4.16 (1 H, d, J = 12.8 Hz), 7.04 (1 H, dd, J = 3.4, 8.9 Hz), 7.09 (1 H, dd, J = 2.6, 6.6 Hz), 7.13-7.20 (1 H, m), 7.20-7.29 (1 H, m), 7.61-7.72 (1 H, m), 7.96 (1 H, d, J = 2.9 Hz).
(4aR,6S,8aS)-8a-(2-fluoro-5-((5-fluoropyridin-2-yl)oxy)phenyl)-2-imino-3,6-dimethylhexahydro-1H-pyrano[3,4-d]pyrimidin-4(4aH)-one

| 69 | | 404.1 | 11.01 | 6.78 |

δ (400 MHz, CD$_3$OD): 1.26 (3 H, d, J = 6.0 Hz), 1.69 (1 H, q, J = 12.1 Hz), 1.99 (1 H, dd, J = 3.1, 13.2 Hz), 3.18 (3 H, s), 3.64-3.74 (1 H, m), 3.78 (1 H, d, J = 12.8 Hz), 3.85 (1 H, dd, J = 4.9, 12.1 Hz), 4.19 (1 H, d, J = 12.8 Hz), 7.24-7.41 (3 H, m), 8.45 (1 H, s), 8.64 (1 H, br s).
(4aR,6S,8aS)-8a-(2-fluoro-5-((5-fluoropyrimidin-4-yl)oxy)phenyl)-2-imino-3,6-dimethylhexahydro-1H-pyrano[3,4-d]pyrimidin-4(4aH)-one

| 70 | | 400.2 | 401.7 | 235.2 |

δ (400 MHz, CD$_3$OD): 1.24 (3 H, d, J = 6.0 Hz), 1.66 (1 H, d, J = 12.3 Hz), 1.97 (1 H, dd, J = 3.2, 13.3 Hz), 2.58 (3 H, s), 3.17 (3 H, s), 3.62-3.89 (3 H, m), 4.17 (1 H, d, J = 12.8 Hz), 7.01-7.41 (3 H, m), 7.88 (1 H, d, J = 2.0 Hz), 8.13 (1 H, d, J = 2.4 Hz).
(4aR,6S,8aS)-8a-(2-fluoro-5-((3-methylpyrazin-2-yl)oxy)phenyl)-2-imino-3,6-dimethylhexahydro-1H-pyrano[3,4-d]pyrimidin-4(4aH)-one

| Ex | Structure HNMR IUPAC Name | LCMS m/z | BACE-1 $K_i$ (nM) | BACE-2 $K_i$ (nM) |
|---|---|---|---|---|
| 71 | 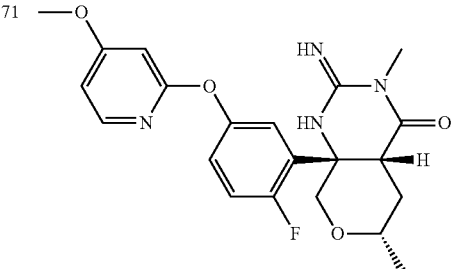 δ (400 MHz, CD$_3$OD): 1.24 (3 H, d, J = 6.0 Hz), 1.65 (1 H, q, J = 12.1 Hz), 1.91-2.02 (1 H, m), 3.16 (3 H, s), 3.63-3.72 (1 H, m), 3.75 (1 H, d, J = 12.8 Hz), 3.81 (1 H, dd, J = 4.9, 12.1 Hz), 3.87 (3 H, s), 4.15 (1 H, d, J = 12.6 Hz), 6.51 (1 H, d, J = 1.8 Hz), 6.70-6.76 (1 H, m), 7.03-7.09 (1 H, m), 7.12-7.19 (1 H, m), 7.20-7.30 (1 H, m), 7.88 (1 H, d, J = 6.0 Hz). (4aR,6S,8aS)-8a-(2-fluoro-5-((4-methoxypyridin-2-yl)oxy)phenyl)-2-imino-3,6-dimethylhexahydro-1H-pyrano[3,4-d]pyrimidin-4(4aH)-one | 415.2 | 39.90 | 14.99 |
| 72 | 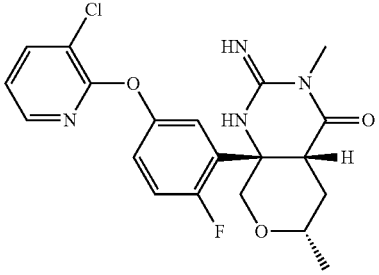 δ (400 MHz, CD$_3$OD): 1.24 (3 H, d, J = 6.0 Hz), 1.66 (1 H, q, J = 12.3 Hz), 1.96 (1 H, dd, J = 3.1, 13.2 Hz), 3.17 (3 H, s), 3.62-3.73 (1 H, m), 3.76 (1 H, d, J = 12.8 Hz), 3.82 (1 H, dd, J = 4.9, 12.1 Hz), 4.16 (1 H, d, J = 12.8 Hz), 7.08-7.14 (2 H, m), 7.16-7.23 (1 H, m), 7.23-7.31 (1 H, m), 7.92 (1 H, d, J = 7.7 Hz), 7.94-7.99 (1 H, m). (4aR,6S,8aS)-8a-(5-((3-chloropyridin-2-yl)oxy)-2-fluorophenyl)-2-imino-3,6-dimethylhexahydro-1H-pyrano[3,4-d]pyrimidin-4(4aH)-one | 419.1 | 37.6 | 9.67 |
| 73 | 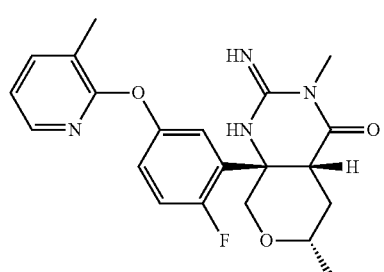 δ (400 MHz, CD$_3$OD): 1.24 (3 H, d, J = 6.0 Hz), 1.65 (1 H, q, J = 12.2 Hz), 1.90-2.01 (1 H, m), 2.30 (3 H, s), 3.16 (3 H, s), 3.63-3.72 (1 H, m), 3.76 (1 H, d, J = 12.6 Hz), 3.81 (1 H, dd, J = 4.9, 12.1 Hz), 4.16 (1 H, d, J = 12.8 Hz), 6.99-7.07 (2 H, m), 7.09-7.16 (1 H, m), 7.19-7.28 (1 H, m), 7.67 (1 H, d, J = 7.1 Hz), 7.85 (1 H, d, J = 3.7 Hz). (4aR,6S,8aS)-8a-(2-fluoro-5-((3-methylpyridin-2-yl)oxy)phenyl)-2-imino-3,6-dimethylhexahydro-1H-pyrano[3,4-d]pyrimidin-4(4aH)-one | 399.1 | 295.30 | 32.29 |

| Ex | Structure HNMR IUPAC Name | LCMS m/z | BACE-1 $K_i$ (nM) | BACE-2 $K_i$ (nM) |
|---|---|---|---|---|
| 74 | 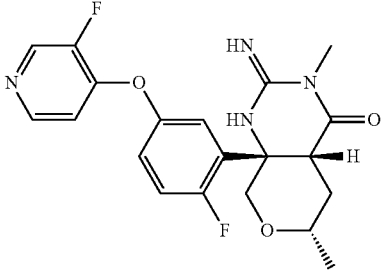 δ (400 MHz, CD$_3$OD): 1.24 (3 H, d, J = 5.1 Hz), 1.66 (1 H, q, J = 12.2 Hz), 1.96 (1 H, d, J = 11.5 Hz), 3.16 (3 H, br s), 3.68 (1 H, br s), 3.74 (1 H, d, J = 12.8 Hz), 3.79-3.90 (1 H, m), 4.17 (1 H, d, J = 12.3 Hz), 6.98 (1 H, br s), 7.17 (1 H, br s), 7.23-7.41 (2 H, m), 8.30 (1 H, br s), 8.60 (1 H, br s). (4aR,6S,8aS)-8a-(2-fluoro-5-((3-fluoropyridin-4-yl)oxy)phenyl)-2-imino-3,6-dimethylhexahydro-1H-pyrano[3,4-d]pyrimidin-4(4aH)-one | 403.1 | 44.34 | 31.50 |
| 75 | 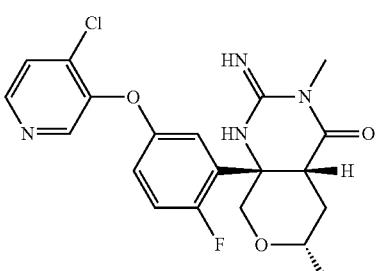 δ (400 MHz, CD$_3$OD): 1.22 (3 H, d, J = 6.0 Hz), 1.63 (1 H, q, J = 12.1 Hz), 1.93 (1 H, dd, J = 3.1, 13.2 Hz), 3.60-3.70 (1 H, m), 3.14 (3 H, s), 3.70-3.81 (2 H, m), 4.12 (1 H, d, J = 12.8 Hz), 6.80-6.92 (1 H, m), 7.03-7.14 (1 H, m), 7.24 (1 H, dd, J = 9.2, 11.4 Hz), 7.65 (1 H, br s), 8.28 (1 H, br s), 8.37 (1 H, br s). (4aR,6S,8aS)-8a-(5-((4-chloropyridin-3-yl)oxy)-2-fluorophenyl)-2-imino-3,6-dimethylhexahydro-1H-pyrano[3,4-d]pyrimidin-4(4aH)-one | 419.1 | 58.18 | 23.27 |
| 76 | 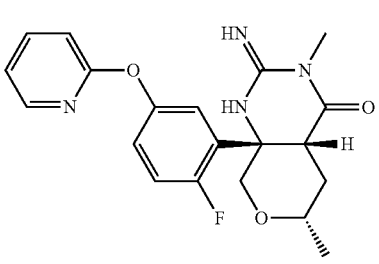 δ (400 MHz, CD$_3$OD): 1.25 (3 H, d, J = 6.2 Hz), 1.66 (1 H, q, J = 12.1 Hz), 1.97 (1 H, dd, J = 3.1, 13.5 Hz), 3.17 (3 H, s), 3.62-3.73 (1 H, m), 3.73-3.87 (2 H, m), 4.16 (1 H, d, J = 12.8 Hz), 7.00 (1 H, d, J = 8.2 Hz), 7.06-7.14 (2 H, m), 7.15-7.21 (1 H, m), 7.21-7.30 (1 H, m), 7.79-7.89 (1 H, m), 8.07 (1 H, d, J = 3.5 Hz). (4aR,6S,8aS)-8a-(2-fluoro-5-(pyridin-2-yloxy)phenyl)-2-imino-3,6-dimethylhexahydro-1H-pyrano[3,4-d]pyrimidin-4(4aH)-one | 385.1 | 31.67 | 13.36 |

TABLE 1-continued

| Ex | Structure HNMR IUPAC Name | LCMS m/z | BACE-1 $K_i$ (nM) | BACE-2 $K_i$ (nM) |
|---|---|---|---|---|

77

435.2  1454.00  241.60

δ (400 MHz, CD$_3$OD): 1.24 (3 H, d, J = 6.2 Hz), 1.58-1.73 (H, m), 1.90-2.00 (1 H, m), 3.18 (3 H, s), 3.63-3.73 (1 H, m), 3.74-3.86 (2 H, m), 4.16 (1 H, d, J = 12.8 Hz), 7.04-7.10 (1 H, m), 7.14-7.21 (1 H, m), 7.22-7.33 (2 H, m), 7.56 (1 H, t, J = 7.4 Hz), 7.72 (1 H, t, J = 7.5 Hz), 7.85 (1 H, d, J = 8.4 Hz), 8.06 (1 H, d, J = 8.4 Hz), 8.98 (1 H, br s).
(4aR,6S,8aS)-8a-(2-fluoro-5-(isoquinolin-3-yloxy)phenyl)-2-imino-3,6-dimethylhexahydro-1H-pyrano[3,4-d]pyrimidin-4(4aH)-one

78

403.1  19.96  32.89

δ (400 MHz, CD$_3$OD): 1.21-1.28 (3 H, m), 1.66 (1 H, q, J = 12.3 Hz), 1.91-2.02 (1 H, m), 3.16 (3 H, s), 3.68 (1 H, dd, J = 6.0, 9.5 Hz), 3.75 (1 H, d, J = 12.8 Hz), 3.82 (1 H, dd, J = 4.9, 12.1 Hz), 4.17 (1 H, d, J = 12.8 Hz), 7.06 (1 H, dd, J = 2.6, 6.4 Hz), 7.24-7.16 (1 H, m), 7.24-7.34 (2 H, m), 8.17 (1 H, br s), 8.31 (1 H, br s).
(4aR,6S,8aS)-8a-(2-fluoro-5-((5-fluoropyridin-3-yl)oxy)phenyl)-2-imino-3,6-dimethylhexahydro-1H-pyrano[3,4-d]pyrimidin-4(4aH)-one

79

421.1  43.46  41.26

δ (400 MHz, CD$_3$OD): 1.24 (3 H, d, J = 6.2 Hz), 1.66 (1 H, q, J = 12.3 Hz), 1.95 (1 H, dd, J = 3.1, 13.2 Hz), 3.16 (3 H, s), 3.61-3.72 (1 H, m), 3.72-3.85 (2 H, m), 4.13 (1 H, d, J = 12.8 Hz), 7.10-7.17 (1 H, m), 7.17-7.29 (2 H, m), 7.67-7.76 (1 H, m), 7.83 (1 H, d, J = 2.2 Hz).
(4aR,6S,8aS)-8a-(5-((3,5-difluoropyridin-2-yl)oxy)-2-fluorophenyl)-2-imino-3,6-dimethylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 80 | 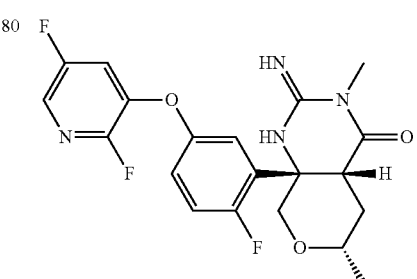 | 421.1 | 8.50 | 22.28 |

δ (400 MHz, CD₃OD): 1.20 (3 H, d, J = 6.0 Hz), 1.43-1.57 (1 H, m), 1.81 (1 H, dd, J = 3.0, 12.9 Hz), 3.04 (3 H, s), 3.48 (1 H, dd, J = 4.9, 12.3 Hz), 3.55-3.69 (1 H, m), 3.74-3.87 (2 H, m), 6.94-7.01 (1 H, m), 7.04-7.12 (1 H, m), 7.13-7.22 (1 H, m), 7.34-7.43 (1 H, m), 7.86 (1 H, br s).
(4aR,6S,8aS)-8a-(5-((2,5-difluoropyridin-3-yl)oxy)-2-fluorophenyl)-2-imino-3,6-dimethylhexahydro-1H-pyrano[3,4-d]pyrimidin-4(4aH)-one

| 81 | 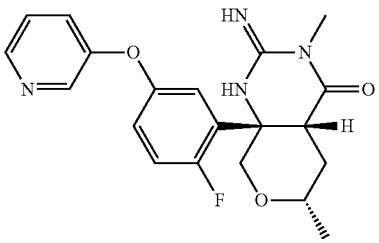 | 385.1 | 26.81 | 20.71 |

δ (400 MHz, CD₃OD): 1.25 (3 H, d, J = 6.0 Hz), 1.60-1.72 (1 H, m), 1.92-2.01 (1 H, m), 3.17 (3 H, s), 3.62-3.72 (1 H, m), 3.75 (1 H, d, J = 12.8 Hz), 3.82 (1 H, dd, J = 4.9, 12.1 Hz), 4.16 (1 H, d, J = 12.6 Hz), 7.02-7.08 (1 H, m), 7.13-7.22 (1 H, m), 7.29 (1 H, dd, J = 9.0, 11.5 Hz), 7.55 (2 H, br s), 8.32 (1 H, br s), 8.38 (1 H, br s).
(4aR,6S,8aS)-8a-(2-fluoro-5-(pyridin-3-yloxy)phenyl)-2-imino-3,6-dimethylhexahydro-1H-pyrano[3,4-d]pyrimidin-4(4aH)-one

| 82 | 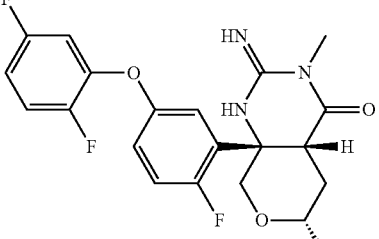 | 420.1 | 45.71 | 23.50 |

δ (400 MHz, CD₃OD): 1.26 (3 H, d, J = 6.0 Hz), 1.61-1.72 (H, m), 1.93-2.01 (1 H, m), 3.17 (3 H, s), 3.65-3.73 (1 H, m), 3.74-3.84 (2 H, m), 4.15 (1 H, d, J = 12.8 Hz), 6.81-7.04 (3 H, m), 7.05-7.14 (1 H, m), 7.19-7.35 (2 H, m).
(4aR,6S,8aS)-8a-(5-(2,5-difluorophenoxy)-2-fluorophenyl)-2-imino-3,6-dimethylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 83 | | 450.0 | 60.53 | 24.18 |

δ (400 MHz, CD$_3$OD): 1.92-2.04 (1 H, m), 2.20 (1 H, d, J = 11.47 Hz), 3.15 (3 H, s), 3.88 (1 H, d, J = 12.79 Hz), 4.06 (1 H, dd, J = 11.80, 4.74 Hz), 4.30 (1 H, d, J = 12.79 Hz), 4.65 (1 H, d, J = 10.80 Hz), 7.06 (2 H, t, J = 8.71 Hz), 7.19 (1 H, dd, J = 11.80, 8.93 Hz), 7.39-7.45 (2 H, m), 7.48-7.55 (1 H, m), 7.59 (1 H, br s).
(4aR,6R,8aS)-8a-(5-bromo-2-fluorophenyl)-6-(4-fluorophenyl)-2-imino-3-methylhexahydro-1H-pyrano[3,4-d]pyrimidin-4(4aH)-one

| 84 | | 388.1 | 70.05 | 17.25 |

δ (400 MHz, CD$_3$OD): 1.97 (1 H, q, J = 12.3 Hz), 2.17-2.25 (1 H, m), 3 17 (3 H, s), 3.91-4.02 (2 H, m), 4.30 (1 H, d, J = 12.8 Hz), 4.64-4.69 (1 H, m), 6.74 (1 H, dd, J = 2.6, 6.4 Hz), 6.76-6.84 (1 H, m), 6.96-7.17 (3 H, m), 7.44 (2 H, dd, J = 5.6, 8.3 Hz).
(4aR,6R,8aS)-8a-(2-fluoro-5-hydroxyphenyl)-6-(4-fluorophenyl)-2-imino-3-methylhexahydro-1H-pyrano[3,4-d]pyrimidin-4(4aH)-one

| 85 | | 442.2 | 3.20 | 0.76 |

δ (400 MHz, CD$_3$OD): 0.31 (2 H, d, J = 5.1 Hz), 0.60 (2 H, d, J = 7.7 Hz), 1.21 (1 H, br s), 1.98 (1 H, q, J = 12.4 Hz), 2.20 (1 H, d, J = 11.2 Hz), 3.15 (3 H, s), 3.77 (2 H, d, J = 6.8 Hz), 3.91 (1 H, d, J = 12.8 Hz), 4.00-4.11 (1 H, m), 4.25-4.37 (1 H, m), 4.60-4.73 (1 H, m), 6.85 (1 H, dd, J = 2.9, 6.4 Hz), 6.95 (1 H, d, J = 8.8 Hz), 7.01-7.17 (2 H, m), 7.12-7.17 (1 H, m), 7.44 (2 H, dd, J = 5.5, 8.2 Hz).
(4aR,6R,8aS)-8a-(5-(cyclopropylmethoxy)-2-fluorophenyl)-6-(4-fluorophenyl)-2-imino-3-methylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 86 | | 356.0 | 1202.00 | 298.00 |

δ (400 MHz, CD₃OD): 1.93-2.07 (2 H, m), 3.30 (3 H, s), 3.59 (1 H, t, J = 10.9 Hz), 3.72 (2 H, d, J = 12.1 Hz), 4.07-4.20 (2 H, m), 7.02 (1 H, t, J = 10.2 Hz), 7.39 (1 H, d, J = 6.3 Hz), 7.49 (1 H, br s).
(4aR,8aS)-8a-(5-bromo-2-fluorophenyl)-2-imino-3-methylhexahydro-1H-pyrano[3,4-d]pyrimidin-4(4aH)-one

| 87 | | 389.2 | 26.97 | 13.51 |

δ (400 MHz, CD₃OD): 1.89-1.98 (1 H, m), 2.06 (1 H, br s), 3.21 (3 H, s), 3.63 (1 H, d, J = 2.0 Hz), 3.76 (1 H, d, J = 12.8 Hz), 3.81 (1 H, dd, J = 5.0, 11.4 Hz), 4.05 (1 H, d, J = 9.5 Hz), 4.13 (1 H, d, J = 12.8 Hz), 7.14-7.34 (4 H, m), 7.70 (1 H, t, J = 8.6 Hz), 7.88 (1 H, d, J = 3.7 Hz).
(4aR,8aS)-8a-(2-fluoro-5-((3-fluoropyridin-2-yl)oxy)phenyl)-2-imino-3-methylhexahydro-1H-pyrano[3,4-d]pyrimidin-4(4aH)-one

| 88 | | 348.2 | 43.95 | 5.96 |

δ (400 MHz, CD₃OD): 0.30-0.37 (2 H, m), 0.58-0.66 (2 H, m), 1.22 (1 H, t, J = 7.1 Hz), 1.89-1.97 (1 H, m), 2.05 (1 H, br s), 3.20 (3 H, s), 3.58-3.73 (2 H, m), 3.76-3.86 (3 H, m), 4.01-4.11 (2 H, m), 6.86 (1 H, dd, J = 2.9, 6.4 Hz), 6.97 (1 H, br s), 7.08-7.16 (1 H, m).
(4aR,8aS)-8a-(5-(cyclopropylmethoxy)-2-fluorophenyl)-2-imino-3-methylhexahydro-1H-pyrano[3,4-d]pyrimidin-4(4aH)-one

| 89 | | 400.0 | 909.60 | 303.80 |

δ (400 MHz, CD₃OD): 1.79-1.86 (1 H, m), 2.00-2.10 (1 H, m), 3.30 (3 H, s), 3.42 (3 H, s), 3.46 (1 H, dd, J = 3.9, 10.2 Hz), 3.58 (1 H, dd, J = 5.5, 10.2 Hz), 3.71-3.88 (3 H, m), 4.20 (1 H, d, J = 12.5 Hz), 7.02 (1 H, dd, J = 8.8, 11.5 Hz), 7.38 (1 H, d, J = 5.1 Hz), 7.50 (1 H, d, J = 7.0 Hz).
(4aR,6R,8aS)-8a-(5-bromo-2-fluorophenyl)-2-imino-6-(methoxymethyl)-3-methylhexahydro-1H-pyrano[3,4-d]pyrimidin-4(4aH)-one

TABLE 1-continued

| Ex | Structure HNMR IUPAC Name | LCMS m/z | BACE-1 $K_i$ (nM) | BACE-2 $K_i$ (nM) |
|---|---|---|---|---|
| 90 | | 392.2 | 21.04 | 8.84 |

δ (400 MHz, CD$_3$OD): 0.26-0.39 (2 H, m), 0.53-0.69 (2 H, m), 1.14-1.27 (1 H, m), 1.69-1.80 (1 H, m), 2.04 (1 H, dd, J = 3.4, 13.2 Hz), 3.28 (3 H, s), 3.41 (3 H, s), 3.43-3.49 (1 H, m), 3.55-3.61 (1 H, m), 3.67-3.89 (5 H, m), 4.17 (1 H, d, J = 12.8 Hz), 6.80-6.87 (2 H, m), 7.01 (1 H, dd, J = 8.8, 11.8 Hz).

(4aR,6R,8aS)-8a-(5-(cyclopropylmethoxy)-2-fluorophenyl)-2-imino-6-(methoxymethyl)-3-methylhexahydro-1H-pyrano[3,4-d]pyrimidin-4(4aH)-one

| 91 | | 323.1 | 467.80 | 155.10 |

δ (400 MHz, CD$_3$OD): 1.28 (3 H, d, J = 6.2 Hz), 1.69 (1 H, q, J = 12.4 Hz), 2.01 (1 H, dd, J = 3.1, 13.5 Hz), 3.19 (3 H, s), 3.66-3.72 (1 H, m), 3.76 (1 H, d, J = 13.0 Hz), 3.83 (1 H, dd, J = 4.9, 12.1 Hz), 3.89 (3 H, s), 4.14 (1 H, d, J = 12.6 Hz), 6.72 (1 H, d, J = 5.3 Hz), 8.09 (1 H, d, J = 3.1 Hz).

(4aR,6S,8aS)-8a-(5-fluoro-2-methoxypyridin-4-yl)-2-imino-3,6-dimethylhexahydro-1H-pyrano[3,4-d]pyrimidin-4(4aH)-one

| 92 | | 363.2 | 11.08 | 2.19 |

δ (400 MHz, CD$_3$OD): 0.33 (2 H, d, J = 4.6 Hz), 0.61 (2 H, d, J = 7.3 Hz), 1.19-1.25 (1 H, m), 1.27 (3 H, d, J = 6.2 Hz), 1.56 (1 H, d, J = 12.3 Hz), 1.87 (1 H, d, J = 9.9 Hz), 3.13 (3 H, s), 3.49 (1 H, dd, J = 4.9, 12.6 Hz), 3.63 (1 H, dd, J = 5.8, 9.6 Hz), 3.82 (2 H, s), 4.04 (2 H, d, J = 7.1 Hz), 6.80 (1 H, d, J = 5.3 Hz), 7.88 (1 H, d, J = 2.9 Hz).

(4aR,6S,8aS)-8a-(2-(cyclopropylmethoxy)-5-fluoropyridin-4-yl)-2-imino-3,6-dimethylhexahydro-1H-pyrano[3,4-d]pyrimidin-4(4aH)-one TABLE 1-continued

| Ex | Structure HNMR IUPAC Name | LCMS m/z | BACE-1 $K_i$ (nM) | BACE-2 $K_i$ (nM) |
|---|---|---|---|---|
| 93 | δ (400 MHz, CD₃OD): 1.25 (3 H, d, J = 6.0 Hz), 1.54 (1 H, d, J = 12.1 Hz), 1.85 (1 H, d, J = 9.7 Hz), 2.48 (2 H, q, J = 6.5 Hz), 3.11 (3 H, s), 3.46 (1 H, dd, J = 4.9, 12.3 Hz), 3.55-3.66 (1 H, m), 3.80 (2 H, s), 4.19-4.34 (2 H, m), 5.03-5.19 (2 H, m), 5.78-5.91 (1 H, m), 6.72 (1 H, d, J = 5.1 Hz), 7.88 (1 H, d, J = 2.9 Hz). (4aR,6S,8aS)-8a-(2-(but-3-en-1-yloxy)-5-fluoropyridin-4-yl)-2-imino-3,6-dimethylhexahydro-1H-pyrano[3,4-d]pyrimidin-4(4aH)-one | 363.2 | 16.09 | 4.46 |
| 94 | δ (400 MHz, CD₃OD): 0.37-0.42 (2 H, m), 0.64-0.69 (2 H, m), 1.14-1.20 (1 H, m), 1.27 (3 H, d, J = 6.0 Hz), 1.50-1.62 (1 H, m), 1.83-1.90 (1 H, m), 3.17 (3 H, s), 3.40 (1 H, dd, J = 4.7, 12.2 Hz), 3.55-3.65 (1 H, m), 3.71 (2 H, d, J = 6.6 Hz), 3.80-3.91 (2 H, m), 6.61 (1 H, d, J = 7.5 Hz), 7.33 (1 H, d, J = 6.8 Hz). (4aR,6S,8aS)-8a-(1-(cyclopropylmethyl)-5-fluoro-2-oxo-1,2-dihydropyridin-4-yl)-2-imino-3,6-dimethylhexahydro-1H-pyrano[3,4-d]pyrimidin-4(4aH)-one | 363.2 | 4181.0 | 1588.0 |
| 95 | δ (400 MHz, CD₃OD): 1.26 (3 H, d, J = 6.2 Hz), 1.48-1.61 (1 H, m), 1.85 (1 H, dd, J = 3.2, 13.1 Hz), 2.47 (2 H, q, J = 6.8 Hz), 3.15 (3 H, s), 3.37 (1 H, dd, J = 5.0, 12.5 Hz), 3.55-3.60 (1 H, m), 3.77-3.98 (4 H, m), 5.08-5.11 (2 H, m), 5.70-5.83 (1 H, m), 6.60 (1 H, d, J = 7.3 Hz), 7.13 (1 H, d, J = 6.8 Hz). (4aR,6S,8aS)-8a-(1-(but-3-en-1-yl)-5-fluoro-2-oxo-1,2-dihydropyridin-4-yl)-2-imino-3,6-dimethylhexahydro-1H-pyrano[3,4-d]pyrimidin-4(4aH)-one | 363.2 | 8404.0 | 1594.0 |

TABLE 1-continued

| Ex | Structure HNMR IUPAC Name | LCMS m/z | BACE-1 $K_i$ (nM) | BACE-2 $K_i$ (nM) |
|---|---|---|---|---|
| 96 | | 404.1 | 144.60 | 31.28 |

δ (400 MHz, CDCl₃): 1.33 (3 H, d, J = 6.0 Hz), 1.65 (1 H, q, J = 11.9 Hz), 2.02 (1 H, br s), 3.31 (3 H, s), 3.62-3.78 (2 H, m), 3.84 (1 H, d, J = 12.8 Hz), 4.21 (1 H, d, J = 12.6 Hz), 7.05 (1 H, d, J = 5.1 Hz), 7.15-7.24 (1 H, m), 7.55 (1 H, t, J = 8.2 Hz), 8.01-8.13 (3 H, m), 11.05 (1 H, br s).
(4aR,6S,8aS)-8a-(5-fluoro-2-((3-fluoropyridin-2-yl)oxy)pyridin-4-yl)-2-imino-3,6-dimethylhexahydro-1H-pyrano[3,4-d]pyrimidin-4(4aH)-one Assays Protocols used to determine the recited potency values for the compounds of the invention are described below.

BACE1 HTRF FRET Assay

Reagents: Na⁺-Acetate pH 5.0; 1% Brij-35; Glycerol; Dimethyl Sulfoxide (DMSO); Recombinant human soluble BACE1 catalytic domain (>95% pure); APP Swedish mutant peptide substrate (QSY7-APP$^{swe}$-Eu): QSY7-EISEVNLDAEFC-Europium-amide.

A homogeneous time-resolved FRET assay can be used to determine IC₅₀ values for inhibitors of the soluble human BACE1 catalytic domain. This assay monitors the increase of 620 nm fluorescence that resulted from BACE1 cleavage of an APPswedish APP$^{swe}$ mutant peptide FRET substrate (QSY7-EISEVNLDAEFC-Europium-amide). This substrate contains an N-terminal QSY7 moiety that serves as a quencher of the C-terminal Europium fluorophore (620 nm Em). In the absence of enzyme activity, 620 nm fluorescence is low in the assay and increased linearly over 3 hours in the presence of uninhibited BACE1 enzyme. Inhibition of BACE1 cleavage of the QSY7-APP$^{swe}$-Eu substrate by inhibitors is manifested as a suppression of 620 nm fluorescence.

Varying concentrations of inhibitors at 3× the final desired concentration in a volume of 10 ul are preincubated with purified human BACE1 catalytic domain (3 nM in 10 μl) for 30 minutes at 30° C. in reaction buffer containing 20 mM Na-Acetate pH 5.0, 10% glycerol, 0.1% Brij-35 and 7.5% DSMO. Reactions are initiated by addition of 10 μl of 600 nM QSY7-APP$^{swe}$-Eu substrate (200 nM final) to give a final reaction volume of 30 μl in a 384 well Nunc HTRF plate. The reactions are incubated at 30° C. for 1.5 hours. The 620 nm fluorescence is then read on a Rubystar HTRF plate reader (BMG Labtechnologies) using a 50 millisecond delay followed by a 400 millisecond acquisition time window. Inhibitor IC₅₀ values are derived from non-linear regression analysis of concentration response curves. $K_i$ values are then calculated from IC₅₀ values using the Cheng-Prusoff equation using a previously determined m value of 8 μM for the QSY7-APP$^{swe}$-Eu substrate at BACE1. Observed $K_i$ values for the non-limiting examples are reported in the tables above.

BACE-2 Assay

Inhibitor IC₅₀ₛ at purified human autoBACE-2 are determined in a time-resolved endpoint proteolysis assay that measures hydrolysis of the QSY7-EISEVNLDAEFC-Eu-amide FRET peptide substrate (BACE-HTRF assay). BACE-mediated hydrolysis of this peptide results in an increase in relative fluorescence (RFU) at 620 nm after excitation with 320 nm light. Inhibitor compounds, prepared at 3× the desired final concentration in 1×BACE assay buffer (20 mM sodium acetate pH 5.0, 10% glycerol, 0.1% Brij-35) supplemented with 7.5% DMSO are preincubated with an equal volume of autoBACE-2 enzyme diluted in 1×BACE assay buffer (final enzyme concentration 1 nM) in black 384-well NUNC plates for 30 minutes at 30° C. The assay is initiated by addition of an equal volume of the QSY7-EISEVNLDAEFC-Eu-amide substrate (200 nM final concentration, $K_m$=8 LM for 4 μM for autoBACE-2) prepared in 1×BACE assay buffer supplemented with 7.5% DMSO and incubated for 90 minutes at 30° C. DMSO is present at 5% final concentration in the assay. Following laser excitation of sample wells at 320 nm, the fluorescence signal at 620 nm is collected for 400 ms following a 50 μs delay on a RUBYstar HTRF plate reader (BMG Labtechnologies). Raw RFU data is normalized to maximum (1.0 nM BACE/DMSO) and minimum (no enzyme/DMSO) RFU values. IC₅₀ₛ are determined by nonlinear regression analysis (sigmoidal dose response, variable slope) of percent inhibition data with minimum and maximum values set to 0 and 100 percent respectively. Similar IC₅₀ₛ are obtained when using raw RFU data. The $K_i$ values are calculated from the IC₅₀ using the Cheng-Prusoff equation.

We claim:

1. A compound, or a pharmaceutically acceptable salt thereof, said compound having the structural Formula (I):

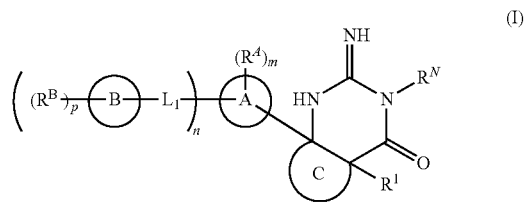

or a tautomer thereof having the structural Formula (I'):

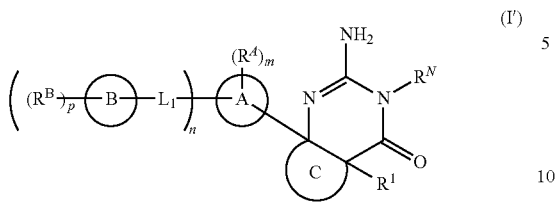

or pharmaceutically acceptable salt thereof, wherein:
ring C is selected from the group consisting of tetrahydrofuranyl and tetrahydropyranyl, wherein 1 or 2 of the ring carbon atoms having two available substitutable hydrogen atoms of said tetrahydrofuranyl and tetrahydropyranyl rings are optionally independently replaced with a —C($R^{C1}R^{C2}$)— group,
  wherein $R^{C1}$ and $R^{C2}$ are each independently selected from the group consisting of H, halogen, —$CO_2$-(lower alkyl), alkyl, cycloalkyl, -alkyl-cycloalkyl, -heterocycloalkyl, -alkyl-heterocycloalkyl, aryl, -alkyl-aryl, heteroaryl, and -alkyl-heteroaryl,
    wherein said alkyl, cycloalkyl, -alkyl-cycloalkyl, -heterocycloalkyl, -alkyl-heterocycloalkyl, aryl, -alkyl-aryl, heteroaryl, and -alkyl-heteroaryl of $R^{C1}$ and $R^{C2}$ are optionally substituted with one or more $R^3$, and
    wherein 1 to 2 non-adjacent, non-terminal carbon atoms in each said alkyl of $R^{C1}$ and $R^{C2}$ are optionally independently replaced with —O—, —NH—, —N(alkyl)-, —S—, —S(O)—, or —S(O)$_2$—,
  or, alternatively, wherein said $R^{C1}$ and $R^{C2}$ of one said —C($R^{C1}R^{C2}$)— group are taken together with the carbon to which they are attached form a spirocyclic ring consisting of from 3 to 6 carbon atoms, wherein 1 of said carbon atoms may be replaced with —O—, —NH—, —N(lower alkyl)-, —N(lower haloalkyl)-, —S—, —S(O)—, or —S(O)$_2$—, and
    wherein each of the carbon atoms of said spirocyclic ring may be optionally independently substituted with 1 to 4 fluorine, lower alkyl, lower haloalkyl, or —$CH_2$O-(lower alkyl);
$R^N$ is selected from the group consisting of H, alkyl, cycloalkyl, and -alkyl-cycloalkyl,
  wherein said alkyl, cycloalkyl, and -alkyl-cycloalkyl are optionally substituted with one or more fluorine, and
  wherein 1 to 2 non-adjacent, non-terminal carbon atoms in said alkyl are optionally independently replaced with —O—, —NH—, —N(alkyl)-, —S—, —S(O)—, or —S(O)$_2$—,
$R^1$ is selected from the group consisting of H, halogen, and alkyl,
  wherein said alkyl is optionally substituted with one or more fluorine, and
  wherein 1 to 2 non-adjacent, non-terminal carbon atoms in said alkyl are optionally independently replaced with —O—, —NH—, —N(alkyl)-, —S—, —S(O)—, or —S(O)$_2$—,
ring A is selected from the group consisting of aryl and heteroaryl;
m is 0 or more, with the proviso that the value of m does not exceed the number of available substitutable hydrogen atoms on ring A;
each $R^A$ (when present) is independently selected from the group consisting of halogen, oxo, —OH, —CN, lower alkyl, —O-(lower alkyl), lower alkenyl, —O-(lower alkenyl), and -(lower alkyl)-(lower cycloalkyl);
  wherein said lower alkyl, —O-(lower alkyl), lower alkenyl, —O-(lower alkenyl), and -(lower alkyl)-(lower cycloalkyl) of $R^A$ are each optionally independently unsubstituted or substituted with one or more fluorine, and
  wherein 1 to 2 non-adjacent, non-terminal carbon atoms in said lower alkyl and are optionally independently replaced with —O—, —NH—, —N(alkyl)-, —S—, —S(O)—, or —S(O)$_2$—;
n is 0 or 1;
-$L_1$- (when present) independently represents a bond or a divalent moiety selected from the group consisting of —O—, —$CH_2$—O—, —$CH(CH_3)$—O—, —CH($CF_3$)—O—, and —CH($CHF_2$)—O—;
ring B is selected from the group consisting of aryl, heteroaryl, cycloalkyl, and heterocycloalkyl;
p is 0 or more, with the proviso that the value of p does not exceed the number of available substitutable hydrogen atoms on ring B; and
each $R^B$ (when present) is independently selected from the group consisting of halogen, oxo, —OH, —CN, —$SF_5$, —$OSF_5$, —$OR^{2B}$, —$SR^{2B}$, alkyl, alkenyl, alkynyl, cycloalkyl, -alkyl-cycloalkyl, heterocycloalkyl, -alkyl-heterocycloalkyl, aryl, and heteroaryl,
  wherein said alkyl, alkenyl, alkynyl, cycloalkyl, -alkyl-cycloalkyl, heterocycloalkyl, -alkyl-heterocycloalkyl, aryl, and heteroaryl of $R^B$ are each optionally independently unsubstituted or substituted with one or more groups independently selected from $R^3$, and wherein 1 to 2 non-adjacent, non-terminal carbon atoms in said alkyl are optionally independently replaced with —O—, —NH—, —N(alkyl)-, —S—, —S(O)—, or —S(O)$_2$—;
each $R^{2B}$ is independently selected from the group consisting of H, alkyl, alkenyl, alkynyl, cycloalkyl, -alkyl-cycloalkyl, heterocycloalkyl, and -alkyl-heterocycloalkyl,
  wherein each said alkyl, alkenyl, alkynyl, cycloalkyl, -alkyl-cycloalkyl, heterocycloalkyl, and -alkyl-heterocycloalkyl of $R^{2B}$ is unsubstituted or optionally substituted with one or more fluorine, and
  wherein 1 to 2 non-adjacent, non-terminal carbon atoms in said alkyl are optionally independently replaced with —O—, —NH—, —N(alkyl)-, —S—, —S(O)—, or —S(O)$_2$—;
each $R^3$ (when present) is independently selected from the group consisting of halogen, —OH, —CN, alkyl, -alkyl-OH, —O-alkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl,
  wherein each said alkyl, -alkyl-OH, —O-alkyl, cycloalkyl, -alkyl-cycloalkyl, —O-cycloalkyl, —O-alkyl-cycloalkyl, -heterocycloalkyl, -alkyl-heterocycloalkyl, —O-heterocycloalkyl and —O-alkyl-heterocycloalkyl, are optionally substituted with one or more halogen,
  and wherein 1 to 2 non-adjacent, non-terminal carbon atoms in said alkyl and —O-alkyl, are optionally independently replaced with —O—, —NH—, —N(alkyl)-, —S—, —S(O)—, or —S(O)$_2$—.

2. A compound of claim 1, or a tautomer thereof, or a pharmaceutically acceptable salt of said compound or said tautomer, wherein:
$R^N$ is methyl; and
$R^1$ is H.

3. A compound of claim 2, or a tautomer thereof, or a pharmaceutically acceptable salt of said compound or said tautomer, wherein:
ring C is

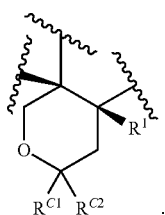

4. A compound of claim 3, or a tautomer thereof, or a pharmaceutically acceptable salt of said compound or said tautomer, wherein:
$R^{C1}$ and $R^{C2}$ are each independently selected from the group consisting of H, —CO$_2$CH$_3$, methyl, —CHF$_2$, cyclopropyl, —CH$_2$OCH$_3$, phenyl, and isoxazoyl, wherein each said phenyl and isoxazoyl of $R^{C1}$ and $R^{C2}$ is unsubstituted or substituted with one or more fluoro or methyl groups.

5. A compound of claim 4, or a tautomer thereof, or a pharmaceutically acceptable salt of said compound or said tautomer, wherein:
n=1;
-L$_1$- is —O—;
ring B is selected from the group consisting of cyclobutyl, cyclopentyl, cyclopropyl, isoquinolinyl, phenyl, piperidinyl, pyrazinyl, pyrazolyl, pyridazinyl, pyridinyl, pyrimidinyl, pyrrolidinyl, quinolinyl, tetrahydrofuranyl, and tetrahydropyranyl;
p is 0, 1, 2, or 3, with the proviso that the value of p does not exceed the number of available substitutable hydrogen atoms on ring B; and
each $R^B$ group (when present) is independently selected from the group consisting of fluoro, chloro, —CN, —OCH$_3$, —O—CH$_2$-cyclopropyl, OCH$_2$—C≡C—H, —OCH$_2$—C≡C—CH$_3$, methyl, ethyl, cyclopropyl, —CH$_2$-cyclopropyl, —CH$_2$OCH$_3$, —C≡CH, —C≡C—CH$_3$, —CF$_3$, —CHF$_2$, —OCF$_3$, —OCHF$_2$, oxadiazolyl, isoxazolyl, oxazolyl, pyrazolyl, pyrrolyl, and triazolyl,
wherein each said oxadiazolyl, isoxazolyl, oxazolyl, pyrazolyl, pyrrolyl, and triazolyl, is optionally substituted with one substituent from the group consisting of fluoro and methyl.

6. A compound of claim 4, or a tautomer thereof, or a pharmaceutically acceptable salt of said compound or said tautomer, wherein:
n=1;
-L$_1$- is —CH$_2$O—;
ring B is selected from the group consisting of [1.1.1]-bicyclopentane, cyclobutyl, cyclopropyl, oxazolyl, phenyl, pyrazinyl, pyridinyl, pyrimidinyl, tetrahydropyranyl, and thiazolyl;
p is 0, 1, 2, or 3, with the proviso that the value of p does not exceed the number of available substitutable hydrogen atoms on ring B; and each $R^B$ group (when present) is independently selected from the group consisting of fluoro, chloro, —CN, —OCH$_3$, —OCH$_2$—C≡C—H, —OCH$_2$—C≡C—CH$_3$, methyl, cyclopropyl, —CH$_2$OCH$_3$, —C≡CH, —C≡C—CH$_3$, —CH$_3$, —CHF$_2$, —OCF$_3$, and —OCHF$_2$.

7. A compound of claim 4, or a tautomer thereof, or a pharmaceutically acceptable salt of said compound or said tautomer, wherein:
n=1;
-L$_1$- is a bond;
ring A is selected from the group consisting of phenyl, pyridinyl, and thienyl;
m is 0, 1, 2, or 3;
each $R^A$ (when present) is independently selected from the group consisting of fluoro, chloro, methyl, and —CHF$_2$;
ring B is selected from the group consisting of phenyl, pyridinyl, and pyrimidinyl;
p is 0, 1, or 2; and
each $R^B$ group (when present) is independently selected from the group consisting of fluoro, chloro, methyl, —CN, —OMe, —C≡CH, —C≡C—CH$_3$, and —CHF$_2$.

8. A compound of claim 4, or a tautomer thereof, or a pharmaceutically acceptable salt of said compound or said tautomer, wherein:
n=0;
ring A is selected from the group consisting of phenyl, pyridazinyl, pyridinyl, pyrimidinyl, pyrazinyl, pyrazolyl, triazinyl, thiazolyl, and thienyl;
m is 0, 1, 2, 3, or 4, with the proviso that the value of m does not exceed the number of available substitutable hydrogen atoms on ring A; and
each $R^A$ (when present) is independently selected from the group consisting of fluoro, chloro, bromo, oxo, —OH, —CN, methyl, ethyl, propyl, butyl, —CH$_2$-cyclopropyl, —CH$_2$CH$_2$CH═CH$_2$, —CH$_2$OCH$_3$, —CH$_2$OCF$_3$, —CH$_2$OCH$_2$CH$_3$, —CH$_2$CH$_2$OCH$_3$, —CH$_2$NHCH$_3$, —CH$_2$NHCH$_2$CH$_3$, —CH$_2$NHCH$_2$CF$_3$, —CF$_3$, —CHF$_2$, —CH$_2$F, —OCH$_3$, —OCH$_2$CH$_3$, —OCH$_2$CH$_2$CH$_3$, —OCH$_2$CH(CH$_3$)$_2$, —OCH$_2$CH$_2$OCH$_3$, —OCF$_3$, —OCHF$_2$, —OCH$_2$F, —OCH$_2$CF$_3$, —OCH$_2$CHF$_2$, —OCH$_2$CH$_2$F, and —OCH$_2$CH$_2$CF$_3$.

9. A compound of claim 1, or a tautomer thereof, or a pharmaceutically acceptable salt of said compound or said tautomer, said compound selected from the group consisting of:

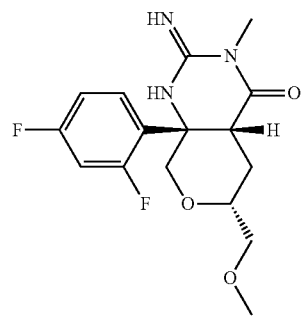 [SMILES: COC[C@H]1C[C@H]2C(=O)N(C)C(=N)N[C@@]2(c2ccc(F)cc2F)CO1]

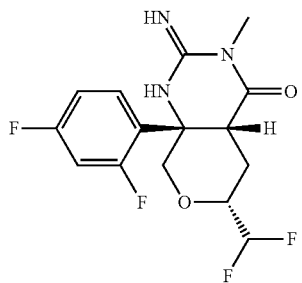
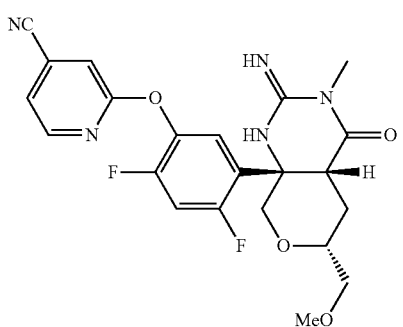 [SMILES: COC[C@H]1C[C@H]2C(=O)N(C)C(=N)N[C@@]2(c2cc(Oc3cc(C#N)ccn3)c(F)cc2F)CO1]
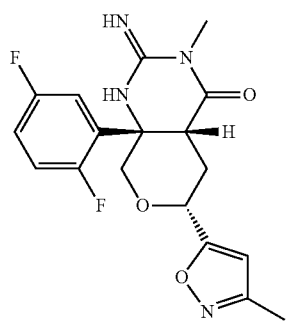
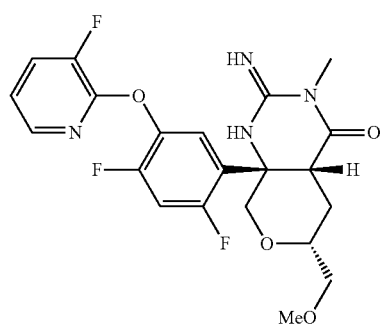 [SMILES: COC[C@H]1C[C@H]2C(=O)N(C)C(=N)N[C@@]2(c2cc(Oc3ncccc3F)c(F)cc2F)CO1]
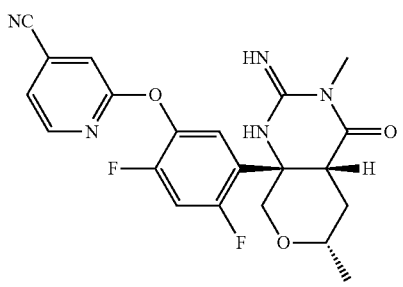
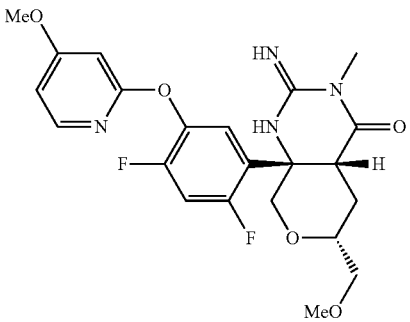 [SMILES: COC[C@H]1C[C@H]2C(=O)N(C)C(=N)N[C@@]2(c2cc(Oc3cc(OC)ccn3)c(F)cc2F)CO1]
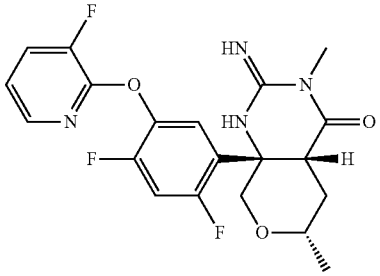
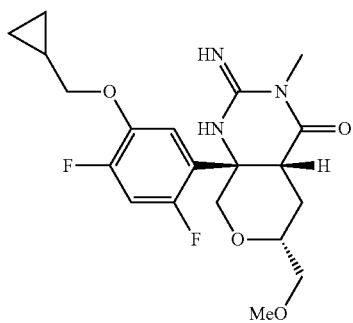 [SMILES: COC[C@H]1C[C@H]2C(=O)N(C)C(=N)N[C@@]2(c2cc(OCC3CC3)c(F)cc2F)CO1]
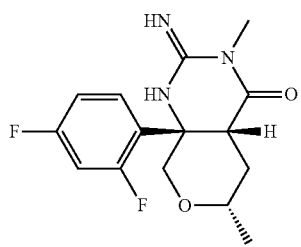
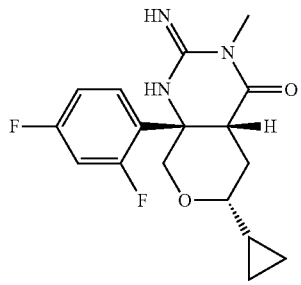 [SMILES: CN1C(=N)N[C@@]2(c3ccc(F)cc3F)CO[C@@H](C3CC3)C[C@H]2C1=O]
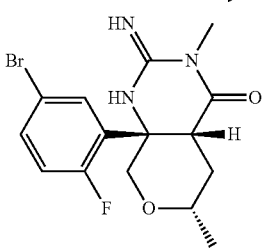

195
-continued
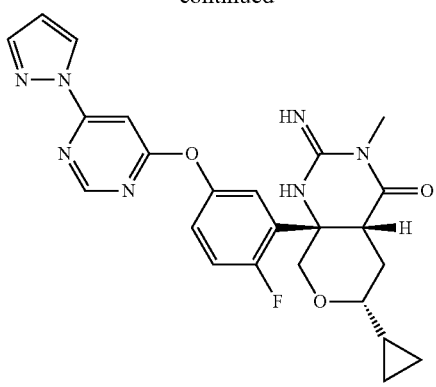
196
-continued
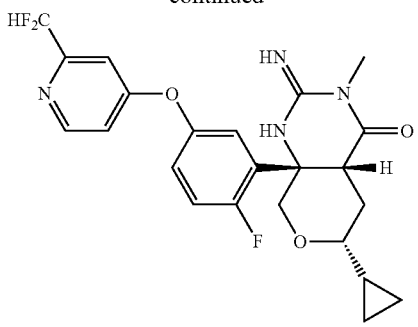
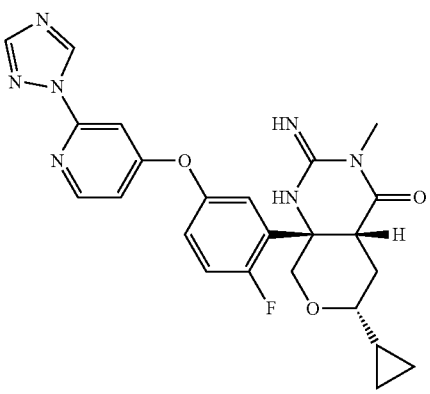
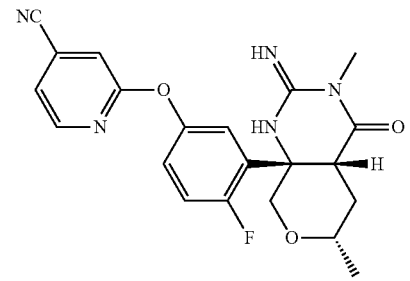
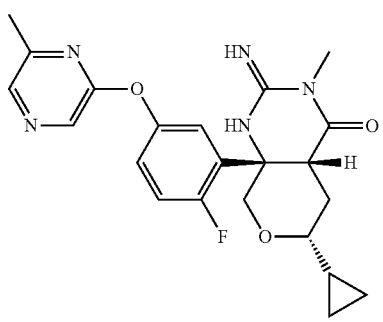 [SMILES: Cc1cncc(Oc2ccc(F)c([C@]34CO[C@@H](C5CC5)C[C@H]3C(=O)N(C)C(=N)N4)c2)n1]
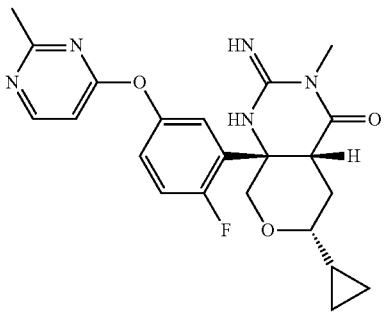 [SMILES: Cc1nccc(Oc2ccc(F)c([C@]34CO[C@@H](C5CC5)C[C@H]3C(=O)N(C)C(=N)N4)c2)n1]

197
-continued
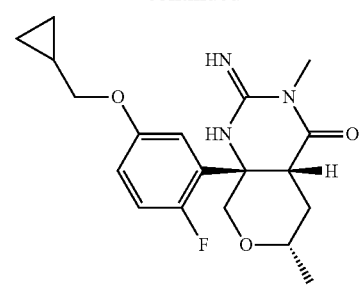 [SMILES: C[C@H]1C[C@H]2C(=O)N(C)C(=N)N[C@@]2(c2cc(OCC3CC3)ccc2F)CO1]
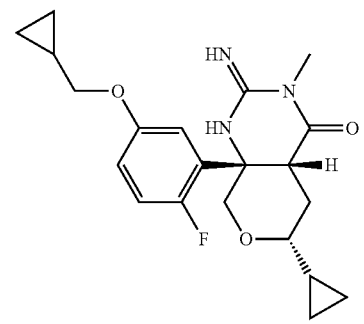 [SMILES: CN1C(=N)N[C@@]2(c3cc(OCC4CC4)ccc3F)CO[C@@H](C3CC3)C[C@H]2C1=O]
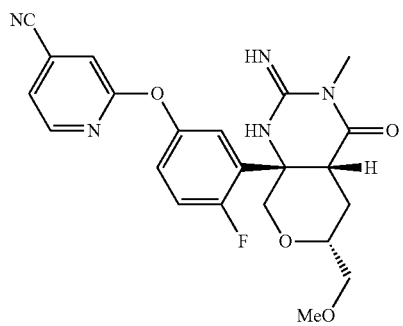
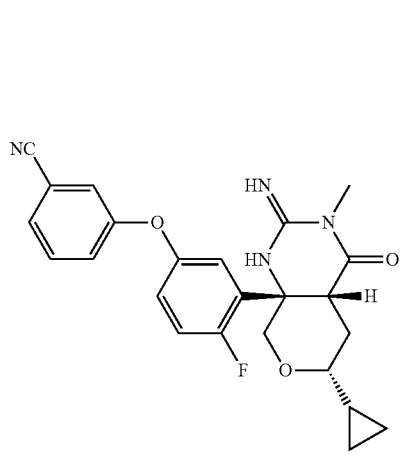
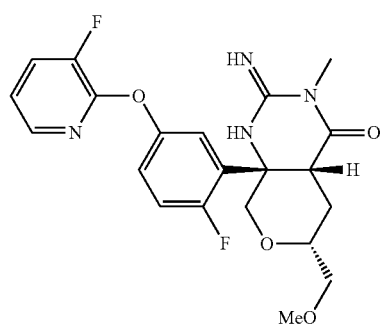
198
-continued
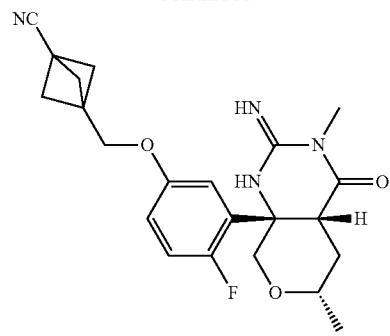 [SMILES: C[C@H]1C[C@H]2C(=O)N(C)C(=N)N[C@@]2(c2cc(OCC34CC(C#N)(C3)C4)ccc2F)CO1]
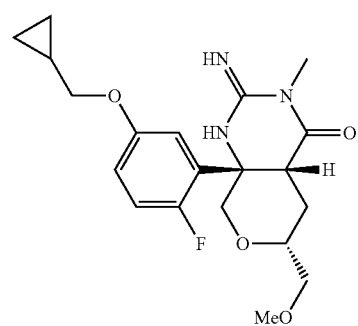
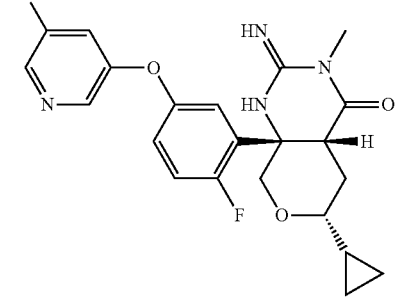
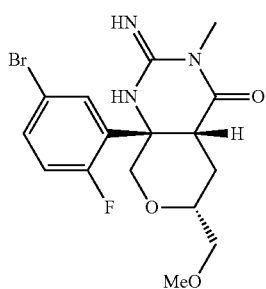 [SMILES: COC[C@H]1C[C@H]2C(=O)N(C)C(=N)N[C@@]2(c2cc(Br)ccc2F)CO1]
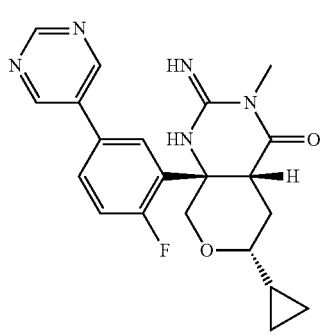

199
-continued
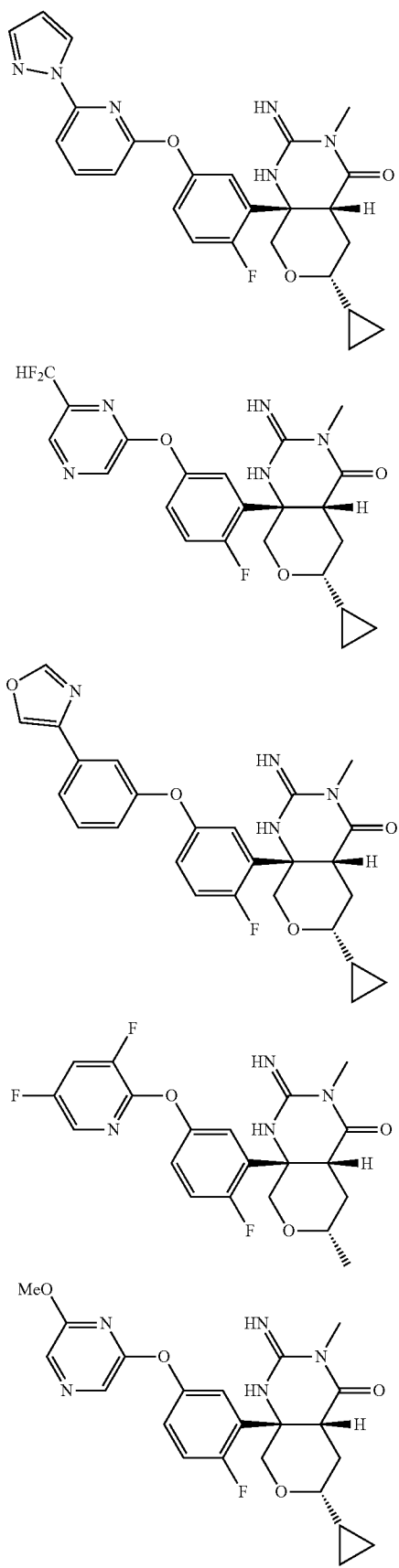
200
-continued
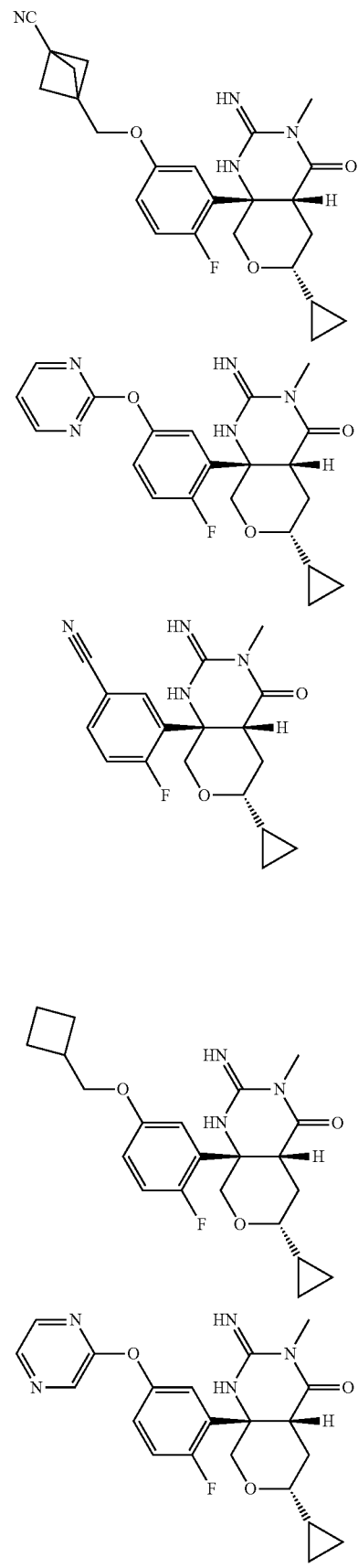

201
-continued
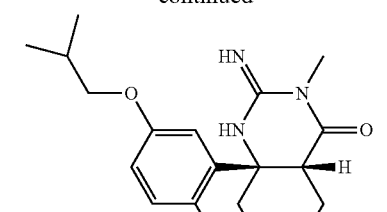
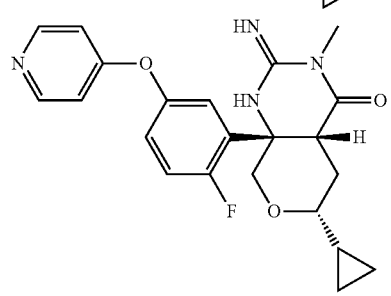
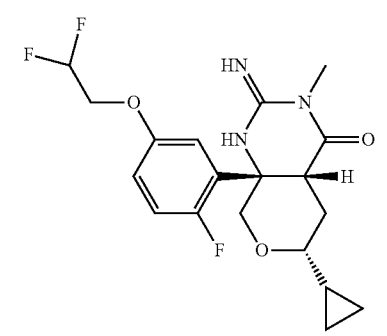
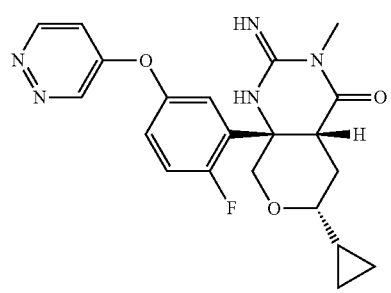 [SMILES: CN1C(=N)N[C@@]2(c3cc(Oc4ccncc4)ccc3F)CO[C@@H](C3CC3)C[C@H]2C1=O]
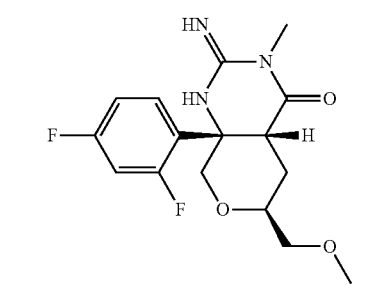 [SMILES: COC[C@@H]1C[C@H]2C(=O)N(C)C(=N)N[C@@]2(c2ccc(F)cc2F)CO1]
202
-continued
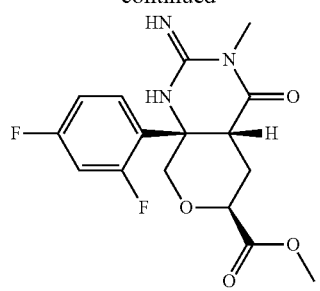
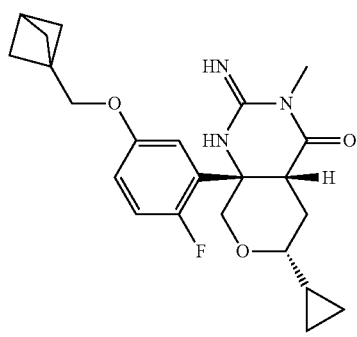 [SMILES: CN1C(=N)N[C@@]2(c3cc(OCC45CC(C4)C5)ccc3F)CO[C@@H](C3CC3)C[C@H]2C1=O]
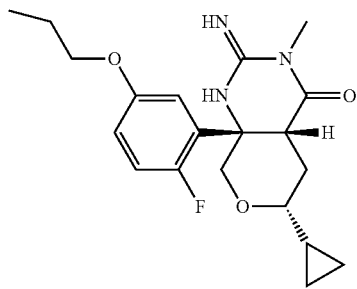
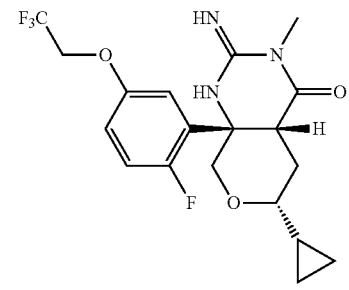 [SMILES: CN1C(=N)N[C@@]2(c3cc(OCC(F)(F)F)ccc3F)CO[C@@H](C3CC3)C[C@H]2C1=O]
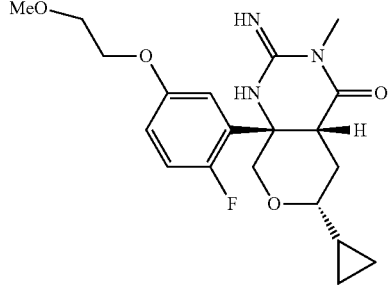

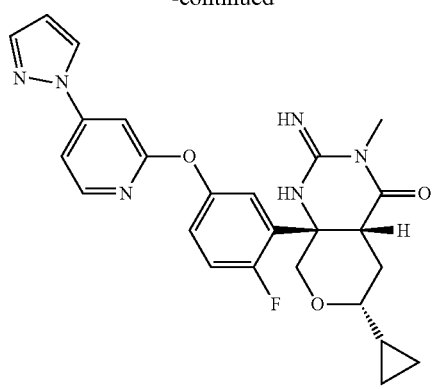
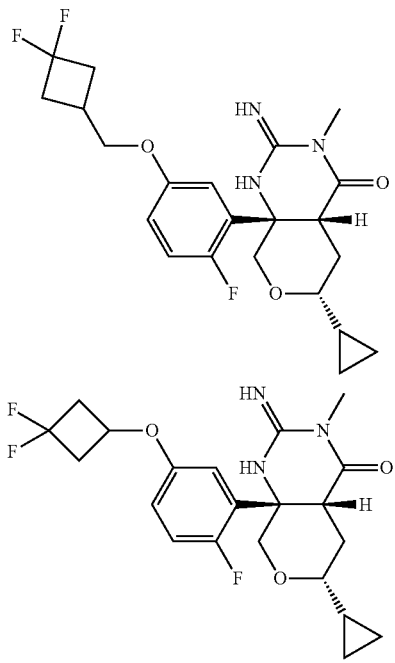
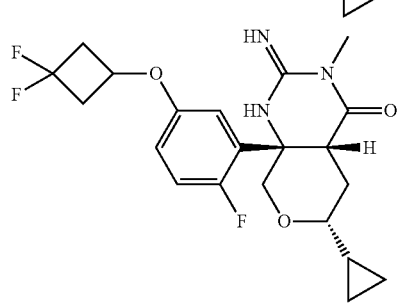
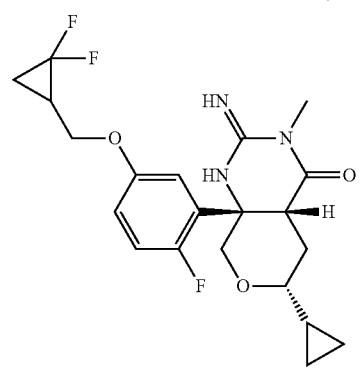
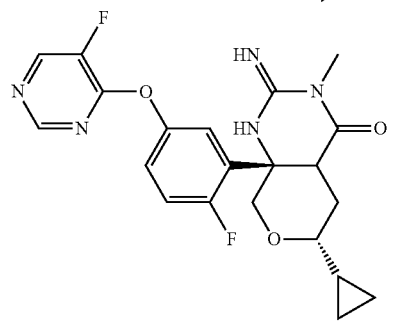
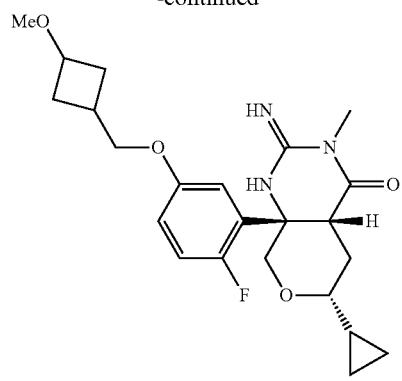
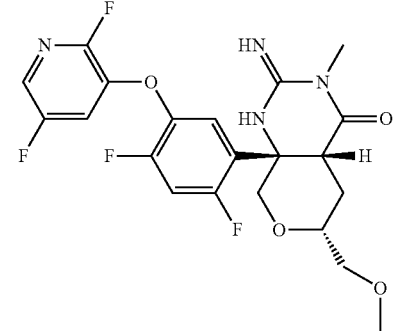 [SMILES: COC[C@H]1C[C@H]2C(=O)N(C)C(=N)N[C@@]2(c2cc(Oc3cc(F)cnc3F)c(F)cc2F)CO1]
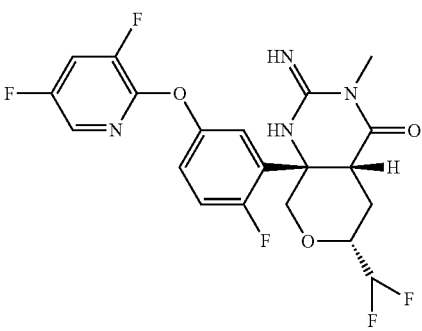 [SMILES: CN1C(=N)N[C@@]2(c3cc(Oc4ncc(F)cc4F)ccc3F)CO[C@@H](C(F)F)C[C@H]2C1=O]
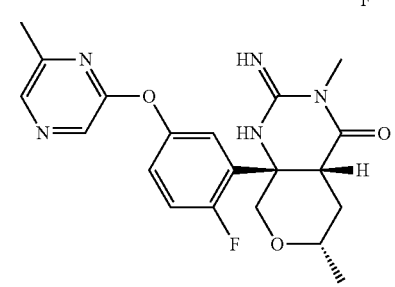
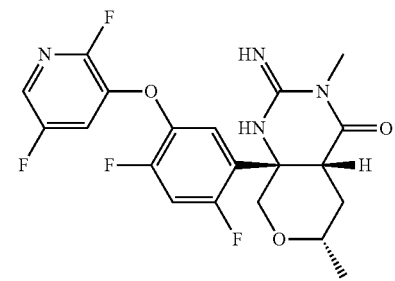 [SMILES: C[C@H]1C[C@H]2C(=O)N(C)C(=N)N[C@@]2(c2cc(Oc3cc(F)cnc3F)c(F)cc2F)CO1]

205
-continued
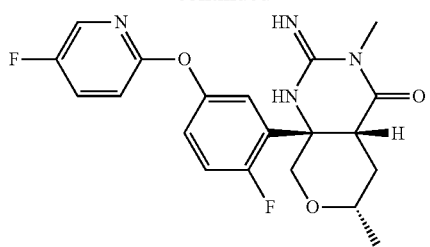
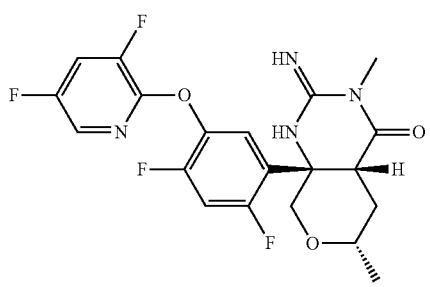 [SMILES: C[C@H]1C[C@H]2C(=O)N(C)C(=N)N[C@@]2(c2cc(Oc3ncc(F)cc3F)c(F)cc2F)CO1]
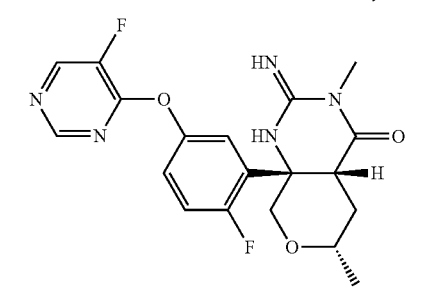
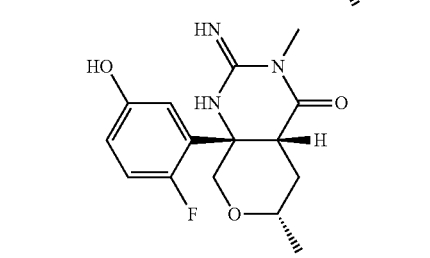
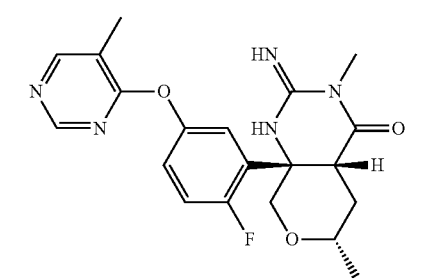
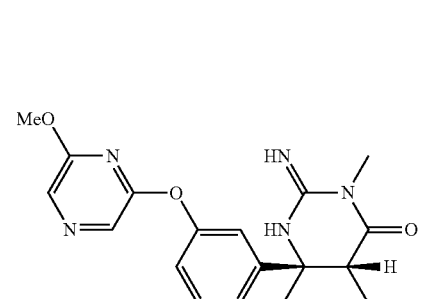
206
-continued
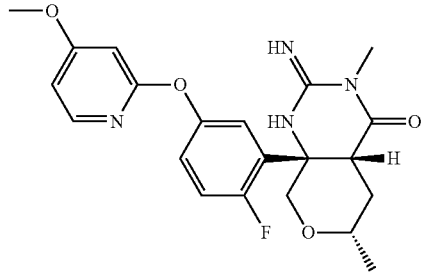 [SMILES: COc1ccnc(Oc2ccc(F)c([C@]34CO[C@@H](C)C[C@H]3C(=O)N(C)C(=N)N4)c2)c1]
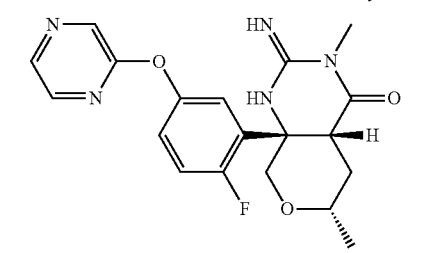
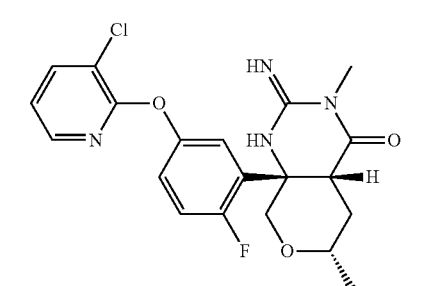
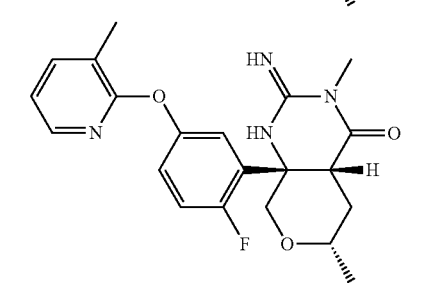
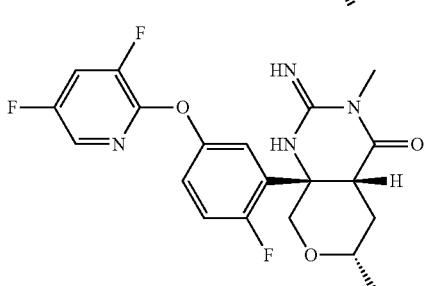
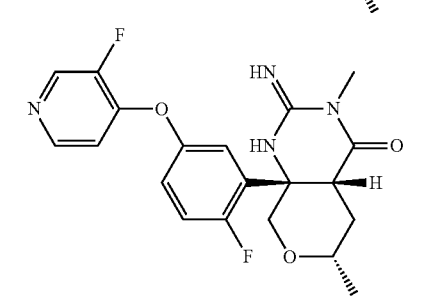

207
-continued
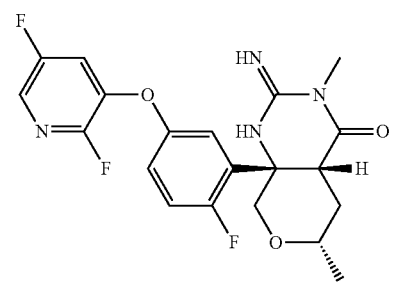
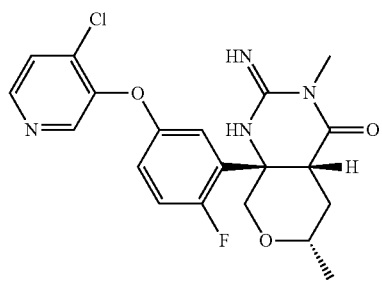 [SMILES: C[C@H]1C[C@H]2C(=O)N(C)C(=N)N[C@@]2(c2cc(Oc3cnccc3Cl)ccc2F)CO1]
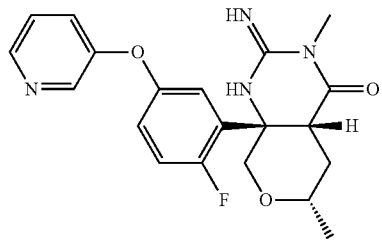
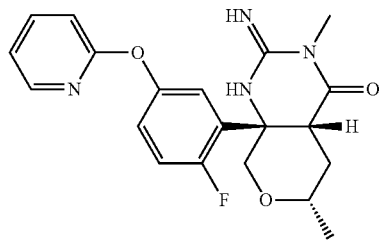 [SMILES: C[C@H]1C[C@H]2C(=O)N(C)C(=N)N[C@@]2(c2cc(Oc3ccccn3)ccc2F)CO1]
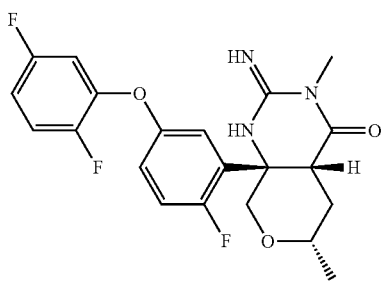
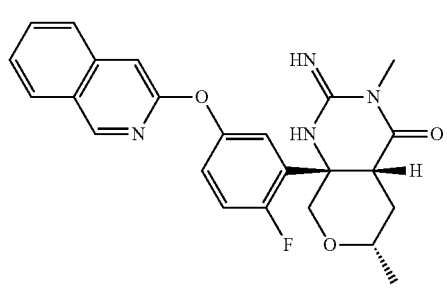 [SMILES: C[C@H]1C[C@H]2C(=O)N(C)C(=N)N[C@@]2(c2cc(Oc3cc4ccccc4cn3)ccc2F)CO1]
208
-continued
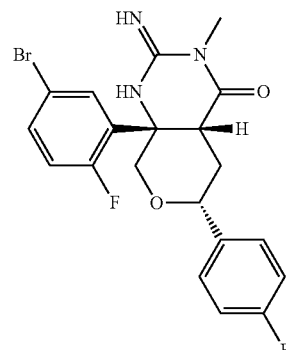
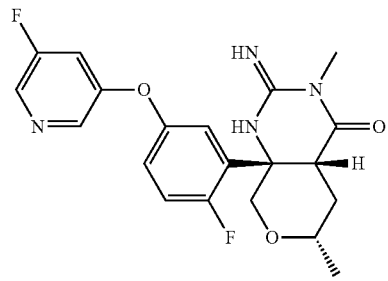 [SMILES: C[C@H]1C[C@H]2C(=O)N(C)C(=N)N[C@@]2(c2cc(Oc3cncc(F)c3)ccc2F)CO1]
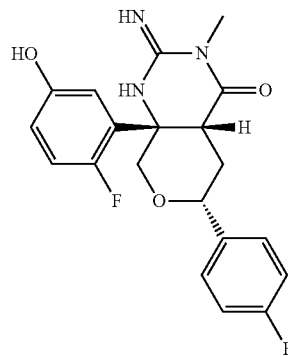
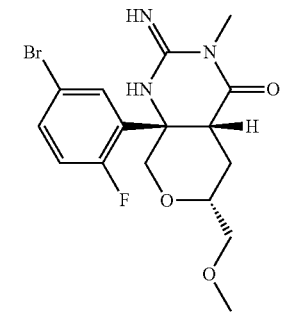
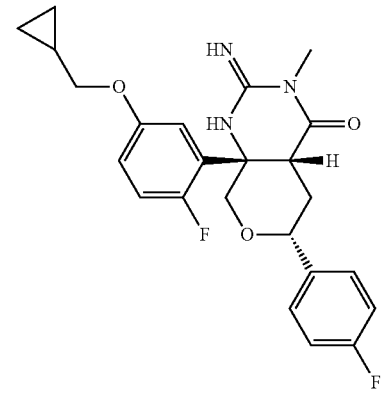 [SMILES: CN1C(=N)N[C@@]2(c3cc(OCC4CC4)ccc3F)CO[C@@H](c3ccc(F)cc3)C[C@H]2C1=O]

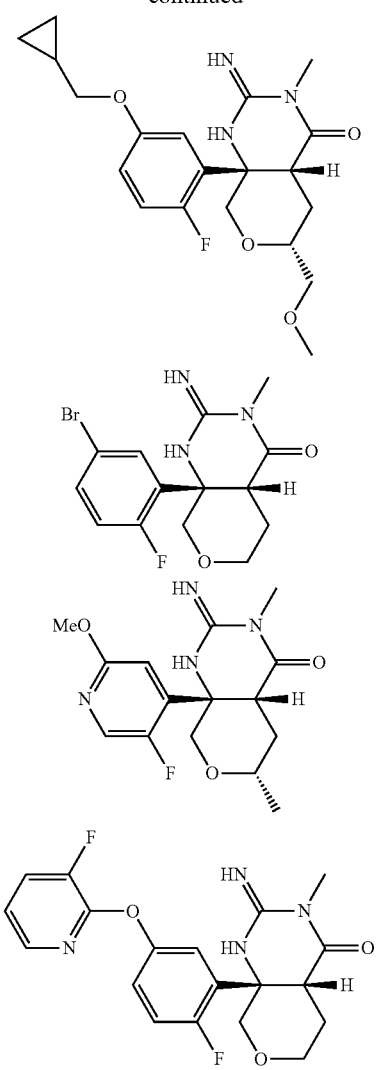

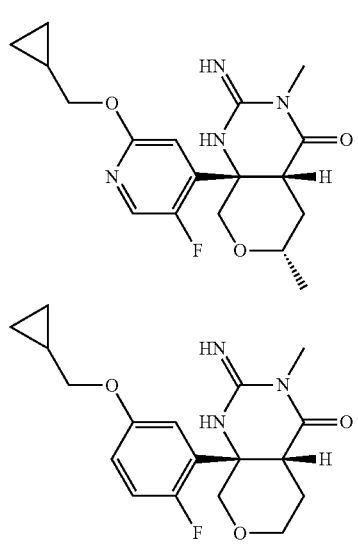

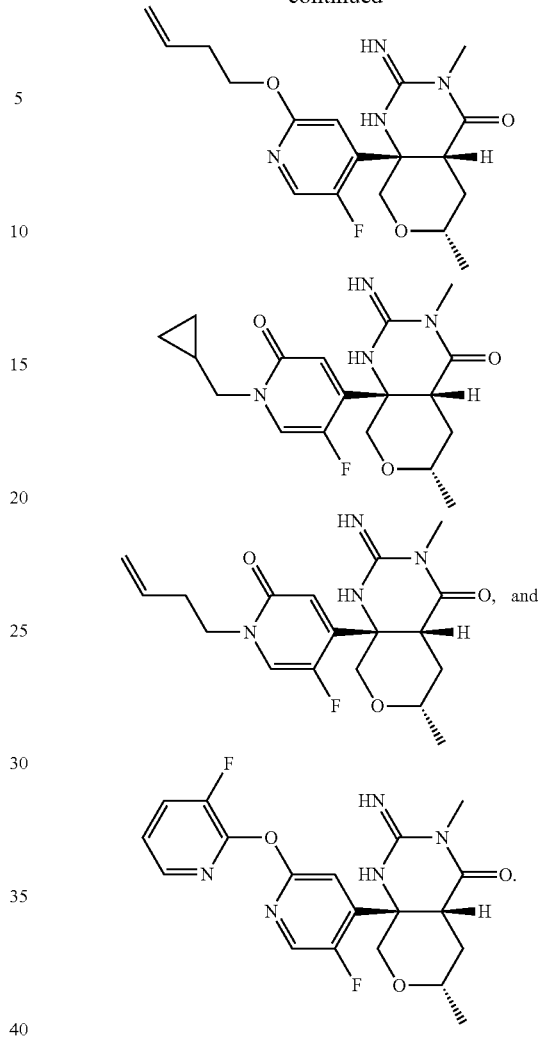

10. A pharmaceutical composition comprising a compound according to claim 1, or a tautomer thereof, or a pharmaceutically acceptable salt of said compound or said tautomer, and a pharmaceutically acceptable carrier or diluent.

11. A method of treating a disease or pathology, wherein said disease or pathology is Alzheimer's disease, olfactory impairment associated with Alzheimer's disease, Down's syndrome, olfactory impairment associated with Down's syndrome, Parkinson's disease, olfactory impairment associated with Parkinson's disease, stroke, microgliosis brain inflammation, pre-senile dementia, senile dementia, progressive supranuclear palsy, cortical basal degeneration, β-amyloid angiopathy, cerebral amyloid angiopathy, hereditary cerebral hemorrhage, mild cognitive impairment, glaucoma, amyloidosis, type II diabetes, diabetes-associated amyloidogenesis, scrapie, bovine spongiform encephalitis, traumatic brain injury, or Creutzfeld-Jakob disease, said method comprising administering a compound according to claim 1, or a tautomer thereof, or a pharmaceutically acceptable salt of said compound or said tautomer, to a patient in need thereof in an amount effective to treat said disease or pathology.

12. The method of claim 11, wherein said disease or pathology is Alzheimer's disease.

* * * * *